US009114131B2

(12) United States Patent
Watanabe et al.

(10) Patent No.: US 9,114,131 B2
(45) Date of Patent: Aug. 25, 2015

(54) ANTIBODY TARGETING OSTEOCLAST-RELATED PROTEIN SIGLEC-15

(75) Inventors: Ichiro Watanabe, Tokyo (JP); Yoshiharu Hiruma, Tokyo (JP); Eisuke Tsuda, Tokyo (JP); Tatsuji Matsuoka, Tokyo (JP); Toshiaki Ohtsuka, Tokyo (JP); Tohru Takahashi, Tokyo (JP); Toshinori Agatsuma, Tokyo (JP); Sandra Miller, Munich (DE); Robert Mühlbacher, Martinsried/Planegg (DE); Kathrin-Ladetzki Baehs, Martinsried/Planegg (DE); Steffen Runz, Martinsried/Planegg (DE); Ulrike Schubert, Munich (DE); Ingrid Schuster, Munich (DE); Dirk Ponsel, Germering (DE)

(73) Assignee: Daiichi Sankyo Company, Limited, Tokyo (JP)

(*) Notice: Subject to any disclaimer, the term of this patent is extended or adjusted under 35 U.S.C. 154(b) by 32 days.

(21) Appl. No.: 13/877,779

(22) PCT Filed: Oct. 4, 2011

(86) PCT No.: PCT/EP2011/005219
§ 371 (c)(1),
(2), (4) Date: Jul. 12, 2013

(87) PCT Pub. No.: WO2012/045481
PCT Pub. Date: Apr. 12, 2012

(65) Prior Publication Data
US 2013/0280276 A1    Oct. 24, 2013

(30) Foreign Application Priority Data

Oct. 5, 2010    (EP) .................................... 10251744

(51) Int. Cl.
| A61K 39/00 | (2006.01) |
| A61K 39/395 | (2006.01) |
| C07K 16/00 | (2006.01) |
| C07K 16/22 | (2006.01) |
| C12N 5/10 | (2006.01) |
| C12N 15/11 | (2006.01) |
| C12N 15/63 | (2006.01) |
| C07K 16/28 | (2006.01) |
| A61K 45/06 | (2006.01) |

(52) U.S. Cl.
CPC ............. *A61K 39/3955* (2013.01); *A61K 45/06* (2013.01); *C07K 16/2803* (2013.01); *A61K 2039/505* (2013.01); *C07K 2317/21* (2013.01); *C07K 2317/55* (2013.01); *C07K 2317/92* (2013.01)

(58) Field of Classification Search
None
See application file for complete search history.

(56) References Cited

U.S. PATENT DOCUMENTS

| 6,855,808 B2 | 2/2005 | Goto et al. |
| 7,125,686 B1 | 10/2006 | Goto et al. |
| 7,205,397 B2 | 4/2007 | Goto et al. |
| 7,276,344 B2 | 10/2007 | Goto et al. |
| 7,405,037 B2 | 7/2008 | Greenwalt |
| 7,468,268 B2 | 12/2008 | Goto et al. |
| 7,608,704 B2 | 10/2009 | Yue et al. |
| 7,989,160 B2 | 8/2011 | Sooknanan et al. |
| 8,540,988 B2 | 9/2013 | Sooknanan et al. |
| 8,546,540 B2 | 10/2013 | Hiruma et al. |
| 2004/0023313 A1 | 2/2004 | Boyle et al. |
| 2004/0033535 A1 | 2/2004 | Boyle et al. |
| 2004/0076992 A1 | 4/2004 | Nakamura et al. |
| 2009/0298763 A1 | 12/2009 | Sooknanan et al. |
| 2010/0104575 A1 | 4/2010 | Sooknanan et al. |
| 2011/0268733 A1 | 11/2011 | Hiruma et al. |
| 2011/0311526 A1 | 12/2011 | Sooknanan et al. |
| 2012/0230988 A1 | 9/2012 | Hiruma et al. |
| 2012/0251485 A1 | 10/2012 | Hiruma et al. |

FOREIGN PATENT DOCUMENTS

| CA | 2 225 366 C | 10/2006 |
| EP | 1 580 263 A1 | 9/2005 |
| EP | 1 715 038 | 10/2006 |
| JP | 2007-020403 | 2/2007 |
| RU | 2 228 335 C2 | 8/1999 |

(Continued)

OTHER PUBLICATIONS

Paul, Fundamental Immunology, 1993, Raven Press, NY, pp. 292-295.*
Casset et al. (Biochem Biophys Res Comm. 2003; 307:198-205).*
MacCallum et al. (J Mol Biol. 1996; 262:732-745).*
Vajdos et al. (J Mol Biol. 2002; 320(2):415-428).*
Holm et al. (Mol Immunol. 2007; 44(6):1075-1084).*
Chen et al. (J Mol Biol. 1999; 293:865-881).*
Protest to the Grant of a Patent dated Apr. 2, 2014, filed against Canadian Patent Application No. 2698326, 11 pages.

(Continued)

*Primary Examiner* — Elizabeth C Kemmerer
(74) *Attorney, Agent, or Firm* — Foley & Lardner LLP

(57) ABSTRACT

An isolated antibody capable of binding Siglec-15 which inhibits osteoclast formation and/or osteoclastic bone resorption, or a functional fragment thereof. The heavy chain of the antibody comprises a CDRH1 comprising a sequence having at least 80% sequence identity to SEQ ID NO: 106, a CDRH2 comprising a sequence having at least 80% sequence identity to SEQ ID NO: 107, and a CDRH3 comprising a sequence having at least 80% sequence identity to one of SEQ ID NOS: 35, 45, 55, 65 or 80. The light chain of the antibody comprises a CDRL1 comprising a sequence having at least 80% sequence identity to SEQ ID NO: 73 or 83, a CDRL2 comprising a sequence having at least 80% sequence identity to SEQ ID NO: 108, and a CDRL3 comprising a sequence having at least 80% sequence identity to one of SEQ ID NOS: 40, 50, 60, 70, 90, 100 or 109.

42 Claims, 39 Drawing Sheets

(56) References Cited

FOREIGN PATENT DOCUMENTS

| RU | 2 238 948 C2 | 3/2004 |
|---|---|---|
| RU | 2238949 C2 | 10/2004 |
| WO | WO 98/46644 A1 | 10/1998 |
| WO | WO 02/38602 | 5/2002 |
| WO | WO 02/064771 | 8/2002 |
| WO | WO 03/048305 | 6/2003 |
| WO | WO 2005/113794 A1 | 12/2005 |
| WO | WO 2007/093042 | 8/2007 |
| WO | WO 2009/048072 | 4/2009 |
| WO | WO 2010/117011 A1 | 10/2010 |
| WO | WO 2011/041894 A1 | 4/2011 |

OTHER PUBLICATIONS

Decision to Grant dated Aug. 13, 2014 in RU 2011128332, 24 pages, with English translation, 20 pages.
Buckley et al., "Human Osteoclast Culture From Peripheral Blood Monocytes," Methods in Molecular Medicine, 107:55-68, Human Cell Culture Protocols, Second Edition, 2005.
Collin-Osdoby et al., "RANKL-Mediated Osteoclast Formation from Murine RAW 264.7 Cells," Methods in Molecular Medicine, 80:153-166, Bone Research Protocols, 2003.
U.S. Appl. No. 14/041,479, filed Sep. 30, 2013, Hiruma et al.
Abaza et al., "Effects of amino acid substitutions outside an antigenic site on protein binding to monoclonal antibodies of predetermined specificity obtained by peptide immunization: demonstration with region 94-100 (antigenic site 3) of myoglobin," J. Protein Chem., Oct. 1992, 11(5):433-444.
Akatsu et al., "Osteoclastogenesis inhibitory factor suppresses osteoclast survival by interfering in the interaction of stromal cells with osteoclast," Biochemical and Biophysical Research Communications, Sep. 18, 1998, 250(2):229-234.
Angata et al., "Siglec-15: an immune system Siglec c observed throughout vertebrate evolution," Glycobiology, Aug. 2007, 17(8):838-846.
Bird et al., "Single-chain antigen-binding proteins," Science, 1988, 242(4877):423-426.
Casset et al., "A peptide mimetic of an anti-CD4 monoclonal antibody by rational design," Biochemical and Biophysical Research Communications, 2003, 307:198-205.
Chen et al., "Selection and Analysis of an Optimized Anti-VEGF Antibody: Crystal Structure of an Affinity-matured Fab in Complex with Antigen," J. Mol. Biol., 1999, 293:865-881.
Clackson et al., "Making antibody fragments using phage display libraries," 1991, Nature 352:624-628.
Colman, P.M., "Effects of amino acid sequence changes on antibody-antigen interactions," Res. Immunol., 1994, 145(1):33-36.
Daugherty et al., "Antibody affinity maturation using bacterial surface display," 1998, Protein Eng., 11:825-832.
Decision to Grant issued in Russian Application No. 2010106639/10 on Sep. 17, 2012, with an English translation.
Duquesnoy, R.J., "Structural and functional definitions of epitopes reacting with mouse monoclonal antibodies," 2008, suppl. www/hlamatchmaker.net, 14 pages.
Gen Bank: BAA08453, human bone morphogenetic protein-3b (*Homo sapiens*), Dec. 27, 2006.
Harlow et al., Antibodies A Laboratory Manual, Cold Spring Harbor, New York, Cold Spring Harbor Laboratory Press, 1989, 141-155.
Hino et al., "cDNA Cloning and Genomic Structure of Human Bone Morphogenetic Protein-3b (BMP-3b)," Biochemical and Biophysical Research Communications, 1996, 223:304-310.
Hiruma et al., "Siglec-15, a member of the sialic acid-binding lectin is a novel regulator for osteoclast differentiation," Biochemical and Biophysical Research Communications, 2011, 409:424-429.
Holm et al., "Functional mapping and single chain construction of the anti-cytokeratin 8 monoclona antibody TS1," Molecular Immunology, 2007, 44:1075-1084.
Kania et al., "CD44 antibodies inhibit osteoclast formation," J. Bone Miner. Res., 1997, 12(8):1155-1164.

Kitaura et al., "An anti-c-Fms antibody inhibits orthodontic tooth movement," J. Dent. Res., 2008, 87(4):395-400.
Kussie et al., "A Single Engineered Amino Acid Substitution changes Antibody Fine Specificity," 1994, J. Immunology, 152(1):146-152.
Lederman et al., "A single amino acid substitution in a common African allele of the CD4 molecule ablates binding of the monoclonal antibody, OKT4," Mol. Immunol., 1991, 28(11):1171-1181.
Li et al., "Beta-Endorphin omission analogs: dissociation of immunoreactivity from other biological activities," PNAS USA, 1980, 77(6):3211-3214.
MacCallum et al., "Antibody-antigen Interactions: Contact Analysis and Binding Site Topography," J. Mol. Biol., 1996, 262:732-745.
Mirny et al., "Protein folding theory: From Lattice to All-Atom Models," Annu. Rev. Biophys. Biomol. Struct., 2001, 30:361-396.
Nakagawa et al., "RANK is the Essential Signaling Receptor for Osteoclast Differentiation Factor in Osteoclastogenesis," Biochemical and Biophysical Research Communications, 1998, 253:395-400.
Ngo et al., "Computational complexity, protein structure prediction, and the Levinthal paradox," The Protein Folding Problem, Birkhauser, 1994, Ch. 14:491-494.
Notice of Opposition to Grant of Patent dated Jun. 29, 2012, filed by Alethia Biotherapeutics Inc. against New Zealand Application 583397, 3 pages.
Owens et al., "The genetic engineering of monoclonal antibodies," J. Immunol. Methods, 1994, 168(2):149-165.
Paul et al., Fundamental Immunology, $3^{rd}$ Ed., 1993, 292-295.
Presta et al., "Antibody engineering for therapeutics," Current Opinion in Structural Biology, 2003, 13:519-525.
Russian Office Action dated Mar. 22, 2013 in Russian Appln. No. 2011128332/10(041966), English translation, 7 pages.
Siegel et al., "Antibody affinity optimization using yeast cell surface display," 2009, Methods Mol. Biol., 504:351-383.
Statement of Grounds and Particulars to Each Ground dated Jun. 1, 2012, filed by Alethia Biotherapeutics Inc. against Australian Patent Application 2008311698, 10 pages.
Takahashi et al., "A new treatment for osteoporosis using fully human monoclonal antibody to RANKL, AMG 162," Clin. Calcium, 2005, 15(1):43-48, with English summary on first page.
Teitelbaum, S.L., "Osteoclasts: What Do They Do and How Do They Do It?" 2007, AJP, 170(2):427-435.
Third Party Observations dated Aug. 20, 2012, filed by Alethia Biotherapeutics Inc. against European Patent Application 08838427.6, 4 pages.
Third Party Observations dated Aug. 13, 2012, filed by Alethia Biotherapeutics Inc. against European Patent Application 08838427.6, 5 pages.
Third Party Observations dated Dec. 10, 2012, filed by Alethia Biotherapeutics Inc. against European Patent Application 08838427.6, 7 pages.
Tsuda, Eisuke, "Hone Kyushi Yokuseiyaku Koho to shite no Hakotso Saibo Keisei Yokusei Inshi OCIF/OPG, Ko-RANKL Kotai, Oyobi sono hoka no RANKL/RANK System Modulator," J. Jpn. Orthop. Assoc., 2005, 79(8):S753 (1-4-S6-3).
Tsuda, Eisuke, "Waga Kuni ni Okeru Hone Ryoki no Soyaku no Rekishi Kaihatsu Chu no Hinmoke 6. Hakotsu Saibo Keisei Yokusei Inshi (OCIF/OPG), Ko RANKL Kotai, Oyobi Sono Ta no RANKL/RANK System Modulator," Bone, Jan. 2005, 19(1):85-92, Abstract only.
Vajdos et al., "Comprehensive Functional Maps of the Antigen-binding Site of an Anti-ErbB2 Antibody Obtained with Shotgun Scanning Mutanesis," J. Mol. Biol., 2002, 320:415-428.
Wada et al., "New bone density conservation agents for osteoporosis under research and development: Anti-RANKL antibody," Nihon Rinsho, 2007, 65(Suppl.9):459-462.
Woo et al., "Pharmacological Topics of Bone Metabolism: Antiresorptive Microbial Compounds That Inhibit Osteoclast Differentiation, Function, and Survival," J. Pharmacol. Sci., 2008, 106:547-554.

\* cited by examiner

Assay: Day 4
RANKL: 20 ng/mL

SEQ ID NO: 1

ATGAAACACCTGTGGTTCTTCCTCCTGCTGGTGGCAGCTCCCAGATGGGT
CCTGTCCCAGGTGCAATTGGTGGAAAGCGGCGGCGGCCTGGTGCAACCG
GCGGCAGCCTGCGTCTGAGCTGCGCGGCCTCCGGATTTACCTTTTCTAA
TTATTGGATGACTTGGGTGCGCCAAGCCCCTGGGAAGGGTCTCGAGTGG
GTGAGCTTTATCTCTTATTCTGGTAGCACTACCTATTATGCGGATAGCGTG
AAAGGCCGTTTTACCATTTCACGTGATAATTCGAAAAACACCCTGTATCTG
CAAATGAACAGCCTGCGTGCGGAAGATACGGCCGTGTATTATTGCGCGCG
TGAGGGTACTTCTTCTATGTTTGATGTTTGGGGCCAAGGCACCCTGGTGA
CGGTTAGCTCAGCCAGCACCAAGGGCCCCAGCGTGTTCCCCCTGGCCCC
CTGCAGCAGAAGCACCAGCGAGAGCACAGCCGCCCTGGGCTGCCTGGTG
AAGGACTACTTCCCCGAGCCCGTGACCGTGAGCTGGAACAGCGGAGCCC
TGACCAGCGGCGTGCACACCTTCCCCGCCGTGCTGCAGAGCAGCGGCCT
GTACAGCCTGAGCAGCGTGGTGACCGTGCCCAGCAGCAACTTCGGCACC
CAGACCTACACCTGCAACGTGGACCACAAGCCCAGCAACACCAAGGTGG
ACAAGACCGTGGAGCGGAAGTGCTGCGTGGAGTGCCCCCCCTGCCCTGC
CCCTCCTGTGGCCGGACCCTCCGTGTTCCTGTTCCCCCCCAAGCCCAAG
GACACCCTGATGATCAGCCGGACCCCCGAGGTGACCTGCGTGGTGGTGG
ACGTGAGCCACGAGGACCCCGAGGTGCAGTTTAATTGGTACGTGGACGG
CGTGGAGGTGCACAACGCCAAGACCAAGCCCCGGGAGGAACAGTTCAAC
AGCACCTTCCGGGTGGTGTCCGTGCTGACCGTGGTGCACCAGGACTGGC
TGAACGGCAAAGAATACAAGTGCAAGGTGTCCAACAAGGGCCTGCCTGCC
CCCATCGAGAAAACCATCAGCAAGACAAAGGGCCAGCCCAGGGAACCCC
AGGTGTACACCCTGCCCCCCAGCCGGGAGGAAATGACCAAGAACCAGGT
GTCCCTGACCTGTCTGGTGAAGGGCTTCTACCCCAGCGACATCGCCGTG
GAGTGGGAGAGCAACGGCCAGCCCGAGAACAACTACAAGACCACCCCCC
CCATGCTGGACAGCGACGGCAGCTTCTTCCTGTACAGCAAGCTGACAGTG
GACAAGAGCCGGTGGCAGCAGGGCAACGTGTTCAGCTGCAGCGTGATGC
ACGAGGCCCTGCACAACCACTACACCCAGAAGAGCCTGAGCCTGTCCCC
CGGCAAA

Figure 14

SEQ ID NO: 2

MKHLWFFLLLVAAPRWVLSQVQLVESGGGLVQPGGSLRLSCAASGFTFSNY
WMTWVRQAPGKGLEWVSFISYSGSTTYYADSVKGRFTISRDNSKNTLYLQM
NSLRAEDTAVYYCAREGTSSMFDVWGQGTLVTVSSASTKGPSVFPLAPCSR
STSESTAALGCLVKDYFPEPVTVSWNSGALTSGVHTFPAVLQSSGLYSLSSV
VTVPSSNFGTQTYTCNVDHKPSNTKVDKTVERKCCVECPPCPAPPVAGPSVF
LFPPKPKDTLMISRTPEVTCVVVDVSHEDPEVQFNWYVDGVEVHNAKTKPRE
EQFNSTFRVVSVLTVVHQDWLNGKEYKCKVSNKGLPAPIEKTISKTKGQPREP
QVYTLPPSREEMTKNQVSLTCLVKGFYPSDIAVEWESNGQPENNYKTTPPML
DSDGSFFLYSKLTVDKSRWQQGNVFSCSVMHEALHNHYTQKSLSLSPGK

Figure 15

SEQ ID NO: 6

ATGGCCTGGGCTCTGCTGCTCCTCACCCTCCTCACTCAGGGCACAGGA
TCCTGGGCTGATATCGAACTGACCCAGCCGCCTTCAGTGAGCGTTGCA
CCAGGTCAGACCGCGCGTATCTCGTGTAGCGGCGATGCTCTTCGTTCT
TATTATGCTTCTTGGTACCAGCAGAAACCCGGGCAGGCGCCAGTTCTT
GTGATTTATGATGATAATAAGCGTCCCTCAGGCATCCCGGAACGCTTTA
GCGGATCCAACAGCGGCAACACCGCGACCCTGACCATTAGCGGCACT
CAGGCGGAAGACGAAGCGGATTATTATTGCGGTTCTTATGATGGTACT
GTTCATGTGTTTGGCGGCGGCACGAAGTTAACCGTCCTAGGTCAGCCC
AAGGCTGCCCCCTCGGTCACTCTGTTCCCGCCCTCCTCTGAGGAGCTT
CAAGCCAACAAGGCCACACTGGTGTGTCTCATAAGTGACTTCTACCCG
GGAGCCGTGACAGTGGCCTGGAAGGCAGATAGCAGCCCCGTCAAGGC
GGGAGTGGAGACCACCACACCCTCCAAACAAAGCAACAACAAGTACGC
GGCCAGCAGCTATCTGAGCCTGACGCCTGAGCAGTGGAAGTCCCACA
GAAGCTACAGCTGCCAGGTCACGCATGAAGGGAGCACCGTGGAGAAG
ACAGTGGCCCCTACAGAATGTTCA

Figure 16

SEQ ID NO: 7

MAWALLLLTLLTQGTGSWADIELTQPPSVSVAPGQTARISCSGDALRSY
YASWYQQKPGQAPVLVIYDDNKRPSGIPERFSGSNSGNTATLTISGTQA
EDEADYYCGSYDGTVHVFGGGTKLTVLGQPKAAPSVTLFPPSSEELQA
NKATLVCLISDFYPGAVTVAWKADSSPVKAGVETTTPSKQSNNKYAASS
YLSLTPEQWKSHRSYSCQVTHEGSTVEKTVAPTECS

Figure 17

SEQ ID NO: 11

ATGAAACACCTGTGGTTCTTCCTCCTGCTGGTGGCAGCTCC
CAGATGGGTCCTGTCCCAGGTGCAATTGGTGGAAAGCGGC
GGCGGCCTGGTGCAACCGGGCGGCAGCCTGCGTCTGAGCT
GCGCGGCCTCCGGATTTACCTTTACTAATTATGCTATGAATT
GGGTGCGCCAAGCCCCTGGGAAGGGTCTCGAGTGGGTGAG
CACTATCTCTTATATTGGTAGCAATACCTATTATGCGGATAG
CGTGAAAGGCCGTTTTACCATTTCACGTGATAATTCGAAAAA
CACCCTGTATCTGCAAATGAACAGCCTGCGTGCGGAAGATA
CGGCCGTGTATTATTGCGCGCGTGGTGCTGGTCTTGGTTAT
GATGTTTGGGGCCAAGGCACCCTGGTGACGGTTAGCTCAG
CCAGCACCAAGGGCCCCAGCGTGTTCCCCCTGGCCCCCTG
CAGCAGAAGCACCAGCGAGAGCACAGCCGCCCTGGGCTGC
CTGGTGAAGGACTACTTCCCCGAGCCCGTGACCGTGAGCT
GGAACAGCGGAGCCCTGACCAGCGGCGTGCACACCTTCCC
CGCCGTGCTGCAGAGCAGCGGCCTGTACAGCCTGAGCAGC
GTGGTGACCGTGCCCAGCAGCAACTTCGGCACCCAGACCT
ACACCTGCAACGTGGACCACAAGCCCAGCAACACCAAGGTG
GACAAGACCGTGGAGCGGAAGTGCTGCGTGGAGTGCCCCC
CCTGCCCTGCCCCTCCTGTGGCCGGACCCTCCGTGTTCCTG
TTCCCCCCCAAGCCCAAGGACACCCTGATGATCAGCCGGAC
CCCCGAGGTGACCTGCGTGGTGGTGGACGTGAGCCACGAG
GACCCCGAGGTGCAGTTTAATTGGTACGTGGACGGCGTGG
AGGTGCACAACGCCAAGACCAAGCCCCGGGAGGAACAGTT
CAACAGCACCTTCCGGGTGGTGTCCGTGCTGACCGTGGTG
CACCAGGACTGGCTGAACGGCAAGAATACAAGTGCAAGGT
GTCCAACAAGGGCCTGCCTGCCCCATCGAGAAAACCATCA
GCAAGACAAAGGGCCAGCCCAGGGAACCCCAGGTGTACAC
CCTGCCCCCAGCCGGGAGGAAATGACCAAGAACCAGGTG
TCCCTGACCTGTCTGGTGAAGGGCTTCTACCCCAGCGACAT
CGCCGTGGAGTGGGAGAGCAACGGCCAGCCCGAGAACAAC
TACAAGACCACCCCCCCCATGCTGGACAGCGACGGCAGCTT
CTTCCTGTACAGCAAGCTGACAGTGGACAAGAGCCGGTGGC
AGCAGGGCAACGTGTTCAGCTGCAGCGTGATGCACGAGGC
CCTGCACAACCACTACACCCAGAAGAGCCTGAGCCTGTCCC
CCGGCAAA

Figure 18

SEQ ID NO: 12

MKHLWFFLLLVAAPRWVLSQVQLVESGGGLVQPGGSLRLSCAASGFT
FTNYAMNWVRQAPGKGLEWVSTISYIGSNTYYADSVKGRFTISRDNSK
NTLYLQMNSLRAEDTAVYYCARGAGLGYDVWGQGTLVTVSSASTKGP
SVFPLAPCSRSTSESTAALGCLVKDYFPEPVTVSWNSGALTSGVHTFP
AVLQSSGLYSLSSVVTVPSSNFGTQTYTCNVDHKPSNTKVDKTVERKC
CVECPPCPAPPVAGPSVFLFPPKPKDTLMISRTPEVTCVVVDVSHEDP
EVQFNWYVDGVEVHNAKTKPREEQFNSTFRVVSVLTVVHQDWLNGK
EYKCKVSNKGLPAPIEKTISKTKGQPREPQVYTLPPSREEMTKNQVSLT
CLVKGFYPSDIAVEWESNGQPENNYKTTPPMLDSDGSFFLYSKLTVDK
SRWQQGNVFSCSVMHEALHNHYTQKSLSLSPGK

Figure 19

SEQ ID NO: 16

ATGGCCTGGGCTCTGCTGCTCCTCACCCTCCTCACTCAGGGCACAGGA
TCCTGGGCTGATATCGAACTGACCCAGCCGCCTTCAGTGAGCGTTGCA
CCAGGTCAGACCGCGCGTATCTCGTGTAGCGGCGATAATCTTCGTTCTA
AGTATGTTTATTGGTACCAGCAGAAACCCGGGCAGGCGCCAGTTCTTGT
GATTTATGATACTAATGATCGTCCCTCAGGCATCCCGGAACGCTTTAGC
GGATCCAACAGCGGCAACACCGCGACCCTGACCATTAGCGGCACTCAG
GCGGAAGACGAAGCGGATTATTATTGCCAGACTTATGATATGACTTCTC
AGGATGTGTTTGGCGGCGGCACGAAGTTAACCGTCCTAGGTCAGCCCA
AGGCTGCCCCCTCGGTCACTCTGTTCCCGCCCTCCTCTGAGGAGCTTC
AAGCCAACAAGGCCACACTGGTGTGTCTCATAAGTGACTTCTACCCGG
GAGCCGTGACAGTGGCCTGGAAGGCAGATAGCAGCCCCGTCAAGGCG
GGAGTGGAGACCACCACACCCTCCAAACAAAGCAACAACAAGTACGCG
GCCAGCAGCTATCTGAGCCTGACGCCTGAGCAGTGGAAGTCCCACAGA
AGCTACAGCTGCCAGGTCACGCATGAAGGGAGCACCGTGGAGAAGACA
GTGGCCCCTACAGAATGTTCA

Figure 20

SEQ ID NO: 17

MAWALLLLTLLTQGTGSWADIELTQPPSVSVAPGQTARISCSGDNLRSKYVYWYQQKPG
QAPVLVIYDTNDRPSGIPERFSGSNSGNTATLTISGTQAEDEADYYCQTYDMTSQDVFG
GGTKLTVLGQPKAAPSVTLFPPSSEELQANKATLVCLISDFYPGAVTVAWKADSSPVKAG
VETTTPSKQSNNKYAASSYLSLTPEQWKSHRSYSCQVTHEGSTVEKTVAPTECS

Figure 21

SEQ ID NO: 21

ATGAAACACCTGTGGTTCTTCCTCCTGCTGGTGGCAGCTCCCAGATGG
GTCCTGTCCCAGGTGCAATTGGTGGAAAGCGGCGGCGGCCTGGTGCA
ACCGGGCGGCAGCCTGCGTCTGAGCTGCGCGGCCTCCGGATTTACCTT
TTCTTCTTATGCTATGCATTGGGTGCGCCAAGCCCCTGGGAAGGGTCTC
GAGTGGGTGAGCTATATCTCTTATTCTGGTAGCAATACCTATTATGCGG
ATAGCGTGAAAGGCCGTTTTACCATTTCACGTGATAATTCGAAAAACAC
CCTGTATCTGCAAATGAACAGCCTGCGTGCGGAAGATACGGCCGTGTA
TTATTGCGCGCGTGGTTGGGGTGGTTTTGATTATTGGGGCCAAGGCAC
CCTGGTGACGGTTAGCTCAGCCAGCACCAAGGGCCCCAGCGTGTTCCC
CCTGGCCCCCTGCAGCAGAAGCACCAGCGAGAGCACAGCCGCCCTGG
GCTGCCTGGTGAAGGACTACTTCCCCGAGCCCGTGACCGTGAGCTGGA
ACAGCGGAGCCCTGACCAGCGGCGTGCACACCTTCCCCGCCGTGCTG
CAGAGCAGCGGCCTGTACAGCCTGAGCAGCGTGGTGACCGTGCCCAG
CAGCAACTTCGGCACCCAGACCTACACCTGCAACGTGGACCACAAGCC
CAGCAACACCAAGGTGGACAAGACCGTGGAGCGGAAGTGCTGCGTGG
AGTGCCCCCCCTGCCCTGCCCCTCCTGTGGCCGGACCCTCCGTGTTCC
TGTTCCCCCCCAAGCCCAAGGACACCCTGATGATCAGCCGGACCCCCG
AGGTGACCTGCGTGGTGGTGGACGTGAGCCACGAGGACCCCGAGGTG
CAGTTTAATTGGTACGTGGACGGCGTGGAGGTGCACAACGCCAAGACC
AAGCCCCGGGAGGAACAGTTCAACAGCACCTTCCGGGTGGTGTCCGTG
CTGACCGTGGTGCACCAGGACTGGCTGAACGGCAAAGAATACAAGTGC
AAGGTGTCCAACAAGGGCCTGCCTGCCCCCATCGAGAAAACCATCAGC
AAGACAAAGGGCCAGCCCAGGGAACCCCAGGTGTACACCCTGCCCCC
CAGCCGGGAGGAAATGACCAAGAACCAGGTGTCCCTGACCTGTCTGGT
GAAGGGCTTCTACCCCAGCGACATCGCCGTGGAGTGGGAGAGCAACG
GCCAGCCCGAGAACAACTACAAGACCACCCCCCCCATGCTGGACAGCG
ACGGCAGCTTCTTCCTGTACAGCAAGCTGACAGTGGACAAGAGCCGGT
GGCAGCAGGGCAACGTGTTCAGCTGCAGCGTGATGCACGAGGCCCTG
CACAACCACTACACCCAGAAGAGCCTGAGCCTGTCCCCCGGCAAA

Figure 22

SEQ ID NO: 22

MKHLWFFLLLVAAPRWVLSQVQLVESGGGLVQPGGSLRLSCAASGFT
FSSYAMHWVRQAPGKGLEWVSYISYSGSNTYYADSVKGRFTISRDNS
KNTLYLQMNSLRAEDTAVYYCARGWGGFDYWGQGTLVTVSSASTKG
PSVFPLAPCSRSTSESTAALGCLVKDYFPEPVTVSWNSGALTSGVHTF
PAVLQSSGLYSLSSVVTVPSSNFGTQTYTCNVDHKPSNTKVDKTVERK
CCVECPPCPAPPVAGPSVFLFPPKPKDTLMISRTPEVTCVVVDVSHED
PEVQFNWYVDGVEVHNAKTKPREEQFNSTFRVVSVLTVVHQDWLNG
KEYKCKVSNKGLPAPIEKTISKTKGQPREPQVYTLPPSREEMTKNQVSL
TCLVKGFYPSDIAVEWESNGQPENNYKTTPPMLDSDGSFFLYSKLTVD
KSRWQQGNVFSCSVMHEALHNHYTQKSLSLSPGK

Figure 23

SEQ ID NO: 26

ATGGCCTGGGCTCTGCTGCTCCTCACCCTCCTCACTCAG
GGCACAGGATCCTGGGCTGATATCGAACTGACCCAGCC
GCCTTCAGTGAGCGTTGCACCAGGTCAGACCGCGCGTAT
CTCGTGTAGCGGCGATAATCTTCCTAATCGTTATGTTCAT
TGGTACCAGCAGAAACCCGGGCAGGCGCCAGTTCTTGT
GATTTATGATGATAATAATCGTCCCTCAGGCATCCCGGAA
CGCTTTAGCGGATCCAACAGCGGCAACACCGCGACCCT
GACCATTAGCGGCACTCAGGCGGAAGACGAAGCGGATT
ATTATTGCCAGACTTATGATATGTTTTCTATGTCTGATGTG
TTTGGCGGCGGCACGAAGTTAACCGTCCTAGGTCAGCCC
AAGGCTGCCCCTCGGTCACTCTGTTCCCGCCCTCCTCT
GAGGAGCTTCAAGCCAACAAGGCCACACTGGTGTGTCTC
ATAAGTGACTTCTACCCGGGAGCCGTGACAGTGGCCTGG
AAGGCAGATAGCAGCCCCGTCAAGGCGGGAGTGGAGAC
CACCACACCCTCCAAACAAAGCAACAACAAGTACGCGGC
CAGCAGCTATCTGAGCCTGACGCCTGAGCAGTGGAAGTC
CCACAGAAGCTACAGCTGCCAGGTCACGCATGAAGGGA
GCACCGTGGAGAAGACAGTGGCCCCTACAGAATGTTCA

Figure 24

SEQ ID NO: 27

MAWALLLLTLLTQGTGSWADIELTQPPSVSVAPGQTARISCSGDNLPNRYVH
WYQQKPGQAPVLVIYDDNNRPSGIPERFSGSNSGNTATLTISGTQAEDEADY
YCQTYDMFSMSDVFGGGTKLTVLGQPKAAPSVTLFPPSSEELQANKATLVCL
ISDFYPGAVTVAWKADSSPVKAGVETTTPSKQSNNKYAASSYLSLTPEQWKS

HRSYSCQVTHEGSTVEKTVAPTECS

Figure 25

SEQ ID NO: 31

```
ATGAAACACCTGTGGTTCTTCCTCCTGCTGGTGGCAGCTCCCAGATGGGTCC
TGTCCCAGGTGCAATTGGTGGAAAGCGGCGGCGGCCTGGTGCAACCGGGC
GGCAGCCTGCGTCTGAGCTGCGCGGCCTCCGGATTTACCTTTTCTAATTATT
GGATGTCTTGGGTGCGCCAAGCCCCTGGGAAGGGTCTCGAGTGGGTGAGC
CTTATCTCTTATTCTGGTAGCACTACCTATTATGCGGATAGCGTGAAAGGCCG
TTTTACCATTTCACGTGATAATTCGAAAAACACCCTGTATCTGCAAATGAACA
GCCTGCGTGCGGAAGATACGGCCGTGTATTATTGCGCGCGTGATACTCCTAT
TGGTATGGATTTTTTGGGGCCAAGGCACCCTGGTGACGGTTAGCTCAGCCAG
CACCAAGGGCCCCAGCGTGTTCCCCCTGGCCCCCTGCAGCAGAAGCACCAG
CGAGAGCACAGCCGCCCTGGGCTGCCTGGTGAAGGACTACTTCCCCGAGCC
CGTGACCGTGAGCTGGAACAGCGGAGCCCTGACCAGCGGCGTGCACACCTT
CCCCGCCGTGCTGCAGAGCAGCGGCCTGTACAGCCTGAGCAGCGTGGTGA
CCGTGCCCAGCAGCAACTTCGGCACCCAGACCTACACCTGCAACGTGGACC
ACAAGCCCAGCAACACCAAGGTGGACAAGACCGTGGAGCGGAAGTGCTGCG
TGGAGTGCCCCCCCTGCCCTGCCCCTCCTGTGGCCGGACCCTCCGTGTTCC
TGTTCCCCCCCAAGCCCAAGGACACCCTGATGATCAGCCGGACCCCCGAGG
TGACCTGCGTGGTGGTGGACGTGAGCCACGAGGACCCCGAGGTGCAGTTTA
ATTGGTACGTGGACGGCGTGGAGGTGCACAACGCCAAGACCAAGCCCCGG
GAGGAACAGTTCAACAGCACCTTCCGGGTGGTGTCCGTGCTGACCGTGGTG
CACCAGGACTGGCTGAACGGCAAAGAATACAAGTGCAAGGTGTCCAACAAG
GGCCTGCCTGCCCCCATCGAGAAAACCATCAGCAAGACAAAGGGCCAGCCC
AGGGAACCCCAGGTGTACACCCTGCCCCCCAGCCGGGAGGAAATGACCAAG
AACCAGGTGTCCCTGACCTGTCTGGTGAAGGGCTTCTACCCCAGCGACATCG
CCGTGGAGTGGGAGAGCAACGGCCAGCCCGAGAACAACTACAAGACCACCC
CCCCCATGCTGGACAGCGACGGCAGCTTCTTCCTGTACAGCAAGCTGACAGT
GGACAAGAGCCGGTGGCAGCAGGGCAACGTGTTCAGCTGCAGCGTGATGCA
CGAGGCCCTGCACAACCACTACACCCAGAAGAGCCTGAGCCTGTCCCCCGG
CAAA
```

Figure 26

SEQ ID NO: 32

MKHLWFFLLLVAAPRWVLSQVQLVESGGGLVQPGGSLRLSCAASGFTF
SNYWMSWVRQAPGKGLEWVSLISYSGSTTYYADSVKGRFTISRDNSKN
TLYLQMNSLRAEDTAVYYCARDTPIGMDFWGQGTLVTVSSASTKGPSVF
PLAPCSRSTSESTAALGCLVKDYFPEPVTVSWNSGALTSGVHTFPAVLQ
SSGLYSLSSVVTVPSSNFGTQTYTCNVDHKPSNTKVDKTVERKCCVECP
PCPAPPVAGPSVFLFPPKPKDTLMISRTPEVTCVVVDVSHEDPEVQFNW
YVDGVEVHNAKTKPREEQFNSTFRVVSVLTVVHQDWLNGKEYKCKVSN
KGLPAPIEKTISKTKGQPREPQVYTLPPSREEMTKNQVSLTCLVKGFYPS
DIAVEWESNGQPENNYKTTPPMLDSDGSFFLYSKLTVDKSRWQQGNVF
SCSVMHEALHNHYTQKSLSLSPGK

Figure 27

SEQ ID NO: 36

ATGGCCTGGGCTCTGCTGCTCCTCACCCTCCTCACTCAGGGCACAGGATCC
TGGGCTGATATCGAACTGACCCAGCCGCCTTCAGTGAGCGTTGCACCAGGT
CAGATCGCGCGTATCTCGTGTAGCGGCGATAATCTTGGTTCTTATTATGCTT
ATTGGTACCAGCAGAAACCCGGGCAGGCGCCAGTTCTTGTGATTTATGGTG
ATAATGATCGTCCCTCAGGCATCCCGGAACGCTTTAGCGGATCCAACAGCG
GCAACACCGCGACCCTGACCATTAGCGGCACTCAGGCGGAAGACGAAGCG
GATTATTATTGCTCTTCTTATGATATTGTTCAGCCTTATGTGTTTGGCGGCGG
CACGAAGTTAACCGTCCTAGGTCAGCCCAAGGCTGCCCCCTCGGTCACTCT
GTTCCCGCCCTCCTCTGAGGAGCTTCAAGCCAACAAGGCCACACTGGTGTG
TCTCATAAGTGACTTCTACCCGGGAGCCGTGACAGTGGCCTGGAAGGCAGA
TAGCAGCCCCGTCAAGGCGGGAGTGGAGACCACCACACCCTCCAAACAAA
GCAACAACAAGTACGCGGCCAGCAGCTATCTGAGCCTGACGCCTGAGCAGT
GGAAGTCCCACAGAAGCTACAGCTGCCAGGTCACGCATGAAGGGAGCACC
GTGGAGAAGACAGTGGCCCCTACAGAATGTTCA

Figure 28

SEQ ID NO: 37

MAWALLLLTLLTQGTGSWADIELTQPPSVSVAPGQIARISCSGDNLGSYYAYWYQQ
KPGQAPVLVIYGDNDRPSGIPERFSGSNSGNTATLTISGTQAEDEADYYCSSYDIV
QPYVFGGGTKLTVLGQPKAAPSVTLFPPSSEELQANKATLVCLISDFYPGAVTVAW
KADSSPVKAGVETTTPSKQSNNKYAASSYLSLTPEQWKSHRSYSCQVTHEGSTVE
KTVAPTECS

Figure 29

SEQ ID NO: 41

```
ATGAAACACCTGTGGTTCTTCCTCCTGCTGGTGGCAGCTCCCAGATGGGT
CCTGTCCCAGGTGCAATTGGTGGAAAGCGGCGGCGGCCTGGTGCAACCG
GGCGGCAGCCTGCGTCTGAGCTGCGCGGCCTCCGGATTTACCTTTTCTTC
TTATGCTATGCATTGGGTGCGCCAAGCCCCTGGGAAGGGTCTCGAGTGGG
TGAGCTATATCTCTTATTCTGGTAGCAATACCTATTATGCGGATAGCGTGAA
AGGCCGTTTTACCATTTCACGTGATAATTCGAAAAACACCCTGTATCTGCAA
ATGAACAGCCTGCGTGCGGAAGATACGGCCGTGTATTATTGCGCGCGTGG
TTGGGGTGGTTTTGATTATTGGGGCCAAGGCACCCTGGTGACGGTTAGCT
CAGCCAGCACCAAGGGCCCCAGCGTGTTCCCCCTGGCCCCCTGCAGCAG
AAGCACCAGCGAGAGCACAGCCGCCCTGGGCTGCCTGGTGAAGGACTAC
TTCCCCGAGCCCGTGACCGTGAGCTGGAACAGCGGAGCCCTGACCAGCG
GCGTGCACACCTTCCCCGCCGTGCTGCAGAGCAGCGGCCTGTACAGCCT
GAGCAGCGTGGTGACCGTGCCCAGCAGCAACTTCGGCACCCAGACCTACA
CCTGCAACGTGGACCACAAGCCCAGCAACACCAAGGTGGACAAGACCGTG
GAGCGGAAGTGCTGCGTGGAGTGCCCCCCCTGCCCTGCCCCTCCTGTGG
CCCGGACCCTCCGTGTTCCTGTTCCCCCCCAAGCCCAAGGACACCCTGATG
ATCAGCCGGACCCCCGAGGTGACCTGCGTGGTGGTGGACGTGAGCCACG
AGGACCCCGAGGTGCAGTTTAATTGGTACGTGGACGGCGTGGAGGTGCAC
AACGCCAAGACCAAGCCCCGGGAGGAACAGTTCAACAGCACCTTCCGGGT
GGTGTCCGTGCTGACCGTGGTGCACCAGGACTGGCTGAACGGCAAAGAAT
ACAAGTGCAAGGTGTCCAACAAGGGCCTGCCTGCCCCATCGAGAAAACC
ATCAGCAAGACAAAGGGCCAGCCCAGGGAACCCCAGGTGTACACCCTGCC
CCCCAGCCGGGAGGAAATGACCAAGAACCAGGTGTCCCTGACCTGTCTGG
TGAAGGGCTTCTACCCCAGCGACATCGCCGTGGAGTGGGAGAGCAACGG
CCAGCCCGAGAACAACTACAAGACCACCCCCCCATGCTGGACAGCGACG
GCAGCTTCTTCCTGTACAGCAAGCTGACAGTGGACAAGAGCCGGTGGCAG
CAGGGCAACGTGTTCAGCTGCAGCGTGATGCACGAGGCCCTGCACAACCA
CTACACCCAGAAGAGCCTGAGCCTGTCCCCGGCAAA
```

Figure 30

SEQ ID NO: 42

MKHLWFFLLLVAAPRWVLSQVQLVESGGGLVQPGGSLRLSCAASGFTFSSYAMH
WVRQAPGKGLEWVSYISYSGSNTYYADSVKGRFTISRDNSKNTLYLQMNSLRAE
DTAVYYCARGWGGFDYWGQGTLVTVSSASTKGPSVFPLAPCSRSTSESTAALG
CLVKDYFPEPVTVSWNSGALTSGVHTFPAVLQSSGLYSLSSVVTVPSSNFGTQTY
TCNVDHKPSNTKVDKTVERKCCVECPPCPAPPVAGPSVFLFPPKPKDTLMISRTP
EVTCVVVDVSHEDPEVQFNWYVDGVEVHNAKTKPREEQFNSTFRVVSVLTVVHQ
DWLNGKEYKCKVSNKGLPAPIEKTISKTKGQPREPQVYTLPPSREEMTKNQVSLT
CLVKGFYPSDIAVEWESNGQPENNYKTTPPMLDSDGSFFLYSKLTVDKSRWQQG
NVFSCSVMHEALHNHYTQKSLSLSPGK

Figure 31

SEQ ID NO: 46

ATGGCCTGGGCTCTGCTGCTCCTCACCCTCCTCACTCAGGGCACAGG
ATCCTGGGCTGATATCGAACTGACCCAGCCGCCTTCAGTGAGCGTTG
CACCAGGTCAGACCGCGCGTATCTCGTGTAGCGGCGATAATCTTCCT
AATCGTTATGTTCATTGGTACCAGCAGAAACCCGGGCAGGCGCCAGT
TCTTGTGATTTATGATGATAATAATCGTCCCTCAGGCATCCCGGAACG
CTTTAGCGGATCCAACAGCGGCAACACCGCGACCCTGACCATTAGCG
GCACTCAGGCGGAAGACGAAGCGGATTATTATTGCCAGTCTCGTGAT
CTTCATTATTCTCCTGTGTTTGGCGGCGGCACGAAGTTAACCGTCCTA
GGTCAGCCCAAGGCTGCCCCCTCGGTCACTCTGTTCCCGCCCTCCTC
TGAGGAGCTTCAAGCCAACAAGGCCACACTGGTGTGTCTCATAAGTG
ACTTCTACCCGGGAGCCGTGACAGTGGCCTGGAAGGCAGATAGCAG
CCCCGTCAAGGCGGGAGTGGAGACCACCACACCCTCCAAACAAAGC
AACAACAAGTACGCGGCCAGCAGCTATCTGAGCCTGACGCCTGAGCA
GTGGAAGTCCCACAGAAGCTACAGCTGCCAGGTCACGCATGAAGGG
AGCACCGTGGAGAAGACAGTGGCCCCTACAGAATGTTCA

Figure 32

SEQ ID NO: 47

MAWALLLLTLLTQGTGSWADIELTQPPSVSVAPGQTARISCSGDNL
PNRYVHWYQQKPGQAPVLVIYDDNNRPSGIPERFSGSNSGNTATL
TISGTQAEDEADYYCQSRDLHYSPVFGGGTKLTVLGQPKAAPSVTL
FPPSSEELQANKATLVCLISDFYPGAVTVAWKADSSPVKAGVETTT
PSKQSNNKYAASSYLSLTPEQWKSHRSYSCQVTHEGSTVEKTVAP
TECS

Figure 33

SEQ ID NO: 51

ATGAAACACCTGTGGTTCTTCCTCCTGCTGGTGGCAGCTCCCAGA
TGGGTCCTGTCCCAGGTGCAATTGGTGGAAAGCGGCGGCGGCCT
GGTGCAACCGGGCGGCAGCCTGCGTCTGAGCTGCGCGGCCTCC
GGATTTACCTTTTCTAATTATTGGATGACTTGGGTGCGCCAAGCCC
CTGGGAAGGGTCTCGAGTGGGTGAGCTTTATCTCTTATTCTGGTA
GCACTACCTATTATGCGGATAGCGTGAAAGGCCGTTTTACCATTTC
ACGTGATAATTCGAAAAACACCCTGTATCTGCAAATGAACAGCCTG
CGTGCGGAAGATACGGCCGTGTATTATTGCGCGCGTGAGGGTACT
TCTTCTATGTTTGATGTTTGGGGCCAAGGCACCCTGGTGACGGTT
AGCTCAGCCAGCACCAAGGGCCCCAGCGTGTTCCCCCTGGCCCC
CTGCAGCAGAAGCACCAGCGAGAGCACAGCCGCCCTGGGCTGCC
TGGTGAAGGACTACTTCCCCGAGCCCGTGACCGTGAGCTGGAACA
GCGGAGCCCTGACCAGCGGCGTGCACACCTTCCCGCCGTGCTG
CAGAGCAGCGGCCTGTACAGCCTGAGCAGCGTGGTGACCGTGCC
CAGCAGCAACTTCGGCACCCAGACCTACACCTGCAACGTGGACCA
CAAGCCCAGCAACACCAAGGTGGACAAGACCGTGGAGCGGAAGT
GCTGCGTGGAGTGCCCCCCTGCCCTGCCCCTCCTGTGGCCGGA
CCCTCCGTGTTCCTGTTCCCCCCAAGCCCAAGGACACCCTGATG
ATCAGCCGGACCCCCGAGGTGACCTGCGTGGTGGTGGACGTGAG
CCACGAGGACCCCGAGGTGCAGTTTAATTGGTACGTGGACGGCG
TGGAGGTGCACAACGCCAAGACCAAGCCCCGGGAGGAACAGTTC
AACAGCACCTTCCGGGTGGTGTCCGTGCTGACCGTGGTGCACCA
GGACTGGCTGAACGGCAAAGAATACAAGTGCAAGGTGTCCAACAA
GGGCCTGCCTGCCCCATCGAGAAAACCATCAGCAAGACAAAGG
GCCAGCCCAGGGAACCCCAGGTGTACACCCTGCCCCCAGCCGG
GAGGAAATGACCAAGAACCAGGTGTCCCTGACCTGTCTGGTGAAG
GGCTTCTACCCCAGCGACATCGCCGTGGAGTGGGAGAGCAACGG
CCAGCCCGAGAACAACTACAAGACCACCCCCCCCATGCTGGACAG
CGACGGCAGCTTCTTCCTGTACAGCAAGCTGACAGTGGACAAGAG
CCGGTGGCAGCAGGGCAACGTGTTCAGCTGCAGCGTGATGCACG
AGGCCCTGCACAACCACTACACCCAGAAGAGCCTGAGCCTGTCCC
CCGGCAAA

Figure 34

SEQ ID NO: 52

MKHLWFFLLLVAAPRWVLSQVQLVESGGGLVQPGGSLRLSCAASGFTFSN
YWMTWVRQAPGKGLEWVSFISYSGSTTYYADSVKGRFTISRDNSKNTLYL
QMNSLRAEDTAVYYCAREGTSSMFDVWGQGTLVTVSSASTKGPSVFPLA
PCSRSTSESTAALGCLVKDYFPEPVTVSWNSGALTSGVHTFPAVLQSSGLY
SLSSVVTVPSSNFGTQTYTCNVDHKPSNTKVDKTVERKCCVECPPCPAPP
VAGPSVFLFPPKPKDTLMISRTPEVTCVVVDVSHEDPEVQFNWYVDGVEV
HNAKTKPREEQFNSTFRVVSVLTVVHQDWLNGKEYKCKVSNKGLPAPIEKT
ISKTKGQPREPQVYTLPPSREEMTKNQVSLTCLVKGFYPSDIAVEWESNGQ
PENNYKTTPPMLDSDGSFFLYSKLTVDKSRWQQGNVFSCSVMHEALHNH
YTQKSLSLSPGK

Figure 35

SEQ ID NO: 56

ATGGCCTGGGCTCTGCTGCTCCTCACCCTCCTCACTCAGGGCACA
GGATCCTGGGCTGATATCGAACTGACCCAGCCGCCTTCAGTGAGC
GTTGCACCAGGTCAGACCGCGCGTATCTCGTGTAGCGGCGATGCT
CTTCGTTCTTATTATGCTTCTTGGTACCAGCAGAAACCCGGGCAGG
CGCCAGTTCTTGTGATTTATGATGATAATAAGCGTCCCTCAGGCATC
CCGGAACGCTTTAGCGGATCCAACAGCGGCAACACCGCGACCCTG
ACCATTAGCGGCACTCAGGCGGAAGACGAAGCGGATTATTATTGCG
CTTCTTTTACTTATATGTCTGATTTTGTGTTTGGCGGCGGCACGAAG
TTAACCGTCCTAGGTCAGCCCAAGGCTGCCCCCTCGGTCACTCTGT
TCCCGCCCTCCTCTGAGGAGCTTCAAGCCAACAAGGCCACACTGGT
GTGTCTCATAAGTGACTTCTACCCGGGAGCCGTGACAGTGGCCTG
GAAGGCAGATAGCAGCCCCGTCAAGGCGGGAGTGGAGACCACCA
CACCCTCCAAACAAAGCAACAACAAGTACGCGGCCAGCAGCTATCT
GAGCCTGACGCCTGAGCAGTGGAAGTCCCACAGAAGCTACAGCTG
CCAGGTCACGCATGAAGGGAGCACCGTGGAGAAGACAGTGGCCCC
TACAGAATGTTCA

Figure 36

SEQ ID NO: 57

MAWALLLLTLLTQGTGSWADIELTQPPSVSVAPGQTARISCSGDALRSYYAS
WYQQKPGQAPVLVIYDDNKRPSGIPERFSGSNSGNTATLTISGTQAEDEAD
YYCASFTYMSDFVFGGGTKLTVLGQPKAAPSVTLFPPSSEELQANKATLVCL
ISDFYPGAVTVAWKADSSPVKAGVETTTPSKQSNNKYAASSYLSLTPEQWK
SHRSYSCQVTHEGSTVEKTVAPTECS

Figure 37

SEQ ID NO: 61

ATGAAACACCTGTGGTTCTTCCTCCTGCTGGTGGCAGCTCCCAGATGG
GTCCTGTCCCAGGTGCAATTGGTGGAAAGCGGCGGCGGCCTGGTGCA
ACCGGGCGGCAGCCTGCGTCTGAGCTGCGCGGCCTCCGGATTTACCT
TTACTAATTATGCTATGAATTGGGTGCGCCAAGCCCCTGGGAAGGGTC
TCGAGTGGGTGAGCTATATCTCTTATTCTTCTAGCAATACCTATTATGC
GGATAGCGTGAAAGGCCGTTTTACCATTTCACGTGATAATTCGAAAAAC
ACCCTGTATCTGCAAATGAACAGCCTGCGTGCGGAAGATACGGCCGT
GTATTATTGCGCGCGTGGTGCTGGTCTTGGTTATGATGTTTGGGGCCA
AGGCACCCTGGTGACGGTTAGCTCAGCCAGCACCAAGGGCCCCAGCG
TGTTCCCCCTGGCCCCTGCAGCAGAAGCACCAGCGAGAGCACAGCC
GCCCTGGGCTGCCTGGTGAAGGACTACTTCCCCGAGCCCGTGACCGT
GAGCTGGAACAGCGGAGCCCTGACCAGCGGCGTGCACACCTTCCCCG
CCGTGCTGCAGAGCAGCGGCCTGTACAGCCTGAGCAGCGTGGTGACC
GTGCCCAGCAGCAACTTCGGCACCCAGACCTACACCTGCAACGTGGA
CCACAAGCCCAGCAACACCAAGGTGGACAAGACCGTGGAGCGGAAGT
GCTGCGTGGAGTGCCCCCCCTGCCCTGCCCCTCCTGTGGCCGGACCC
TCCGTGTTCCTGTTCCCCCCCAAGCCCAAGGACACCCTGATGATCAGC
CGGACCCCCGAGGTGACCTGCGTGGTGGTGGACGTGAGCCACGAGG
ACCCCGAGGTGCAGTTTAATTGGTACGTGGACGGCGTGGAGGTGCAC
AACGCCAAGACCAAGCCCCGGGAGGAACAGTTCAACAGCACCTTCCG
GGTGGTGTCCGTGCTGACCGTGGTGCACCAGGACTGGCTGAACGGCA
AAGAATACAAGTGCAAGGTGTCCAACAAGGGCCTGCCTGCCCCCATC
GAGAAAACCATCAGCAAGACAAAGGGCCAGCCCAGGGAACCCCAGGT
GTACACCCTGCCCCCCAGCCGGGAGGAAATGACCAAGAACCAGGTGT
CCCTGACCTGTCTGGTGAAGGGCTTCTACCCCAGCGACATCGCCGTG
GAGTGGGAGAGCAACGGCCAGCCCGAGAACAACTACAAGACCACCCC
CCCCATGCTGGACAGCGACGGCAGCTTCTTCCTGTACAGCAAGCTGA
CAGTGGACAAGAGCCGGTGGCAGCAGGGCAACGTGTTCAGCTGCAGC
GTGATGCACGAGGCCCTGCACAACCACTACACCCAGAAGAGCCTGAG
CCTGTCCCCCGGCAAA

Figure 38

SEQ ID NO: 62

MKHLWFFLLLVAAPRWVLSQVQLVESGGGLVQPGGSLRLSCAASGFTFTN
YAMNWVRQAPGKGLEWVSYISYSSSNTYYADSVKGRFTISRDNSKNTLYL
QMNSLRAEDTAVYYCARGAGLGYDVWGQGTLVTVSSASTKGPSVFPLAP
CSRSTSESTAALGCLVKDYFPEPVTVSWNSGALTSGVHTFPAVLQSSGLYS
LSSVVTVPSSNFGTQTYTCNVDHKPSNTKVDKTVERKCCVECPPCPAPPV
AGPSVFLFPPKPKDTLMISRTPEVTCVVVDVSHEDPEVQFNWYVDGVEVH
NAKTKPREEQFNSTFRVVSVLTVVHQDWLNGKEYKCKVSNKGLPAPIEKTI
SKTKGQPREPQVYTLPPSREEMTKNQVSLTCLVKGFYPSDIAVEWESNGQ
PENNYKTTPPMLDSDGSFFLYSKLTVDKSRWQQGNVFSCSVMHEALHNH
YTQKSLSLSPGK

Figure 39

SEQ ID NO: 66

ATGGCCTGGGCTCTGCTGCTCCTCACCCTCCTCACTCAGGGCACA
GGATCCTGGGCTGATATCGAACTGACCCAGCCGCCTTCAGTGAGC
GTTGCACCAGGTCAGACCGCGCGTATCTCGTGTAGCGGCGATAAT
CTTCGTTCTAAGTATGTTTATTGGTACCAGCAGAAACCCGGGCAGG
CGCCAGTTCTTGTGATTTATGATACTAATGATCGTCCCTCAGGCATC
CCGGAACGCTTTAGCGGATCCAACAGCGGCAACACCGCGACCCTG
ACCATTAGCGGCACTCAGGCGGAAGACGAAGCGGATTATTATTGCC
AGACTTATGATATGACTTCTCAGGATGTGTTTGGCGGCGGCACGAA
GTTAACCGTCCTAGGTCAGCCCAAGGCTGCCCCCTCGGTCACTCTG
TTCCCGCCCTCCTCTGAGGAGCTTCAAGCCAACAAGGCCACACTGG
TGTGTCTCATAAGTGACTTCTACCCGGGAGCCGTGACAGTGGCCTG
GAAGGCAGATAGCAGCCCCGTCAAGGCGGGAGTGGAGACCACCA
CACCCTCCAAACAAAGCAACAACAAGTACGCGGCCAGCAGCTATCT
GAGCCTGACGCCTGAGCAGTGGAAGTCCCACAGAAGCTACAGCTG
CCAGGTCACGCATGAAGGGAGCACCGTGGAGAAGACAGTGGCCCC
TACAGAATGTTCA

Figure 40

SEQ ID NO: 67

MAWALLLLTLLTQGTGSWADIELTQPPSVSVAPGQTARISCSGDNLRSKYVYW
YQQKPGQAPVLVIYDTNDRPSGIPERFSGSNSGNTATLTISGTQAEDEADYYCQ
TYDMTSQDVFGGGTKLTVLGQPKAAPSVTLFPPSSEELQANKATLVCLISDFYP
GAVTVAWKADSSPVKAGVETTTPSKQSNNKYAASSYLSLTPEQWKSHRSYSC
QVTHEGSTVEKTVAPTECS

Figure 41

SEQ ID NO: 76

ATGAAACACCTGTGGTTCTTCCTCCTGCTGGTGGCAGCTCCCAGATGGGT
CCTGTCCCAGGTGCAATTGGTGGAAAGCGGCGGCGGCCTGGTGCAACCG
GGCGGCAGCCTGCGTCTGAGCTGCGCGGCCTCCGGATTTACCTTTACTA
CTTATGCTATGCATTGGGTGCGCCAAGCCCCTGGGAAGGGTCTCGAGTG
GGTGAGCAATATCGCTTATTCTGGTAGCGTTACCTATTATGCGGATAGCG
TGAAAGGCCGTTTTACCATTTCACGTGATAATTCGAAAAACACCCTGTATC
TGCAAATGAACAGCCTGCGTGCGGAAGATACGGCCGTGTATTATTGCGCG
CGTCGTGGTCCTGGTATGGGTAATATGGATATTTGGGGCCAAGGCACCCT
GGTGACGGTTAGCTCAGCCAGCACCAAGGGCCCCAGCGTGTTCCCCCTG
GCCCCCTGCAGCAGAAGCACCAGCGAGAGCACAGCCGCCCTGGGCTGC
CTGGTGAAGGACTACTTCCCCGAGCCCGTGACCGTGAGCTGGAACAGCG
GAGCCCTGACCAGCGGCGTGCACACCTTCCCCGCCGTGCTGCAGAGCAG
CGGCCTGTACAGCCTGAGCAGCGTGGTGACCGTGCCCAGCAGCAACTTC
GGCACCCAGACCTACACCTGCAACGTGGACCACAAGCCCAGCAACACCA
AGGTGGACAAGACCGTGGAGCGGAAGTGCTGCGTGGAGTGCCCCCCCT
GCCCTGCCCCTCCTGTGGCCGGACCCTCCGTGTTCCTGTTCCCCCCCAA
GCCCAAGGACACCCTGATGATCAGCCGGACCCCCGAGGTGACCTGCGTG
GTGGTGGACGTGAGCCACGAGGACCCCGAGGTGCAGTTTAATTGGTACG
TGGACGGCGTGGAGGTGCACAACGCCAAGACCAAGCCCCGGGAGGAAC
AGTTCAACAGCACCTTCCGGGTGGTGTCCGTGCTGACCGTGGTGCACCA
GGACTGGCTGAACGGCAAAGAATACAAGTGCAAGGTGTCCAACAAGGGC
CTGCCTGCCCCCATCGAGAAAACCATCAGCAAGACAAAGGGCCAGCCCA
GGGAACCCCAGGTGTACACCCTGCCCCCAGCCGGGAGGAAATGACCAA
GAACCAGGTGTCCCTGACCTGTCTGGTGAAGGGCTTCTACCCCAGCGAC
ATCGCCGTGGAGTGGGAGAGCAACGGCCAGCCCGAGAACAACTACAAGA
CCACCCCCCCCATGCTGGACAGCGACGGCAGCTTCTTCCTGTACAGCAA
GCTGACAGTGGACAAGAGCCGGTGGCAGCAGGGCAACGTGTTCAGCTGC
AGCGTGATGCACGAGGCCCTGCACAACCACTACACCCAGAAGAGCCTGA
GCCTGTCCCCGGCAAA

Figure 46

SEQ ID NO: 77

MKHLWFFLLLVAAPRWVLSQVQLVESGGGLVQPGGSLRLSCAASGFTFTTY
AMHWVRQAPGKGLEWVSNIAYSGSVTYYADSVKGRFTISRDNSKNTLYLQ
MNSLRAEDTAVYYCARRGPGMGNMDIWGQGTLVTVSSASTKGPSVFPLAP
CSRSTSESTAALGCLVKDYFPEPVTVSWNSGALTSGVHTFPAVLQSSGLYS
LSSVVTVPSSNFGTQTYTCNVDHKPSNTKVDKTVERKCCVECPPCPAPPVA
GPSVFLFPPKPKDTLMISRTPEVTCVVVDVSHEDPEVQFNWYVDGVEVHNA
KTKPREEQFNSTFRVVSVLTVVHQDWLNGKEYKCKVSNKGLPAPIEKTISKT
KGQPREPQVYTLPPSREEMTKNQVSLTCLVKGFYPSDIAVEWESNGQPEN
NYKTTPPMLDSDGSFFLYSKLTVDKSRWQQGNVFSCSVMHEALHNHYTQK
SLSLSPGK

Figure 47

SEQ ID NO: 81

ATGGCCTGGGCTCTGCTGCTCCTCACCCTCCTCACTCAGGGCACAGG
ATCCTGGGCTGATATCGCACTGACCCAGCCAGCTTCAGTGAGCGGCT
CACCAGGTCAGAGCATTACCATCTCGTGTACGGGTACTAGCAGCGATG
TTGGTGATTATAATTATGTGTCTTGGTACCAGCAGCATCCCGGGAAGG
CGCCGAAACTTATGATTTATTATGTTACTAATCGTCCCTCAGGCGTGAG
CAACCGTTTTAGCGGATCCAAAAGCGGCAACACCGCGAGCCTGACCAT
TAGCGGCCTGCAAGCGGAAGACGAAGCGGATTATTATTGCCAGTCTTA
TGATACTGGTTCTTTTGCTATGGTGTTTGGCGGCGGCACGAAGTTAAC
CGTCCTAGGTCAGCCCAAGGCTGCCCCTCGGTCACTCTGTTCCCGC
CCTCCTCTGAGGAGCTTCAAGCCAACAAGGCCACACTGGTGTGTCTCA
TAAGTGACTTCTACCCGGGAGCCGTGACAGTGGCCTGGAAGGCAGAT
AGCAGCCCCGTCAAGGCGGGAGTGGAGACCACCACACCCTCCAAACA
AAGCAACAACAAGTACGCGGCCAGCAGCTATCTGAGCCTGACGCCTG
AGCAGTGGAAGTCCCACAGAAGCTACAGCTGCCAGGTCACGCATGAA
GGGAGCACCGTGGAGAAGACAGTGGCCCCTACAGAATGTTCA

Figure 48

SEQ ID NO: 82

MAWALLLLTLLTQGTGSWADIALTQPASVSGSPGQSITISCTGTSSDVGDY
NYVSWYQQHPGKAPKLMIYYVTNRPSGVSNRFSGSKSGNTASLTISGLQA
EDEADYYCQSYDTGSFAMVFGGGTKLTVLGQPKAAPSVTLFPPSSEELQA
NKATLVCLISDFYPGAVTVAWKADSSPVKAGVETTTPSKQSNNKYAASSYL
SLTPEQWKSHRSYSCQVTHEGSTVEKTVAPTECS

Figure 49

SEQ ID NO: 86

ATGGCCTGGGCTCTGCTGCTCCTCACCCTCCTCACTCAGGGCA
CAGGATCCTGGGCTGATATCGCACTGACCCAGCCAGCTTCAGT
GAGCGGCTCACCAGGTCAGAGCATTACCATCTCGTGTACGGGT
ACTAGCAGCGATGTTGGTGATTATAATTATGTGTCTTGGTACCAG
CAGCATCCCGGGAAGGCGCCGAAACTTATGATTTATTATGTTAC
TAATCGTCCCTCAGGCGTGAGCAACCGTTTTAGCGGATCCAAAA
GCGGCAACACCGCGAGCCTGACCATTAGCGGCCTGCAAGCGGA
AGACGAAGCGGATTATTATTGCCAGTCTTATGCTCCTCTTCCTTC
TTCTCATATTGTGTTTGGCGGCGGCACGAAGTTAACCGTCCTAG
GTCAGCCCAAGGCTGCCCCTCGGTCACTCTGTTCCCGCCCTC
CTCTGAGGAGCTTCAAGCCAACAAGGCCACACTGGTGTGTCTCA
TAAGTGACTTCTACCCGGGAGCCGTGACAGTGGCCTGGAAGGC
AGATAGCAGCCCCGTCAAGGCGGGAGTGGAGACCACCACACCC
TCCAAACAAAGCAACAACAAGTACGCGGCCAGCAGCTATCTGAG
CCTGACGCCTGAGCAGTGGAAGTCCCACAGAAGCTACAGCTGC
CAGGTCACGCATGAAGGGAGCACCGTGGAGAAGACAGTGGCCC
CTACAGAATGTTCA

Figure 50

SEQ ID NO: 87

MAWALLLLTLLTQGTGSWADIALTQPASVSGSPGQSITISCTGTSSDV
GDYNYVSWYQQHPGKAPKLMIYYVTNRPSGVSNRFSGSKSGNTASL
TISGLQAEDEADYYCQSYAPLPSSHIVFGGGTKLTVLGQPKAAPSVTL
FPPSSEELQANKATLVCLISDFYPGAVTVAWKADSSPVKAGVETTTPS
KQSNNKYAASSYLSLTPEQWKSHRSYSCQVTHEGSTVEKTVAPTEC
S

Figure 51

SEQ ID NO: 91

```
ATGAAACACCTGTGGTTCTTCCTCCTGCTGGTGGCAGCTCCCAGATGG
GTCCTGTCCCAGGTGCAATTGGTGGAAAGCGGCGGCGGCCTGGTGCA
ACCGGGCGGCAGCCTGCGTCTGAGCTGCGCGGCCTCCGGATTTACCTT
TACTACTTATGCTATGCATTGGGTGCGCCAAGCCCCTGGGAAGGGTCT
CGAGTGGGTGAGCACTATCTTTGGTTCTTCTAGCTCTACCTATTATGCG
GATAGCGTGAAAGGCCGTTTTACCATTTCACGTGATAATTCGAAAAACA
CCCTGTATCTGCAAATGAACAGCCTGCGTGCGGAAGATACGGCCGTGT
ATTATTGCGCGCGTCGTGGTCCTGGTATGGGTAATATGGATATTTGGGG
CCAAGGCACCCTGGTGACGGTTAGCTCAGCCAGCACCAAGGGCCCCA
GCGTGTTCCCCCTGGCCCCCTGCAGCAGAAGCACCAGCGAGAGCACA
GCCGCCCTGGGCTGCCTGGTGAAGGACTACTTCCCCGAGCCCGTGAC
CGTGAGCTGGAACAGCGGAGCCCTGACCAGCGGCGTGCACACCTTCC
CCGCCGTGCTGCAGAGCAGCGGCCTGTACAGCCTGAGCAGCGTGGTG
ACCGTGCCCAGCAGCAACTTCGGCACCCAGACCTACACCTGCAACGTG
GACCACAAGCCCAGCAACACCAAGGTGGACAAGACCGTGGAGCGGAA
GTGCTGCGTGGAGTGCCCCCCCTGCCCTGCCCCTCCTGTGGCCGGAC
CCTCCGTGTTCCTGTTCCCCCCCAAGCCCAAGGACACCCTGATGATCA
GCCGGACCCCCGAGGTGACCTGCGTGGTGGTGGACGTGAGCCACGAG
GACCCCGAGGTGCAGTTTAATTGGTACGTGGACGGCGTGGAGGTGCAC
AACGCCAAGACCAAGCCCCGGGAGGAACAGTTCAACAGCACCTTCCGG
GTGGTGTCCGTGCTGACCGTGGTGCACCAGGACTGGCTGAACGGCAAA
GAATACAAGTGCAAGGTGTCCAACAAGGGCCTGCCTGCCCCCATCGAG
AAAACCATCAGCAAGACAAAGGGCCAGCCCAGGGAACCCCAGGTGTAC
ACCCTGCCCCCAGCCGGGAGGAAATGACCAAGAACCAGGTGTCCCTG
ACCTGTCTGGTGAAGGGCTTCTACCCCAGCGACATCGCCGTGGAGTGG
GAGAGCAACGGCCAGCCCGAGAACAACTACAAGACCACCCCCCCCATG
CTGGACAGCGACGGCAGCTTCTTCCTGTACAGCAAGCTGACAGTGGAC
AAGAGCCGGTGGCAGCAGGGCAACGTGTTCAGCTGCAGCGTGATGCA
CGAGGCCCTGCACAACCACTACACCCAGAAGAGCCTGAGCCTGTCCCC
CGGCAAA
```

Figure 52

SEQ ID NO: 92

MKHLWFFLLLVAAPRWVLSQVQLVESGGGLVQPGGSLRLSCAASGFTF
TTYAMHWVRQAPGKGLEWVSTIFGSSSSTYYADSVKGRFTISRDNSKNT
LYLQMNSLRAEDTAVYYCARRGPGMGNMDIWGQGTLVTVSSASTKGPS
VFPLAPCSRSTSESTAALGCLVKDYFPEPVTVSWNSGALTSGVHTFPAVL
QSSGLYSLSSVVTVPSSNFGTQTYTCNVDHKPSNTKVDKTVERKCCVEC
PPCPAPPVAGPSVFLFPPKPKDTLMISRTPEVTCVVVDVSHEDPEVQFN
WYVDGVEVHNAKTKPREEQFNSTFRVVSVLTVVHQDWLNGKEYKCKVS
NKGLPAPIEKTISKTKGQPREPQVYTLPPSREEMTKNQVSLTCLVKGFYP
SDIAVEWESNGQPENNYKTTPPMLDSDGSFFLYSKLTVDKSRWQQGNV
FSCSVMHEALHNHYTQKSLSLSPGK

Figure 53

SEQ ID NO: 96

ATGGCCTGGGCTCTGCTGCTCCTCACCCTCCTCACTCAGGGCACAG
GATCCTGGGCTGATATCGCACTGACCCAGCCAGCTTCAGTGAGCGG
CTCACCAGGTCAGAGCATTACCATCTCGTGTACGGGTACTAGCAGC
GATGTTGGTGATTATAATTATGTGTCTTGGTACCAGCAGCATCCCGG
GAAGGCGCCGAAACTTATGATTTATTATGTTACTAATCGTCCCTCAG
GCGTGAGCAACCGTTTTAGCGGATCCAAAAGCGGCAACACCGCGAG
CCTGACCATTAGCGGCCTGCAAGCGGAAGACGAAGCGGATTATTAT
TGCCAGTCTTATGCTGGTGCTTCTTTTAATCTTGTGTTTGGCGGCGG
CACGAAGTTAACCGTCCTAGGTCAGCCCAAGGCTGCCCCCTCGGTC
ACTCTGTTCCCGCCCTCCTCTGAGGAGCTTCAAGCCAACAAGGCCA
CACTGGTGTGTCTCATAAGTGACTTCTACCCGGGAGCCGTGACAGT
GGCCTGGAAGGCAGATAGCAGCCCCGTCAAGGCGGGAGTGGAGAC
CACCACACCCTCCAAACAAAGCAACAACAAGTACGCGGCCAGCAGC
TATCTGAGCCTGACGCCTGAGCAGTGGAAGTCCCACAGAAGCTACA
GCTGCCAGGTCACGCATGAAGGGAGCACCGTGGAGAAGACAGTGG
CCCCTACAGAATGTTCA

Figure 54

SEQ ID NO: 97
MAWALLLLTLLTQGTGSWADIALTQPASVSGSPGQSITISCTGTSSDV
GDYNYVSWYQQHPGKAPKLMIYYVTNRPSGVSNRFSGSKSGNTASL
TISGLQAEDEADYYCQSYAGASFNLVFGGGTKLTVLGQPKAAPSVTL
FPPSSEELQANKATLVCLISDFYPGAVTVAWKADSSPVKAGVETTTPS
KQSNNKYAASSYLSLTPEQWKSHRSYSCQVTHEGSTVEKTVAPTEC
S

Figure 55

SEQ ID NO: 101

ATGAAACACCTGTGGTTCTTCCTCCTGCTGGTGGCAGCTCCCAGATGGG
TCCTGTCCCAGGTGCAATTGGTGGAAAGCGGCGGCGGCCTGGTGCAAC
CGGGCGGCAGCCTGCGTCTGAGCTGCGCGGCCTCCGGATTTACCTTTA
CTACTTATGCTATGCATTGGGTGCGCCAAGCCCCTGGGAAGGGTCTCGA
GTGGGTGAGCACTATTGAGATTAAGGAGGCTGGTTATGCTACTAATTATG
CTGCTGGTGTTAAGGGTCGTTTTACCATTTCACGTGATAATTCGAAAAAC
ACCCTGTATCTGCAAATGAACAGCCTGCGTGCGGAAGATACGGCCGTGT
ATTATTGCGCGCGTCGTGGTCCTGGTATGGGTAATATGGATATTTGGGG
CCAAGGCACCCTGGTGACGGTTAGCTCAGCCAGCACCAAGGGCCCCAG
CGTGTTCCCCCTGGCCCCCTGCAGCAGAAGCACCAGCGAGAGCACAGC
CGCCCTGGGCTGCCTGGTGAAGGACTACTTCCCCGAGCCCGTGACCGT
GAGCTGGAACAGCGGAGCCCTGACCAGCGGCGTGCACACCTTCCCCGC
CGTGCTGCAGAGCAGCGGCCTGTACAGCCTGAGCAGCGTGGTGACCGT
GCCCAGCAGCAACTTCGGCACCCAGACCTACACCTGCAACGTGGACCAC
AAGCCCAGCAACACCAAGGTGGACAAGACCGTGGAGCGGAAGTGCTGC
GTGGAGTGCCCCCCCTGCCCTGCCCCTCCTGTGGCCGGACCCTCCGTG
TTCCTGTTCCCCCCCAAGCCCAAGGACACCCTGATGATCAGCCGGACCC
CCGAGGTGACCTGCGTGGTGGTGGACGTGAGCCACGAGGACCCCGAG
GTGCAGTTTAATTGGTACGTGGACGGCGTGGAGGTGCACAACGCCAAGA
CCAAGCCCCGGGAGGAACAGTTCAACAGCACCTTCCGGGTGGTGTCCG
TGCTGACCGTGGTGCACCAGGACTGGCTGAACGGCAAAGAATACAAGTG
CAAGGTGTCCAACAAGGGCCTGCCTGCCCCCATCGAGAAAACCATCAGC
AAGACAAAGGGCCAGCCCAGGGAACCCCAGGTGTACACCCTGCCCCCC
AGCCGGGAGGAAATGACCAAGAACCAGGTGTCCCTGACCTGTCTGGTG
AAGGGCTTCTACCCCAGCGACATCGCCGTGGAGTGGGAGAGCAACGGC
CAGCCCGAGAACAACTACAAGACCACCCCCCCCATGCTGGACAGCGAC
GGCAGCTTCTTCCTGTACAGCAAGCTGACAGTGGACAAGAGCCGGTGG
CAGCAGGGCAACGTGTTCAGCTGCAGCGTGATGCACGAGGCCCTGCAC
AACCACTACACCCAGAAGAGCCTGAGCCTGTCCCCCGGCAAA

Figure 56

SEQ ID NO: 102

MKHLWFFLLLVAAPRWVLSQVQLVESGGGLVQPGGSLRLSCAASGFTF
TTYAMHWVRQAPGKGLEWVSTIEIKEAGYATNYAAGVKGRFTISRDNS
KNTLYLQMNSLRAEDTAVYYCARRGPGMGNMDIWGQGTLVTVSSAST
KGPSVFPLAPCSRSTSESTAALGCLVKDYFPEPVTVSWNSGALTSGVH
TFPAVLQSSGLYSLSSVVTVPSSNFGTQTYTCNVDHKPSNTKVDKTVER
KCCVECPPCPAPPVAGPSVFLFPPKPKDTLMISRTPEVTCVVVDVSHED
PEVQFNWYVDGVEVHNAKTKPREEQFNSTFRVVSVLTVVHQDWLNGK
EYKCKVSNKGLPAPIEKTISKTKGQPREPQVYTLPPSREEMTKNQVSLT
CLVKGFYPSDIAVEWESNGQPENNYKTTPPMLDSDGSFFLYSKLTVDK
SRWQQGNVFSCSVMHEALHNHYTQKSLSLSPGK

Figure 57

SEQUENCE LISTING

```
<160> NUMBER OF SEQ ID NOS: 109

<210> SEQ ID NO 1
<211> LENGTH: 1389
<212> TYPE: DNA
<213> ORGANISM: Homo sapiens
<220> FEATURE:
<221> NAME/KEY: CDS
<222> LOCATION: (1)..(1389)
<220> FEATURE:
<221> NAME/KEY: sig_peptide
<222> LOCATION: (1)..(57)
<220> FEATURE:
<221> NAME/KEY: V_region
<222> LOCATION: (58)..(411)
<220> FEATURE:
<221> NAME/KEY: misc_feature
<222> LOCATION: (148)..(162)
<223> OTHER INFORMATION: CDR1
<220> FEATURE:
<221> NAME/KEY: misc_feature
<222> LOCATION: (205)..(255)
<223> OTHER INFORMATION: CDR2
```

```
<220> FEATURE:
<221> NAME/KEY: misc_feature
<222> LOCATION: (352)..(378)
<223> OTHER INFORMATION: CDR3

<400> SEQUENCE: 1 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtc ctg tcc cag gtg caa ttg gtg gaa agc ggc ggc ggc ctg gtg caa      96
Val Leu Ser Gln Val Gln Leu Val Glu Ser Gly Gly Gly Leu Val Gln
            20                  25                  30 ccg ggc ggc agc ctg cgt ctg agc tgc gcg gcc tcc gga ttt acc ttt     144
Pro Gly Gly Ser Leu Arg Leu Ser Cys Ala Ala Ser Gly Phe Thr Phe
        35                  40                  45 tct aat tat tgg atg act tgg gtg cgc caa gcc cct ggg aag ggt ctc     192
Ser Asn Tyr Trp Met Thr Trp Val Arg Gln Ala Pro Gly Lys Gly Leu
    50                  55                  60 gag tgg gtg agc ttt atc tct tat tct ggt agc act acc tat tat gcg     240
Glu Trp Val Ser Phe Ile Ser Tyr Ser Gly Ser Thr Thr Tyr Tyr Ala
65                  70                  75                  80 gat agc gtg aaa ggc cgt ttt acc att tca cgt gat aat tcg aaa aac     288
Asp Ser Val Lys Gly Arg Phe Thr Ile Ser Arg Asp Asn Ser Lys Asn
                85                  90                  95 acc ctg tat ctg caa atg aac agc ctg cgt gcg gaa gat acg gcc gtg     336
Thr Leu Tyr Leu Gln Met Asn Ser Leu Arg Ala Glu Asp Thr Ala Val
            100                 105                 110 tat tat tgc gcg cgt gag ggt act tct tct atg ttt gat gtt tgg ggc     384
Tyr Tyr Cys Ala Arg Glu Gly Thr Ser Ser Met Phe Asp Val Trp Gly
        115                 120                 125 caa ggc acc ctg gtg acg gtt agc tca gcc agc acc aag ggc ccc agc     432
Gln Gly Thr Leu Val Thr Val Ser Ser Ala Ser Thr Lys Gly Pro Ser
    130                 135                 140 gtg ttc ccc ctg gcc ccc tgc agc aga agc acc agc gag agc aca gcc     480
Val Phe Pro Leu Ala Pro Cys Ser Arg Ser Thr Ser Glu Ser Thr Ala
145                 150                 155                 160 gcc ctg ggc tgc ctg gtg aag gac tac ttc ccc gag ccc gtg acc gtg     528
Ala Leu Gly Cys Leu Val Lys Asp Tyr Phe Pro Glu Pro Val Thr Val
                165                 170                 175 agc tgg aac agc gga gcc ctg acc agc ggc gtg cac acc ttc ccc gcc     576
Ser Trp Asn Ser Gly Ala Leu Thr Ser Gly Val His Thr Phe Pro Ala
            180                 185                 190 gtg ctg cag agc agc ggc ctg tac agc ctg agc agc gtg gtg acc gtg     624
Val Leu Gln Ser Ser Gly Leu Tyr Ser Leu Ser Ser Val Val Thr Val
        195                 200                 205 ccc agc agc aac ttc ggc acc cag acc tac acc tgc aac gtg gac cac     672
Pro Ser Ser Asn Phe Gly Thr Gln Thr Tyr Thr Cys Asn Val Asp His
    210                 215                 220 aag ccc agc aac acc aag gtg gac aag acc gtg gag cgg aag tgc tgc     720
Lys Pro Ser Asn Thr Lys Val Asp Lys Thr Val Glu Arg Lys Cys Cys
225                 230                 235                 240 gtg gag tgc ccc ccc tgc cct gcc cct cct gtg gcc gga ccc tcc gtg     768
Val Glu Cys Pro Pro Cys Pro Ala Pro Pro Val Ala Gly Pro Ser Val
                245                 250                 255 ttc ctg ttc ccc ccc aag ccc aag gac acc ctg atg atc agc cgg acc     816
Phe Leu Phe Pro Pro Lys Pro Lys Asp Thr Leu Met Ile Ser Arg Thr
            260                 265                 270 ccc gag gtg acc tgc gtg gtg gtg gac gtg agc cac gag gac ccc gag     864
Pro Glu Val Thr Cys Val Val Val Asp Val Ser His Glu Asp Pro Glu
        275                 280                 285
```

| | | | | | | | | | | | | | | | |
|---|---|---|---|---|---|---|---|---|---|---|---|---|---|---|---|
| gtg | cag | ttt | aat | tgg | tac | gtg | gac | ggc | gtg | gag | gtg | cac | aac | gcc | aag | 912 |
| Val | Gln | Phe | Asn | Trp | Tyr | Val | Asp | Gly | Val | Glu | Val | His | Asn | Ala | Lys |
| | 290 | | | | 295 | | | | 300 | | | | | | |

| acc | aag | ccc | cgg | gag | gaa | cag | ttc | aac | agc | acc | ttc | cgg | gtg | gtg | tcc | 960 |
|---|---|---|---|---|---|---|---|---|---|---|---|---|---|---|---|---|
| Thr | Lys | Pro | Arg | Glu | Glu | Gln | Phe | Asn | Ser | Thr | Phe | Arg | Val | Val | Ser |
| 305 | | | | | 310 | | | | | 315 | | | | | 320 |

| gtg | ctg | acc | gtg | gtg | cac | cag | gac | tgg | ctg | aac | ggc | aaa | gaa | tac | aag | 1008 |
|---|---|---|---|---|---|---|---|---|---|---|---|---|---|---|---|---|
| Val | Leu | Thr | Val | Val | His | Gln | Asp | Trp | Leu | Asn | Gly | Lys | Glu | Tyr | Lys |
| | | | | 325 | | | | | 330 | | | | | 335 | |

| tgc | aag | gtg | tcc | aac | aag | ggc | ctg | cct | gcc | ccc | atc | gag | aaa | acc | atc | 1056 |
|---|---|---|---|---|---|---|---|---|---|---|---|---|---|---|---|---|
| Cys | Lys | Val | Ser | Asn | Lys | Gly | Leu | Pro | Ala | Pro | Ile | Glu | Lys | Thr | Ile |
| | | | 340 | | | | | 345 | | | | | 350 | | |

| agc | aag | aca | aag | ggc | cag | ccc | agg | gaa | ccc | cag | gtg | tac | acc | ctg | ccc | 1104 |
|---|---|---|---|---|---|---|---|---|---|---|---|---|---|---|---|---|
| Ser | Lys | Thr | Lys | Gly | Gln | Pro | Arg | Glu | Pro | Gln | Val | Tyr | Thr | Leu | Pro |
| | | 355 | | | | | 360 | | | | | 365 | | | |

| ccc | agc | cgg | gag | gaa | atg | acc | aag | aac | cag | gtg | tcc | ctg | acc | tgt | ctg | 1152 |
|---|---|---|---|---|---|---|---|---|---|---|---|---|---|---|---|---|
| Pro | Ser | Arg | Glu | Glu | Met | Thr | Lys | Asn | Gln | Val | Ser | Leu | Thr | Cys | Leu |
| | 370 | | | | | 375 | | | | | 380 | | | | |

| gtg | aag | ggc | ttc | tac | ccc | agc | gac | atc | gcc | gtg | gag | tgg | gag | agc | aac | 1200 |
|---|---|---|---|---|---|---|---|---|---|---|---|---|---|---|---|---|
| Val | Lys | Gly | Phe | Tyr | Pro | Ser | Asp | Ile | Ala | Val | Glu | Trp | Glu | Ser | Asn |
| 385 | | | | | 390 | | | | | 395 | | | | | 400 |

| ggc | cag | ccc | gag | aac | aac | tac | aag | acc | acc | ccc | ccc | atg | ctg | gac | agc | 1248 |
|---|---|---|---|---|---|---|---|---|---|---|---|---|---|---|---|---|
| Gly | Gln | Pro | Glu | Asn | Asn | Tyr | Lys | Thr | Thr | Pro | Pro | Met | Leu | Asp | Ser |
| | | | | 405 | | | | | 410 | | | | | 415 | |

| gac | ggc | agc | ttc | ttc | ctg | tac | agc | aag | ctg | aca | gtg | gac | aag | agc | cgg | 1296 |
|---|---|---|---|---|---|---|---|---|---|---|---|---|---|---|---|---|
| Asp | Gly | Ser | Phe | Phe | Leu | Tyr | Ser | Lys | Leu | Thr | Val | Asp | Lys | Ser | Arg |
| | | | 420 | | | | | 425 | | | | | 430 | | |

| tgg | cag | cag | ggc | aac | gtg | ttc | agc | tgc | agc | gtg | atg | cac | gag | gcc | ctg | 1344 |
|---|---|---|---|---|---|---|---|---|---|---|---|---|---|---|---|---|
| Trp | Gln | Gln | Gly | Asn | Val | Phe | Ser | Cys | Ser | Val | Met | His | Glu | Ala | Leu |
| | | 435 | | | | | 440 | | | | | 445 | | | |

| cac | aac | cac | tac | acc | cag | aag | agc | ctg | agc | ctg | tcc | ccc | ggc | aaa | | 1389 |
|---|---|---|---|---|---|---|---|---|---|---|---|---|---|---|---|---|
| His | Asn | His | Tyr | Thr | Gln | Lys | Ser | Leu | Ser | Leu | Ser | Pro | Gly | Lys | |
| | 450 | | | | | 455 | | | | | 460 | | | | |

```
<210> SEQ ID NO 2
<211> LENGTH: 463
<212> TYPE: PRT
<213> ORGANISM: Homo sapiens

<400> SEQUENCE: 2
```

| Met | Lys | His | Leu | Trp | Phe | Phe | Leu | Leu | Leu | Val | Ala | Ala | Pro | Arg | Trp |
|---|---|---|---|---|---|---|---|---|---|---|---|---|---|---|---|
| 1 | | | | 5 | | | | | 10 | | | | | 15 | |

| Val | Leu | Ser | Gln | Val | Gln | Leu | Val | Glu | Ser | Gly | Gly | Gly | Leu | Val | Gln |
|---|---|---|---|---|---|---|---|---|---|---|---|---|---|---|---|
| | | | 20 | | | | | 25 | | | | | 30 | | |

| Pro | Gly | Gly | Ser | Leu | Arg | Leu | Ser | Cys | Ala | Ala | Ser | Gly | Phe | Thr | Phe |
|---|---|---|---|---|---|---|---|---|---|---|---|---|---|---|---|
| | | 35 | | | | | 40 | | | | | 45 | | | |

| Ser | Asn | Tyr | Trp | Met | Thr | Trp | Val | Arg | Gln | Ala | Pro | Gly | Lys | Gly | Leu |
|---|---|---|---|---|---|---|---|---|---|---|---|---|---|---|---|
| | 50 | | | | | 55 | | | | | 60 | | | | |

| Glu | Trp | Val | Ser | Phe | Ile | Ser | Tyr | Ser | Gly | Ser | Thr | Thr | Tyr | Ala |
|---|---|---|---|---|---|---|---|---|---|---|---|---|---|---|
| 65 | | | | | 70 | | | | | 75 | | | | 80 |

| Asp | Ser | Val | Lys | Gly | Arg | Phe | Thr | Ile | Ser | Arg | Asp | Asn | Ser | Lys | Asn |
|---|---|---|---|---|---|---|---|---|---|---|---|---|---|---|---|
| | | | | 85 | | | | | 90 | | | | | 95 | |

| Thr | Leu | Tyr | Leu | Gln | Met | Asn | Ser | Leu | Arg | Ala | Glu | Asp | Thr | Ala | Val |
|---|---|---|---|---|---|---|---|---|---|---|---|---|---|---|---|
| | | | 100 | | | | | 105 | | | | | 110 | | |

| Tyr | Tyr | Cys | Ala | Arg | Glu | Gly | Thr | Ser | Ser | Met | Phe | Asp | Val | Trp | Gly |
|---|---|---|---|---|---|---|---|---|---|---|---|---|---|---|---|
| | | 115 | | | | | 120 | | | | | 125 | | | |

| Gln | Gly | Thr | Leu | Val | Thr | Val | Ser | Ser | Ala | Ser | Thr | Lys | Gly | Pro | Ser |
|---|---|---|---|---|---|---|---|---|---|---|---|---|---|---|---|
| | 130 | | | | | 135 | | | | | 140 | | | | |

```
Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
        180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 3
<211> LENGTH: 5
<212> TYPE: PRT
<213> ORGANISM: Homo sapiens

<400> SEQUENCE: 3

Asn Tyr Trp Met Thr
1               5

<210> SEQ ID NO 4
<211> LENGTH: 17
<212> TYPE: PRT
<213> ORGANISM: Homo sapiens

<400> SEQUENCE: 4
```

```
Phe Ile Ser Tyr Ser Gly Ser Thr Thr Tyr Tyr Ala Asp Ser Val Lys
1               5                   10                  15

Gly
```

<210> SEQ ID NO 5
<211> LENGTH: 9
<212> TYPE: PRT
<213> ORGANISM: Homo sapiens

<400> SEQUENCE: 5

```
Glu Gly Thr Ser Ser Met Phe Asp Val
1               5
```

<210> SEQ ID NO 6
<211> LENGTH: 693
<212> TYPE: DNA
<213> ORGANISM: Homo sapiens
<220> FEATURE:
<221> NAME/KEY: CDS
<222> LOCATION: (1)..(693)
<220> FEATURE:
<221> NAME/KEY: sig_peptide
<222> LOCATION: (1)..(57)
<220> FEATURE:
<221> NAME/KEY: V_region
<222> LOCATION: (58)..(384)
<220> FEATURE:
<221> NAME/KEY: misc_feature
<222> LOCATION: (124)..(156)
<223> OTHER INFORMATION: CDR1
<220> FEATURE:
<221> NAME/KEY: misc_feature
<222> LOCATION: (202)..(222)
<223> OTHER INFORMATION: CDR2
<220> FEATURE:
<221> NAME/KEY: misc_feature
<222> LOCATION: (319)..(345)
<223> OTHER INFORMATION: CDR3

<400> SEQUENCE: 6

```
atg gcc tgg gct ctg ctg ctc ctc acc ctc ctc act cag ggc aca gga        48
Met Ala Trp Ala Leu Leu Leu Leu Thr Leu Leu Thr Gln Gly Thr Gly
1               5                   10                  15 tcc tgg gct gat atc gaa ctg acc cag ccg cct tca gtg agc gtt gca        96
Ser Trp Ala Asp Ile Glu Leu Thr Gln Pro Pro Ser Val Ser Val Ala
                20                  25                  30 cca ggt cag acc gcg cgt atc tcg tgt agc ggc gat gct ctt cgt tct       144
Pro Gly Gln Thr Ala Arg Ile Ser Cys Ser Gly Asp Ala Leu Arg Ser
            35                  40                  45 tat tat gct tct tgg tac cag cag aaa ccc ggg cag gcg cca gtt ctt       192
Tyr Tyr Ala Ser Trp Tyr Gln Gln Lys Pro Gly Gln Ala Pro Val Leu
        50                  55                  60 gtg att tat gat gat aat aag cgt ccc tca ggc atc ccg gaa cgc ttt       240
Val Ile Tyr Asp Asp Asn Lys Arg Pro Ser Gly Ile Pro Glu Arg Phe
65                  70                  75                  80 agc gga tcc aac agc ggc aac acc gcg acc ctg acc att agc ggc act       288
Ser Gly Ser Asn Ser Gly Asn Thr Ala Thr Leu Thr Ile Ser Gly Thr
                85                  90                  95 cag gcg gaa gac gaa gcg gat tat tat tgc ggt tct tat gat ggt act       336
Gln Ala Glu Asp Glu Ala Asp Tyr Tyr Cys Gly Ser Tyr Asp Gly Thr
            100                 105                 110 gtt cat gtg ttt ggc ggc ggc acg aag tta acc gtc cta ggt cag ccc       384
Val His Val Phe Gly Gly Gly Thr Lys Leu Thr Val Leu Gly Gln Pro
        115                 120                 125 aag gct gcc ccc tcg gtc act ctg ttc ccg ccc tcc tct gag gag ctt       432
Lys Ala Ala Pro Ser Val Thr Leu Phe Pro Pro Ser Ser Glu Glu Leu
```

```
                    130                 135                 140
caa gcc aac aag gcc aca ctg gtg tgt ctc ata agt gac ttc tac ccg       480
Gln Ala Asn Lys Ala Thr Leu Val Cys Leu Ile Ser Asp Phe Tyr Pro
145                 150                 155                 160 gga gcc gtg aca gtg gcc tgg aag gca gat agc agc ccc gtc aag gcg       528
Gly Ala Val Thr Val Ala Trp Lys Ala Asp Ser Ser Pro Val Lys Ala
                165                 170                 175 gga gtg gag acc acc aca ccc tcc aaa caa agc aac aac aag tac gcg       576
Gly Val Glu Thr Thr Thr Pro Ser Lys Gln Ser Asn Asn Lys Tyr Ala
            180                 185                 190 gcc agc agc tat ctg agc ctg acg cct gag cag tgg aag tcc cac aga       624
Ala Ser Ser Tyr Leu Ser Leu Thr Pro Glu Gln Trp Lys Ser His Arg
        195                 200                 205 agc tac agc tgc cag gtc acg cat gaa ggg agc acc gtg gag aag aca       672
Ser Tyr Ser Cys Gln Val Thr His Glu Gly Ser Thr Val Glu Lys Thr
    210                 215                 220 gtg gcc cct aca gaa tgt tca                                           693
Val Ala Pro Thr Glu Cys Ser
225                 230
```

<210> SEQ ID NO 7
<211> LENGTH: 231
<212> TYPE: PRT
<213> ORGANISM: Homo sapiens

<400> SEQUENCE: 7

```
Met Ala Trp Ala Leu Leu Leu Thr Leu Leu Thr Gln Gly Thr Gly
1               5                   10                  15

Ser Trp Ala Asp Ile Glu Leu Thr Gln Pro Ser Val Ser Val Ala
            20                  25                  30

Pro Gly Gln Thr Ala Arg Ile Ser Cys Ser Gly Asp Ala Leu Arg Ser
        35                  40                  45

Tyr Tyr Ala Ser Trp Tyr Gln Gln Lys Pro Gly Gln Ala Pro Val Leu
    50                  55                  60

Val Ile Tyr Asp Asp Asn Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Glu Asp Glu Ala Asp Tyr Tyr Cys Gly Ser Tyr Asp Gly Thr
            100                 105                 110

Val His Val Phe Gly Gly Gly Thr Lys Leu Thr Val Leu Gly Gln Pro
        115                 120                 125

Lys Ala Ala Pro Ser Val Thr Leu Phe Pro Pro Ser Ser Glu Glu Leu
130                 135                 140

Gln Ala Asn Lys Ala Thr Leu Val Cys Leu Ile Ser Asp Phe Tyr Pro
145                 150                 155                 160

Gly Ala Val Thr Val Ala Trp Lys Ala Asp Ser Ser Pro Val Lys Ala
                165                 170                 175

Gly Val Glu Thr Thr Thr Pro Ser Lys Gln Ser Asn Asn Lys Tyr Ala
            180                 185                 190

Ala Ser Ser Tyr Leu Ser Leu Thr Pro Glu Gln Trp Lys Ser His Arg
        195                 200                 205

Ser Tyr Ser Cys Gln Val Thr His Glu Gly Ser Thr Val Glu Lys Thr
    210                 215                 220

Val Ala Pro Thr Glu Cys Ser
225                 230
```

-continued

```
<210> SEQ ID NO 8
<211> LENGTH: 11
<212> TYPE: PRT
<213> ORGANISM: Homo sapiens

<400> SEQUENCE: 8

Ser Gly Asp Ala Leu Arg Ser Tyr Tyr Ala Ser
1               5                   10

<210> SEQ ID NO 9
<211> LENGTH: 7
<212> TYPE: PRT
<213> ORGANISM: Homo sapiens

<400> SEQUENCE: 9

Asp Asp Asn Lys Arg Pro Ser
1               5

<210> SEQ ID NO 10
<211> LENGTH: 9
<212> TYPE: PRT
<213> ORGANISM: Homo sapiens

<400> SEQUENCE: 10

Gly Ser Tyr Asp Gly Thr Val His Val
1               5

<210> SEQ ID NO 11
<211> LENGTH: 1386
<212> TYPE: DNA
<213> ORGANISM: Homo sapiens
<220> FEATURE:
<221> NAME/KEY: CDS
<222> LOCATION: (1)..(1386)
<220> FEATURE:
<221> NAME/KEY: sig_peptide
<222> LOCATION: (1)..(57)
<220> FEATURE:
<221> NAME/KEY: V_region
<222> LOCATION: (58)..(408)
<220> FEATURE:
<221> NAME/KEY: misc_feature
<222> LOCATION: (148)..(162)
<223> OTHER INFORMATION: CDR1
<220> FEATURE:
<221> NAME/KEY: misc_feature
<222> LOCATION: (205)..(255)
<223> OTHER INFORMATION: CDR2
<220> FEATURE:
<221> NAME/KEY: misc_feature
<222> LOCATION: (352)..(375)
<223> OTHER INFORMATION: CDR3

<400> SEQUENCE: 11 atg aaa cac ctg tgg ttc ttc ctc ctg ctg gtg gca gct ccc aga tgg     48
Met Lys His Leu Trp Phe Phe Leu Leu Leu Val Ala Ala Pro Arg Trp
1               5                   10                  15 gtc ctg tcc cag gtg caa ttg gtg gaa agc ggc ggc ggc ctg gtg caa     96
Val Leu Ser Gln Val Gln Leu Val Glu Ser Gly Gly Gly Leu Val Gln
                20                  25                  30 ccg ggc ggc agc ctg cgt ctg agc tgc gcg gcc tcc gga ttt acc ttt    144
Pro Gly Gly Ser Leu Arg Leu Ser Cys Ala Ala Ser Gly Phe Thr Phe
            35                  40                  45 act aat tat gct atg aat tgg gtg cgc caa gcc cct ggg aag ggt ctc    192
Thr Asn Tyr Ala Met Asn Trp Val Arg Gln Ala Pro Gly Lys Gly Leu
        50                  55                  60 gag tgg gtg agc act atc tct tat att ggt agc aat acc tat tat gcg    240
```

-continued

```
              Glu Trp Val Ser Thr Ile Ser Tyr Ile Gly Ser Asn Thr Tyr Tyr Ala
              65                  70                  75                  80 gat agc gtg aaa ggc cgt ttt acc att tca cgt gat aat tcg aaa aac            288
Asp Ser Val Lys Gly Arg Phe Thr Ile Ser Arg Asp Asn Ser Lys Asn
                85                  90                  95 acc ctg tat ctg caa atg aac agc ctg cgt gcg gaa gat acg gcc gtg            336
Thr Leu Tyr Leu Gln Met Asn Ser Leu Arg Ala Glu Asp Thr Ala Val
        100                 105                 110 tat tat tgc gcg cgt ggt gct ggt ctt ggt tat gat gtt tgg ggc caa            384
Tyr Tyr Cys Ala Arg Gly Ala Gly Leu Gly Tyr Asp Val Trp Gly Gln
            115                 120                 125 ggc acc ctg gtg acg gtt agc tca gcc agc acc aag ggc ccc agc gtg            432
Gly Thr Leu Val Thr Val Ser Ser Ala Ser Thr Lys Gly Pro Ser Val
    130                 135                 140 ttc ccc ctg gcc ccc tgc agc aga agc acc agc gag agc aca gcc gcc            480
Phe Pro Leu Ala Pro Cys Ser Arg Ser Thr Ser Glu Ser Thr Ala Ala
145                 150                 155                 160 ctg ggc tgc ctg gtg aag gac tac ttc ccc gag ccc gtg acc gtg agc            528
Leu Gly Cys Leu Val Lys Asp Tyr Phe Pro Glu Pro Val Thr Val Ser
                165                 170                 175 tgg aac agc gga gcc ctg acc agc ggc gtg cac acc ttc ccc gcc gtg            576
Trp Asn Ser Gly Ala Leu Thr Ser Gly Val His Thr Phe Pro Ala Val
        180                 185                 190 ctg cag agc agc ggc ctg tac agc ctg agc agc gtg gtg acc gtg ccc            624
Leu Gln Ser Ser Gly Leu Tyr Ser Leu Ser Ser Val Val Thr Val Pro
            195                 200                 205 agc agc aac ttc ggc acc cag acc tac acc tgc aac gtg gac cac aag            672
Ser Ser Asn Phe Gly Thr Gln Thr Tyr Thr Cys Asn Val Asp His Lys
    210                 215                 220 ccc agc aac acc aag gtg gac aag acc gtg gag cgg aag tgc tgc gtg            720
Pro Ser Asn Thr Lys Val Asp Lys Thr Val Glu Arg Lys Cys Cys Val
225                 230                 235                 240 gag tgc ccc ccc tgc cct gcc cct cct gtg gcc gga ccc tcc gtg ttc            768
Glu Cys Pro Pro Cys Pro Ala Pro Pro Val Ala Gly Pro Ser Val Phe
                245                 250                 255 ctg ttc ccc ccc aag ccc aag gac acc ctg atg atc agc cgg acc ccc            816
Leu Phe Pro Pro Lys Pro Lys Asp Thr Leu Met Ile Ser Arg Thr Pro
        260                 265                 270 gag gtg acc tgc gtg gtg gtg gac gtg agc cac gag gac ccc gag gtg            864
Glu Val Thr Cys Val Val Val Asp Val Ser His Glu Asp Pro Glu Val
            275                 280                 285 cag ttt aat tgg tac gtg gac ggc gtg gag gtg cac aac gcc aag acc            912
Gln Phe Asn Trp Tyr Val Asp Gly Val Glu Val His Asn Ala Lys Thr
    290                 295                 300 aag ccc cgg gag gaa cag ttc aac agc acc ttc cgg gtg gtg tcc gtg            960
Lys Pro Arg Glu Glu Gln Phe Asn Ser Thr Phe Arg Val Val Ser Val
305                 310                 315                 320 ctg acc gtg gtg cac cag gac tgg ctg aac ggc aaa gaa tac aag tgc           1008
Leu Thr Val Val His Gln Asp Trp Leu Asn Gly Lys Glu Tyr Lys Cys
                325                 330                 335 aag gtg tcc aac aag ggc ctg cct gcc ccc atc gag aaa acc atc agc           1056
Lys Val Ser Asn Lys Gly Leu Pro Ala Pro Ile Glu Lys Thr Ile Ser
        340                 345                 350 aag aca aag ggc cag ccc agg gaa ccc cag gtg tac acc ctg ccc ccc           1104
Lys Thr Lys Gly Gln Pro Arg Glu Pro Gln Val Tyr Thr Leu Pro Pro
            355                 360                 365 agc cgg gag gaa atg acc aag aac cag gtg tcc ctg acc tgt ctg gtg           1152
Ser Arg Glu Glu Met Thr Lys Asn Gln Val Ser Leu Thr Cys Leu Val
    370                 375                 380
```

```
aag ggc ttc tac ccc agc gac atc gcc gtg gag tgg gag agc aac ggc    1200
Lys Gly Phe Tyr Pro Ser Asp Ile Ala Val Glu Trp Glu Ser Asn Gly
385                 390                 395                 400 cag ccc gag aac aac tac aag acc acc ccc ccc atg ctg gac agc gac    1248
Gln Pro Glu Asn Asn Tyr Lys Thr Thr Pro Pro Met Leu Asp Ser Asp
                405                 410                 415 ggc agc ttc ttc ctg tac agc aag ctg aca gtg gac aag agc cgg tgg    1296
Gly Ser Phe Phe Leu Tyr Ser Lys Leu Thr Val Asp Lys Ser Arg Trp
            420                 425                 430 cag cag ggc aac gtg ttc agc tgc agc gtg atg cac gag gcc ctg cac    1344
Gln Gln Gly Asn Val Phe Ser Cys Ser Val Met His Glu Ala Leu His
        435                 440                 445 aac cac tac acc cag aag agc ctg agc ctg tcc ccc ggc aaa            1386
Asn His Tyr Thr Gln Lys Ser Leu Ser Leu Ser Pro Gly Lys
    450                 455                 460

<210> SEQ ID NO 12
<211> LENGTH: 462
<212> TYPE: PRT
<213> ORGANISM: Homo sapiens

<400> SEQUENCE: 12

Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asn Tyr Ala Met Asn Trp Val Arg Gln Ala Pro Gly Lys Gly Leu
    50                  55                  60

Glu Trp Val Ser Thr Ile Ser Tyr Ile Gly Ser Asn Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Ala Gly Leu Gly Tyr Asp Val Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Asn Phe Gly Thr Gln Thr Tyr Thr Cys Asn Val Asp His Lys
    210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
            260                 265                 270
```

-continued

Glu Val Thr Cys Val Val Asp Val Ser His Glu Asp Pro Glu Val
            275                 280                 285

Gln Phe Asn Trp Tyr Val Asp Gly Val Glu Val His Asn Ala Lys Thr
290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
            325                 330                 335

Lys Val Ser Asn Lys Gly Leu Pro Ala Pro Ile Glu Lys Thr Ile Ser
            340                 345                 350

Lys Thr Lys Gly Gln Pro Arg Glu Pro Gln Val Tyr Thr Leu Pro Pro
            355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
            405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
    450                 455                 460

<210> SEQ ID NO 13
<211> LENGTH: 5
<212> TYPE: PRT
<213> ORGANISM: Homo sapiens

<400> SEQUENCE: 13

Asn Tyr Ala Met Asn
1               5

<210> SEQ ID NO 14
<211> LENGTH: 17
<212> TYPE: PRT
<213> ORGANISM: Homo sapiens

<400> SEQUENCE: 14

Thr Ile Ser Tyr Ile Gly Ser Asn Thr Tyr Tyr Ala Asp Ser Val Lys
1               5                   10                  15
Gly

<210> SEQ ID NO 15
<211> LENGTH: 8
<212> TYPE: PRT
<213> ORGANISM: Homo sapiens

<400> SEQUENCE: 15

Gly Ala Gly Leu Gly Tyr Asp Val
1               5

<210> SEQ ID NO 16
<211> LENGTH: 696
<212> TYPE: DNA
<213> ORGANISM: Homo sapiens
<220> FEATURE:
<221> NAME/KEY: CDS
<222> LOCATION: (1)..(696)

<220> FEATURE:
<221> NAME/KEY: sig_peptide
<222> LOCATION: (1)..(57)
<220> FEATURE:
<221> NAME/KEY: V_region
<222> LOCATION: (58)..(387)
<220> FEATURE:
<221> NAME/KEY: misc_feature
<222> LOCATION: (124)..(156)
<223> OTHER INFORMATION: CDR1
<220> FEATURE:
<221> NAME/KEY: misc_feature
<222> LOCATION: (202)..(222)
<223> OTHER INFORMATION: CDR2
<220> FEATURE:
<221> NAME/KEY: misc_feature
<222> LOCATION: (319)..(348)
<223> OTHER INFORMATION: CDR3

<400> SEQUENCE: 16

| | | | | | | | | | | | | | | | | |
|---|---|---|---|---|---|---|---|---|---|---|---|---|---|---|---|---|
| atg | gcc | tgg | gct | ctg | ctg | ctc | ctc | acc | ctc | ctc | act | cag | ggc | aca | gga | 48 |
| Met | Ala | Trp | Ala | Leu | Leu | Leu | Leu | Thr | Leu | Leu | Thr | Gln | Gly | Thr | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tcc | tgg | gct | gat | atc | gaa | ctg | acc | cag | ccg | cct | tca | gtg | agc | gtt | gca | 96 |
| Ser | Trp | Ala | Asp | Ile | Glu | Leu | Thr | Gln | Pro | Pro | Ser | Val | Ser | Val | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| cca | ggt | cag | acc | gcg | cgt | atc | tcg | tgt | agc | ggc | gat | aat | ctt | cgt | tct | 144 |
| Pro | Gly | Gln | Thr | Ala | Arg | Ile | Ser | Cys | Ser | Gly | Asp | Asn | Leu | Arg | Ser | |
| | | 35 | | | | | 40 | | | | | 45 | | | | |

| | | | | | | | | | | | | | | | | |
|---|---|---|---|---|---|---|---|---|---|---|---|---|---|---|---|---|
| aag | tat | gtt | tat | tgg | tac | cag | cag | aaa | ccc | ggg | cag | gcg | cca | gtt | ctt | 192 |
| Lys | Tyr | Val | Tyr | Trp | Tyr | Gln | Gln | Lys | Pro | Gly | Gln | Ala | Pro | Val | Leu | |
| 50 | | | | | 55 | | | | | 60 | | | | | | |

| | | | | | | | | | | | | | | | | |
|---|---|---|---|---|---|---|---|---|---|---|---|---|---|---|---|---|
| gtg | att | tat | gat | act | aat | gat | cgt | ccc | tca | ggc | atc | ccg | gaa | cgc | ttt | 240 |
| Val | Ile | Tyr | Asp | Thr | Asn | Asp | Arg | Pro | Ser | Gly | Ile | Pro | Glu | Arg | Phe | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| agc | gga | tcc | aac | agc | ggc | aac | acc | gcg | acc | ctg | acc | att | agc | ggc | act | 288 |
| Ser | Gly | Ser | Asn | Ser | Gly | Asn | Thr | Ala | Thr | Leu | Thr | Ile | Ser | Gly | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| cag | gcg | gaa | gac | gaa | gcg | gat | tat | tat | tgc | cag | act | tat | gat | atg | act | 336 |
| Gln | Ala | Glu | Asp | Glu | Ala | Asp | Tyr | Tyr | Cys | Gln | Thr | Tyr | Asp | Met | Thr | |
| | | | 100 | | | | | 105 | | | | | 110 | | | |

| | | | | | | | | | | | | | | | | |
|---|---|---|---|---|---|---|---|---|---|---|---|---|---|---|---|---|
| tct | cag | gat | gtg | ttt | ggc | ggc | ggc | acg | aag | tta | acc | gtc | cta | ggt | cag | 384 |
| Ser | Gln | Asp | Val | Phe | Gly | Gly | Gly | Thr | Lys | Leu | Thr | Val | Leu | Gly | Gln | |
| | | 115 | | | | | 120 | | | | | 125 | | | | |

| | | | | | | | | | | | | | | | | |
|---|---|---|---|---|---|---|---|---|---|---|---|---|---|---|---|---|
| ccc | aag | gct | gcc | ccc | tcg | gtc | act | ctg | ttc | ccg | ccc | tcc | tct | gag | gag | 432 |
| Pro | Lys | Ala | Ala | Pro | Ser | Val | Thr | Leu | Phe | Pro | Pro | Ser | Ser | Glu | Glu | |
| | 130 | | | | | 135 | | | | | 140 | | | | | |

| | | | | | | | | | | | | | | | | |
|---|---|---|---|---|---|---|---|---|---|---|---|---|---|---|---|---|
| ctt | caa | gcc | aac | aag | gcc | aca | ctg | gtg | tgt | ctc | ata | agt | gac | ttc | tac | 480 |
| Leu | Gln | Ala | Asn | Lys | Ala | Thr | Leu | Val | Cys | Leu | Ile | Ser | Asp | Phe | Tyr | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| ccg | gga | gcc | gtg | aca | gtg | gcc | tgg | aag | gca | gat | agc | agc | ccc | gtc | aag | 528 |
| Pro | Gly | Ala | Val | Thr | Val | Ala | Trp | Lys | Ala | Asp | Ser | Ser | Pro | Val | Lys | |
| | | | | 165 | | | | | 170 | | | | | 175 | | |

| | | | | | | | | | | | | | | | | |
|---|---|---|---|---|---|---|---|---|---|---|---|---|---|---|---|---|
| gcg | gga | gtg | gag | acc | acc | aca | ccc | tcc | aaa | caa | agc | aac | aac | aag | tac | 576 |
| Ala | Gly | Val | Glu | Thr | Thr | Thr | Pro | Ser | Lys | Gln | Ser | Asn | Asn | Lys | Tyr | |
| | | | 180 | | | | | 185 | | | | | 190 | | | |

| | | | | | | | | | | | | | | | | |
|---|---|---|---|---|---|---|---|---|---|---|---|---|---|---|---|---|
| gcg | gcc | agc | agc | tat | ctg | agc | ctg | acg | cct | gag | cag | tgg | aag | tcc | cac | 624 |
| Ala | Ala | Ser | Ser | Tyr | Leu | Ser | Leu | Thr | Pro | Glu | Gln | Trp | Lys | Ser | His | |
| | | 195 | | | | | 200 | | | | | 205 | | | | |

| | | | | | | | | | | | | | | | | |
|---|---|---|---|---|---|---|---|---|---|---|---|---|---|---|---|---|
| aga | agc | tac | agc | tgc | cag | gtc | acg | cat | gaa | ggg | agc | acc | gtg | gag | aag | 672 |
| Arg | Ser | Tyr | Ser | Cys | Gln | Val | Thr | His | Glu | Gly | Ser | Thr | Val | Glu | Lys | |
| | 210 | | | | | 215 | | | | | 220 | | | | | |

| | | | | | | |
|---|---|---|---|---|---|---|
| aca | gtg | gcc | cct | aca | gaa | tgt | tca | 696 |
| Thr | Val | Ala | Pro | Thr | Glu | Cys | Ser | |

```
                          225                 230

<210> SEQ ID NO 17
<211> LENGTH: 232
<212> TYPE: PRT
<213> ORGANISM: Homo sapiens

<400> SEQUENCE: 17

Met Ala Trp Ala Leu Leu Leu Thr Leu Leu Thr Gln Gly Thr Gly
1               5                   10                  15

Ser Trp Ala Asp Ile Glu Leu Thr Gln Pro Pro Ser Val Ser Val Ala
            20                  25                  30

Pro Gly Gln Thr Ala Arg Ile Ser Cys Ser Gly Asp Asn Leu Arg Ser
        35                  40                  45

Lys Tyr Val Tyr Trp Tyr Gln Gln Lys Pro Gly Gln Ala Pro Val Leu
    50                  55                  60

Val Ile Tyr Asp Thr Asn Asp Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Glu Asp Glu Ala Asp Tyr Tyr Cys Gln Thr Tyr Asp Met Thr
            100                 105                 110

Ser Gln Asp Val Phe Gly Gly Gly Thr Lys Leu Thr Val Leu Gly Gln
        115                 120                 125

Pro Lys Ala Ala Pro Ser Val Thr Leu Phe Pro Pro Ser Ser Glu Glu
    130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
        195                 200                 205

Arg Ser Tyr Ser Cys Gln Val Thr His Glu Gly Ser Thr Val Glu Lys
    210                 215                 220

Thr Val Ala Pro Thr Glu Cys Ser
225                 230

<210> SEQ ID NO 18
<211> LENGTH: 11
<212> TYPE: PRT
<213> ORGANISM: Homo sapiens

<400> SEQUENCE: 18

Ser Gly Asp Asn Leu Arg Ser Lys Tyr Val Tyr
1               5                   10

<210> SEQ ID NO 19
<211> LENGTH: 7
<212> TYPE: PRT
<213> ORGANISM: Homo sapiens

<400> SEQUENCE: 19

Asp Thr Asn Asp Arg Pro Ser
1               5

<210> SEQ ID NO 20
```

```
<211> LENGTH: 10
<212> TYPE: PRT
<213> ORGANISM: Homo sapiens

<400> SEQUENCE: 20

Gln Thr Tyr Asp Met Thr Ser Gln Asp Val
1               5                   10

<210> SEQ ID NO 21
<211> LENGTH: 1383
<212> TYPE: DNA
<213> ORGANISM: Homo sapiens
<220> FEATURE:
<221> NAME/KEY: CDS
<222> LOCATION: (1)..(1383)
<220> FEATURE:
<221> NAME/KEY: sig_peptide
<222> LOCATION: (1)..(57)
<220> FEATURE:
<221> NAME/KEY: V_region
<222> LOCATION: (58)..(405)
<220> FEATURE:
<221> NAME/KEY: misc_feature
<222> LOCATION: (148)..(162)
<223> OTHER INFORMATION: CDR1
<220> FEATURE:
<221> NAME/KEY: misc_feature
<222> LOCATION: (205)..(255)
<223> OTHER INFORMATION: CDR2
<220> FEATURE:
<221> NAME/KEY: misc_feature
<222> LOCATION: (352)..(372)
<223> OTHER INFORMATION: CDR3

<400> SEQUENCE: 21
```

| | | | | | | | | | | | | | | | | |
|---|---|---|---|---|---|---|---|---|---|---|---|---|---|---|---|---|
| atg | aaa | cac | ctg | tgg | ttc | ttc | ctc | ctg | ctg | gtg | gca | gct | ccc | aga | tgg | 48 |
| Met | Lys | His | Leu | Trp | Phe | Phe | Leu | Leu | Leu | Val | Ala | Ala | Pro | Arg | Trp | |
| 1 | | | | 5 | | | | | 10 | | | | | 15 | | |
| gtc | ctg | tcc | cag | gtg | caa | ttg | gtg | gaa | agc | ggc | ggc | ggc | ctg | gtg | caa | 96 |
| Val | Leu | Ser | Gln | Val | Gln | Leu | Val | Glu | Ser | Gly | Gly | Gly | Leu | Val | Gln | |
| | | | 20 | | | | | 25 | | | | | 30 | | | |
| ccg | ggc | ggc | agc | ctg | cgt | ctg | agc | tgc | gcg | gcc | tcc | gga | ttt | acc | ttt | 144 |
| Pro | Gly | Gly | Ser | Leu | Arg | Leu | Ser | Cys | Ala | Ala | Ser | Gly | Phe | Thr | Phe | |
| | | 35 | | | | | 40 | | | | | 45 | | | | |
| tct | tct | tat | gct | atg | cat | tgg | gtg | cgc | caa | gcc | cct | ggg | aag | ggt | ctc | 192 |
| Ser | Ser | Tyr | Ala | Met | His | Trp | Val | Arg | Gln | Ala | Pro | Gly | Lys | Gly | Leu | |
| | 50 | | | | | 55 | | | | | 60 | | | | | |
| gag | tgg | gtg | agc | tat | atc | tct | tat | tct | ggt | agc | aat | acc | tat | tat | gcg | 240 |
| Glu | Trp | Val | Ser | Tyr | Ile | Ser | Tyr | Ser | Gly | Ser | Asn | Thr | Tyr | Tyr | Ala | |
| 65 | | | | | 70 | | | | | 75 | | | | | 80 | |
| gat | agc | gtg | aaa | ggc | cgt | ttt | acc | att | tca | cgt | gat | aat | tcg | aaa | aac | 288 |
| Asp | Ser | Val | Lys | Gly | Arg | Phe | Thr | Ile | Ser | Arg | Asp | Asn | Ser | Lys | Asn | |
| | | | | 85 | | | | | 90 | | | | | 95 | | |
| acc | ctg | tat | ctg | caa | atg | aac | agc | ctg | cgt | gcg | gaa | gat | acg | gcc | gtg | 336 |
| Thr | Leu | Tyr | Leu | Gln | Met | Asn | Ser | Leu | Arg | Ala | Glu | Asp | Thr | Ala | Val | |
| | | | 100 | | | | | 105 | | | | | 110 | | | |
| tat | tat | tgc | gcg | cgt | ggt | tgg | ggt | ggt | ttt | gat | tat | tgg | ggc | caa | ggc | 384 |
| Tyr | Tyr | Cys | Ala | Arg | Gly | Trp | Gly | Gly | Phe | Asp | Tyr | Trp | Gly | Gln | Gly | |
| | | 115 | | | | | 120 | | | | | 125 | | | | |
| acc | ctg | gtg | acg | gtt | agc | tca | gcc | agc | acc | aag | ggc | ccc | agc | gtg | ttc | 432 |
| Thr | Leu | Val | Thr | Val | Ser | Ser | Ala | Ser | Thr | Lys | Gly | Pro | Ser | Val | Phe | |
| | 130 | | | | | 135 | | | | | 140 | | | | | |
| ccc | ctg | gcc | ccc | tgc | agc | aga | agc | acc | agc | gag | agc | aca | gcc | gcc | ctg | 480 |
| Pro | Leu | Ala | Pro | Cys | Ser | Arg | Ser | Thr | Ser | Glu | Ser | Thr | Ala | Ala | Leu | |
| 145 | | | | | 150 | | | | | 155 | | | | | 160 | |
| ggc | tgc | ctg | gtg | aag | gac | tac | ttc | ccc | gag | ccc | gtg | acc | gtg | agc | tgg | 528 |

|  |  |  |  |  |  |  |  |  |  |  |  |  |
|---|---|---|---|---|---|---|---|---|---|---|---|---|
| Gly | Cys | Leu | Val | Lys | Asp | Tyr | Phe | Pro | Glu | Pro | Val | Thr | Val | Ser | Trp |
|  |  |  | 165 |  |  |  |  | 170 |  |  |  | 175 |

```
aac agc gga gcc ctg acc agc ggc gtg cac acc ttc ccc gcc gtg ctg       576
Asn Ser Gly Ala Leu Thr Ser Gly Val His Thr Phe Pro Ala Val Leu
            180                 185                 190 cag agc agc ggc ctg tac agc ctg agc agc gtg gtg acc gtg ccc agc       624
Gln Ser Ser Gly Leu Tyr Ser Leu Ser Ser Val Val Thr Val Pro Ser
        195                 200                 205 agc aac ttc ggc acc cag acc tac acc tgc aac gtg gac cac aag ccc       672
Ser Asn Phe Gly Thr Gln Thr Tyr Thr Cys Asn Val Asp His Lys Pro
    210                 215                 220 agc aac acc aag gtg gac aag acc gtg gag cgg aag tgc tgc gtg gag       720
Ser Asn Thr Lys Val Asp Lys Thr Val Glu Arg Lys Cys Cys Val Glu
225                 230                 235                 240 tgc ccc ccc tgc cct gcc cct cct gtg gcc gga ccc tcc gtg ttc ctg       768
Cys Pro Pro Cys Pro Ala Pro Pro Val Ala Gly Pro Ser Val Phe Leu
                245                 250                 255 ttc ccc ccc aag ccc aag gac acc ctg atg atc agc cgg acc ccc gag       816
Phe Pro Pro Lys Pro Lys Asp Thr Leu Met Ile Ser Arg Thr Pro Glu
            260                 265                 270 gtg acc tgc gtg gtg gtg gac gtg agc cac gag gac ccc gag gtg cag       864
Val Thr Cys Val Val Val Asp Val Ser His Glu Asp Pro Glu Val Gln
        275                 280                 285 ttt aat tgg tac gtg gac ggc gtg gag gtg cac aac gcc aag acc aag       912
Phe Asn Trp Tyr Val Asp Gly Val Glu Val His Asn Ala Lys Thr Lys
    290                 295                 300 ccc cgg gag gaa cag ttc aac agc acc ttc cgg gtg gtg tcc gtg ctg       960
Pro Arg Glu Glu Gln Phe Asn Ser Thr Phe Arg Val Val Ser Val Leu
305                 310                 315                 320 acc gtg gtg cac cag gac tgg ctg aac ggc aaa gaa tac aag tgc aag      1008
Thr Val Val His Gln Asp Trp Leu Asn Gly Lys Glu Tyr Lys Cys Lys
                325                 330                 335 gtg tcc aac aag ggc ctg cct gcc ccc atc gag aaa acc atc agc aag      1056
Val Ser Asn Lys Gly Leu Pro Ala Pro Ile Glu Lys Thr Ile Ser Lys
            340                 345                 350 aca aag ggc cag ccc agg gaa ccc cag gtg tac acc ctg ccc ccc agc      1104
Thr Lys Gly Gln Pro Arg Glu Pro Gln Val Tyr Thr Leu Pro Pro Ser
        355                 360                 365 cgg gag gaa atg acc aag aac cag gtg tcc ctg acc tgt ctg gtg aag      1152
Arg Glu Glu Met Thr Lys Asn Gln Val Ser Leu Thr Cys Leu Val Lys
    370                 375                 380 ggc ttc tac ccc agc gac atc gcc gtg gag tgg gag agc aac ggc cag      1200
Gly Phe Tyr Pro Ser Asp Ile Ala Val Glu Trp Glu Ser Asn Gly Gln
385                 390                 395                 400 ccc gag aac aac tac aag acc acc ccc ccc atg ctg gac agc gac ggc      1248
Pro Glu Asn Asn Tyr Lys Thr Thr Pro Pro Met Leu Asp Ser Asp Gly
                405                 410                 415 agc ttc ttc ctg tac agc aag ctg aca gtg gac aag agc cgg tgg cag      1296
Ser Phe Phe Leu Tyr Ser Lys Leu Thr Val Asp Lys Ser Arg Trp Gln
            420                 425                 430 cag ggc aac gtg ttc agc tgc agc gtg atg cac gag gcc ctg cac aac      1344
Gln Gly Asn Val Phe Ser Cys Ser Val Met His Glu Ala Leu His Asn
        435                 440                 445 cac tac acc cag aag agc ctg agc ctg tcc ccc ggc aaa                  1383
His Tyr Thr Gln Lys Ser Leu Ser Leu Ser Pro Gly Lys
    450                 455                 460

<210> SEQ ID NO 22
<211> LENGTH: 461
<212> TYPE: PRT
```

<213> ORGANISM: Homo sapiens

<400> SEQUENCE: 22

```
Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met His Trp Val Arg Gln Ala Pro Gly Lys Gly Leu
    50                  55                  60

Glu Trp Val Ser Tyr Ile Ser Tyr Ser Gly Ser Asn Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Trp Gly Gly Phe Asp Tyr Trp Gly Gln Gly
        115                 120                 125

Thr Leu Val Thr Val Ser Ser Ala Ser Thr Lys Gly Pro Ser Val Phe
130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400
```

```
Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460
```

<210> SEQ ID NO 23
<211> LENGTH: 5
<212> TYPE: PRT
<213> ORGANISM: Homo sapiens

<400> SEQUENCE: 23

```
Ser Tyr Ala Met His
1               5
```

<210> SEQ ID NO 24
<211> LENGTH: 17
<212> TYPE: PRT
<213> ORGANISM: Homo sapiens

<400> SEQUENCE: 24

```
Tyr Ile Ser Tyr Ser Gly Ser Asn Thr Tyr Tyr Ala Asp Ser Val Lys
1               5                   10                  15

Gly
```

<210> SEQ ID NO 25
<211> LENGTH: 7
<212> TYPE: PRT
<213> ORGANISM: Homo sapiens

<400> SEQUENCE: 25

```
Gly Trp Gly Gly Phe Asp Tyr
1               5
```

<210> SEQ ID NO 26
<211> LENGTH: 699
<212> TYPE: DNA
<213> ORGANISM: Homo sapiens
<220> FEATURE:
<221> NAME/KEY: CDS
<222> LOCATION: (1)..(699)
<220> FEATURE:
<221> NAME/KEY: sig_peptide
<222> LOCATION: (1)..(57)
<220> FEATURE:
<221> NAME/KEY: V_region
<222> LOCATION: (58)..(390)
<220> FEATURE:
<221> NAME/KEY: misc_feature
<222> LOCATION: (124)..(156)
<223> OTHER INFORMATION: CDR1
<220> FEATURE:
<221> NAME/KEY: misc_feature
<222> LOCATION: (202)..(222)
<223> OTHER INFORMATION: CDR2
<220> FEATURE:
<221> NAME/KEY: misc_feature
<222> LOCATION: (319)..(351)
<223> OTHER INFORMATION: CDR3

<400> SEQUENCE: 26

```
atg gcc tgg gct ctg ctg ctc ctc acc ctc ctc act cag ggc aca gga      48
Met Ala Trp Ala Leu Leu Leu Leu Thr Leu Leu Thr Gln Gly Thr Gly
1               5                   10                  15
```

```
tcc tgg gct gat atc gaa ctg acc cag ccg cct tca gtg agc gtt gca      96
Ser Trp Ala Asp Ile Glu Leu Thr Gln Pro Pro Ser Val Ser Val Ala
         20                  25                  30 cca ggt cag acc gcg cgt atc tcg tgt agc ggc gat aat ctt cct aat     144
Pro Gly Gln Thr Ala Arg Ile Ser Cys Ser Gly Asp Asn Leu Pro Asn
 35                  40                  45 cgt tat gtt cat tgg tac cag cag aaa ccc ggg cag gcg cca gtt ctt     192
Arg Tyr Val His Trp Tyr Gln Gln Lys Pro Gly Gln Ala Pro Val Leu
 50                  55                  60 gtg att tat gat gat aat aat cgt ccc tca ggc atc ccg gaa cgc ttt     240
Val Ile Tyr Asp Asp Asn Asn Arg Pro Ser Gly Ile Pro Glu Arg Phe
65                  70                  75                  80 agc gga tcc aac agc ggc aac acc gcg acc ctg acc att agc ggc act     288
Ser Gly Ser Asn Ser Gly Asn Thr Ala Thr Leu Thr Ile Ser Gly Thr
             85                  90                  95 cag gcg gaa gac gaa gcg gat tat tat tgc cag act tat gat atg ttt     336
Gln Ala Glu Asp Glu Ala Asp Tyr Tyr Cys Gln Thr Tyr Asp Met Phe
        100                 105                 110 tct atg tct gat gtg ttt ggc ggc ggc acg aag tta acc gtc cta ggt     384
Ser Met Ser Asp Val Phe Gly Gly Gly Thr Lys Leu Thr Val Leu Gly
    115                 120                 125 cag ccc aag gct gcc ccc tcg gtc act ctg ttc ccg ccc tcc tct gag     432
Gln Pro Lys Ala Ala Pro Ser Val Thr Leu Phe Pro Pro Ser Ser Glu
130                 135                 140 gag ctt caa gcc aac aag gcc aca ctg gtg tgt ctc ata agt gac ttc     480
Glu Leu Gln Ala Asn Lys Ala Thr Leu Val Cys Leu Ile Ser Asp Phe
145                 150                 155                 160 tac ccg gga gcc gtg aca gtg gcc tgg aag gca gat agc agc ccc gtc     528
Tyr Pro Gly Ala Val Thr Val Ala Trp Lys Ala Asp Ser Ser Pro Val
                165                 170                 175 aag gcg gga gtg gag acc acc aca ccc tcc aaa caa agc aac aac aag     576
Lys Ala Gly Val Glu Thr Thr Thr Pro Ser Lys Gln Ser Asn Asn Lys
            180                 185                 190 tac gcg gcc agc agc tat ctg agc ctg acg cct gag cag tgg aag tcc     624
Tyr Ala Ala Ser Ser Tyr Leu Ser Leu Thr Pro Glu Gln Trp Lys Ser
        195                 200                 205 cac aga agc tac agc tgc cag gtc acg cat gaa ggg agc acc gtg gag     672
His Arg Ser Tyr Ser Cys Gln Val Thr His Glu Gly Ser Thr Val Glu
    210                 215                 220 aag aca gtg gcc cct aca gaa tgt tca                                 699
Lys Thr Val Ala Pro Thr Glu Cys Ser
225                 230
```

<210> SEQ ID NO 27
<211> LENGTH: 233
<212> TYPE: PRT
<213> ORGANISM: Homo sapiens

<400> SEQUENCE: 27

```
Met Ala Trp Ala Leu Leu Leu Leu Thr Leu Leu Thr Gln Gly Thr Gly
1               5                   10                  15

Ser Trp Ala Asp Ile Glu Leu Thr Gln Pro Pro Ser Val Ser Val Ala
            20                  25                  30

Pro Gly Gln Thr Ala Arg Ile Ser Cys Ser Gly Asp Asn Leu Pro Asn
        35                  40                  45

Arg Tyr Val His Trp Tyr Gln Gln Lys Pro Gly Gln Ala Pro Val Leu
    50                  55                  60

Val Ile Tyr Asp Asp Asn Asn Arg Pro Ser Gly Ile Pro Glu Arg Phe
65                  70                  75                  80
```

-continued

Ser Gly Ser Asn Ser Gly Asn Thr Ala Thr Leu Thr Ile Ser Gly Thr
            85                  90                  95

Gln Ala Glu Asp Glu Ala Asp Tyr Tyr Cys Gln Thr Tyr Asp Met Phe
        100                 105                 110

Ser Met Ser Asp Val Phe Gly Gly Thr Lys Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 28
<211> LENGTH: 11
<212> TYPE: PRT
<213> ORGANISM: Homo sapiens

<400> SEQUENCE: 28

Ser Gly Asp Asn Leu Pro Asn Arg Tyr Val His
1               5                   10

<210> SEQ ID NO 29
<211> LENGTH: 7
<212> TYPE: PRT
<213> ORGANISM: Homo sapiens

<400> SEQUENCE: 29

Asp Asp Asn Asn Arg Pro Ser
1               5

<210> SEQ ID NO 30
<211> LENGTH: 11
<212> TYPE: PRT
<213> ORGANISM: Homo sapiens

<400> SEQUENCE: 30

Gln Thr Tyr Asp Met Phe Ser Met Ser Asp Val
1               5                   10

<210> SEQ ID NO 31
<211> LENGTH: 1386
<212> TYPE: DNA
<213> ORGANISM: Homo sapiens
<220> FEATURE:
<221> NAME/KEY: CDS
<222> LOCATION: (1)..(1386)
<220> FEATURE:
<221> NAME/KEY: sig_peptide
<222> LOCATION: (1)..(57)
<220> FEATURE:
<221> NAME/KEY: V_region
<222> LOCATION: (58)..(408)
<220> FEATURE:

```
<221> NAME/KEY: misc_feature
<222> LOCATION: (148)..(162)
<223> OTHER INFORMATION: CDR1
<220> FEATURE:
<221> NAME/KEY: misc_feature
<222> LOCATION: (205)..(255)
<223> OTHER INFORMATION: CDR2
<220> FEATURE:
<221> NAME/KEY: misc_feature
<222> LOCATION: (352)..(375)
<223> OTHER INFORMATION: CDR3

<400> SEQUENCE: 31
```

| | | | | | | | | | | | | | | | | |
|---|---|---|---|---|---|---|---|---|---|---|---|---|---|---|---|---|
| atg | aaa | cac | ctg | tgg | ttc | ttc | ctc | ctg | ctg | gtg | gca | gct | ccc | aga | tgg | 48 |
| Met | Lys | His | Leu | Trp | Phe | Phe | Leu | Leu | Leu | Val | Ala | Ala | Pro | Arg | Trp | |
| 1 | | | | 5 | | | | | 10 | | | | | 15 | | |
| gtc | ctg | tcc | cag | gtg | caa | ttg | gtg | gaa | agc | ggc | ggc | ggc | ctg | gtg | caa | 96 |
| Val | Leu | Ser | Gln | Val | Gln | Leu | Val | Glu | Ser | Gly | Gly | Gly | Leu | Val | Gln | |
| | | | | 20 | | | | | 25 | | | | | 30 | | |
| ccg | ggc | ggc | agc | ctg | cgt | ctg | agc | tgc | gcg | gcc | tcc | gga | ttt | acc | ttt | 144 |
| Pro | Gly | Gly | Ser | Leu | Arg | Leu | Ser | Cys | Ala | Ala | Ser | Gly | Phe | Thr | Phe | |
| | | 35 | | | | | 40 | | | | | 45 | | | | |
| tct | aat | tat | tgg | atg | tct | tgg | gtg | cgc | caa | gcc | cct | ggg | aag | ggt | ctc | 192 |
| Ser | Asn | Tyr | Trp | Met | Ser | Trp | Val | Arg | Gln | Ala | Pro | Gly | Lys | Gly | Leu | |
| | 50 | | | | | 55 | | | | | 60 | | | | | |
| gag | tgg | gtg | agc | ctt | atc | tct | tat | tct | ggt | agc | act | acc | tat | tat | gcg | 240 |
| Glu | Trp | Val | Ser | Leu | Ile | Ser | Tyr | Ser | Gly | Ser | Thr | Thr | Tyr | Tyr | Ala | |
| 65 | | | | | 70 | | | | | 75 | | | | | 80 | |
| gat | agc | gtg | aaa | ggc | cgt | ttt | acc | att | tca | cgt | gat | aat | tcg | aaa | aac | 288 |
| Asp | Ser | Val | Lys | Gly | Arg | Phe | Thr | Ile | Ser | Arg | Asp | Asn | Ser | Lys | Asn | |
| | | | | 85 | | | | | 90 | | | | | 95 | | |
| acc | ctg | tat | ctg | caa | atg | aac | agc | ctg | cgt | gcg | gaa | gat | acg | gcc | gtg | 336 |
| Thr | Leu | Tyr | Leu | Gln | Met | Asn | Ser | Leu | Arg | Ala | Glu | Asp | Thr | Ala | Val | |
| | | | 100 | | | | | 105 | | | | | 110 | | | |
| tat | tat | tgc | gcg | cgt | gat | act | cct | att | ggt | atg | gat | ttt | tgg | ggc | caa | 384 |
| Tyr | Tyr | Cys | Ala | Arg | Asp | Thr | Pro | Ile | Gly | Met | Asp | Phe | Trp | Gly | Gln | |
| | | 115 | | | | | 120 | | | | | 125 | | | | |
| ggc | acc | ctg | gtg | acg | gtt | agc | tca | gcc | agc | acc | aag | ggc | ccc | agc | gtg | 432 |
| Gly | Thr | Leu | Val | Thr | Val | Ser | Ser | Ala | Ser | Thr | Lys | Gly | Pro | Ser | Val | |
| | 130 | | | | | 135 | | | | | 140 | | | | | |
| ttc | ccc | ctg | gcc | ccc | tgc | agc | aga | agc | acc | agc | gag | agc | aca | gcc | gcc | 480 |
| Phe | Pro | Leu | Ala | Pro | Cys | Ser | Arg | Ser | Thr | Ser | Glu | Ser | Thr | Ala | Ala | |
| 145 | | | | | 150 | | | | | 155 | | | | | 160 | |
| ctg | ggc | tgc | ctg | gtg | aag | gac | tac | ttc | ccc | gag | ccc | gtg | acc | gtg | agc | 528 |
| Leu | Gly | Cys | Leu | Val | Lys | Asp | Tyr | Phe | Pro | Glu | Pro | Val | Thr | Val | Ser | |
| | | | 165 | | | | | 170 | | | | | 175 | | | |
| tgg | aac | agc | gga | gcc | ctg | acc | agc | ggc | gtg | cac | acc | ttc | ccc | gcc | gtg | 576 |
| Trp | Asn | Ser | Gly | Ala | Leu | Thr | Ser | Gly | Val | His | Thr | Phe | Pro | Ala | Val | |
| | | 180 | | | | | 185 | | | | | 190 | | | | |
| ctg | cag | agc | agc | ggc | ctg | tac | agc | ctg | agc | agc | gtg | gtg | acc | gtg | ccc | 624 |
| Leu | Gln | Ser | Ser | Gly | Leu | Tyr | Ser | Leu | Ser | Ser | Val | Val | Thr | Val | Pro | |
| | 195 | | | | | 200 | | | | | 205 | | | | | |
| agc | agc | aac | ttc | ggc | acc | cag | acc | tac | acc | tgc | aac | gtg | gac | cac | aag | 672 |
| Ser | Ser | Asn | Phe | Gly | Thr | Gln | Thr | Tyr | Thr | Cys | Asn | Val | Asp | His | Lys | |
| | | 210 | | | | | 215 | | | | | 220 | | | | |
| ccc | agc | aac | acc | aag | gtg | gac | aag | acc | gtg | gag | cgg | aag | tgc | tgc | gtg | 720 |
| Pro | Ser | Asn | Thr | Lys | Val | Asp | Lys | Thr | Val | Glu | Arg | Lys | Cys | Cys | Val | |
| 225 | | | | | 230 | | | | | 235 | | | | | 240 | |
| gag | tgc | ccc | ccc | tgc | cct | gcc | cct | cct | gtg | gcc | gga | ccc | tcc | gtg | ttc | 768 |
| Glu | Cys | Pro | Pro | Cys | Pro | Ala | Pro | Pro | Val | Ala | Gly | Pro | Ser | Val | Phe | |
| | | | 245 | | | | | 250 | | | | | 255 | | | |
| ctg | ttc | ccc | ccc | aag | ccc | aag | gac | acc | ctg | atg | atc | agc | cgg | acc | ccc | 816 |

```
Leu Phe Pro Pro Lys Pro Lys Asp Thr Leu Met Ile Ser Arg Thr Pro
                260                 265                 270 gag gtg acc tgc gtg gtg gtg gac gtg agc cac gag gac ccc gag gtg         864
Glu Val Thr Cys Val Val Val Asp Val Ser His Glu Asp Pro Glu Val
            275                 280                 285 cag ttt aat tgg tac gtg gac ggc gtg gag gtg cac aac gcc aag acc         912
Gln Phe Asn Trp Tyr Val Asp Gly Val Glu Val His Asn Ala Lys Thr
        290                 295                 300 aag ccc cgg gag gaa cag ttc aac agc acc ttc cgg gtg gtg tcc gtg         960
Lys Pro Arg Glu Glu Gln Phe Asn Ser Thr Phe Arg Val Val Ser Val
305                 310                 315                 320 ctg acc gtg gtg cac cag gac tgg ctg aac ggc aaa gaa tac aag tgc        1008
Leu Thr Val Val His Gln Asp Trp Leu Asn Gly Lys Glu Tyr Lys Cys
                325                 330                 335 aag gtg tcc aac aag ggc ctg cct gcc ccc atc gag aaa acc atc agc        1056
Lys Val Ser Asn Lys Gly Leu Pro Ala Pro Ile Glu Lys Thr Ile Ser
            340                 345                 350 aag aca aag ggc cag ccc agg gaa ccc cag gtg tac acc ctg ccc cca        1104
Lys Thr Lys Gly Gln Pro Arg Glu Pro Gln Val Tyr Thr Leu Pro Pro
        355                 360                 365 agc cgg gag gaa atg acc aag aac cag gtg tcc ctg acc tgt ctg gtg        1152
Ser Arg Glu Glu Met Thr Lys Asn Gln Val Ser Leu Thr Cys Leu Val
370                 375                 380 aag ggc ttc tac ccc agc gac atc gcc gtg gag tgg gag agc aac ggc        1200
Lys Gly Phe Tyr Pro Ser Asp Ile Ala Val Glu Trp Glu Ser Asn Gly
385                 390                 395                 400 cag ccc gag aac aac tac aag acc acc ccc ccc atg ctg gac agc gac        1248
Gln Pro Glu Asn Asn Tyr Lys Thr Thr Pro Pro Met Leu Asp Ser Asp
                405                 410                 415 ggc agc ttc ttc ctg tac agc aag ctg aca gtg gac aag agc cgg tgg        1296
Gly Ser Phe Phe Leu Tyr Ser Lys Leu Thr Val Asp Lys Ser Arg Trp
            420                 425                 430 cag cag ggc aac gtg ttc agc tgc agc gtg atg cac gag gcc ctg cac        1344
Gln Gln Gly Asn Val Phe Ser Cys Ser Val Met His Glu Ala Leu His
        435                 440                 445 aac cac tac acc cag aag agc ctg agc ctg tcc ccc ggc aaa                1386
Asn His Tyr Thr Gln Lys Ser Leu Ser Leu Ser Pro Gly Lys
    450                 455                 460

<210> SEQ ID NO 32
<211> LENGTH: 462
<212> TYPE: PRT
<213> ORGANISM: Homo sapiens

<400> SEQUENCE: 32

Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Trp Met Ser Trp Val Arg Gln Ala Pro Gly Lys Gly Leu
    50                  55                  60

Glu Trp Val Ser Leu Ile Ser Tyr Ser Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110
```

-continued

```
Tyr Tyr Cys Ala Arg Asp Thr Pro Ile Gly Met Asp Phe Trp Gly Gln
            115                 120                 125

Gly Thr Leu Val Thr Val Ser Ser Ala Ser Thr Lys Gly Pro Ser Val
130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
            195                 200                 205

Ser Ser Asn Phe Gly Thr Gln Thr Tyr Thr Cys Asn Val Asp His Lys
        210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
                325                 330                 335

Lys Val Ser Asn Lys Gly Leu Pro Ala Pro Ile Glu Lys Thr Ile Ser
            340                 345                 350

Lys Thr Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 33
<211> LENGTH: 5
<212> TYPE: PRT
<213> ORGANISM: Homo sapiens

<400> SEQUENCE: 33

Asn Tyr Trp Met Ser
1               5
```

```
<210> SEQ ID NO 34
<211> LENGTH: 17
<212> TYPE: PRT
<213> ORGANISM: Homo sapiens

<400> SEQUENCE: 34

Leu Ile Ser Tyr Ser Gly Ser Thr Thr Tyr Ala Asp Ser Val Lys
1               5                   10                  15

Gly

<210> SEQ ID NO 35
<211> LENGTH: 8
<212> TYPE: PRT
<213> ORGANISM: Homo sapiens

<400> SEQUENCE: 35

Asp Thr Pro Ile Gly Met Asp Phe
1               5

<210> SEQ ID NO 36
<211> LENGTH: 696
<212> TYPE: DNA
<213> ORGANISM: Homo sapiens
<220> FEATURE:
<221> NAME/KEY: CDS
<222> LOCATION: (1)..(696)
<220> FEATURE:
<221> NAME/KEY: sig_peptide
<222> LOCATION: (1)..(57)
<220> FEATURE:
<221> NAME/KEY: V_region
<222> LOCATION: (58)..(387)
<220> FEATURE:
<221> NAME/KEY: misc_feature
<222> LOCATION: (124)..(156)
<223> OTHER INFORMATION: CDR1
<220> FEATURE:
<221> NAME/KEY: misc_feature
<222> LOCATION: (202)..(222)
<223> OTHER INFORMATION: CDR2
<220> FEATURE:
<221> NAME/KEY: misc_feature
<222> LOCATION: (319)..(348)
<223> OTHER INFORMATION: CDR3

<400> SEQUENCE: 36 atg gcc tgg gct ctg ctg ctc ctc acc ctc ctc act cag ggc aca gga      48
Met Ala Trp Ala Leu Leu Leu Leu Thr Leu Leu Thr Gln Gly Thr Gly
1               5                   10                  15 tcc tgg gct gat atc gaa ctg acc cag ccg cct tca gtg agc gtt gca      96
Ser Trp Ala Asp Ile Glu Leu Thr Gln Pro Pro Ser Val Ser Val Ala
                20                  25                  30 cca ggt cag atc gcg cgt atc tcg tgt agc ggc gat aat ctt ggt tct     144
Pro Gly Gln Ile Ala Arg Ile Ser Cys Ser Gly Asp Asn Leu Gly Ser
            35                  40                  45 tat tat gct tat tgg tac cag cag aaa ccc ggg cag gcg cca gtt ctt     192
Tyr Tyr Ala Tyr Trp Tyr Gln Gln Lys Pro Gly Gln Ala Pro Val Leu
        50                  55                  60 gtg att tat ggt gat aat gat cgt ccc tca ggc atc ccg gaa cgc ttt     240
Val Ile Tyr Gly Asp Asn Asp Arg Pro Ser Gly Ile Pro Glu Arg Phe
65                  70                  75                  80 agc gga tcc aac agc ggc aac acc gcg acc ctg acc att agc ggc act     288
Ser Gly Ser Asn Ser Gly Asn Thr Ala Thr Leu Thr Ile Ser Gly Thr
                85                  90                  95 cag gcg gaa gac gaa gcg gat tat tgc tct tct tat gat att gtt         336
Gln Ala Glu Asp Glu Ala Asp Tyr Tyr Cys Ser Ser Tyr Asp Ile Val
                100                 105                 110
```

```
cag cct tat gtg ttt ggc ggc ggc acg aag tta acc gtc cta ggt cag      384
Gln Pro Tyr Val Phe Gly Gly Gly Thr Lys Leu Thr Val Leu Gly Gln
        115                 120                 125 ccc aag gct gcc ccc tcg gtc act ctg ttc ccg ccc tcc tct gag gag      432
Pro Lys Ala Ala Pro Ser Val Thr Leu Phe Pro Pro Ser Ser Glu Glu
        130                 135                 140 ctt caa gcc aac aag gcc aca ctg gtg tgt ctc ata agt gac ttc tac      480
Leu Gln Ala Asn Lys Ala Thr Leu Val Cys Leu Ile Ser Asp Phe Tyr
145                 150                 155                 160 ccg gga gcc gtg aca gtg gcc tgg aag gca gat agc agc ccc gtc aag      528
Pro Gly Ala Val Thr Val Ala Trp Lys Ala Asp Ser Ser Pro Val Lys
                165                 170                 175 gcg gga gtg gag acc acc aca ccc tcc aaa caa agc aac aac aag tac      576
Ala Gly Val Glu Thr Thr Thr Pro Ser Lys Gln Ser Asn Asn Lys Tyr
        180                 185                 190 gcg gcc agc agc tat ctg agc ctg acg cct gag cag tgg aag tcc cac      624
Ala Ala Ser Ser Tyr Leu Ser Leu Thr Pro Glu Gln Trp Lys Ser His
        195                 200                 205 aga agc tac agc tgc cag gtc acg cat gaa ggg agc acc gtg gag aag      672
Arg Ser Tyr Ser Cys Gln Val Thr His Glu Gly Ser Thr Val Glu Lys
        210                 215                 220 aca gtg gcc cct aca gaa tgt tca                                      696
Thr Val Ala Pro Thr Glu Cys Ser
225                 230

<210> SEQ ID NO 37
<211> LENGTH: 232
<212> TYPE: PRT
<213> ORGANISM: Homo sapiens

<400> SEQUENCE: 37

Met Ala Trp Ala Leu Leu Leu Leu Thr Leu Leu Thr Gln Gly Thr Gly
1               5                   10                  15

Ser Trp Ala Asp Ile Glu Leu Thr Gln Pro Pro Ser Val Ser Val Ala
            20                  25                  30

Pro Gly Gln Ile Ala Arg Ile Ser Cys Ser Gly Asp Asn Leu Gly Ser
        35                  40                  45

Tyr Tyr Ala Tyr Trp Tyr Gln Gln Lys Pro Gly Gln Ala Pro Val Leu
    50                  55                  60

Val Ile Tyr Gly Asp Asn Asp Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Glu Asp Glu Ala Asp Tyr Tyr Cys Ser Ser Tyr Asp Ile Val
            100                 105                 110

Gln Pro Tyr Val Phe Gly Gly Gly Thr Lys Leu Thr Val Leu Gly Gln
        115                 120                 125

Pro Lys Ala Ala Pro Ser Val Thr Leu Phe Pro Pro Ser Ser Glu Glu
        130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
        195                 200                 205
```

Arg Ser Tyr Ser Cys Gln Val Thr His Glu Gly Ser Thr Val Glu Lys
    210                 215                 220

Thr Val Ala Pro Thr Glu Cys Ser
225                 230

<210> SEQ ID NO 38
<211> LENGTH: 11
<212> TYPE: PRT
<213> ORGANISM: Homo sapiens

<400> SEQUENCE: 38

Ser Gly Asp Asn Leu Gly Ser Tyr Tyr Ala Tyr
1               5                   10

<210> SEQ ID NO 39
<211> LENGTH: 7
<212> TYPE: PRT
<213> ORGANISM: Homo sapiens

<400> SEQUENCE: 39

Gly Asp Asn Asp Arg Pro Ser
1               5

<210> SEQ ID NO 40
<211> LENGTH: 10
<212> TYPE: PRT
<213> ORGANISM: Homo sapiens

<400> SEQUENCE: 40

Ser Ser Tyr Asp Ile Val Gln Pro Tyr Val
1               5                   10

<210> SEQ ID NO 41
<211> LENGTH: 1383
<212> TYPE: DNA
<213> ORGANISM: Homo sapiens
<220> FEATURE:
<221> NAME/KEY: CDS
<222> LOCATION: (1)..(1383)
<220> FEATURE:
<221> NAME/KEY: sig_peptide
<222> LOCATION: (1)..(57)
<220> FEATURE:
<221> NAME/KEY: V_region
<222> LOCATION: (58)..(405)
<220> FEATURE:
<221> NAME/KEY: misc_feature
<222> LOCATION: (148)..(162)
<223> OTHER INFORMATION: CDR1
<220> FEATURE:
<221> NAME/KEY: misc_feature
<222> LOCATION: (205)..(255)
<223> OTHER INFORMATION: CDR2
<220> FEATURE:
<221> NAME/KEY: misc_feature
<222> LOCATION: (352)..(372)
<223> OTHER INFORMATION: CDR3

<400> SEQUENCE: 41 atg aaa cac ctg tgg ttc ttc ctc ctg ctg gtg gca gct ccc aga tgg    48
Met Lys His Leu Trp Phe Phe Leu Leu Leu Val Ala Ala Pro Arg Trp
1               5                   10                  15 gtc ctg tcc cag gtg caa ttg gtg gaa agc ggc ggc ggc ctg gtg caa    96
Val Leu Ser Gln Val Gln Leu Val Glu Ser Gly Gly Gly Leu Val Gln
            20                  25                  30 ccg ggc ggc agc ctg cgt ctg agc tgc gcg gcc tcc gga ttt acc ttt   144
Pro Gly Gly Ser Leu Arg Leu Ser Cys Ala Ala Ser Gly Phe Thr Phe -continued

```
              35                  40                  45
tct tct tat gct atg cat tgg gtg cgc caa gcc cct ggg aag ggt ctc    192
Ser Ser Tyr Ala Met His Trp Val Arg Gln Ala Pro Gly Lys Gly Leu
    50                  55                  60 gag tgg gtg agc tat atc tct tat tct ggt agc aat acc tat tat gcg    240
Glu Trp Val Ser Tyr Ile Ser Tyr Ser Gly Ser Asn Thr Tyr Tyr Ala
65                  70                  75                  80 gat agc gtg aaa ggc cgt ttt acc att tca cgt gat aat tcg aaa aac    288
Asp Ser Val Lys Gly Arg Phe Thr Ile Ser Arg Asp Asn Ser Lys Asn
                85                  90                  95 acc ctg tat ctg caa atg aac agc ctg cgt gcg gaa gat acg gcc gtg    336
Thr Leu Tyr Leu Gln Met Asn Ser Leu Arg Ala Glu Asp Thr Ala Val
            100                 105                 110 tat tat tgc gcg cgt ggt tgg ggt ggt ttt gat tat tgg ggc caa ggc    384
Tyr Tyr Cys Ala Arg Gly Trp Gly Gly Phe Asp Tyr Trp Gly Gln Gly
        115                 120                 125 acc ctg gtg acg gtt agc tca gcc agc acc aag ggc ccc agc gtg ttc    432
Thr Leu Val Thr Val Ser Ser Ala Ser Thr Lys Gly Pro Ser Val Phe
    130                 135                 140 ccc ctg gcc ccc tgc agc aga agc acc agc gag agc aca gcc gcc ctg    480
Pro Leu Ala Pro Cys Ser Arg Ser Thr Ser Glu Ser Thr Ala Ala Leu
145                 150                 155                 160 ggc tgc ctg gtg aag gac tac ttc ccc gag ccc gtg acc gtg agc tgg    528
Gly Cys Leu Val Lys Asp Tyr Phe Pro Glu Pro Val Thr Val Ser Trp
                165                 170                 175 aac agc gga gcc ctg acc agc ggc gtg cac acc ttc ccc gcc gtg ctg    576
Asn Ser Gly Ala Leu Thr Ser Gly Val His Thr Phe Pro Ala Val Leu
            180                 185                 190 cag agc agc ggc ctg tac agc ctg agc agc gtg gtg acc gtg ccc agc    624
Gln Ser Ser Gly Leu Tyr Ser Leu Ser Ser Val Val Thr Val Pro Ser
        195                 200                 205 agc aac ttc ggc acc cag acc tac acc tgc aac gtg gac cac aag ccc    672
Ser Asn Phe Gly Thr Gln Thr Tyr Thr Cys Asn Val Asp His Lys Pro
    210                 215                 220 agc aac acc aag gtg gac aag acc gtg gag cgg aag tgc tgc gtg gag    720
Ser Asn Thr Lys Val Asp Lys Thr Val Glu Arg Lys Cys Cys Val Glu
225                 230                 235                 240 tgc ccc ccc tgc cct gcc cct cct gtg gcc gga ccc tcc gtg ttc ctg    768
Cys Pro Pro Cys Pro Ala Pro Pro Val Ala Gly Pro Ser Val Phe Leu
                245                 250                 255 ttc ccc ccc aag ccc aag gac acc ctg atg atc agc cgg acc ccc gag    816
Phe Pro Pro Lys Pro Lys Asp Thr Leu Met Ile Ser Arg Thr Pro Glu
            260                 265                 270 gtg acc tgc gtg gtg gtg gac gtg agc cac gag gac ccc gag gtg cag    864
Val Thr Cys Val Val Val Asp Val Ser His Glu Asp Pro Glu Val Gln
        275                 280                 285 ttt aat tgg tac gtg gac ggc gtg gag gtg cac aac gcc aag acc aag    912
Phe Asn Trp Tyr Val Asp Gly Val Glu Val His Asn Ala Lys Thr Lys
    290                 295                 300 ccc cgg gag gaa cag ttc aac agc acc ttc cgg gtg gtg tcc gtg ctg    960
Pro Arg Glu Glu Gln Phe Asn Ser Thr Phe Arg Val Val Ser Val Leu
305                 310                 315                 320 acc gtg gtg cac cag gac tgg ctg aac ggc aaa gaa tac aag tgc aag   1008
Thr Val Val His Gln Asp Trp Leu Asn Gly Lys Glu Tyr Lys Cys Lys
                325                 330                 335 gtg tcc aac aag ggc ctg cct gcc ccc atc gag aaa acc atc agc aag   1056
Val Ser Asn Lys Gly Leu Pro Ala Pro Ile Glu Lys Thr Ile Ser Lys
            340                 345                 350 aca aag ggc cag ccc agg gaa ccc cag gtg tac acc ctg ccc ccc agc   1104
```

```
Thr Lys Gly Gln Pro Arg Glu Pro Gln Val Tyr Thr Leu Pro Pro Ser
            355                 360                 365 cgg gag gaa atg acc aag aac cag gtg tcc ctg acc tgt ctg gtg aag       1152
Arg Glu Glu Met Thr Lys Asn Gln Val Ser Leu Thr Cys Leu Val Lys
    370                 375                 380 ggc ttc tac ccc agc gac atc gcc gtg gag tgg gag agc aac ggc cag       1200
Gly Phe Tyr Pro Ser Asp Ile Ala Val Glu Trp Glu Ser Asn Gly Gln
385                 390                 395                 400 ccc gag aac aac tac aag acc acc ccc ccc atg ctg gac agc gac ggc       1248
Pro Glu Asn Asn Tyr Lys Thr Thr Pro Pro Met Leu Asp Ser Asp Gly
                405                 410                 415 agc ttc ttc ctg tac agc aag ctg aca gtg gac aag agc cgg tgg cag       1296
Ser Phe Phe Leu Tyr Ser Lys Leu Thr Val Asp Lys Ser Arg Trp Gln
            420                 425                 430 cag ggc aac gtg ttc agc tgc agc gtg atg cac gag gcc ctg cac aac       1344
Gln Gly Asn Val Phe Ser Cys Ser Val Met His Glu Ala Leu His Asn
        435                 440                 445 cac tac acc cag aag agc ctg agc ctg tcc ccc ggc aaa                   1383
His Tyr Thr Gln Lys Ser Leu Ser Leu Ser Pro Gly Lys
    450                 455                 460

<210> SEQ ID NO 42
<211> LENGTH: 461
<212> TYPE: PRT
<213> ORGANISM: Homo sapiens

<400> SEQUENCE: 42

Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met His Trp Val Arg Gln Ala Pro Gly Lys Gly Leu
    50                  55                  60

Glu Trp Val Ser Tyr Ile Ser Tyr Ser Gly Ser Asn Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Trp Gly Gly Phe Asp Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240
```

```
Cys Pro Pro Cys Pro Ala Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 43
<211> LENGTH: 5
<212> TYPE: PRT
<213> ORGANISM: Homo sapiens

<400> SEQUENCE: 43

Ser Tyr Ala Met His
1               5

<210> SEQ ID NO 44
<211> LENGTH: 17
<212> TYPE: PRT
<213> ORGANISM: Homo sapiens

<400> SEQUENCE: 44

Tyr Ile Ser Tyr Ser Gly Ser Asn Thr Tyr Tyr Ala Asp Ser Val Lys
1               5                   10                  15

Gly

<210> SEQ ID NO 45
<211> LENGTH: 7
<212> TYPE: PRT
<213> ORGANISM: Homo sapiens

<400> SEQUENCE: 45

Gly Trp Gly Gly Phe Asp Tyr
1               5
```

<210> SEQ ID NO 46
<211> LENGTH: 696
<212> TYPE: DNA
<213> ORGANISM: Homo sapiens
<220> FEATURE:
<221> NAME/KEY: CDS
<222> LOCATION: (1)..(696)
<220> FEATURE:
<221> NAME/KEY: sig_peptide
<222> LOCATION: (1)..(57)
<220> FEATURE:
<221> NAME/KEY: V_region
<222> LOCATION: (58)..(387)
<220> FEATURE:
<221> NAME/KEY: misc_feature
<222> LOCATION: (124)..(156)
<223> OTHER INFORMATION: CDR1
<220> FEATURE:
<221> NAME/KEY: misc_feature
<222> LOCATION: (202)..(222)
<223> OTHER INFORMATION: CDR2
<220> FEATURE:
<221> NAME/KEY: misc_feature
<222> LOCATION: (319)..(348)
<223> OTHER INFORMATION: CDR3

<400> SEQUENCE: 46

| | | | | | | | | | | | | | | | | |
|---|---|---|---|---|---|---|---|---|---|---|---|---|---|---|---|---|
| atg | gcc | tgg | gct | ctg | ctg | ctc | ctc | acc | ctc | ctc | act | cag | ggc | aca | gga | 48 |
| Met | Ala | Trp | Ala | Leu | Leu | Leu | Thr | Leu | Leu | Thr | Gln | Gly | Thr | Gly | | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tcc | tgg | gct | gat | atc | gaa | ctg | acc | cag | ccg | cct | tca | gtg | agc | gtt | gca | 96 |
| Ser | Trp | Ala | Asp | Ile | Glu | Leu | Thr | Gln | Pro | Pro | Ser | Val | Ser | Val | Ala | |
| | | 20 | | | | | 25 | | | | | 30 | | | | |

| | | | | | | | | | | | | | | | | |
|---|---|---|---|---|---|---|---|---|---|---|---|---|---|---|---|---|
| cca | ggt | cag | acc | gcg | cgt | atc | tcg | tgt | agc | ggc | gat | aat | ctt | cct | aat | 144 |
| Pro | Gly | Gln | Thr | Ala | Arg | Ile | Ser | Cys | Ser | Gly | Asp | Asn | Leu | Pro | Asn | |
| | | | 35 | | | | | 40 | | | | | 45 | | | |

| | | | | | | | | | | | | | | | | |
|---|---|---|---|---|---|---|---|---|---|---|---|---|---|---|---|---|
| cgt | tat | gtt | cat | tgg | tac | cag | cag | aaa | ccc | ggg | cag | gcg | cca | gtt | ctt | 192 |
| Arg | Tyr | Val | His | Trp | Tyr | Gln | Gln | Lys | Pro | Gly | Gln | Ala | Pro | Val | Leu | |
| | 50 | | | | | 55 | | | | | 60 | | | | | |

| | | | | | | | | | | | | | | | | |
|---|---|---|---|---|---|---|---|---|---|---|---|---|---|---|---|---|
| gtg | att | tat | gat | gat | aat | aat | cgt | ccc | tca | ggc | atc | ccg | gaa | cgc | ttt | 240 |
| Val | Ile | Tyr | Asp | Asp | Asn | Asn | Arg | Pro | Ser | Gly | Ile | Pro | Glu | Arg | Phe | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| agc | gga | tcc | aac | agc | ggc | aac | acc | gcg | acc | ctg | acc | att | agc | ggc | act | 288 |
| Ser | Gly | Ser | Asn | Ser | Gly | Asn | Thr | Ala | Thr | Leu | Thr | Ile | Ser | Gly | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| cag | gcg | gaa | gac | gaa | gcg | gat | tat | tat | tgc | cag | tct | cgt | gat | ctt | cat | 336 |
| Gln | Ala | Glu | Asp | Glu | Ala | Asp | Tyr | Tyr | Cys | Gln | Ser | Arg | Asp | Leu | His | |
| | | | 100 | | | | | 105 | | | | | 110 | | | |

| | | | | | | | | | | | | | | | | |
|---|---|---|---|---|---|---|---|---|---|---|---|---|---|---|---|---|
| tat | tct | cct | gtg | ttt | ggc | ggc | ggc | acg | aag | tta | acc | gtc | cta | ggt | cag | 384 |
| Tyr | Ser | Pro | Val | Phe | Gly | Gly | Gly | Thr | Lys | Leu | Thr | Val | Leu | Gly | Gln | |
| | | 115 | | | | | 120 | | | | | 125 | | | | |

| | | | | | | | | | | | | | | | | |
|---|---|---|---|---|---|---|---|---|---|---|---|---|---|---|---|---|
| ccc | aag | gct | gcc | ccc | tcg | gtc | act | ctg | ttc | ccg | ccc | tcc | tct | gag | gag | 432 |
| Pro | Lys | Ala | Ala | Pro | Ser | Val | Thr | Leu | Phe | Pro | Pro | Ser | Ser | Glu | Glu | |
| | 130 | | | | | 135 | | | | | 140 | | | | | |

| | | | | | | | | | | | | | | | | |
|---|---|---|---|---|---|---|---|---|---|---|---|---|---|---|---|---|
| ctt | caa | gcc | aac | aag | gcc | aca | ctg | gtg | tgt | ctc | ata | agt | gac | ttc | tac | 480 |
| Leu | Gln | Ala | Asn | Lys | Ala | Thr | Leu | Val | Cys | Leu | Ile | Ser | Asp | Phe | Tyr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ccg | gga | gcc | gtg | aca | gtg | gcc | tgg | aag | gca | gat | agc | agc | ccc | gtc | aag | 528 |
| Pro | Gly | Ala | Val | Thr | Val | Ala | Trp | Lys | Ala | Asp | Ser | Ser | Pro | Val | Lys | |
| | | | | 165 | | | | | 170 | | | | | 175 | | |

| | | | | | | | | | | | | | | | | |
|---|---|---|---|---|---|---|---|---|---|---|---|---|---|---|---|---|
| gcg | gga | gtg | gag | acc | acc | aca | ccc | tcc | aaa | caa | agc | aac | aac | aag | tac | 576 |
| Ala | Gly | Val | Glu | Thr | Thr | Thr | Pro | Ser | Lys | Gln | Ser | Asn | Asn | Lys | Tyr | |
| | | | 180 | | | | | 185 | | | | | 190 | | | |

| | | | | | | | | | | | | | | | | |
|---|---|---|---|---|---|---|---|---|---|---|---|---|---|---|---|---|
| gcg | gcc | agc | agc | tat | ctg | agc | ctg | acg | cct | gag | cag | tgg | aag | tcc | cac | 624 |
| Ala | Ala | Ser | Ser | Tyr | Leu | Ser | Leu | Thr | Pro | Glu | Gln | Trp | Lys | Ser | His | |
| | | 195 | | | | | 200 | | | | | 205 | | | | |

```
aga agc tac agc tgc cag gtc acg cat gaa ggg agc acc gtg gag aag         672
Arg Ser Tyr Ser Cys Gln Val Thr His Glu Gly Ser Thr Val Glu Lys
    210                 215                 220 aca gtg gcc cct aca gaa tgt tca                                         696
Thr Val Ala Pro Thr Glu Cys Ser
225                 230
```

<210> SEQ ID NO 47
<211> LENGTH: 232
<212> TYPE: PRT
<213> ORGANISM: Homo sapiens

<400> SEQUENCE: 47

```
Met Ala Trp Ala Leu Leu Leu Thr Leu Leu Thr Gln Gly Thr Gly
1               5                   10                  15

Ser Trp Ala Asp Ile Glu Leu Thr Gln Pro Ser Val Ser Val Ala
                20                  25                  30

Pro Gly Gln Thr Ala Arg Ile Ser Cys Ser Gly Asp Asn Leu Pro Asn
                35                  40                  45

Arg Tyr Val His Trp Tyr Gln Gln Lys Pro Gly Gln Ala Pro Val Leu
    50                  55                  60

Val Ile Tyr Asp Asp Asn Asn Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Glu Asp Glu Ala Asp Tyr Tyr Cys Gln Ser Arg Asp Leu His
                100                 105                 110

Tyr Ser Pro Val Phe Gly Gly Gly Thr Lys Leu Thr Val Leu Gly Gln
            115                 120                 125

Pro Lys Ala Ala Pro Ser Val Thr Leu Phe Pro Pro Ser Ser Glu Glu
            130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
                180                 185                 190

Ala Ala Ser Ser Tyr Leu Ser Leu Thr Pro Glu Gln Trp Lys Ser His
            195                 200                 205

Arg Ser Tyr Ser Cys Gln Val Thr His Glu Gly Ser Thr Val Glu Lys
    210                 215                 220

Thr Val Ala Pro Thr Glu Cys Ser
225                 230
```

<210> SEQ ID NO 48
<211> LENGTH: 11
<212> TYPE: PRT
<213> ORGANISM: Homo sapiens

<400> SEQUENCE: 48

```
Ser Gly Asp Asn Leu Pro Asn Arg Tyr Val His
1               5                   10
```

<210> SEQ ID NO 49
<211> LENGTH: 7
<212> TYPE: PRT
<213> ORGANISM: Homo sapiens

```
<400> SEQUENCE: 49

Asp Asp Asn Asn Arg Pro Ser
1               5

<210> SEQ ID NO 50
<211> LENGTH: 10
<212> TYPE: PRT
<213> ORGANISM: Homo sapiens

<400> SEQUENCE: 50

Gln Ser Arg Asp Leu His Tyr Ser Pro Val
1               5                   10

<210> SEQ ID NO 51
<211> LENGTH: 1389
<212> TYPE: DNA
<213> ORGANISM: Homo sapiens
<220> FEATURE:
<221> NAME/KEY: CDS
<222> LOCATION: (1)..(1389)
<220> FEATURE:
<221> NAME/KEY: sig_peptide
<222> LOCATION: (1)..(57)
<220> FEATURE:
<221> NAME/KEY: V_region
<222> LOCATION: (58)..(411)
<220> FEATURE:
<221> NAME/KEY: misc_feature
<222> LOCATION: (148)..(162)
<223> OTHER INFORMATION: CDR1
<220> FEATURE:
<221> NAME/KEY: misc_feature
<222> LOCATION: (205)..(255)
<223> OTHER INFORMATION: CDR2
<220> FEATURE:
<221> NAME/KEY: misc_feature
<222> LOCATION: (352)..(378)
<223> OTHER INFORMATION: CDR3

<400> SEQUENCE: 51 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtc ctg tcc cag gtg caa ttg gtg gaa agc ggc ggc ggc ctg gtg caa      96
Val Leu Ser Gln Val Gln Leu Val Glu Ser Gly Gly Gly Leu Val Gln
            20                  25                  30 ccg ggc ggc agc ctg cgt ctg agc tgc gcg gcc tcc gga ttt acc ttt     144
Pro Gly Gly Ser Leu Arg Leu Ser Cys Ala Ala Ser Gly Phe Thr Phe
        35                  40                  45 tct aat tat tgg atg act tgg gtg cgc caa gcc cct ggg aag ggt ctc     192
Ser Asn Tyr Trp Met Thr Trp Val Arg Gln Ala Pro Gly Lys Gly Leu
    50                  55                  60 gag tgg gtg agc ttt atc tct tat tct ggt agc act acc tat tat gcg     240
Glu Trp Val Ser Phe Ile Ser Tyr Ser Gly Ser Thr Thr Tyr Tyr Ala
65                  70                  75                  80 gat agc gtg aaa ggc cgt ttt acc att tca cgt gat aat tcg aaa aac     288
Asp Ser Val Lys Gly Arg Phe Thr Ile Ser Arg Asp Asn Ser Lys Asn
                85                  90                  95 acc ctg tat ctg caa atg aac agc ctg cgt gcg gaa gat acg gcc gtg     336
Thr Leu Tyr Leu Gln Met Asn Ser Leu Arg Ala Glu Asp Thr Ala Val
            100                 105                 110 tat tat tgc gcg cgt gag ggt act tct tct atg ttt gat gtt tgg ggc     384
Tyr Tyr Cys Ala Arg Glu Gly Thr Ser Ser Met Phe Asp Val Trp Gly
        115                 120                 125 caa ggc acc ctg gtg acg gtt agc tca gcc agc acc aag ggc ccc agc     432
Gln Gly Thr Leu Val Thr Val Ser Ser Ala Ser Thr Lys Gly Pro Ser
```

-continued

| | | | | | | | | | | | | | | | |
|---|---|---|---|---|---|---|---|---|---|---|---|---|---|---|---|
| | | 130 | | | | | 135 | | | | | 140 | | | |
| gtg | ttc | ccc | ctg | gcc | ccc | tgc | agc | aga | agc | acc | agc | gag | agc | aca | gcc | 480 |
| Val | Phe | Pro | Leu | Ala | Pro | Cys | Ser | Arg | Ser | Thr | Ser | Glu | Ser | Thr | Ala | |
| 145 | | | | | 150 | | | | | 155 | | | | | 160 | |
| gcc | ctg | ggc | tgc | ctg | gtg | aag | gac | tac | ttc | ccc | gag | ccc | gtg | acc | gtg | 528 |
| Ala | Leu | Gly | Cys | Leu | Val | Lys | Asp | Tyr | Phe | Pro | Glu | Pro | Val | Thr | Val | |
| | | | | 165 | | | | | 170 | | | | | 175 | | |
| agc | tgg | aac | agc | gga | gcc | ctg | acc | agc | ggc | gtg | cac | acc | ttc | ccc | gcc | 576 |
| Ser | Trp | Asn | Ser | Gly | Ala | Leu | Thr | Ser | Gly | Val | His | Thr | Phe | Pro | Ala | |
| | | | 180 | | | | | 185 | | | | | 190 | | | |
| gtg | ctg | cag | agc | agc | ggc | ctg | tac | agc | ctg | agc | agc | gtg | gtg | acc | gtg | 624 |
| Val | Leu | Gln | Ser | Ser | Gly | Leu | Tyr | Ser | Leu | Ser | Ser | Val | Val | Thr | Val | |
| | | 195 | | | | | 200 | | | | | 205 | | | | |
| ccc | agc | agc | aac | ttc | ggc | acc | cag | acc | tac | acc | tgc | aac | gtg | gac | cac | 672 |
| Pro | Ser | Ser | Asn | Phe | Gly | Thr | Gln | Thr | Tyr | Thr | Cys | Asn | Val | Asp | His | |
| | 210 | | | | | 215 | | | | | 220 | | | | | |
| aag | ccc | agc | aac | acc | aag | gtg | gac | aag | acc | gtg | gag | cgg | aag | tgc | tgc | 720 |
| Lys | Pro | Ser | Asn | Thr | Lys | Val | Asp | Lys | Thr | Val | Glu | Arg | Lys | Cys | Cys | |
| 225 | | | | | 230 | | | | | 235 | | | | | 240 | |
| gtg | gag | tgc | ccc | ccc | tgc | cct | gcc | cct | cct | gtg | gcc | gga | ccc | tcc | gtg | 768 |
| Val | Glu | Cys | Pro | Pro | Cys | Pro | Ala | Pro | Pro | Val | Ala | Gly | Pro | Ser | Val | |
| | | | | 245 | | | | | 250 | | | | | 255 | | |
| ttc | ctg | ttc | ccc | ccc | aag | ccc | aag | gac | acc | ctg | atg | atc | agc | cgg | acc | 816 |
| Phe | Leu | Phe | Pro | Pro | Lys | Pro | Lys | Asp | Thr | Leu | Met | Ile | Ser | Arg | Thr | |
| | | | 260 | | | | | 265 | | | | | 270 | | | |
| ccc | gag | gtg | acc | tgc | gtg | gtg | gtg | gac | gtg | agc | cac | gag | gac | ccc | gag | 864 |
| Pro | Glu | Val | Thr | Cys | Val | Val | Val | Asp | Val | Ser | His | Glu | Asp | Pro | Glu | |
| | | 275 | | | | | 280 | | | | | 285 | | | | |
| gtg | cag | ttt | aat | tgg | tac | gtg | gac | ggc | gtg | gag | gtg | cac | aac | gcc | aag | 912 |
| Val | Gln | Phe | Asn | Trp | Tyr | Val | Asp | Gly | Val | Glu | Val | His | Asn | Ala | Lys | |
| | 290 | | | | | 295 | | | | | 300 | | | | | |
| acc | aag | ccc | cgg | gag | gaa | cag | ttc | aac | agc | acc | ttc | cgg | gtg | gtg | tcc | 960 |
| Thr | Lys | Pro | Arg | Glu | Glu | Gln | Phe | Asn | Ser | Thr | Phe | Arg | Val | Val | Ser | |
| 305 | | | | | 310 | | | | | 315 | | | | | 320 | |
| gtg | ctg | acc | gtg | gtg | cac | cag | gac | tgg | ctg | aac | ggc | aaa | gaa | tac | aag | 1008 |
| Val | Leu | Thr | Val | Val | His | Gln | Asp | Trp | Leu | Asn | Gly | Lys | Glu | Tyr | Lys | |
| | | | | 325 | | | | | 330 | | | | | 335 | | |
| tgc | aag | gtg | tcc | aac | aag | ggc | ctg | cct | gcc | ccc | atc | gag | aaa | acc | atc | 1056 |
| Cys | Lys | Val | Ser | Asn | Lys | Gly | Leu | Pro | Ala | Pro | Ile | Glu | Lys | Thr | Ile | |
| | | | 340 | | | | | 345 | | | | | 350 | | | |
| agc | aag | aca | aag | ggc | cag | ccc | agg | gaa | ccc | cag | gtg | tac | acc | ctg | ccc | 1104 |
| Ser | Lys | Thr | Lys | Gly | Gln | Pro | Arg | Glu | Pro | Gln | Val | Tyr | Thr | Leu | Pro | |
| | | 355 | | | | | 360 | | | | | 365 | | | | |
| ccc | agc | cgg | gag | gaa | atg | acc | aag | aac | cag | gtg | tcc | ctg | acc | tgt | ctg | 1152 |
| Pro | Ser | Arg | Glu | Glu | Met | Thr | Lys | Asn | Gln | Val | Ser | Leu | Thr | Cys | Leu | |
| | 370 | | | | | 375 | | | | | 380 | | | | | |
| gtg | aag | ggc | ttc | tac | ccc | agc | gac | atc | gcc | gtg | gag | tgg | gag | agc | aac | 1200 |
| Val | Lys | Gly | Phe | Tyr | Pro | Ser | Asp | Ile | Ala | Val | Glu | Trp | Glu | Ser | Asn | |
| 385 | | | | | 390 | | | | | 395 | | | | | 400 | |
| ggc | cag | ccc | gag | aac | aac | tac | aag | acc | acc | ccc | ccc | atg | ctg | gac | agc | 1248 |
| Gly | Gln | Pro | Glu | Asn | Asn | Tyr | Lys | Thr | Thr | Pro | Pro | Met | Leu | Asp | Ser | |
| | | | | 405 | | | | | 410 | | | | | 415 | | |
| gac | ggc | agc | ttc | ttc | ctg | tac | agc | aag | ctg | aca | gtg | gac | aag | agc | cgg | 1296 |
| Asp | Gly | Ser | Phe | Phe | Leu | Tyr | Ser | Lys | Leu | Thr | Val | Asp | Lys | Ser | Arg | |
| | | | | 420 | | | | | 425 | | | | | 430 | | |
| tgg | cag | cag | ggc | aac | gtg | ttc | agc | tgc | agc | gtg | atg | cac | gag | gcc | ctg | 1344 |
| Trp | Gln | Gln | Gly | Asn | Val | Phe | Ser | Cys | Ser | Val | Met | His | Glu | Ala | Leu | |
| | | | 435 | | | | | 440 | | | | | 445 | | | |
| cac | aac | cac | tac | acc | cag | aag | agc | ctg | agc | ctg | tcc | ccc | ggc | aaa | | 1389 |

His Asn His Tyr Thr Gln Lys Ser Leu Ser Leu Ser Pro Gly Lys
        450                 455                 460

<210> SEQ ID NO 52
<211> LENGTH: 463
<212> TYPE: PRT
<213> ORGANISM: Homo sapiens

<400> SEQUENCE: 52

Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Trp Met Thr Trp Val Arg Gln Ala Pro Gly Lys Gly Leu
    50                  55                  60

Glu Trp Val Ser Phe Ile Ser Tyr Ser Gly Ser Thr Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Glu Gly Thr Ser Ser Met Phe Asp Val Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

```
Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 53
<211> LENGTH: 5
<212> TYPE: PRT
<213> ORGANISM: Homo sapiens

<400> SEQUENCE: 53

Asn Tyr Trp Met Thr
1               5

<210> SEQ ID NO 54
<211> LENGTH: 17
<212> TYPE: PRT
<213> ORGANISM: Homo sapiens

<400> SEQUENCE: 54

Phe Ile Ser Tyr Ser Gly Ser Thr Thr Tyr Tyr Ala Asp Ser Val Lys
1               5                   10                  15

Gly

<210> SEQ ID NO 55
<211> LENGTH: 9
<212> TYPE: PRT
<213> ORGANISM: Homo sapiens

<400> SEQUENCE: 55

Glu Gly Thr Ser Ser Met Phe Asp Val
1               5

<210> SEQ ID NO 56
<211> LENGTH: 696
<212> TYPE: DNA
<213> ORGANISM: Homo sapiens
<220> FEATURE:
<221> NAME/KEY: CDS
<222> LOCATION: (1)..(696)
<220> FEATURE:
<221> NAME/KEY: sig_peptide
<222> LOCATION: (1)..(57)
<220> FEATURE:
<221> NAME/KEY: V_region
<222> LOCATION: (58)..(387)
<220> FEATURE:
<221> NAME/KEY: misc_feature
<222> LOCATION: (124)..(156)
<223> OTHER INFORMATION: CDR1
<220> FEATURE:
<221> NAME/KEY: misc_feature
<222> LOCATION: (202)..(222)
<223> OTHER INFORMATION: CDR2
<220> FEATURE:
<221> NAME/KEY: misc_feature
<222> LOCATION: (319)..(348)
```

<223> OTHER INFORMATION: CDR3

<400> SEQUENCE: 56

```
atg gcc tgg gct ctg ctg ctc ctc acc ctc ctc act cag ggc aca gga        48
Met Ala Trp Ala Leu Leu Leu Leu Thr Leu Leu Thr Gln Gly Thr Gly
1               5                   10                  15 tcc tgg gct gat atc gaa ctg acc cag ccg cct tca gtg agc gtt gca        96
Ser Trp Ala Asp Ile Glu Leu Thr Gln Pro Pro Ser Val Ser Val Ala
                20                  25                  30 cca ggt cag acc gcg cgt atc tcg tgt agc ggc gat gct ctt cgt tct       144
Pro Gly Gln Thr Ala Arg Ile Ser Cys Ser Gly Asp Ala Leu Arg Ser
            35                  40                  45 tat tat gct tct tgg tac cag cag aaa ccc ggg cag gcg cca gtt ctt       192
Tyr Tyr Ala Ser Trp Tyr Gln Gln Lys Pro Gly Gln Ala Pro Val Leu
        50                  55                  60 gtg att tat gat gat aat aag cgt ccc tca ggc atc ccg gaa cgc ttt       240
Val Ile Tyr Asp Asp Asn Lys Arg Pro Ser Gly Ile Pro Glu Arg Phe
65                  70                  75                  80 agc gga tcc aac agc ggc aac acc gcg acc ctg acc att agc ggc act       288
Ser Gly Ser Asn Ser Gly Asn Thr Ala Thr Leu Thr Ile Ser Gly Thr
                85                  90                  95 cag gcg gaa gac gaa gcg gat tat tat tgc gct tct ttt act tat atg       336
Gln Ala Glu Asp Glu Ala Asp Tyr Tyr Cys Ala Ser Phe Thr Tyr Met
            100                 105                 110 tct gat ttt gtg ttt ggc ggc ggc acg aag tta acc gtc cta ggt cag       384
Ser Asp Phe Val Phe Gly Gly Gly Thr Lys Leu Thr Val Leu Gly Gln
        115                 120                 125 ccc aag gct gcc ccc tcg gtc act ctg ttc ccg ccc tcc tct gag gag       432
Pro Lys Ala Ala Pro Ser Val Thr Leu Phe Pro Pro Ser Ser Glu Glu
    130                 135                 140 ctt caa gcc aac aag gcc aca ctg gtg tgt ctc ata agt gac ttc tac       480
Leu Gln Ala Asn Lys Ala Thr Leu Val Cys Leu Ile Ser Asp Phe Tyr
145                 150                 155                 160 ccg gga gcc gtg aca gtg gcc tgg aag gca gat agc agc ccc gtc aag       528
Pro Gly Ala Val Thr Val Ala Trp Lys Ala Asp Ser Ser Pro Val Lys
                165                 170                 175 gcg gga gtg gag acc acc aca ccc tcc aaa caa agc aac aac aag tac       576
Ala Gly Val Glu Thr Thr Thr Pro Ser Lys Gln Ser Asn Asn Lys Tyr
            180                 185                 190 gcg gcc agc agc tat ctg agc ctg acg cct gag cag tgg aag tcc cac       624
Ala Ala Ser Ser Tyr Leu Ser Leu Thr Pro Glu Gln Trp Lys Ser His
        195                 200                 205 aga agc tac agc tgc cag gtc acg cat gaa ggg agc acc gtg gag aag       672
Arg Ser Tyr Ser Cys Gln Val Thr His Glu Gly Ser Thr Val Glu Lys
    210                 215                 220 aca gtg gcc cct aca gaa tgt tca                                       696
Thr Val Ala Pro Thr Glu Cys Ser
225                 230
```

<210> SEQ ID NO 57
<211> LENGTH: 232
<212> TYPE: PRT
<213> ORGANISM: Homo sapiens

<400> SEQUENCE: 57

```
Met Ala Trp Ala Leu Leu Leu Leu Thr Leu Leu Thr Gln Gly Thr Gly
1               5                   10                  15

Ser Trp Ala Asp Ile Glu Leu Thr Gln Pro Pro Ser Val Ser Val Ala
                20                  25                  30

Pro Gly Gln Thr Ala Arg Ile Ser Cys Ser Gly Asp Ala Leu Arg Ser
```

```
                35                  40                  45
Tyr Tyr Ala Ser Trp Tyr Gln Gln Lys Pro Gly Gln Ala Pro Val Leu
 50                  55                  60

Val Ile Tyr Asp Asp Asn Lys Arg Pro Ser Gly Ile Pro Glu Arg Phe
 65                  70                  75                  80

Ser Gly Ser Asn Ser Gly Asn Thr Ala Thr Leu Thr Ile Ser Gly Thr
                 85                  90                  95

Gln Ala Glu Asp Glu Ala Asp Tyr Tyr Cys Ala Ser Phe Thr Tyr Met
                100                 105                 110

Ser Asp Phe Val Phe Gly Gly Gly Thr Lys Leu Thr Val Leu Gly Gln
                115                 120                 125

Pro Lys Ala Ala Pro Ser Val Thr Leu Phe Pro Pro Ser Ser Glu Glu
            130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
        195                 200                 205

Arg Ser Tyr Ser Cys Gln Val Thr His Glu Gly Ser Thr Val Glu Lys
    210                 215                 220

Thr Val Ala Pro Thr Glu Cys Ser
225                 230

<210> SEQ ID NO 58
<211> LENGTH: 11
<212> TYPE: PRT
<213> ORGANISM: Homo sapiens

<400> SEQUENCE: 58

Ser Gly Asp Ala Leu Arg Ser Tyr Tyr Ala Ser
1               5                   10

<210> SEQ ID NO 59
<211> LENGTH: 7
<212> TYPE: PRT
<213> ORGANISM: Homo sapiens

<400> SEQUENCE: 59

Asp Asp Asn Lys Arg Pro Ser
1               5

<210> SEQ ID NO 60
<211> LENGTH: 10
<212> TYPE: PRT
<213> ORGANISM: Homo sapiens

<400> SEQUENCE: 60

Ala Ser Phe Thr Tyr Met Ser Asp Phe Val
1               5                   10

<210> SEQ ID NO 61
<211> LENGTH: 1386
<212> TYPE: DNA
<213> ORGANISM: Homo sapiens
<220> FEATURE:
<221> NAME/KEY: CDS
<222> LOCATION: (1)..(1386)
```

```
<220> FEATURE:
<221> NAME/KEY: sig_peptide
<222> LOCATION: (1)..(57)
<220> FEATURE:
<221> NAME/KEY: V_region
<222> LOCATION: (58)..(408)
<220> FEATURE:
<221> NAME/KEY: misc_feature
<222> LOCATION: (148)..(162)
<223> OTHER INFORMATION: CDR1
<220> FEATURE:
<221> NAME/KEY: misc_feature
<222> LOCATION: (205)..(255)
<223> OTHER INFORMATION: CDR2
<220> FEATURE:
<221> NAME/KEY: misc_feature
<222> LOCATION: (352)..(375)
<223> OTHER INFORMATION: CDR3

<400> SEQUENCE: 61 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtc ctg tcc cag gtg caa ttg gtg gaa agc ggc ggc ggc ctg gtg caa      96
Val Leu Ser Gln Val Gln Leu Val Glu Ser Gly Gly Gly Leu Val Gln
            20                  25                  30 ccg ggc ggc agc ctg cgt ctg agc tgc gcg gcc tcc gga ttt acc ttt     144
Pro Gly Gly Ser Leu Arg Leu Ser Cys Ala Ala Ser Gly Phe Thr Phe
        35                  40                  45 act aat tat gct atg aat tgg gtg cgc caa gcc cct ggg aag ggt ctc     192
Thr Asn Tyr Ala Met Asn Trp Val Arg Gln Ala Pro Gly Lys Gly Leu
    50                  55                  60 gag tgg gtg agc tat atc tct tat tct tct agc aat acc tat tat gcg     240
Glu Trp Val Ser Tyr Ile Ser Tyr Ser Ser Ser Asn Thr Tyr Tyr Ala
65                  70                  75                  80 gat agc gtg aaa ggc cgt ttt acc att tca cgt gat aat tcg aaa aac     288
Asp Ser Val Lys Gly Arg Phe Thr Ile Ser Arg Asp Asn Ser Lys Asn
                85                  90                  95 acc ctg tat ctg caa atg aac agc ctg cgt gcg gaa gat acg gcc gtg     336
Thr Leu Tyr Leu Gln Met Asn Ser Leu Arg Ala Glu Asp Thr Ala Val
            100                 105                 110 tat tat tgc gcg cgt ggt gct ggt ctt ggt tat gat gtt tgg ggc caa     384
Tyr Tyr Cys Ala Arg Gly Ala Gly Leu Gly Tyr Asp Val Trp Gly Gln
        115                 120                 125 ggc acc ctg gtg acg gtt agc tca gcc agc acc aag ggc ccc agc gtg     432
Gly Thr Leu Val Thr Val Ser Ser Ala Ser Thr Lys Gly Pro Ser Val
    130                 135                 140 ttc ccc ctg gcc ccc tgc agc aga agc acc agc gag agc aca gcc gcc     480
Phe Pro Leu Ala Pro Cys Ser Arg Ser Thr Ser Glu Ser Thr Ala Ala
145                 150                 155                 160 ctg ggc tgc ctg gtg aag gac tac ttc ccc gag ccc gtg acc gtg agc     528
Leu Gly Cys Leu Val Lys Asp Tyr Phe Pro Glu Pro Val Thr Val Ser
                165                 170                 175 tgg aac agc gga gcc ctg acc agc ggc gtg cac acc ttc ccc gcc gtg     576
Trp Asn Ser Gly Ala Leu Thr Ser Gly Val His Thr Phe Pro Ala Val
            180                 185                 190 ctg cag agc agc ggc ctg tac agc ctg agc agc gtg gtg acc gtg ccc     624
Leu Gln Ser Ser Gly Leu Tyr Ser Leu Ser Ser Val Val Thr Val Pro
        195                 200                 205 agc agc aac ttc ggc acc cag acc tac acc tgc aac gtg gac cac aag     672
Ser Ser Asn Phe Gly Thr Gln Thr Tyr Thr Cys Asn Val Asp His Lys
    210                 215                 220 ccc agc aac acc aag gtg gac aag acc gtg gag cgg aag tgc tgc gtg     720
Pro Ser Asn Thr Lys Val Asp Lys Thr Val Glu Arg Lys Cys Cys Val
```

```
                225                 230                 235                 240
gag tgc ccc ccc tgc cct gcc cct cct gtg gcc gga ccc tcc gtg ttc    768
Glu Cys Pro Pro Cys Pro Ala Pro Pro Val Ala Gly Pro Ser Val Phe
                    245                 250                 255 ctg ttc ccc ccc aag ccc aag gac acc ctg atg atc agc cgg acc ccc    816
Leu Phe Pro Pro Lys Pro Lys Asp Thr Leu Met Ile Ser Arg Thr Pro
                260                 265                 270 gag gtg acc tgc gtg gtg gtg gac gtg agc cac gag gac ccc gag gtg    864
Glu Val Thr Cys Val Val Val Asp Val Ser His Glu Asp Pro Glu Val
            275                 280                 285 cag ttt aat tgg tac gtg gac ggc gtg gag gtg cac aac gcc aag acc    912
Gln Phe Asn Trp Tyr Val Asp Gly Val Glu Val His Asn Ala Lys Thr
        290                 295                 300 aag ccc cgg gag gaa cag ttc aac agc acc ttc cgg gtg gtg tcc gtg    960
Lys Pro Arg Glu Glu Gln Phe Asn Ser Thr Phe Arg Val Val Ser Val
305                 310                 315                 320 ctg acc gtg gtg cac cag gac tgg ctg aac ggc aaa gaa tac aag tgc    1008
Leu Thr Val Val His Gln Asp Trp Leu Asn Gly Lys Glu Tyr Lys Cys
                325                 330                 335 aag gtg tcc aac aag ggc ctg cct gcc ccc atc gag aaa acc atc agc    1056
Lys Val Ser Asn Lys Gly Leu Pro Ala Pro Ile Glu Lys Thr Ile Ser
            340                 345                 350 aag aca aag ggc cag ccc agg gaa ccc cag gtg tac acc ctg ccc ccc    1104
Lys Thr Lys Gly Gln Pro Arg Glu Pro Gln Val Tyr Thr Leu Pro Pro
        355                 360                 365 agc cgg gag gaa atg acc aag aac cag gtg tcc ctg acc tgt ctg gtg    1152
Ser Arg Glu Glu Met Thr Lys Asn Gln Val Ser Leu Thr Cys Leu Val
    370                 375                 380 aag ggc ttc tac ccc agc gac atc gcc gtg gag tgg gag agc aac ggc    1200
Lys Gly Phe Tyr Pro Ser Asp Ile Ala Val Glu Trp Glu Ser Asn Gly
385                 390                 395                 400 cag ccc gag aac aac tac aag acc acc ccc ccc atg ctg gac agc gac    1248
Gln Pro Glu Asn Asn Tyr Lys Thr Thr Pro Pro Met Leu Asp Ser Asp
                405                 410                 415 ggc agc ttc ttc ctg tac agc aag ctg aca gtg gac aag agc cgg tgg    1296
Gly Ser Phe Phe Leu Tyr Ser Lys Leu Thr Val Asp Lys Ser Arg Trp
            420                 425                 430 cag cag ggc aac gtg ttc agc tgc agc gtg atg cac gag gcc ctg cac    1344
Gln Gln Gly Asn Val Phe Ser Cys Ser Val Met His Glu Ala Leu His
        435                 440                 445 aac cac tac acc cag aag agc ctg agc ctg tcc ccc ggc aaa            1386
Asn His Tyr Thr Gln Lys Ser Leu Ser Leu Ser Pro Gly Lys
    450                 455                 460

<210> SEQ ID NO 62
<211> LENGTH: 462
<212> TYPE: PRT
<213> ORGANISM: Homo sapiens

<400> SEQUENCE: 62

Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Asn Tyr Ala Met Asn Trp Val Arg Gln Ala Pro Gly Lys Gly Leu
    50                  55                  60

Glu Trp Val Ser Tyr Ile Ser Tyr Ser Ser Ser Asn Thr Tyr Tyr Ala
```

```
                65                  70                  75                  80
Asp Ser Val Lys Gly Arg Phe Thr Ile Ser Arg Asp Asn Ser Lys Asn
                        85                  90                  95
Thr Leu Tyr Leu Gln Met Asn Ser Leu Arg Ala Glu Asp Thr Ala Val
                        100                 105                 110
Tyr Tyr Cys Ala Arg Gly Ala Gly Leu Gly Tyr Asp Val Trp Gly Gln
                        115                 120                 125
Gly Thr Leu Val Thr Val Ser Ser Ala Ser Thr Lys Gly Pro Ser Val
            130                 135                 140
Phe Pro Leu Ala Pro Cys Ser Arg Ser Thr Ser Glu Ser Thr Ala Ala
145                 150                 155                 160
Leu Gly Cys Leu Val Lys Asp Tyr Phe Pro Glu Pro Val Thr Val Ser
                    165                 170                 175
Trp Asn Ser Gly Ala Leu Thr Ser Gly Val His Thr Phe Pro Ala Val
                180                 185                 190
Leu Gln Ser Ser Gly Leu Tyr Ser Leu Ser Ser Val Val Thr Val Pro
            195                 200                 205
Ser Ser Asn Phe Gly Thr Gln Thr Tyr Thr Cys Asn Val Asp His Lys
    210                 215                 220
Pro Ser Asn Thr Lys Val Asp Lys Thr Val Glu Arg Lys Cys Cys Val
225                 230                 235                 240
Glu Cys Pro Pro Cys Pro Ala Pro Pro Val Ala Gly Pro Ser Val Phe
                    245                 250                 255
Leu Phe Pro Pro Lys Pro Lys Asp Thr Leu Met Ile Ser Arg Thr Pro
                260                 265                 270
Glu Val Thr Cys Val Val Val Asp Val Ser His Glu Asp Pro Glu Val
            275                 280                 285
Gln Phe Asn Trp Tyr Val Asp Gly Val Glu Val His Asn Ala Lys Thr
        290                 295                 300
Lys Pro Arg Glu Glu Gln Phe Asn Ser Thr Phe Arg Val Val Ser Val
305                 310                 315                 320
Leu Thr Val Val His Gln Asp Trp Leu Asn Gly Lys Glu Tyr Lys Cys
                    325                 330                 335
Lys Val Ser Asn Lys Gly Leu Pro Ala Pro Ile Glu Lys Thr Ile Ser
                340                 345                 350
Lys Thr Lys Gly Gln Pro Arg Glu Pro Gln Val Tyr Thr Leu Pro Pro
            355                 360                 365
Ser Arg Glu Glu Met Thr Lys Asn Gln Val Ser Leu Thr Cys Leu Val
    370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Met Leu Asp Ser Asp
                    405                 410                 415
Gly Ser Phe Phe Leu Tyr Ser Lys Leu Thr Val Asp Lys Ser Arg Trp
                420                 425                 430
Gln Gln Gly Asn Val Phe Ser Cys Ser Val Met His Glu Ala Leu His
            435                 440                 445
Asn His Tyr Thr Gln Lys Ser Leu Ser Leu Ser Pro Gly Lys
    450                 455                 460

<210> SEQ ID NO 63
<211> LENGTH: 5
<212> TYPE: PRT
<213> ORGANISM: Homo sapiens
```

<400> SEQUENCE: 63

Asn Tyr Ala Met Asn
1               5

<210> SEQ ID NO 64
<211> LENGTH: 17
<212> TYPE: PRT
<213> ORGANISM: Homo sapiens

<400> SEQUENCE: 64

Tyr Ile Ser Tyr Ser Ser Ser Asn Thr Tyr Tyr Ala Asp Ser Val Lys
1               5                   10                  15

Gly

<210> SEQ ID NO 65
<211> LENGTH: 8
<212> TYPE: PRT
<213> ORGANISM: Homo sapiens

<400> SEQUENCE: 65

Gly Ala Gly Leu Gly Tyr Asp Val
1               5

<210> SEQ ID NO 66
<211> LENGTH: 696
<212> TYPE: DNA
<213> ORGANISM: Homo sapiens
<220> FEATURE:
<221> NAME/KEY: CDS
<222> LOCATION: (1)..(696)
<220> FEATURE:
<221> NAME/KEY: sig_peptide
<222> LOCATION: (1)..(57)
<220> FEATURE:
<221> NAME/KEY: V_region
<222> LOCATION: (58)..(387)
<220> FEATURE:
<221> NAME/KEY: misc_feature
<222> LOCATION: (124)..(156)
<223> OTHER INFORMATION: CDR1
<220> FEATURE:
<221> NAME/KEY: misc_feature
<222> LOCATION: (202)..(222)
<223> OTHER INFORMATION: CDR2
<220> FEATURE:
<221> NAME/KEY: misc_feature
<222> LOCATION: (319)..(348)
<223> OTHER INFORMATION: CDR3

<400> SEQUENCE: 66

| atg gcc tgg gct ctg ctg ctc ctc acc ctc ctc act cag ggc aca gga | 48 |
| Met Ala Trp Ala Leu Leu Leu Leu Thr Leu Leu Thr Gln Gly Thr Gly | |
| 1               5                   10                  15 | |

| tcc tgg gct gat atc gaa ctg acc cag ccg cct tca gtg agc gtt gca | 96 |
| Ser Trp Ala Asp Ile Glu Leu Thr Gln Pro Pro Ser Val Ser Val Ala | |
|                 20                  25                  30 | |

| cca ggt cag acc gcg cgt atc tcg tgt agc ggc gat aat ctt cgt tct | 144 |
| Pro Gly Gln Thr Ala Arg Ile Ser Cys Ser Gly Asp Asn Leu Arg Ser | |
|         35                  40                  45 | |

| aag tat gtt tat tgg tac cag cag aaa ccc ggg cag gcg cca gtt ctt | 192 |
| Lys Tyr Val Tyr Trp Tyr Gln Gln Lys Pro Gly Gln Ala Pro Val Leu | |
|     50                  55                  60 | |

| gtg att tat gat act aat gat cgt ccc tca ggc atc ccg gaa cgc ttt | 240 |
| Val Ile Tyr Asp Thr Asn Asp Arg Pro Ser Gly Ile Pro Glu Arg Phe | |
| 65                  70                  75                  80 | |

```
                                                    -continued agc gga tcc aac agc ggc aac acc gcg acc ctg acc att agc ggc act       288
Ser Gly Ser Asn Ser Gly Asn Thr Ala Thr Leu Thr Ile Ser Gly Thr
                 85                  90                  95 cag gcg gaa gac gaa gcg gat tat tat tgc cag act tat gat atg act       336
Gln Ala Glu Asp Glu Ala Asp Tyr Tyr Cys Gln Thr Tyr Asp Met Thr
            100                 105                 110 tct cag gat gtg ttt ggc ggc ggc acg aag tta acc gtc cta ggt cag       384
Ser Gln Asp Val Phe Gly Gly Gly Thr Lys Leu Thr Val Leu Gly Gln
        115                 120                 125 ccc aag gct gcc ccc tcg gtc act ctg ttc ccg ccc tcc tct gag gag       432
Pro Lys Ala Ala Pro Ser Val Thr Leu Phe Pro Pro Ser Ser Glu Glu
    130                 135                 140 ctt caa gcc aac aag gcc aca ctg gtg tgt ctc ata agt gac ttc tac       480
Leu Gln Ala Asn Lys Ala Thr Leu Val Cys Leu Ile Ser Asp Phe Tyr
145                 150                 155                 160 ccg gga gcc gtg aca gtg gcc tgg aag gca gat agc agc ccc gtc aag       528
Pro Gly Ala Val Thr Val Ala Trp Lys Ala Asp Ser Ser Pro Val Lys
                165                 170                 175 gcg gga gtg gag acc acc aca ccc tcc aaa caa agc aac aac aag tac       576
Ala Gly Val Glu Thr Thr Thr Pro Ser Lys Gln Ser Asn Asn Lys Tyr
            180                 185                 190 gcg gcc agc agc tat ctg agc ctg acg cct gag cag tgg aag tcc cac       624
Ala Ala Ser Ser Tyr Leu Ser Leu Thr Pro Glu Gln Trp Lys Ser His
        195                 200                 205 aga agc tac agc tgc cag gtc acg cat gaa ggg agc acc gtg gag aag       672
Arg Ser Tyr Ser Cys Gln Val Thr His Glu Gly Ser Thr Val Glu Lys
    210                 215                 220 aca gtg gcc cct aca gaa tgt tca                                       696
Thr Val Ala Pro Thr Glu Cys Ser
225                 230

<210> SEQ ID NO 67
<211> LENGTH: 232
<212> TYPE: PRT
<213> ORGANISM: Homo sapiens

<400> SEQUENCE: 67

Met Ala Trp Ala Leu Leu Leu Leu Thr Leu Leu Thr Gln Gly Thr Gly
1               5                   10                  15

Ser Trp Ala Asp Ile Glu Leu Thr Gln Pro Pro Ser Val Ser Val Ala
            20                  25                  30

Pro Gly Gln Thr Ala Arg Ile Ser Cys Ser Gly Asp Asn Leu Arg Ser
        35                  40                  45

Lys Tyr Val Tyr Trp Tyr Gln Gln Lys Pro Gly Gln Ala Pro Val Leu
    50                  55                  60

Val Ile Tyr Asp Thr Asn Asp Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Glu Asp Glu Ala Asp Tyr Tyr Cys Gln Thr Tyr Asp Met Thr
            100                 105                 110

Ser Gln Asp Val Phe Gly Gly Gly Thr Lys Leu Thr Val Leu Gly Gln
        115                 120                 125

Pro Lys Ala Ala Pro Ser Val Thr Leu Phe Pro Pro Ser Ser Glu Glu
    130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
```

```
                     165                 170                 175
Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
            195                 200                 205

Arg Ser Tyr Ser Cys Gln Val Thr His Glu Gly Ser Thr Val Glu Lys
            210                 215                 220

Thr Val Ala Pro Thr Glu Cys Ser
225                 230

<210> SEQ ID NO 68
<211> LENGTH: 11
<212> TYPE: PRT
<213> ORGANISM: Homo sapiens

<400> SEQUENCE: 68

Ser Gly Asp Asn Leu Arg Ser Lys Tyr Val Tyr
1               5                   10

<210> SEQ ID NO 69
<211> LENGTH: 7
<212> TYPE: PRT
<213> ORGANISM: Homo sapiens

<400> SEQUENCE: 69

Asp Thr Asn Asp Arg Pro Ser
1               5

<210> SEQ ID NO 70
<211> LENGTH: 10
<212> TYPE: PRT
<213> ORGANISM: Homo sapiens

<400> SEQUENCE: 70

Gln Thr Tyr Asp Met Thr Ser Gln Asp Val
1               5                   10

<210> SEQ ID NO 71
<211> LENGTH: 5
<212> TYPE: PRT
<213> ORGANISM: Homo sapiens
<220> FEATURE:
<221> NAME/KEY: VARIANT
<222> LOCATION: (1)..(1)
<223> OTHER INFORMATION: /replace="Asn"
      /replace="Ser"
<220> FEATURE:
<221> NAME/KEY: VARIANT
<222> LOCATION: (3)..(3)
<223> OTHER INFORMATION: /replace="Trp"
      /replace="Ala"
<220> FEATURE:
<221> NAME/KEY: VARIANT
<222> LOCATION: (5)..(5)
<223> OTHER INFORMATION: /replace="Ser"
      /replace="His"
      /replace="Thr"
      /replace="Asn"

<400> SEQUENCE: 71

Xaa Tyr Xaa Met Xaa
1               5

<210> SEQ ID NO 72
<211> LENGTH: 17
<212> TYPE: PRT
```

```
<213> ORGANISM: Homo sapiens
<220> FEATURE:
<221> NAME/KEY: VARIANT
<222> LOCATION: (1)..(1)
<223> OTHER INFORMATION: /replace="Leu"
      /replace="Tyr"
      /replace="Phe"
<220> FEATURE:
<221> NAME/KEY: VARIANT
<222> LOCATION: (6)..(6)
<223> OTHER INFORMATION: /replace="Ser"
      /replace="Gly"
<220> FEATURE:
<221> NAME/KEY: VARIANT
<222> LOCATION: (8)..(8)
<223> OTHER INFORMATION: /replace="Thr"
      /replace="Asn"

<400> SEQUENCE: 72

Xaa Ile Ser Tyr Ser Xaa Ser Xaa Thr Tyr Tyr Ala Asp Ser Val Lys
1               5                   10                  15

Gly

<210> SEQ ID NO 73
<211> LENGTH: 11
<212> TYPE: PRT
<213> ORGANISM: Homo sapiens
<220> FEATURE:
<221> NAME/KEY: VARIANT
<222> LOCATION: (4)..(4)
<223> OTHER INFORMATION: /replace="Asn"
      /replace="Ala"
<220> FEATURE:
<221> NAME/KEY: VARIANT
<222> LOCATION: (6)..(6)
<223> OTHER INFORMATION: /replace="Gly"
      /replace="Pro"
      /replace="Arg"
<220> FEATURE:
<221> NAME/KEY: VARIANT
<222> LOCATION: (7)..(7)
<223> OTHER INFORMATION: /replace="Ser"
      /replace="Asn"
<220> FEATURE:
<221> NAME/KEY: VARIANT
<222> LOCATION: (8)..(8)
<223> OTHER INFORMATION: /replace="Tyr"
      /replace="Arg"
      /replace="Lys"
<220> FEATURE:
<221> NAME/KEY: VARIANT
<222> LOCATION: (10)..(10)
<223> OTHER INFORMATION: /replace="Ala"
      /replace="Val"
<220> FEATURE:
<221> NAME/KEY: VARIANT
<222> LOCATION: (11)..(11)
<223> OTHER INFORMATION: /replace="Tyr"
      /replace="His"
      /replace="Ser"

<400> SEQUENCE: 73

Ser Gly Asp Xaa Leu Xaa Xaa Xaa Tyr Xaa Xaa
1               5                   10

<210> SEQ ID NO 74
<211> LENGTH: 7
<212> TYPE: PRT
<213> ORGANISM: Homo sapiens
<220> FEATURE:
<221> NAME/KEY: VARIANT
<222> LOCATION: (1)..(1)
<223> OTHER INFORMATION: /replace="Gly"
      /replace="Asp"
```

```
<220> FEATURE:
<221> NAME/KEY: VARIANT
<222> LOCATION: (2)..(2)
<223> OTHER INFORMATION: /replace="Thr"
      /replace="Asp"
<220> FEATURE:
<221> NAME/KEY: VARIANT
<222> LOCATION: (4)..(4)
<223> OTHER INFORMATION: /replace="Asn"
      /replace="Asp"
      /replace="Lys"

<400> SEQUENCE: 74

Xaa Xaa Asn Xaa Arg Pro Ser
1               5

<210> SEQ ID NO 75
<211> LENGTH: 5
<212> TYPE: PRT
<213> ORGANISM: Artificial
<220> FEATURE:
<223> OTHER INFORMATION: Complementarity Determining Region 1

<400> SEQUENCE: 75

Asn Tyr Ala Met Ser
1               5

<210> SEQ ID NO 76
<211> LENGTH: 1392
<212> TYPE: DNA
<213> ORGANISM: Homo sapiens
<220> FEATURE:
<221> NAME/KEY: CDS
<222> LOCATION: (1)..(1392)
<220> FEATURE:
<221> NAME/KEY: sig_peptide
<222> LOCATION: (1)..(57)
<220> FEATURE:
<221> NAME/KEY: V_region
<222> LOCATION: (58)..(414)
<220> FEATURE:
<221> NAME/KEY: misc_feature
<222> LOCATION: (148)..(162)
<223> OTHER INFORMATION: CDR1
<220> FEATURE:
<221> NAME/KEY: misc_feature
<222> LOCATION: (205)..(255)
<223> OTHER INFORMATION: CDR2
<220> FEATURE:
<221> NAME/KEY: misc_feature
<222> LOCATION: (352)..(381)
<223> OTHER INFORMATION: CDR3

<400> SEQUENCE: 76
```

| | | | | | | | | | | | | | | | | |
|---|---|---|---|---|---|---|---|---|---|---|---|---|---|---|---|---|
| atg | aaa | cac | ctg | tgg | ttc | ttc | ctc | ctg | ctg | gtg | gca | gct | ccc | aga | tgg | 48 |
| Met | Lys | His | Leu | Trp | Phe | Phe | Leu | Leu | Leu | Val | Ala | Ala | Pro | Arg | Trp | |
| 1 | | | | 5 | | | | | 10 | | | | | 15 | | |
| gtc | ctg | tcc | cag | gtg | caa | ttg | gtg | gaa | agc | ggc | ggc | ggc | ctg | gtg | caa | 96 |
| Val | Leu | Ser | Gln | Val | Gln | Leu | Val | Glu | Ser | Gly | Gly | Gly | Leu | Val | Gln | |
| | | 20 | | | | | 25 | | | | | 30 | | | | |
| ccg | ggc | ggc | agc | ctg | cgt | ctg | agc | tgc | gcg | gcc | tcc | gga | ttt | acc | ttt | 144 |
| Pro | Gly | Gly | Ser | Leu | Arg | Leu | Ser | Cys | Ala | Ala | Ser | Gly | Phe | Thr | Phe | |
| | | | 35 | | | | | 40 | | | | | 45 | | | |
| act | act | tat | gct | atg | cat | tgg | gtg | cgc | caa | gcc | cct | ggg | aag | ggt | ctc | 192 |
| Thr | Thr | Tyr | Ala | Met | His | Trp | Val | Arg | Gln | Ala | Pro | Gly | Lys | Gly | Leu | |
| | | 50 | | | | | 55 | | | | | 60 | | | | |
| gag | tgg | gtg | agc | aat | atc | gct | tat | tct | ggt | agc | gtt | acc | tat | tat | gcg | 240 |
| Glu | Trp | Val | Ser | Asn | Ile | Ala | Tyr | Ser | Gly | Ser | Val | Thr | Tyr | Tyr | Ala | |
| 65 | | | | 70 | | | | | 75 | | | | | 80 | | |

-continued

| | |
|---|---|
| gat agc gtg aaa ggc cgt ttt acc att tca cgt gat aat tcg aaa aac<br>Asp Ser Val Lys Gly Arg Phe Thr Ile Ser Arg Asp Asn Ser Lys Asn<br>                85                    90                    95 | 288 |
| acc ctg tat ctg caa atg aac agc ctg cgt gcg gaa gat acg gcc gtg<br>Thr Leu Tyr Leu Gln Met Asn Ser Leu Arg Ala Glu Asp Thr Ala Val<br>               100                  105                  110 | 336 |
| tat tat tgc gcg cgt cgt ggt cct ggt atg ggt aat atg gat att tgg<br>Tyr Tyr Cys Ala Arg Arg Gly Pro Gly Met Gly Asn Met Asp Ile Trp<br>           115                  120                  125 | 384 |
| ggc caa ggc acc ctg gtg acg gtt agc tca gcc agc acc aag ggc ccc<br>Gly Gln Gly Thr Leu Val Thr Val Ser Ser Ala Ser Thr Lys Gly Pro<br>130                  135                  140 | 432 |
| agc gtg ttc ccc ctg gcc ccc tgc agc aga agc acc agc gag agc aca<br>Ser Val Phe Pro Leu Ala Pro Cys Ser Arg Ser Thr Ser Glu Ser Thr<br>145                  150                  155                  160 | 480 |
| gcc gcc ctg ggc tgc ctg gtg aag gac tac ttc ccc gag ccc gtg acc<br>Ala Ala Leu Gly Cys Leu Val Lys Asp Tyr Phe Pro Glu Pro Val Thr<br>               165                  170                  175 | 528 |
| gtg agc tgg aac agc gga gcc ctg acc agc ggc gtg cac acc ttc ccc<br>Val Ser Trp Asn Ser Gly Ala Leu Thr Ser Gly Val His Thr Phe Pro<br>                  180                  185                  190 | 576 |
| gcc gtg ctg cag agc agc ggc ctg tac agc ctg agc agc gtg gtg acc<br>Ala Val Leu Gln Ser Ser Gly Leu Tyr Ser Leu Ser Ser Val Val Thr<br>           195                  200                  205 | 624 |
| gtg ccc agc agc aac ttc ggc acc cag acc tac acc tgc aac gtg gac<br>Val Pro Ser Ser Asn Phe Gly Thr Gln Thr Tyr Thr Cys Asn Val Asp<br>210                  215                  220 | 672 |
| cac aag ccc agc aac acc aag gtg gac aag acc gtg gag cgg aag tgc<br>His Lys Pro Ser Asn Thr Lys Val Asp Lys Thr Val Glu Arg Lys Cys<br>225                  230                  235                  240 | 720 |
| tgc gtg gag tgc ccc ccc tgc cct gcc cct cct gtg gcc gga ccc tcc<br>Cys Val Glu Cys Pro Pro Cys Pro Ala Pro Pro Val Ala Gly Pro Ser<br>               245                  250                  255 | 768 |
| gtg ttc ctg ttc ccc ccc aag ccc aag gac acc ctg atg atc agc cgg<br>Val Phe Leu Phe Pro Pro Lys Pro Lys Asp Thr Leu Met Ile Ser Arg<br>                  260                  265                  270 | 816 |
| acc ccc gag gtg acc tgc gtg gtg gtg gac gtg agc cac gag gac ccc<br>Thr Pro Glu Val Thr Cys Val Val Val Asp Val Ser His Glu Asp Pro<br>           275                  280                  285 | 864 |
| gag gtg cag ttt aat tgg tac gtg gac ggc gtg gag gtg cac aac gcc<br>Glu Val Gln Phe Asn Trp Tyr Val Asp Gly Val Glu Val His Asn Ala<br>           290                  295                  300 | 912 |
| aag acc aag ccc cgg gag gaa cag ttc aac agc acc ttc cgg gtg gtg<br>Lys Thr Lys Pro Arg Glu Glu Gln Phe Asn Ser Thr Phe Arg Val Val<br>305                  310                  315                  320 | 960 |
| tcc gtg ctg acc gtg gtg cac cag gac tgg ctg aac ggc aaa gaa tac<br>Ser Val Leu Thr Val Val His Gln Asp Trp Leu Asn Gly Lys Glu Tyr<br>                 325                  330                  335 | 1008 |
| aag tgc aag gtg tcc aac aag ggc ctg cct gcc ccc atc gag aaa acc<br>Lys Cys Lys Val Ser Asn Lys Gly Leu Pro Ala Pro Ile Glu Lys Thr<br>           340                  345                  350 | 1056 |
| atc agc aag aca aag ggc cag ccc agg gaa ccc cag gtg tac acc ctg<br>Ile Ser Lys Thr Lys Gly Gln Pro Arg Glu Pro Gln Val Tyr Thr Leu<br>               355                  360                  365 | 1104 |
| ccc ccc agc cgg gag gaa atg acc aag aac cag gtg tcc ctg acc tgt<br>Pro Pro Ser Arg Glu Glu Met Thr Lys Asn Gln Val Ser Leu Thr Cys<br>370                  375                  380 | 1152 |
| ctg gtg aag ggc ttc tac ccc agc gac atc gcc gtg gag tgg gag agc<br>Leu Val Lys Gly Phe Tyr Pro Ser Asp Ile Ala Val Glu Trp Glu Ser<br>385                  390                  395                  400 | 1200 |

```
aac ggc cag ccc gag aac aac tac aag acc acc ccc ccc atg ctg gac      1248
Asn Gly Gln Pro Glu Asn Asn Tyr Lys Thr Thr Pro Pro Met Leu Asp
            405                 410                 415 agc gac ggc agc ttc ttc ctg tac agc aag ctg aca gtg gac aag agc      1296
Ser Asp Gly Ser Phe Phe Leu Tyr Ser Lys Leu Thr Val Asp Lys Ser
            420                 425                 430 cgg tgg cag cag ggc aac gtg ttc agc tgc agc gtg atg cac gag gcc      1344
Arg Trp Gln Gln Gly Asn Val Phe Ser Cys Ser Val Met His Glu Ala
435                 440                 445 ctg cac aac cac tac acc cag aag agc ctg agc ctg tcc ccc ggc aaa      1392
Leu His Asn His Tyr Thr Gln Lys Ser Leu Ser Leu Ser Pro Gly Lys
            450                 455                 460

<210> SEQ ID NO 77
<211> LENGTH: 464
<212> TYPE: PRT
<213> ORGANISM: Homo sapiens

<400> SEQUENCE: 77

Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Thr Tyr Ala Met His Trp Val Arg Gln Ala Pro Gly Lys Gly Leu
    50                  55                  60

Glu Trp Val Ser Asn Ile Ala Tyr Ser Gly Ser Val Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Arg Gly Pro Gly Met Gly Asn Met Asp Ile Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285
```

```
Glu Val Gln Phe Asn Trp Tyr Val Asp Gly Val Glu Val His Asn Ala
        290                 295                 300

Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
            340                 345                 350

Ile Ser Lys Thr Lys Gly Gln Pro Arg Glu Pro Gln Val Tyr Thr Leu
        355                 360                 365

Pro Pro Ser Arg Glu Glu Met Thr Lys Asn Gln Val Ser Leu Thr Cys
370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 78
<211> LENGTH: 5
<212> TYPE: PRT
<213> ORGANISM: Homo sapiens

<400> SEQUENCE: 78

Thr Tyr Ala Met His
1               5

<210> SEQ ID NO 79
<211> LENGTH: 17
<212> TYPE: PRT
<213> ORGANISM: Homo sapiens

<400> SEQUENCE: 79

Asn Ile Ala Tyr Ser Gly Ser Val Thr Tyr Tyr Ala Asp Ser Val Lys
1               5                   10                  15

Gly

<210> SEQ ID NO 80
<211> LENGTH: 10
<212> TYPE: PRT
<213> ORGANISM: Homo sapiens

<400> SEQUENCE: 80

Arg Gly Pro Gly Met Gly Asn Met Asp Ile
1               5                   10

<210> SEQ ID NO 81
<211> LENGTH: 708
<212> TYPE: DNA
<213> ORGANISM: Homo sapiens
<220> FEATURE:
<221> NAME/KEY: CDS
<222> LOCATION: (1)..(708)
<220> FEATURE:
<221> NAME/KEY: sig_peptide
<222> LOCATION: (1)..(57)
```

```
<220> FEATURE:
<221> NAME/KEY: V_region
<222> LOCATION: (58)..(399)
<220> FEATURE:
<221> NAME/KEY: misc_feature
<222> LOCATION: (124)..(165)
<223> OTHER INFORMATION: CDR1
<220> FEATURE:
<221> NAME/KEY: misc_feature
<222> LOCATION: (211)..(231)
<223> OTHER INFORMATION: CDR2
<220> FEATURE:
<221> NAME/KEY: misc_feature
<222> LOCATION: (328)..(360)
<223> OTHER INFORMATION: CDR3

<400> SEQUENCE: 81 atg gcc tgg gct ctg ctg ctc ctc acc ctc ctc act cag ggc aca gga     48
Met Ala Trp Ala Leu Leu Leu Leu Thr Leu Leu Thr Gln Gly Thr Gly
1               5                   10                  15 tcc tgg gct gat atc gca ctg acc cag cca gct tca gtg agc ggc tca     96
Ser Trp Ala Asp Ile Ala Leu Thr Gln Pro Ala Ser Val Ser Gly Ser
            20                  25                  30 cca ggt cag agc att acc atc tcg tgt acg ggt act agc agc gat gtt    144
Pro Gly Gln Ser Ile Thr Ile Ser Cys Thr Gly Thr Ser Ser Asp Val
        35                  40                  45 ggt gat tat aat tat gtg tct tgg tac cag cag cat ccc ggg aag gcg    192
Gly Asp Tyr Asn Tyr Val Ser Trp Tyr Gln Gln His Pro Gly Lys Ala
    50                  55                  60 ccg aaa ctt atg att tat tat gtt act aat cgt ccc tca ggc gtg agc    240
Pro Lys Leu Met Ile Tyr Tyr Val Thr Asn Arg Pro Ser Gly Val Ser
65                  70                  75                  80 aac cgt ttt agc gga tcc aaa agc ggc aac acc gcg agc ctg acc att    288
Asn Arg Phe Ser Gly Ser Lys Ser Gly Asn Thr Ala Ser Leu Thr Ile
                85                  90                  95 agc ggc ctg caa gcg gaa gac gaa gcg gat tat tat tgc cag tct tat    336
Ser Gly Leu Gln Ala Glu Asp Glu Ala Asp Tyr Tyr Cys Gln Ser Tyr
            100                 105                 110 gat act ggt tct ttt gct atg gtg ttt ggc ggc ggc acg aag tta acc    384
Asp Thr Gly Ser Phe Ala Met Val Phe Gly Gly Gly Thr Lys Leu Thr
        115                 120                 125 gtc cta ggt cag ccc aag gct gcc ccc tcg gtc act ctg ttc ccg ccc    432
Val Leu Gly Gln Pro Lys Ala Ala Pro Ser Val Thr Leu Phe Pro Pro
    130                 135                 140 tcc tct gag gag ctt caa gcc aac aag gcc aca ctg gtg tgt ctc ata    480
Ser Ser Glu Glu Leu Gln Ala Asn Lys Ala Thr Leu Val Cys Leu Ile
145                 150                 155                 160 agt gac ttc tac ccg gga gcc gtg aca gtg gcc tgg aag gca gat agc    528
Ser Asp Phe Tyr Pro Gly Ala Val Thr Val Ala Trp Lys Ala Asp Ser
                165                 170                 175 agc ccc gtc aag gcg gga gtg gag acc acc aca ccc tcc aaa caa agc    576
Ser Pro Val Lys Ala Gly Val Glu Thr Thr Thr Pro Ser Lys Gln Ser
            180                 185                 190 aac aac aag tac gcg gcc agc agc tat ctg agc ctg acg cct gag cag    624
Asn Asn Lys Tyr Ala Ala Ser Ser Tyr Leu Ser Leu Thr Pro Glu Gln
        195                 200                 205 tgg aag tcc cac aga agc tac agc tgc cag gtc acg cat gaa ggg agc    672
Trp Lys Ser His Arg Ser Tyr Ser Cys Gln Val Thr His Glu Gly Ser
    210                 215                 220 acc gtg gag aag aca gtg gcc cct aca gaa tgt tca                    708
Thr Val Glu Lys Thr Val Ala Pro Thr Glu Cys Ser
225                 230                 235
```

<210> SEQ ID NO 82
<211> LENGTH: 236
<212> TYPE: PRT
<213> ORGANISM: Homo sapiens

<400> SEQUENCE: 82

Met Ala Trp Ala Leu Leu Leu Leu Thr Leu Leu Thr Gln Gly Thr Gly
1               5                   10                  15

Ser Trp Ala Asp Ile Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
        35                  40                  45

Gly Asp Tyr Asn Tyr Val Ser Trp Tyr Gln Gln His Pro Gly Lys Ala
    50                  55                  60

Pro Lys Leu Met Ile Tyr Tyr Val Thr Asn Arg Pro Ser Gly Val Ser
65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Gln Ser Tyr
            100                 105                 110

Asp Thr Gly Ser Phe Ala Met Val Phe Gly Gly Gly Thr Lys Leu Thr
        115                 120                 125

Val Leu Gly Gln Pro Lys Ala Ala Pro Ser Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235

<210> SEQ ID NO 83
<211> LENGTH: 14
<212> TYPE: PRT
<213> ORGANISM: Homo sapiens

<400> SEQUENCE: 83

Thr Gly Thr Ser Ser Asp Val Gly Asp Tyr Asn Tyr Val Ser
1               5                   10

<210> SEQ ID NO 84
<211> LENGTH: 7
<212> TYPE: PRT
<213> ORGANISM: Homo sapiens

<400> SEQUENCE: 84

Tyr Val Thr Asn Arg Pro Ser
1               5

<210> SEQ ID NO 85
<211> LENGTH: 11
<212> TYPE: PRT
<213> ORGANISM: Homo sapiens

<400> SEQUENCE: 85

Gln Ser Tyr Asp Thr Gly Ser Phe Ala Met Val
1               5                   10

<210> SEQ ID NO 86
<211> LENGTH: 711
<212> TYPE: DNA
<213> ORGANISM: Homo sapiens
<220> FEATURE:
<221> NAME/KEY: CDS
<222> LOCATION: (1)..(711)
<220> FEATURE:
<221> NAME/KEY: sig_peptide
<222> LOCATION: (1)..(57)
<220> FEATURE:
<221> NAME/KEY: V_region
<222> LOCATION: (58)..(402)
<220> FEATURE:
<221> NAME/KEY: misc_feature
<222> LOCATION: (124)..(165)
<223> OTHER INFORMATION: CDR1
<220> FEATURE:
<221> NAME/KEY: misc_feature
<222> LOCATION: (211)..(231)
<223> OTHER INFORMATION: CDR2
<220> FEATURE:
<221> NAME/KEY: misc_feature
<222> LOCATION: (328)..(363)
<223> OTHER INFORMATION: CDR3

<400> SEQUENCE: 86

| | | | | | | | | | | | | | | | | |
|---|---|---|---|---|---|---|---|---|---|---|---|---|---|---|---|---|---|
| atg | gcc | tgg | gct | ctg | ctg | ctc | ctc | acc | ctc | ctc | act | cag | ggc | aca | gga | | 48 |
| Met | Ala | Trp | Ala | Leu | Leu | Leu | Leu | Thr | Leu | Leu | Thr | Gln | Gly | Thr | Gly | | |
| 1 | | | | 5 | | | | | 10 | | | | | 15 | | | |
| tcc | tgg | gct | gat | atc | gca | ctg | acc | cag | cca | gct | tca | gtg | agc | ggc | tca | | 96 |
| Ser | Trp | Ala | Asp | Ile | Ala | Leu | Thr | Gln | Pro | Ala | Ser | Val | Ser | Gly | Ser | | |
| | | 20 | | | | | 25 | | | | | 30 | | | | | |
| cca | ggt | cag | agc | att | acc | atc | tcg | tgt | acg | ggt | act | agc | agc | gat | gtt | | 144 |
| Pro | Gly | Gln | Ser | Ile | Thr | Ile | Ser | Cys | Thr | Gly | Thr | Ser | Ser | Asp | Val | | |
| | | | 35 | | | | | 40 | | | | | 45 | | | | |
| ggt | gat | tat | aat | tat | gtg | tct | tgg | tac | cag | cag | cat | ccc | ggg | aag | gcg | | 192 |
| Gly | Asp | Tyr | Asn | Tyr | Val | Ser | Trp | Tyr | Gln | Gln | His | Pro | Gly | Lys | Ala | | |
| 50 | | | | | 55 | | | | | 60 | | | | | | | |
| ccg | aaa | ctt | atg | att | tat | tat | gtt | act | aat | cgt | ccc | tca | ggc | gtg | agc | | 240 |
| Pro | Lys | Leu | Met | Ile | Tyr | Tyr | Val | Thr | Asn | Arg | Pro | Ser | Gly | Val | Ser | | |
| 65 | | | | 70 | | | | | 75 | | | | | 80 | | | |
| aac | cgt | ttt | agc | gga | tcc | aaa | agc | ggc | aac | acc | gcg | agc | ctg | acc | att | | 288 |
| Asn | Arg | Phe | Ser | Gly | Ser | Lys | Ser | Gly | Asn | Thr | Ala | Ser | Leu | Thr | Ile | | |
| | | | | 85 | | | | | 90 | | | | | 95 | | | |
| agc | ggc | ctg | caa | gcg | gaa | gac | gaa | gcg | gat | tat | tat | tgc | cag | tct | tat | | 336 |
| Ser | Gly | Leu | Gln | Ala | Glu | Asp | Glu | Ala | Asp | Tyr | Tyr | Cys | Gln | Ser | Tyr | | |
| | | | 100 | | | | | 105 | | | | | 110 | | | | |
| gct | cct | ctt | cct | tct | tct | cat | att | gtg | ttt | ggc | ggc | ggc | acg | aag | tta | | 384 |
| Ala | Pro | Leu | Pro | Ser | Ser | His | Ile | Val | Phe | Gly | Gly | Gly | Thr | Lys | Leu | | |
| | | | | 115 | | | | | 120 | | | | | 125 | | | |
| acc | gtc | cta | ggt | cag | ccc | aag | gct | gcc | ccc | tcg | gtc | act | ctg | ttc | ccg | | 432 |
| Thr | Val | Leu | Gly | Gln | Pro | Lys | Ala | Ala | Pro | Ser | Val | Thr | Leu | Phe | Pro | | |
| | | | 130 | | | | | 135 | | | | | 140 | | | | |
| ccc | tcc | tct | gag | gag | ctt | caa | gcc | aac | aag | gcc | aca | ctg | gtg | tgt | ctc | | 480 |
| Pro | Ser | Ser | Glu | Glu | Leu | Gln | Ala | Asn | Lys | Ala | Thr | Leu | Val | Cys | Leu | | |
| 145 | | | | | 150 | | | | | 155 | | | | | 160 | | |
| ata | agt | gac | ttc | tac | ccg | gga | gcc | gtg | aca | gtg | gcc | tgg | aag | gca | gat | | 528 |
| Ile | Ser | Asp | Phe | Tyr | Pro | Gly | Ala | Val | Thr | Val | Ala | Trp | Lys | Ala | Asp | | |
| | | | | 165 | | | | | 170 | | | | | 175 | | | |

```
agc agc ccc gtc aag gcg gga gtg gag acc acc aca ccc tcc aaa caa      576
Ser Ser Pro Val Lys Ala Gly Val Glu Thr Thr Thr Pro Ser Lys Gln
            180                 185                 190 agc aac aac aag tac gcg gcc agc agc tat ctg agc ctg acg cct gag      624
Ser Asn Asn Lys Tyr Ala Ala Ser Ser Tyr Leu Ser Leu Thr Pro Glu
            195                 200                 205 cag tgg aag tcc cac aga agc tac agc tgc cag gtc acg cat gaa ggg      672
Gln Trp Lys Ser His Arg Ser Tyr Ser Cys Gln Val Thr His Glu Gly
            210                 215                 220 agc acc gtg gag aag aca gtg gcc cct aca gaa tgt tca                  711
Ser Thr Val Glu Lys Thr Val Ala Pro Thr Glu Cys Ser
225                 230                 235

<210> SEQ ID NO 87
<211> LENGTH: 237
<212> TYPE: PRT
<213> ORGANISM: Homo sapiens

<400> SEQUENCE: 87

Met Ala Trp Ala Leu Leu Leu Thr Leu Leu Thr Gln Gly Thr Gly
1               5                   10                  15

Ser Trp Ala Asp Ile Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
        35                  40                  45

Gly Asp Tyr Asn Tyr Val Ser Trp Tyr Gln Gln His Pro Gly Lys Ala
    50                  55                  60

Pro Lys Leu Met Ile Tyr Tyr Val Thr Asn Arg Pro Ser Gly Val Ser
65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Gln Ser Tyr
            100                 105                 110

Ala Pro Leu Pro Ser Ser His Ile Val Phe Gly Gly Thr Lys Leu
        115                 120                 125

Thr Val Leu Gly Gln Pro Lys Ala Ala Pro Ser Val Thr Leu Phe Pro
    130                 135                 140

Pro Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
            195                 200                 205

Gln Trp Lys Ser His Arg Ser Tyr Ser Cys Gln Val Thr His Glu Gly
        210                 215                 220

Ser Thr Val Glu Lys Thr Val Ala Pro Thr Glu Cys Ser
225                 230                 235

<210> SEQ ID NO 88
<211> LENGTH: 14
<212> TYPE: PRT
<213> ORGANISM: Homo sapiens

<400> SEQUENCE: 88

Thr Gly Thr Ser Ser Asp Val Gly Asp Tyr Asn Tyr Val Ser
1               5                   10
```

<210> SEQ ID NO 89
<211> LENGTH: 7
<212> TYPE: PRT
<213> ORGANISM: Homo sapiens

<400> SEQUENCE: 89

Tyr Val Thr Asn Arg Pro Ser
1               5

<210> SEQ ID NO 90
<211> LENGTH: 12
<212> TYPE: PRT
<213> ORGANISM: Homo sapiens

<400> SEQUENCE: 90

Gln Ser Tyr Ala Pro Leu Pro Ser Ser His Ile Val
1               5                   10

<210> SEQ ID NO 91
<211> LENGTH: 1392
<212> TYPE: DNA
<213> ORGANISM: Homo sapiens
<220> FEATURE:
<221> NAME/KEY: CDS
<222> LOCATION: (1)..(1392)
<220> FEATURE:
<221> NAME/KEY: sig_peptide
<222> LOCATION: (1)..(57)
<220> FEATURE:
<221> NAME/KEY: V_region
<222> LOCATION: (58)..(414)
<220> FEATURE:
<221> NAME/KEY: misc_feature
<222> LOCATION: (148)..(162)
<223> OTHER INFORMATION: CDR1
<220> FEATURE:
<221> NAME/KEY: misc_feature
<222> LOCATION: (205)..(255)
<223> OTHER INFORMATION: CDR2
<220> FEATURE:
<221> NAME/KEY: misc_feature
<222> LOCATION: (352)..(381)
<223> OTHER INFORMATION: CDR3

<400> SEQUENCE: 91

| atg | aaa | cac | ctg | tgg | ttc | ttc | ctc | ctg | ctg | gtg | gca | gct | ccc | aga | tgg | 48 |
| Met | Lys | His | Leu | Trp | Phe | Phe | Leu | Leu | Leu | Val | Ala | Ala | Pro | Arg | Trp |
| 1 | | | | 5 | | | | | 10 | | | | | 15 | | |

| gtc | ctg | tcc | cag | gtg | caa | ttg | gtg | gaa | agc | ggc | ggc | ggc | ctg | gtg | caa | 96 |
| Val | Leu | Ser | Gln | Val | Gln | Leu | Val | Glu | Ser | Gly | Gly | Gly | Leu | Val | Gln |
| | | | 20 | | | | | 25 | | | | | 30 | | | |

| ccg | ggc | ggc | agc | ctg | cgt | ctg | agc | tgc | gcg | gcc | tcc | gga | ttt | acc | ttt | 144 |
| Pro | Gly | Gly | Ser | Leu | Arg | Leu | Ser | Cys | Ala | Ala | Ser | Gly | Phe | Thr | Phe |
| | | 35 | | | | | 40 | | | | | 45 | | | | |

| act | act | tat | gct | atg | cat | tgg | gtg | cgc | caa | gcc | cct | ggg | aag | ggt | ctc | 192 |
| Thr | Thr | Tyr | Ala | Met | His | Trp | Val | Arg | Gln | Ala | Pro | Gly | Lys | Gly | Leu |
| | 50 | | | | | 55 | | | | | 60 | | | | | |

| gag | tgg | gtg | agc | act | atc | ttt | ggt | tct | tct | agc | tct | acc | tat | tat | gcg | 240 |
| Glu | Trp | Val | Ser | Thr | Ile | Phe | Gly | Ser | Ser | Ser | Ser | Thr | Tyr | Tyr | Ala |
| 65 | | | | | 70 | | | | | 75 | | | | | 80 | |

| gat | agc | gtg | aaa | ggc | cgt | ttt | acc | att | tca | cgt | gat | aat | tcg | aaa | aac | 288 |
| Asp | Ser | Val | Lys | Gly | Arg | Phe | Thr | Ile | Ser | Arg | Asp | Asn | Ser | Lys | Asn |
| | | | | 85 | | | | | 90 | | | | | 95 | | |

| acc | ctg | tat | ctg | caa | atg | aac | agc | ctg | cgt | gcg | gaa | gat | acg | gcc | gtg | 336 |
| Thr | Leu | Tyr | Leu | Gln | Met | Asn | Ser | Leu | Arg | Ala | Glu | Asp | Thr | Ala | Val |
| | | | 100 | | | | | 105 | | | | | 110 | | | |

| | | |
|---|---|---|
| tat tat tgc gcg cgt cgt ggt cct ggt atg ggt aat atg gat att tgg<br>Tyr Tyr Cys Ala Arg Arg Gly Pro Gly Met Gly Asn Met Asp Ile Trp<br>            115                 120                 125 | 384 | |
| ggc caa ggc acc ctg gtg acg gtt agc tca gcc agc acc aag ggc ccc<br>Gly Gln Gly Thr Leu Val Thr Val Ser Ser Ala Ser Thr Lys Gly Pro<br>        130                 135                 140 | 432 | |
| agc gtg ttc ccc ctg gcc ccc tgc agc aga agc acc agc gag agc aca<br>Ser Val Phe Pro Leu Ala Pro Cys Ser Arg Ser Thr Ser Glu Ser Thr<br>145                 150                 155                 160 | 480 | |
| gcc gcc ctg ggc tgc ctg gtg aag gac tac ttc ccc gag ccc gtg acc<br>Ala Ala Leu Gly Cys Leu Val Lys Asp Tyr Phe Pro Glu Pro Val Thr<br>                165                 170                 175 | 528 | |
| gtg agc tgg aac agc gga gcc ctg acc agc ggc gtg cac acc ttc ccc<br>Val Ser Trp Asn Ser Gly Ala Leu Thr Ser Gly Val His Thr Phe Pro<br>            180                 185                 190 | 576 | |
| gcc gtg ctg cag agc agc ggc ctg tac agc ctg agc agc gtg gtg acc<br>Ala Val Leu Gln Ser Ser Gly Leu Tyr Ser Leu Ser Ser Val Val Thr<br>        195                 200                 205 | 624 | |
| gtg ccc agc agc aac ttc ggc acc cag acc tac acc tgc aac gtg gac<br>Val Pro Ser Ser Asn Phe Gly Thr Gln Thr Tyr Thr Cys Asn Val Asp<br>    210                 215                 220 | 672 | |
| cac aag ccc agc aac acc aag gtg gac aag acc gtg gag cgg aag tgc<br>His Lys Pro Ser Asn Thr Lys Val Asp Lys Thr Val Glu Arg Lys Cys<br>225                 230                 235                 240 | 720 | |
| tgc gtg gag tgc ccc ccc tgc cct gcc cct cct gtg gcc gga ccc tcc<br>Cys Val Glu Cys Pro Pro Cys Pro Ala Pro Pro Val Ala Gly Pro Ser<br>                245                 250                 255 | 768 | |
| gtg ttc ctg ttc ccc ccc aag ccc aag gac acc ctg atg atc agc cgg<br>Val Phe Leu Phe Pro Pro Lys Pro Lys Asp Thr Leu Met Ile Ser Arg<br>            260                 265                 270 | 816 | |
| acc ccc gag gtg acc tgc gtg gtg gtg gac gtg agc cac gag gac ccc<br>Thr Pro Glu Val Thr Cys Val Val Val Asp Val Ser His Glu Asp Pro<br>        275                 280                 285 | 864 | |
| gag gtg cag ttt aat tgg tac gtg gac ggc gtg gag gtg cac aac gcc<br>Glu Val Gln Phe Asn Trp Tyr Val Asp Gly Val Glu Val His Asn Ala<br>    290                 295                 300 | 912 | |
| aag acc aag ccc cgg gag gaa cag ttc aac agc acc ttc cgg gtg gtg<br>Lys Thr Lys Pro Arg Glu Glu Gln Phe Asn Ser Thr Phe Arg Val Val<br>305                 310                 315                 320 | 960 | |
| tcc gtg ctg acc gtg gtg cac cag gac tgg ctg aac ggc aaa gaa tac<br>Ser Val Leu Thr Val Val His Gln Asp Trp Leu Asn Gly Lys Glu Tyr<br>                325                 330                 335 | 1008 | |
| aag tgc aag gtg tcc aac aag ggc ctg cct gcc ccc atc gag aaa acc<br>Lys Cys Lys Val Ser Asn Lys Gly Leu Pro Ala Pro Ile Glu Lys Thr<br>            340                 345                 350 | 1056 | |
| atc agc aag aca aag ggc cag ccc agg gaa ccc cag gtg tac acc ctg<br>Ile Ser Lys Thr Lys Gly Gln Pro Arg Glu Pro Gln Val Tyr Thr Leu<br>        355                 360                 365 | 1104 | |
| ccc ccc agc cgg gag gaa atg acc aag aac cag gtg tcc ctg acc tgt<br>Pro Pro Ser Arg Glu Glu Met Thr Lys Asn Gln Val Ser Leu Thr Cys<br>    370                 375                 380 | 1152 | |
| ctg gtg aag ggc ttc tac ccc agc gac atc gcc gtg gag tgg gag agc<br>Leu Val Lys Gly Phe Tyr Pro Ser Asp Ile Ala Val Glu Trp Glu Ser<br>385                 390                 395                 400 | 1200 | |
| aac ggc cag ccc gag aac aac tac aag acc acc ccc ccc atg ctg gac<br>Asn Gly Gln Pro Glu Asn Asn Tyr Lys Thr Thr Pro Pro Met Leu Asp<br>                405                 410                 415 | 1248 | |
| agc gac ggc agc ttc ttc ctg tac agc aag ctg aca gtg gac aag agc<br>Ser Asp Gly Ser Phe Phe Leu Tyr Ser Lys Leu Thr Val Asp Lys Ser | 1296 | |

```
                420              425              430
cgg tgg cag cag ggc aac gtg ttc agc tgc agc gtg atg cac gag gcc    1344
Arg Trp Gln Gln Gly Asn Val Phe Ser Cys Ser Val Met His Glu Ala
        435              440              445 ctg cac aac cac tac acc cag aag agc ctg agc ctg tcc ccc ggc aaa    1392
Leu His Asn His Tyr Thr Gln Lys Ser Leu Ser Leu Ser Pro Gly Lys
450              455              460
```

<210> SEQ ID NO 92
<211> LENGTH: 464
<212> TYPE: PRT
<213> ORGANISM: Homo sapiens

<400> SEQUENCE: 92

```
Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Thr Thr Tyr Ala Met His Trp Val Arg Gln Ala Pro Gly Lys Gly Leu
    50                  55                  60

Glu Trp Val Ser Thr Ile Phe Gly Ser Ser Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Arg Gly Pro Gly Met Gly Asn Met Asp Ile Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
```

```
                   325                 330                 335
Lys Cys Lys Val Ser Asn Lys Gly Leu Pro Ala Pro Ile Glu Lys Thr
                340                 345                 350

Ile Ser Lys Thr Lys Gly Gln Pro Arg Glu Pro Gln Val Tyr Thr Leu
            355                 360                 365

Pro Pro Ser Arg Glu Glu Met Thr Lys Asn Gln Val Ser Leu Thr Cys
        370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 93
<211> LENGTH: 5
<212> TYPE: PRT
<213> ORGANISM: Homo sapiens

<400> SEQUENCE: 93

Thr Tyr Ala Met His
1               5

<210> SEQ ID NO 94
<211> LENGTH: 17
<212> TYPE: PRT
<213> ORGANISM: Homo sapiens

<400> SEQUENCE: 94

Thr Ile Phe Gly Ser Ser Ser Thr Tyr Tyr Ala Asp Ser Val Lys
1               5                   10                  15

Gly

<210> SEQ ID NO 95
<211> LENGTH: 10
<212> TYPE: PRT
<213> ORGANISM: Homo sapiens

<400> SEQUENCE: 95

Arg Gly Pro Gly Met Gly Asn Met Asp Ile
1               5                   10

<210> SEQ ID NO 96
<211> LENGTH: 708
<212> TYPE: DNA
<213> ORGANISM: Homo sapiens
<220> FEATURE:
<221> NAME/KEY: CDS
<222> LOCATION: (1)..(708)
<220> FEATURE:
<221> NAME/KEY: sig_peptide
<222> LOCATION: (1)..(57)
<220> FEATURE:
<221> NAME/KEY: V_region
<222> LOCATION: (58)..(399)
<220> FEATURE:
<221> NAME/KEY: misc_feature
<222> LOCATION: (124)..(165)
<223> OTHER INFORMATION: CDR1
```

<220> FEATURE:
<221> NAME/KEY: misc_feature
<222> LOCATION: (211)..(231)
<223> OTHER INFORMATION: CDR2
<220> FEATURE:
<221> NAME/KEY: misc_feature
<222> LOCATION: (328)..(360)
<223> OTHER INFORMATION: CDR3

<400> SEQUENCE: 96

| | | | | | | | | | | | | | | | | |
|---|---|---|---|---|---|---|---|---|---|---|---|---|---|---|---|---|
| atg | gcc | tgg | gct | ctg | ctg | ctc | ctc | acc | ctc | ctc | act | cag | ggc | aca | gga | 48 |
| Met | Ala | Trp | Ala | Leu | Leu | Leu | Leu | Thr | Leu | Leu | Thr | Gln | Gly | Thr | Gly | |
| 1 | | | | 5 | | | | | 10 | | | | | 15 | | |
| tcc | tgg | gct | gat | atc | gca | ctg | acc | cag | cca | gct | tca | gtg | agc | ggc | tca | 96 |
| Ser | Trp | Ala | Asp | Ile | Ala | Leu | Thr | Gln | Pro | Ala | Ser | Val | Ser | Gly | Ser | |
| | | | 20 | | | | | 25 | | | | | 30 | | | |
| cca | ggt | cag | agc | att | acc | atc | tcg | tgt | acg | ggt | act | agc | agc | gat | gtt | 144 |
| Pro | Gly | Gln | Ser | Ile | Thr | Ile | Ser | Cys | Thr | Gly | Thr | Ser | Ser | Asp | Val | |
| | | 35 | | | | | 40 | | | | | 45 | | | | |
| ggt | gat | tat | aat | tat | gtg | tct | tgg | tac | cag | cag | cat | ccc | ggg | aag | gcg | 192 |
| Gly | Asp | Tyr | Asn | Tyr | Val | Ser | Trp | Tyr | Gln | Gln | His | Pro | Gly | Lys | Ala | |
| | 50 | | | | | 55 | | | | | 60 | | | | | |
| ccg | aaa | ctt | atg | att | tat | tat | gtt | act | aat | cgt | ccc | tca | ggc | gtg | agc | 240 |
| Pro | Lys | Leu | Met | Ile | Tyr | Tyr | Val | Thr | Asn | Arg | Pro | Ser | Gly | Val | Ser | |
| 65 | | | | 70 | | | | | 75 | | | | | 80 | | |
| aac | cgt | ttt | agc | gga | tcc | aaa | agc | ggc | aac | acc | gcg | agc | ctg | acc | att | 288 |
| Asn | Arg | Phe | Ser | Gly | Ser | Lys | Ser | Gly | Asn | Thr | Ala | Ser | Leu | Thr | Ile | |
| | | | | 85 | | | | | 90 | | | | | 95 | | |
| agc | ggc | ctg | caa | gcg | gaa | gac | gaa | gcg | gat | tat | tat | tgc | cag | tct | tat | 336 |
| Ser | Gly | Leu | Gln | Ala | Glu | Asp | Glu | Ala | Asp | Tyr | Tyr | Cys | Gln | Ser | Tyr | |
| | | | 100 | | | | | 105 | | | | | 110 | | | |
| gct | ggt | gct | tct | ttt | aat | ctt | gtg | ttt | ggc | ggc | ggc | acg | aag | tta | acc | 384 |
| Ala | Gly | Ala | Ser | Phe | Asn | Leu | Val | Phe | Gly | Gly | Gly | Thr | Lys | Leu | Thr | |
| | | 115 | | | | | 120 | | | | | 125 | | | | |
| gtc | cta | ggt | cag | ccc | aag | gct | gcc | ccc | tcg | gtc | act | ctg | ttc | ccg | ccc | 432 |
| Val | Leu | Gly | Gln | Pro | Lys | Ala | Ala | Pro | Ser | Val | Thr | Leu | Phe | Pro | Pro | |
| | 130 | | | | | 135 | | | | | 140 | | | | | |
| tcc | tct | gag | gag | ctt | caa | gcc | aac | aag | gcc | aca | ctg | gtg | tgt | ctc | ata | 480 |
| Ser | Ser | Glu | Glu | Leu | Gln | Ala | Asn | Lys | Ala | Thr | Leu | Val | Cys | Leu | Ile | |
| 145 | | | | 150 | | | | | 155 | | | | | 160 | | |
| agt | gac | ttc | tac | ccg | gga | gcc | gtg | aca | gtg | gcc | tgg | aag | gca | gat | agc | 528 |
| Ser | Asp | Phe | Tyr | Pro | Gly | Ala | Val | Thr | Val | Ala | Trp | Lys | Ala | Asp | Ser | |
| | | | | 165 | | | | | 170 | | | | | 175 | | |
| agc | ccc | gtc | aag | gcg | gga | gtg | gag | acc | acc | aca | ccc | tcc | aaa | caa | agc | 576 |
| Ser | Pro | Val | Lys | Ala | Gly | Val | Glu | Thr | Thr | Thr | Pro | Ser | Lys | Gln | Ser | |
| | | | 180 | | | | | 185 | | | | | 190 | | | |
| aac | aac | aag | tac | gcg | gcc | agc | agc | tat | ctg | agc | ctg | acg | cct | gag | cag | 624 |
| Asn | Asn | Lys | Tyr | Ala | Ala | Ser | Ser | Tyr | Leu | Ser | Leu | Thr | Pro | Glu | Gln | |
| | | 195 | | | | | 200 | | | | | 205 | | | | |
| tgg | aag | tcc | cac | aga | agc | tac | agc | tgc | cag | gtc | acg | cat | gaa | ggg | agc | 672 |
| Trp | Lys | Ser | His | Arg | Ser | Tyr | Ser | Cys | Gln | Val | Thr | His | Glu | Gly | Ser | |
| | 210 | | | | | 215 | | | | | 220 | | | | | |
| acc | gtg | gag | aag | aca | gtg | gcc | cct | aca | gaa | tgt | tca | | | | | 708 |
| Thr | Val | Glu | Lys | Thr | Val | Ala | Pro | Thr | Glu | Cys | Ser | | | | | |
| 225 | | | | 230 | | | | | 235 | | | | | | | |

<210> SEQ ID NO 97
<211> LENGTH: 236
<212> TYPE: PRT
<213> ORGANISM: Homo sapiens

<400> SEQUENCE: 97

```
Met Ala Trp Ala Leu Leu Leu Thr Leu Thr Gln Gly Thr Gly
1               5                   10                  15

Ser Trp Ala Asp Ile Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
        35                  40                  45

Gly Asp Tyr Asn Tyr Val Ser Trp Tyr Gln Gln His Pro Gly Lys Ala
50                  55                  60

Pro Lys Leu Met Ile Tyr Tyr Val Thr Asn Arg Pro Ser Gly Val Ser
65                  70                  75                  80

Asn Arg Phe Ser Gly Ser Lys Ser Gly Asn Thr Ala Ser Leu Thr Ile
                85                  90                  95

Ser Gly Leu Gln Ala Glu Asp Glu Ala Asp Tyr Tyr Cys Gln Ser Tyr
            100                 105                 110

Ala Gly Ala Ser Phe Asn Leu Val Phe Gly Gly Gly Thr Lys Leu Thr
            115                 120                 125

Val Leu Gly Gln Pro Lys Ala Ala Pro Ser Val Thr Leu Phe Pro Pro
        130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
            195                 200                 205

Trp Lys Ser His Arg Ser Tyr Ser Cys Gln Val Thr His Glu Gly Ser
        210                 215                 220

Thr Val Glu Lys Thr Val Ala Pro Thr Glu Cys Ser
225                 230                 235

<210> SEQ ID NO 98
<211> LENGTH: 14
<212> TYPE: PRT
<213> ORGANISM: Homo sapiens

<400> SEQUENCE: 98

Thr Gly Thr Ser Ser Asp Val Gly Asp Tyr Asn Tyr Val Ser
1               5                   10

<210> SEQ ID NO 99
<211> LENGTH: 7
<212> TYPE: PRT
<213> ORGANISM: Homo sapiens

<400> SEQUENCE: 99

Tyr Val Thr Asn Arg Pro Ser
1               5

<210> SEQ ID NO 100
<211> LENGTH: 11
<212> TYPE: PRT
<213> ORGANISM: Homo sapiens

<400> SEQUENCE: 100

Gln Ser Tyr Ala Gly Ala Ser Phe Asn Leu Val
1               5                   10
```

```
<210> SEQ ID NO 101
<211> LENGTH: 1398
<212> TYPE: DNA
<213> ORGANISM: Homo sapiens
<220> FEATURE:
<221> NAME/KEY: CDS
<222> LOCATION: (1)..(1398)
<220> FEATURE:
<221> NAME/KEY: sig_peptide
<222> LOCATION: (1)..(57)
<220> FEATURE:
<221> NAME/KEY: V_region
<222> LOCATION: (58)..(420)
<220> FEATURE:
<221> NAME/KEY: misc_feature
<222> LOCATION: (148)..(162)
<223> OTHER INFORMATION: CDR1
<220> FEATURE:
<221> NAME/KEY: misc_feature
<222> LOCATION: (205)..(261)
<223> OTHER INFORMATION: CDR2
<220> FEATURE:
<221> NAME/KEY: misc_feature
<222> LOCATION: (358)..(387)
<223> OTHER INFORMATION: CDR3

<400> SEQUENCE: 101 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtc ctg tcc cag gtg caa ttg gtg gaa agc ggc ggc ggc ctg gtg caa      96
Val Leu Ser Gln Val Gln Leu Val Glu Ser Gly Gly Gly Leu Val Gln
            20                  25                  30 ccg ggc ggc agc ctg cgt ctg agc tgc gcg gcc tcc gga ttt acc ttt     144
Pro Gly Gly Ser Leu Arg Leu Ser Cys Ala Ala Ser Gly Phe Thr Phe
        35                  40                  45 act act tat gct atg cat tgg gtg cgc caa gcc cct ggg aag ggt ctc     192
Thr Thr Tyr Ala Met His Trp Val Arg Gln Ala Pro Gly Lys Gly Leu
    50                  55                  60 gag tgg gtg agc act att gag att aag gag gct ggt tat gct act aat     240
Glu Trp Val Ser Thr Ile Glu Ile Lys Glu Ala Gly Tyr Ala Thr Asn
65                  70                  75                  80 tat gct gct ggt gtt aag ggt cgt ttt acc att tca cgt gat aat tcg     288
Tyr Ala Ala Gly Val Lys Gly Arg Phe Thr Ile Ser Arg Asp Asn Ser
                85                  90                  95 aaa aac acc ctg tat ctg caa atg aac agc ctg cgt gcg gaa gat acg     336
Lys Asn Thr Leu Tyr Leu Gln Met Asn Ser Leu Arg Ala Glu Asp Thr
            100                 105                 110 gcc gtg tat tat tgc gcg cgt cgt ggt cct ggt atg ggt aat atg gat     384
Ala Val Tyr Tyr Cys Ala Arg Arg Gly Pro Gly Met Gly Asn Met Asp
        115                 120                 125 att tgg ggc caa ggc acc ctg gtg acg gtt agc tca gcc agc acc aag     432
Ile Trp Gly Gln Gly Thr Leu Val Thr Val Ser Ser Ala Ser Thr Lys
    130                 135                 140 ggc ccc agc gtg ttc ccc ctg gcc ccc tgc agc aga agc acc agc gag     480
Gly Pro Ser Val Phe Pro Leu Ala Pro Cys Ser Arg Ser Thr Ser Glu
145                 150                 155                 160 agc aca gcc gcc ctg ggc tgc ctg gtg aag gac tac ttc ccc gag ccc     528
Ser Thr Ala Ala Leu Gly Cys Leu Val Lys Asp Tyr Phe Pro Glu Pro
                165                 170                 175 gtg acc gtg agc tgg aac agc gga gcc ctg acc agc ggc gtg cac acc     576
Val Thr Val Ser Trp Asn Ser Gly Ala Leu Thr Ser Gly Val His Thr
            180                 185                 190 ttc ccc gcc gtg ctg cag agc agc ggc ctg tac agc ctg agc agc gtg     624
Phe Pro Ala Val Leu Gln Ser Ser Gly Leu Tyr Ser Leu Ser Ser Val
        195                 200                 205
```

```
gtg acc gtg ccc agc agc aac ttc ggc acc cag acc tac acc tgc aac      672
Val Thr Val Pro Ser Ser Asn Phe Gly Thr Gln Thr Tyr Thr Cys Asn
    210                 215                 220 gtg gac cac aag ccc agc aac acc aag gtg gac aag acc gtg gag cgg      720
Val Asp His Lys Pro Ser Asn Thr Lys Val Asp Lys Thr Val Glu Arg
225                 230                 235                 240 aag tgc tgc gtg gag tgc ccc ccc tgc cct gcc cct cct gtg gcc gga      768
Lys Cys Cys Val Glu Cys Pro Pro Cys Pro Ala Pro Pro Val Ala Gly
                245                 250                 255 ccc tcc gtg ttc ctg ttc ccc ccc aag ccc aag gac acc ctg atg atc      816
Pro Ser Val Phe Leu Phe Pro Pro Lys Pro Lys Asp Thr Leu Met Ile
                260                 265                 270 agc cgg acc ccc gag gtg acc tgc gtg gtg gtg gac gtg agc cac gag      864
Ser Arg Thr Pro Glu Val Thr Cys Val Val Val Asp Val Ser His Glu
            275                 280                 285 gac ccc gag gtg cag ttt aat tgg tac gtg gac ggc gtg gag gtg cac      912
Asp Pro Glu Val Gln Phe Asn Trp Tyr Val Asp Gly Val Glu Val His
290                 295                 300 aac gcc aag acc aag ccc cgg gag gaa cag ttc aac agc acc ttc cgg      960
Asn Ala Lys Thr Lys Pro Arg Glu Glu Gln Phe Asn Ser Thr Phe Arg
305                 310                 315                 320 gtg gtg tcc gtg ctg acc gtg gtg cac cag gac tgg ctg aac ggc aaa     1008
Val Val Ser Val Leu Thr Val Val His Gln Asp Trp Leu Asn Gly Lys
                325                 330                 335 gaa tac aag tgc aag gtg tcc aac aag ggc ctg cct gcc ccc atc gag     1056
Glu Tyr Lys Cys Lys Val Ser Asn Lys Gly Leu Pro Ala Pro Ile Glu
                340                 345                 350 aaa acc atc agc aag aca aag ggc cag ccc agg gaa ccc cag gtg tac     1104
Lys Thr Ile Ser Lys Thr Lys Gly Gln Pro Arg Glu Pro Gln Val Tyr
            355                 360                 365 acc ctg ccc ccc agc cgg gag gaa atg acc aag aac cag gtg tcc ctg     1152
Thr Leu Pro Pro Ser Arg Glu Glu Met Thr Lys Asn Gln Val Ser Leu
370                 375                 380 acc tgt ctg gtg aag ggc ttc tac ccc agc gac atc gcc gtg gag tgg     1200
Thr Cys Leu Val Lys Gly Phe Tyr Pro Ser Asp Ile Ala Val Glu Trp
385                 390                 395                 400 gag agc aac ggc cag ccc gag aac aac tac aag acc acc ccc ccc atg     1248
Glu Ser Asn Gly Gln Pro Glu Asn Asn Tyr Lys Thr Thr Pro Pro Met
                405                 410                 415 ctg gac agc gac ggc agc ttc ttc ctg tac agc aag ctg aca gtg gac     1296
Leu Asp Ser Asp Gly Ser Phe Phe Leu Tyr Ser Lys Leu Thr Val Asp
                420                 425                 430 aag agc cgg tgg cag cag ggc aac gtg ttc agc tgc agc gtg atg cac     1344
Lys Ser Arg Trp Gln Gln Gly Asn Val Phe Ser Cys Ser Val Met His
            435                 440                 445 gag gcc ctg cac aac cac tac acc cag aag agc ctg agc ctg tcc ccc     1392
Glu Ala Leu His Asn His Tyr Thr Gln Lys Ser Leu Ser Leu Ser Pro
        450                 455                 460 ggc aaa                                                              1398
Gly Lys
465

<210> SEQ ID NO 102
<211> LENGTH: 466
<212> TYPE: PRT
<213> ORGANISM: Homo sapiens

<400> SEQUENCE: 102

Met Lys His Leu Trp Phe Phe Leu Leu Leu Val Ala Ala Pro Arg Trp
1               5                   10                  15
```

```
Val Leu Ser Gln Val Gln Leu Val Glu Ser Gly Gly Leu Val Gln
            20                  25                  30

Pro Gly Gly Ser Leu Arg Leu Ser Cys Ala Ala Ser Gly Phe Thr Phe
                35                  40                  45

Thr Thr Tyr Ala Met His Trp Val Arg Gln Ala Pro Gly Lys Gly Leu
    50                  55                  60

Glu Trp Val Ser Thr Ile Glu Ile Lys Glu Ala Gly Tyr Ala Thr Asn
65                  70                  75                  80

Tyr Ala Ala Gly Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
                100                 105                 110

Ala Val Tyr Tyr Cys Ala Arg Arg Gly Pro Gly Met Gly Asn Met Asp
            115                 120                 125

Ile Trp Gly Gln Gly Thr Leu Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Asn Phe Gly Thr Gln Thr Tyr Thr Cys Asn
            210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
                260                 265                 270

Ser Arg Thr Pro Glu Val Thr Cys Val Val Val Asp Val Ser His Glu
            275                 280                 285

Asp Pro Glu Val Gln Phe Asn Trp Tyr Val Asp Gly Val Glu Val His
            290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
            370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430
```

```
Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 103
<211> LENGTH: 5
<212> TYPE: PRT
<213> ORGANISM: Homo sapiens

<400> SEQUENCE: 103

Thr Tyr Ala Met His
1               5

<210> SEQ ID NO 104
<211> LENGTH: 19
<212> TYPE: PRT
<213> ORGANISM: Homo sapiens

<400> SEQUENCE: 104

Thr Ile Glu Ile Lys Glu Ala Gly Tyr Ala Thr Asn Tyr Ala Ala Gly
1               5                   10                  15

Val Lys Gly

<210> SEQ ID NO 105
<211> LENGTH: 10
<212> TYPE: PRT
<213> ORGANISM: Homo sapiens

<400> SEQUENCE: 105

Arg Gly Pro Gly Met Gly Asn Met Asp Ile
1               5                   10

<210> SEQ ID NO 106
<211> LENGTH: 5
<212> TYPE: PRT
<213> ORGANISM: Homo sapiens
<220> FEATURE:
<221> NAME/KEY: VARIANT
<222> LOCATION: (1)..(1)
<223> OTHER INFORMATION: /replace="Asn"
      /replace="Ser"
      /replace="Thr"
<220> FEATURE:
<221> NAME/KEY: VARIANT
<222> LOCATION: (3)..(3)
<223> OTHER INFORMATION: /replace="Trp"
      /replace="Ala"
<220> FEATURE:
<221> NAME/KEY: VARIANT
<222> LOCATION: (5)..(5)
<223> OTHER INFORMATION: /replace="Ser"
      /replace="His"
      /replace="Thr"
      /replace="Asn"

<400> SEQUENCE: 106

Xaa Tyr Xaa Met Xaa
1               5

<210> SEQ ID NO 107
<211> LENGTH: 19
<212> TYPE: PRT
<213> ORGANISM: Homo sapiens
<220> FEATURE:
```

```
<221> NAME/KEY: VARIANT
<222> LOCATION: (1)..(1)
<223> OTHER INFORMATION: /replace="Leu"/replace="Tyr"/replace=
      "Phe"/replace="Asn"/replace="Thr"
<220> FEATURE:
<221> NAME/KEY: VARIANT
<222> LOCATION: (3)..(3)
<223> OTHER INFORMATION: /replace="Ser"/replace="Ala"/replace=
      "Phe"/replace="Glu"
<220> FEATURE:
<221> NAME/KEY: VARIANT
<222> LOCATION: (4)..(4)
<223> OTHER INFORMATION: /replace="Tyr"/replace="Gly"/replace="Ile"
<220> FEATURE:
<221> NAME/KEY: VARIANT
<222> LOCATION: (5)..(5)
<223> OTHER INFORMATION: /replace="Lys"/replace=absent
<220> FEATURE:
<221> NAME/KEY: VARIANT
<222> LOCATION: (6)..(6)
<223> OTHER INFORMATION: /replace="Glu"/replace=absent
<220> FEATURE:
<221> NAME/KEY: VARIANT
<222> LOCATION: (7)..(7)
<223> OTHER INFORMATION: /replace="Ser"/replace="Ala"
<220> FEATURE:
<221> NAME/KEY: VARIANT
<222> LOCATION: (8)..(8)
<223> OTHER INFORMATION: /replace="Ser"/replace="Gly"
<220> FEATURE:
<221> NAME/KEY: VARIANT
<222> LOCATION: (9)..(9)
<223> OTHER INFORMATION: /replace="Ser"/replace="Tyr"
<220> FEATURE:
<221> NAME/KEY: VARIANT
<222> LOCATION: (10)..(10)
<223> OTHER INFORMATION: /replace="Thr"/replace="Asn"/replace=
      "Val"/replace="Ser"/replace="Ala"
<220> FEATURE:
<221> NAME/KEY: VARIANT
<222> LOCATION: (12)..(12)
<223> OTHER INFORMATION: /replace="Tyr"/replace="Asn"
<220> FEATURE:
<221> NAME/KEY: VARIANT
<222> LOCATION: (15)..(15)
<223> OTHER INFORMATION: /replace="Asp"/replace="Asn"
<220> FEATURE:
<221> NAME/KEY: VARIANT
<222> LOCATION: (16)..(16)
<223> OTHER INFORMATION: /replace="Ser"/replace="Gly"

<400> SEQUENCE: 107

Xaa Ile Xaa Xaa Xaa Xaa Xaa Xaa Xaa Xaa Thr Xaa Tyr Ala Xaa Xaa
1               5                   10                  15

Val Lys Gly

<210> SEQ ID NO 108
<211> LENGTH: 7
<212> TYPE: PRT
<213> ORGANISM: Homo sapiens
<220> FEATURE:
<221> NAME/KEY: VARIANT
<222> LOCATION: (1)..(1)
<223> OTHER INFORMATION: /replace="Gly"/replace="Asp"/replace="Tyr"
<220> FEATURE:
<221> NAME/KEY: VARIANT
<222> LOCATION: (2)..(2)
<223> OTHER INFORMATION: /replace="Thr"/replace="Asp"/replace="Val"
<220> FEATURE:
<221> NAME/KEY: VARIANT
<222> LOCATION: (3)..(3)
<223> OTHER INFORMATION: /replace="Asn"/replace="Thr"
<220> FEATURE:
<221> NAME/KEY: VARIANT
<222> LOCATION: (4)..(4)
<223> OTHER INFORMATION: /replace="Asn"/replace="Asp"/replace="Lys"
```

```
<400> SEQUENCE: 108

Xaa Xaa Xaa Xaa Arg Pro Ser
1               5

<210> SEQ ID NO 109
<211> LENGTH: 12
<212> TYPE: PRT
<213> ORGANISM: Homo sapiens
<220> FEATURE:
<221> NAME/KEY: VARIANT
<222> LOCATION: (5)..(5)
<223> OTHER INFORMATION: /replace="Pro"/replace="Gly"
<220> FEATURE:
<221> NAME/KEY: VARIANT
<222> LOCATION: (6)..(6)
<223> OTHER INFORMATION: /replace="Leu"/replace="Ala"
<220> FEATURE:
<221> NAME/KEY: VARIANT
<222> LOCATION: (7)..(7)
<223> OTHER INFORMATION: /replace="Ser"/replace="Pro"
<220> FEATURE:
<221> NAME/KEY: VARIANT
<222> LOCATION: (8)..(8)
<223> OTHER INFORMATION: /replace="Ser"/replace="Phe"
<220> FEATURE:
<221> NAME/KEY: VARIANT
<222> LOCATION: (9)..(9)
<223> OTHER INFORMATION: /replace="Ser"/replace="Asn"
<220> FEATURE:
<221> NAME/KEY: VARIANT
<222> LOCATION: (10)..(10)
<223> OTHER INFORMATION: /replace="His"/replace=absent
<220> FEATURE:
<221> NAME/KEY: VARIANT
<222> LOCATION: (11)..(11)
<223> OTHER INFORMATION: /replace="Ile"/replace="Leu"

<400> SEQUENCE: 109

Gln Ser Tyr Ala Xaa Xaa Xaa Xaa Xaa Xaa Xaa Val
1               5                   10
```

ANTIBODY TARGETING OSTEOCLAST-RELATED PROTEIN SIGLEC-15

CROSS-REFERENCE TO RELATED APPLICATIONS

This application is a National Stage application of PCT/EP2011/005219, filed Oct. 4, 2011, which claims priority from European application EP 10 251 744.8, filed Oct. 5, 2010.

SEQUENCE LISTING

The instant application contains a Sequence Listing which has been submitted in ASCII format via EFS-WEB and is hereby incorporated by reference in its entirety. Said ASCII copy, created on Apr. 1, 2013, is named sequence.txt and is 179 KB.

TECHNICAL FIELD

The present invention relates to a substance useful as a therapeutic and/or preventive agent for abnormal bone metabolism. The present invention also relates to a pharmaceutical composition such as an antibody and a polynucleotide encoding such an antibody. In addition, the present invention relates to a method of treating and/or preventing abnormal bone metabolism.

BACKGROUND ART

Bone is known to be a dynamic organ which is continuously remodelled by repeated formation and resorption so as to change its own morphology and maintain blood calcium levels. Healthy bone maintains an equilibrium between bone formation by osteoblasts and bone resorption by osteoclasts, and the bone mass is maintained constant. In contrast, when the equilibrium between bone formation and bone resorption is lost, abnormal bone metabolism such as osteoporosis occurs (Endocrinological Review, (1992) 13, pp. 66-80, Principles of Bone Biology, Academic Press, New York, (1996) pp. 87-102).

As factors which regulate bone metabolism, many systemic hormones and local cytokines have been reported, and these factors collaborate with one another to form and maintain bone (Endocrinological Review, (1992) 13, pp. 66-80, Endocrinological Review, (1996) 17, pp. 308-332). As a change in bone tissue due to aging, the occurrence of osteoporosis is widely known, but the mechanism of its occurrence encompasses various factors such as a decrease in secretion of sex hormones and an abnormality in the receptors for the hormones, variation in cytokine expression locally in bone, expression of aging genes, and osteoclast or osteoblast differentiation failure or dysfunction, and thus, it is difficult to consider it as a simple age-related physiological phenomenon. Primary osteoporosis is largely divided into postmenopausal osteoporosis due to a decrease in secretion of estrogen and senile osteoporosis due to aging, but advancement of basic research on the mechanisms of regulation of bone formation and bone resorption is essential to elucidate the mechanism of its occurrence and to develop a therapeutic agent therefor.

Osteoclasts are multinucleated cells derived from hematopoietic stem cells, and by releasing chloride ions and hydrogen ions on a bone surface to which osteoclasts adhere, osteoclasts acidify a gap between the bone surface and the osteoclasts and also secrete cathepsin K which is an acid protease or the like (American Journal of Physiology, (1991) 260, C1315-C1324). This causes degradation of calcium phosphate, activation of acid proteases and degradation of bone matrix proteins, resulting in bone resorption.

Osteoclast precursor cells have been found to be differentiated into osteoclasts by stimulation with RANKL (receptor activator of NF-κB ligand) expressed on the cell membrane of osteoblasts/stromal cells present on the surface of bone (Proceedings of the National Academy of Science of the United States of America, (1998) 95, pp. 3597-3602, Cell, (1998) 93, pp. 165-176). It has been revealed that RANKL is a membrane protein produced by osteoblasts/stromal cells. Its expression being regulated by a bone resorption factor, RANKL induces differentiation of osteoclast precursor cells into multinucleated osteoclasts, and the like (Proceedings of the National Academy of Science of the United States of America, (1998) 95, pp. 3597-3602, Journal of Bone and Mineral Research, (1998) 23, S222). Further, knockout mice devoid of RANKL have been found to develop an osteopetrosis-like disease, and therefore, RANKL has been proved to be a physiological osteoclast differentiation-inducing factor (Nature, (1999) 397, pp. 315-323).

As drugs for treating bone metabolism diseases or shortening the duration of treatment, bisphosphonates, active vitamin $D_3$, calcitonin and derivatives thereof, hormone preparations such as estradiol, SERMs (selective estrogen receptor modulators), ipriflavone, vitamin $K_2$ (menatetrenone), PTH (parathyroid hormone) preparations, calcium preparations and the like are used. However, these drugs do not always exhibit a satisfactory therapeutic effect and the development of an agent with a more potent therapeutic effect has been demanded.

The cell membranes of immune cells are covered with a dense coating of various glycans, such as sialic acid, which are recognized by various glycan-binding proteins. Sialic-acid-binding immunoglobulin-like lectins (hereinafter referred to as "siglecs") are a family of type I membrane proteins which recognize sialylated glycans and bind thereto. Many siglecs are expressed on the cell membranes of immune cells and recognize sialic acid similarly present on the cell membranes of immune cells and regulate cell interaction or cell function and are considered to be involved in the immune response (Nature Reviews Immunology, (2007) 7, pp. 255-266). However, there are also a lot of siglec molecules whose physiological functions have not been elucidated yet. Siglec-15 (Sialic-acid binding immunoglobulin-like lectin 15) is a molecule which has been newly reported to belong to the Siglecs (Glycobiology, (2007) 17, pp. 838-846) and is identical to a molecule called "CD33 antigen-like 3", "CD33 molecule-like 3", "CD33-like 3" or "CD33L3". This molecule is highly evolutionarily conserved from fish to humans and has been found to be strongly expressed in dendritic cells and/or macrophages of human spleen and lymph nodes. Further, as a result of a binding test using a sialic acid probe, it has also been found that human Siglec-15 binds to Neu5Acα2-6GalNAc, and that mouse Siglec-15 binds to Neu5Acα2-3Galβ1-4Glc in addition to Neu5Acα2-6GalNAc (Glycobiology, (2007) 17, pp. 838-846). Until recently, the physiological role of Siglec-15 was not revealed, however, it has been reported that the expression of Siglec-15 increases with the differentiation and maturation of osteoclasts, and the differentiation of osteoclasts is inhibited by decreasing the expression of Siglec-15 by RNA interference (WO 2007/093042). It has also been reported that the Siglec-15 gene is specifically expressed in giant cell tumors and it has also been found that the expression level of the Siglec-15 gene increases when a monocyte-derived cell line differentiates into osteoclasts (WO2009/048072). Rabbit polyclonal and rat monoclonal anti-mouse Siglec-15 antibodies which can inhibit the differentiation of osteoclasts have been disclosed (WO2009/048072). Anti-Siglec-15 chimeric monoclonal antibodies which can inhibit the differentiation of osteoclasts have also been disclosed (US2010/0104575). However, human antibodies which can be administered to humans have not yet been disclosed.

DISCLOSURE OF THE INVENTION

Problems that the Invention is to Solve

An object of the invention is to provide a substance which inhibits the differentiation and maturation of osteoclasts and the activity thereof and a therapeutic and/or preventive agent for abnormal bone metabolism.

Means for Solving the Problems

The present inventors studied to elucidate the mechanism of osteoclast differentiation, maturation and activation in order to find a substance having a therapeutic and/or preventive effect on abnormal bone metabolism. As a result, they found that the expression of the Siglec-15 gene increases with the differentiation and maturation of osteoclasts and also found that the differentiation of osteoclasts is inhibited by an antibody which specifically binds to Siglec-15, and thus, the invention has been completed. In some instances, antibodies of the invention have a higher potency against osteoclasts than antibodies known in the art.

That is, the invention includes the following aspects.

According to a first aspect of the present invention, there is provided an isolated antibody capable of binding Siglec-15 which inhibits osteoclast formation and/or osteoclastic bone resorption, or a functional fragment thereof comprising (a) a heavy chain comprising a CDRH1 comprising a sequence having at least 80% sequence identity to SEQ ID NO: 71, a CDRH2 comprising a sequence having at least 80% sequence identity to SEQ ID NO: 72, and a CDRH3 comprising a sequence having at least 80% sequence identity to one of SEQ ID NOS: 35, 45, 55 or 65; and (b) a light chain comprising a CDRL1 comprising a sequence having at least 80% sequence identity to SEQ ID NO: 73, a CDRL2 comprising a sequence having at least 80% sequence identity to SEQ ID NO: 74, and a CDRL3 comprising a sequence having at least 80% sequence identity to one of SEQ ID NOS: 40, 50, 60 or 70.

According to a second aspect of the present invention there is provided an isolated antibody capable of binding Siglec-15 which inhibits osteoclast formation and/or osteoclastic bone resorption, or a functional fragment thereof comprising (a) a heavy chain comprising a CDRH1 comprising a sequence having at least 80% sequence identity to SEQ ID NO: 106, a CDRH2 comprising a sequence having at least 80% sequence identity to SEQ ID NO: 107, and a CDRH3 comprising a sequence having at least 80% sequence identity to one of SEQ ID NOS: 55, 35, 45, 65, or 80; and (b) a light chain comprising a CDRL1 comprising a sequence having at least 80% sequence identity to SEQ ID NO: 73 or 83, a CDRL2 comprising a sequence having at least 80% sequence identity to SEQ ID NO: 108, and a CDRL3 comprising a sequence having at least 80% sequence identity to one of SEQ ID NOS: 60, 40, 50, 70, 90, 100 or 109.

It is preferred that the CDRH3 comprises a sequence having at least 80% sequence identity to SEQ ID NO: 35 and the CDRL3 comprises a sequence having at least 80% sequence identity to SEQ ID NO: 40. Alternatively, the CDRH3 comprises a sequence having at least 80% sequence identity to SEQ ID NO: 45 and the CDRL3 comprises a sequence having at least 80% sequence identity to SEQ ID NO: 50. Alternatively, the CDRH3 comprises a sequence having at least 80% sequence identity to SEQ ID NO: 55 and the CDRL3 comprises a sequence having at least 80% sequence identity to SEQ ID NO: 60. Alternatively, the CDRH3 comprises a sequence having at least 80% sequence identity to SEQ ID NO: 65 and the CDRL3 comprises a sequence having at least 80% sequence identity to SEQ ID NO: 70. Alternatively, the CDRH3 comprises a sequence having at least 80% sequence identity to SEQ ID NO: 80 and the CDRL3 comprises a sequence having at least 80% sequence identity to SEQ ID NO: 109, preferably at least 80% sequence identity to any one of SEQ ID NO: 90 or 100.

Conveniently, the CDRH1 comprises a sequence having at least 80% sequence identity to one of SEQ ID NOS: 33, 43, 53, 63 or 78.

Preferably, the CDRH2 comprises a sequence having at least 80% sequence identity to one of SEQ ID NOS: 34, 44, 54, 64, 79, 94 or 104.

Advantageously, the CDRL1 comprises a sequence having at least 80% sequence identity to one of SEQ ID NOS: 38, 48, 58, 68 or 88.

Conveniently, the CDRL2 comprises a sequence having at least 80% sequence identity to one of SEQ ID NOS: 39, 49, 59, 69 or 89.

Preferably, the sequences of CDRH1, CDRH2, CDRH3, CDRL1, CDRL2, and CDRL3 comprise sequences having at least 80% sequence identity to SEQ. ID NOS: 33, 34, 35, 38, 39 and 40 respectively.

Alternatively, the sequences of CDRH1, CDRH2, CDRH3, CDRL1, CDRL2 and CDRL3 comprise sequences having at least 80% sequence identity to SEQ. ID NOS: 43, 44, 45, 48, 49 and 50 respectively.

Alternatively, the sequences of CDRH1, CDRH2, CDRH3, CDRL1, CDRL2 and CDRL3 comprise sequences having at least 80% sequence identity to SEQ. ID NOS: 53, 54, 55, 58, 59 and 60 respectively.

Alternatively, the sequences of CDRH1, CDRH2, CDRH3, CDRL1, CDRL2 and CDRL3 comprise sequences having at least 80% sequence identity to SEQ. ID NOS: 63, 64, 65, 68, 69, and 70, respectively.

Alternatively, the sequences of CDRH1, CDRH2, CDRH3, CDRL1, CDRL2 and CDRL3 comprise sequences having at least 80% sequence identity to SEQ. ID NOS: 78, 79, 80, 88, 89, and 90, respectively.

Alternatively, the sequences of CDRH1, CDRH2, CDRH3, CDRL1, CDRL2 and CDRL3 comprise sequences having at least 80% sequence identity to SEQ. ID NOS: 93, 94, 95, 98, 99, and 100, respectively.

Alternatively, the sequences of CDRH1, CDRH2, CDRH3, CDRL1, CDRL2 and CDRL3 comprise sequences having at least 80% sequence identity to SEQ. ID NOS: 103, 104, 105, 88, 89 and 90, respectively.

It is particularly preferred that the antibody or functional fragment comprises CDRH1, CDRH2, CDRH3, CDRL1, CDRL2 and/or CDRL3 sequences having at least 90% or 95% sequence identity to the sequences set out above.

Preferably, the antibody comprises:
a heavy chain variable region selected from the group consisting of
a1) an amino acid sequence comprising: amino acid residues 20 to 136 of SEQ ID NO: 32, amino acid residues 20 to 135 of SEQ ID NO: 42, amino acid residues 20 to 137 of SEQ ID NO: 52, amino acid residues 20 to 136 of SEQ ID NO: 62, amino acid residues 20 to 138 of SEQ ID NO: 77, amino acid residues 20 to 138 of SEQ ID NO: 92 or amino acid residues 20 to 140 of SEQ ID NO: 102;

a2) an amino acid sequence having at least 90% sequence identity with the amino acid sequence of a1);

a3) an amino acid sequence having at least 95% sequence identity with the amino acid sequence of a1); and a4) an amino acid sequence including addition, deletion or substitution of one or several amino acid residues in the amino acid sequence of a1); and a light chain variable region selected form the group consisting of b1) an amino acid sequence comprising: amino acid residues 20 to 129 of SEQ ID NO: 37, amino acid residues 20 to 129 of SEQ ID NO: 47, amino acid residues 20 to 129 of SEQ ID NO: 57, amino acid residues 20 to 129 of SEQ ID NO: 67, amino acid residues 20 to 134 of SEQ ID NO: 87 or amino acid residues 20 to 133 of SEQ ID NO: 97;

b2) an amino acid sequence having at least 90% sequence identity with the amino acid sequence of b1);

b3) an amino acid sequence having at least 95% sequence identity with the amino acid sequence of b1); and b4) an amino acid sequence including addition, deletion or substitution of one or several amino acid residues in the amino acid sequence of b1).

It is particularly preferred that the heavy and light chain variable regions have at least 99% sequence identity to the sequences set out above.

Advantageously, the antibody comprises:

a heavy chain selected from the group consisting of a1) an amino acid sequence comprising the sequence of one of SEQ ID NOS: 32, 42, 52, 62, 77, 92 or 102;

a2) an amino acid sequence having at least 90% sequence identity with the amino acid sequence of a1);

a3) an amino acid sequence having at least 95% sequence identity with the amino acid sequence of a1); and a4) an amino acid sequence including addition, deletion or substitution of one or several amino acid residues in the amino acid sequence of a1); and a light chain selected from the group consisting of b1) an amino acid sequence comprising the sequence of one of SEQ ID NOS: 37, 47, 57, 67, 87 or 97;

b2) an amino acid sequence having at least 90% sequence identity with the amino acid sequence of b1);

b3) an amino acid sequence having at least 95% sequence identity with the amino acid sequence of b1); and b4) an amino acid sequence including addition, deletion or substitution of one or several amino acid residues in the amino acid sequence of b1).

It is particularly preferred that the heavy and light chains have at least 99% sequence identity to the sequences set out above.

Conveniently, the antibody comprises a heavy chain consisting of an amino acid sequence comprising SEQ ID NO: 32 and a light chain consisting of an amino acid sequence comprising SEQ ID NO: 37.

Alternatively, the antibody comprises a heavy chain consisting of an amino acid sequence comprising SEQ ID NO: 42 and a light chain consisting of an amino acid sequence comprising SEQ ID NO: 47.

Alternatively, the antibody comprises a heavy chain consisting of an amino acid sequence comprising SEQ ID NO: 52 and a light chain consisting of an amino acid sequence comprising SEQ ID NO: 57.

Alternatively, the antibody comprises a heavy chain consisting of an amino acid sequence comprising SEQ ID NO: 62 and a light chain consisting of an amino acid sequence comprising SEQ ID NO: 67.

Alternatively, the antibody comprises a heavy chain consisting of an amino acid sequence comprising SEQ ID NO: 77 and a light chain consisting of an amino acid sequence comprising SEQ ID NO: 87.

Alternatively, the antibody comprises a heavy chain consisting of an amino acid sequence comprising SEQ ID NO: 92 and a light chain consisting of an amino acid sequence comprising SEQ ID NO: 97.

Alternatively, the antibody comprises a heavy chain consisting of an amino acid sequence comprising SEQ ID NO: 102 and a light chain consisting of an amino acid sequence comprising SEQ ID NO: 87.

Conveniently, the functional fragment of the antibody of the invention is selected from the group consisting of Fab, F(ab')2, Fab' and Fv.

Preferably, the antibody is an scFv.

According to a third aspect of the invention there is provided an isolated antibody or a functional fragment thereof according to the first or second aspect of the invention for use in treating and/or preventing abnormal bone metabolism.

According to a fourth aspect of the present invention, there is provided the use of an isolated antibody or a functional fragment thereof according to the first or second aspect of the invention for the manufacture of a medicament for the treatment or prevention of abnormal bone metabolism.

According to a fifth aspect of the present invention, there is provided a method of treatment of a patient suffering from abnormal bone metabolism comprising administering a therapeutically effective amount of an isolated antibody or a functional fragment thereof according to the first or second aspect of the invention.

According to a sixth aspect of the present invention, there is provided a pharmaceutical composition comprising at least one of the antibodies or functional fragments thereof according to the first or second aspect of the invention.

Conveniently, the pharmaceutical composition is a therapeutic and/or preventive agent for abnormal bone metabolism.

According to a seventh aspect of the present invention, there is provided a pharmaceutical composition for treating and/or preventing abnormal bone metabolism characterized by comprising at least one of the antibodies or functional fragments of the antibodies according to the first or second aspect of the invention and at least one member selected from the group consisting of bisphosphonates, active vitamin $D_3$, calcitonin and derivatives thereof, hormone preparations such as estradiol, SERMs (selective estrogen receptor modulators), ipriflavone, vitamin $K_2$ (menatetrenone), calcium preparations, PTH (parathyroid hormone) preparations, non-steroidal anti-inflammatory agents, soluble TNF receptor preparations, anti-TNF-α antibodies or functional fragments of the antibodies, anti-PTHrP (parathyroid hormone-related protein) antibodies or functional fragments of the antibodies, IL-1 receptor antagonists, anti-IL-6 receptor antibodies or functional fragments of the antibodies, anti-RANKL antibodies or functional fragments of the antibodies and OCIF (osteoclastogenesis inhibitory factor).

Preferably, the abnormal bone metabolism is selected from the group consisting of: osteoporosis, bone destruction accompanying rheumatoid arthritis, cancerous hypercalcemia, bone destruction accompanying multiple myeloma or cancer metastasis to bone, giant cell tumor, tooth loss due to periodontitis, osteolysis around a prosthetic joint, bone destruction in chronic osteomyelitis, Paget's disease of bone, renal osteodystrophy and osteogenesis imperfecta.

Advantageously, the abnormal bone metabolism is osteoporosis, bone destruction accompanying rheumatoid arthritis or bone destruction accompanying cancer metastasis to bone.

Conveniently, the osteoporosis is postmenopausal osteoporosis, senile osteoporosis, secondary osteoporosis due to the use of a therapeutic agent such as a steroid or an immunosuppressant, or osteoporosis accompanying rheumatoid arthritis.

According to an eighth aspect of the present invention, there is provided a polynucleotide which comprises:
a) a nucleotide sequence that encodes one of the antibodies or functional fragments thereof according to the first or second aspect of the invention; or
b) a nucleotide sequence of a polynucleotide which hybridizes to a polynucleotide consisting of a nucleotide sequence complementary to the nucleotide sequence of a) under stringent conditions.

Conveniently, the nucleotide sequences which encode the sequences of CDRH1, CDRH2, CDRH3, CDRL1, CDRL2 and CDRL3 comprise:
a) nucleotides 148 to 162 of SEQ ID NO: 31, nucleotides 205 to 255 of SEQ ID NO: 31, nucleotides 352 to 375 of SEQ ID NO: 31, nucleotides 124 to 156 of SEQ ID NO: 36, nucleotides 202 to 222 of SEQ ID NO: 36 and nucleotides 319 to 348 of SEQ ID NO: 36, respectively;
b) nucleotides 148 to 162 of SEQ ID NO: 41, nucleotides 205 to 255 of SEQ ID NO: 41, nucleotides 352 to 372 of SEQ ID NO: 41, nucleotides 124 to 156 of SEQ ID NO: 46, nucleotides 202 to 222 of SEQ ID NO: 46 and nucleotides 319 to 348 of SEQ ID NO: 46, respectively;
c) nucleotides 148 to 162 of SEQ ID NO: 51, nucleotides 205 to 255 of SEQ ID NO: 51, nucleotides 352 to 378 of SEQ ID NO: 51, nucleotides 124 to 156 of SEQ ID NO: 56, nucleotides 202 to 222 of SEQ ID NO: 56 and nucleotides 319 to 348 of SEQ ID NO: 56, respectively;
d) nucleotides 148 to 162 of SEQ ID NO: 61, nucleotides 205 to 255 of SEQ ID NO: 61, nucleotides 352 to 375 of SEQ ID NO: 61, nucleotides 124 to 156 of SEQ ID NO: 66, nucleotides 202 to 222 of SEQ ID NO: 66 and nucleotides 319 to 348 of SEQ ID NO: 66, respectively;
e) nucleotides 148 to 162 of SEQ ID NO: 76, nucleotides 205 to 255 of SEQ ID NO: 76, nucleotides 352 to 381 of SEQ ID NO: 76, nucleotides 124 to 165 of SEQ ID NO: 86, nucleotides 211 to 231 of SEQ ID NO: 86 and nucleotides 328 to 363 of SEQ ID NO: 86, respectively;
f) nucleotides 148 to 162 of SEQ ID NO: 91, nucleotides 205 to 255 of SEQ ID NO: 91, nucleotides 352 to 381 of SEQ ID NO: 91, nucleotides 124 to 165 of SEQ ID NO: 96, nucleotides 211 to 231 of SEQ ID NO: 96 and nucleotides 328 to 360 of SEQ ID NO: 96, respectively; or
g) nucleotides 148 to 162 of SEQ ID NO: 101, nucleotides 205 to 261 of SEQ ID NO: 101, nucleotides 358 to 387 of SEQ ID NO: 101, nucleotides 124 to 165 of SEQ ID NO: 86, nucleotides 211 to 231 of SEQ ID NO: 86 and nucleotides 328 to 363 of SEQ ID NO: 86, respectively.

Preferably, the polynucleotide comprises:
a nucleotide sequence encoding a heavy chain variable region selected from the group consisting of
a1) a nucleotide sequence comprising: nucleotides 58 to 408 of SEQ ID NO: 31, nucleotides 58 to 405 of SEQ ID NO: 41, nucleotides 58 to 411 of SEQ ID NO: 51, nucleotides 58 to 408 of SEQ ID NO: 61, nucleotides 58 to 414 of SEQ ID NO: 76, nucleotides 58 to 414 of SEQ ID NO: 91 or nucleotides 58 to 420 of SEQ ID NO: 101;
a2) a nucleotide sequence of a polynucleotide which hybridizes to a polynucleotide consisting of a nucleotide sequence complementary to the nucleotide sequence of a1) under stringent conditions; and
a3) a nucleotide sequence including addition, deletion or substitution of one or several nucleotides in the nucleotide sequence of a1); and
a nucleotide sequence encoding a light chain variable region selected from the group consisting of
b1) a nucleotide sequence comprising: nucleotides 58 to 387 of SEQ ID NO: 36, nucleotides 58 to 387 of SEQ ID NO: 46, nucleotides 58 to 387 of SEQ ID NO: 56, nucleotides 58 to 387 of SEQ ID NO: 66, nucleotides 58 to 402 of SEQ ID NO: 86 or nucleotides 58 to 399 of SEQ ID NO: 96;
b2) a nucleotide sequence of a polynucleotide which hybridizes to a polynucleotide consisting of a nucleotide sequence complementary to the nucleotide sequence of b1) under stringent conditions; and
b3) a nucleotide sequence including addition, deletion or substitution of one or several nucleotides in the nucleotide sequence of b1).

Advantageously, the polynucleotide comprises:
a nucleotide sequence encoding a heavy chain selected from the group consisting of
a1) a nucleotide sequence the sequence of one of SEQ ID NOS: 31, 41, 51, 61, 76, 91 or 101;
a2) a nucleotide sequence of a polynucleotide which hybridizes to a polynucleotide consisting of a nucleotide sequence complementary to the nucleotide sequence of a1) under stringent conditions; and
a3) a nucleotide sequence including addition, deletion or substitution of one or several nucleotides in the nucleotide sequence of a1); and
a nucleotide sequence encoding a light chain selected from the group consisting of
b1) a nucleotide sequence comprising the sequence of one of SEQ ID NOS: 36, 46, 56, 66, 86 or 96;
b2) a nucleotide sequence of a polynucleotide which hybridizes to a polynucleotide consisting of a nucleotide sequence complementary to the nucleotide sequence of b1) under stringent condition; and
b3) a nucleotide sequence including addition, deletion or addition of one or several nucleotides in the nucleotide sequence of b1).

According to a ninth aspect of the present invention, there is provided a vector comprising at least one polynucleotide according to the eighth aspect of the invention.

According to a tenth aspect of the present invention, there is provided a transformed cell comprising at least one polynucleotide according to the eighth aspect of the invention.

According to an eleventh aspect of the present invention, there is provided a transformed cell comprising at least one vector according to the ninth aspect of the invention.

According to a twelfth aspect of the present invention, there is provided a method of producing antibodies according to the first or second aspect of the invention, comprising the steps of culturing a transformed cell according to the tenth or eleventh aspects of the invention, collecting culturing materials and purifying said antibodies from said culturing materials.

In this specification, the percentage "identity" between two sequences is determined using the BLASTP algorithm version 2.2.2 (Altschul, Stephen F., Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402) using default parameters. In particular, the BLAST algorithm can be accessed on the internet using the URL www.ncbi.nlm.nih.gov/blast.

Advantage of the Invention

According to the invention, a therapeutic and/or preventive agent for abnormal bone metabolism whose mechanism of action is to inhibit the differentiation and maturation of osteoclasts and the activity thereof can be obtained.

BRIEF DESCRIPTION OF THE DRAWINGS

FIG. 14 is the DNA sequence (SEQ ID NO: 1) encoding the heavy chain of antibody MOR08656.

FIG. 15 is the amino acid sequence (SEQ ID NO: 2) for the heavy chain of antibody MOR08656.

FIG. 16 is the DNA sequence (SEQ ID NO: 6) encoding the light chain of antibody MOR08656.

FIG. 17 is the amino acid sequence (SEQ ID NO: 7) for the light chain of antibody MOR08656.

FIG. 18 is the DNA sequence (SEQ ID NO: 11) encoding the heavy chain of antibody MOR08662.

FIG. 19 is the amino acid sequence (SEQ ID NO: 12) for the heavy chain of antibody MOR08662.

FIG. 20 is the DNA sequence (SEQ ID NO: 16) encoding the light chain of antibody MOR08662.

FIG. 21 is the amino acid sequence (SEQ ID NO: 17) for the light chain of antibody MOR08662.

FIG. 22 is the DNA sequence (SEQ ID NO: 21) encoding the heavy chain of antibody MOR09012.

FIG. 23 is the amino acid sequence (SEQ ID NO: 22) for the heavy chain of antibody MOR09012.

FIG. 24 is the DNA sequence (SEQ ID NO: 26) encoding the light chain of antibody MOR09012.

FIG. 25 is the amino acid sequence (SEQ ID NO: 27) for the light chain of antibody MOR09012.

FIG. 26 is the DNA sequence (SEQ ID NO: 31) encoding the heavy chain of antibody MOR09281.

FIG. 27 is the amino acid sequence (SEQ ID NO: 32) for the heavy chain of antibody MOR09281.

FIG. 28 is the DNA sequence (SEQ ID NO: 36) encoding the light chain of antibody MOR09281.

FIG. 29 is the amino acid sequence (SEQ ID NO: 37) for the light chain of antibody MOR09281.

FIG. 30 is the DNA sequence (SEQ ID NO: 41) encoding the heavy chain of antibody MOR09892.

FIG. 31 is the amino acid sequence (SEQ ID NO: 42) for the heavy chain of antibody MOR09892.

FIG. 32 is the DNA sequence (SEQ ID NO: 46) encoding the light chain of antibody MOR09892.

FIG. 33 is the amino acid sequence (SEQ ID NO: 47) for the light chain of antibody MOR09892.

FIG. 34 is the DNA sequence (SEQ ID NO: 51) encoding the heavy chain of antibody MOR09898.

FIG. 35 is the amino acid sequence (SEQ ID NO: 52) for the heavy chain of antibody MOR09898.

FIG. 36 is the DNA sequence (SEQ ID NO: 56) encoding the light chain of antibody MOR09898.

FIG. 37 is the amino acid sequence (SEQ ID NO: 57) for the light chain of antibody MOR09898.

FIG. 38 is the DNA sequence (SEQ ID NO: 61) encoding the heavy chain of antibody MOR10110.

FIG. 39 is the amino acid sequence (SEQ ID NO: 62) for the heavy chain of antibody MOR10110.

FIG. 40 is the DNA sequence (SEQ ID NO: 66) encoding the light chain of antibody MOR10110.

FIG. 41 is the amino acid sequence (SEQ ID NO: 67) for the light chain of antibody MOR10110.

FIG. 46 is the DNA sequence (SEQ ID NO: 76) encoding the heavy chain of antibodies MOR09268 and MOR12574.

FIG. 47 is the amino acid sequence (SEQ ID NO: 77) for the heavy chain of antibodies MOR09268 and MOR12574.

FIG. 48 is the DNA sequence (SEQ ID NO: 81) encoding the light chain of antibody MOR09268.

FIG. 49 is the amino acid sequence (SEQ ID NO: 82) for the light chain of antibody MOR09268.

FIG. 50 is the DNA sequence (SEQ ID NO: 86) encoding the light chain of antibodies MOR12574 and MOR13156.

FIG. 51 is the amino acid sequence (SEQ ID NO: 87) for the light chain of antibodies MOR12574 and MOR13156.

FIG. 52 is the DNA sequence (SEQ ID NO: 91) encoding the heavy chain of antibody MOR13154.

FIG. 53 is the amino acid sequence (SEQ ID NO: 92) for the heavy chain of antibody MOR13154.

FIG. 54 is the DNA sequence (SEQ ID NO: 96) encoding the light chain of antibody MOR13154.

FIG. 55 is the amino acid sequence (SEQ ID NO: 97) for the light chain of antibody MOR13154.

FIG. 56 is the DNA sequence (SEQ ID NO: 101) encoding the heavy chain of antibody MOR13156.

FIG. 57 is the amino acid sequence (SEQ ID NO: 102) for the heavy chain of antibody MOR13156.

BEST MODE FOR CARRYING OUT THE INVENTION

Figure 1:
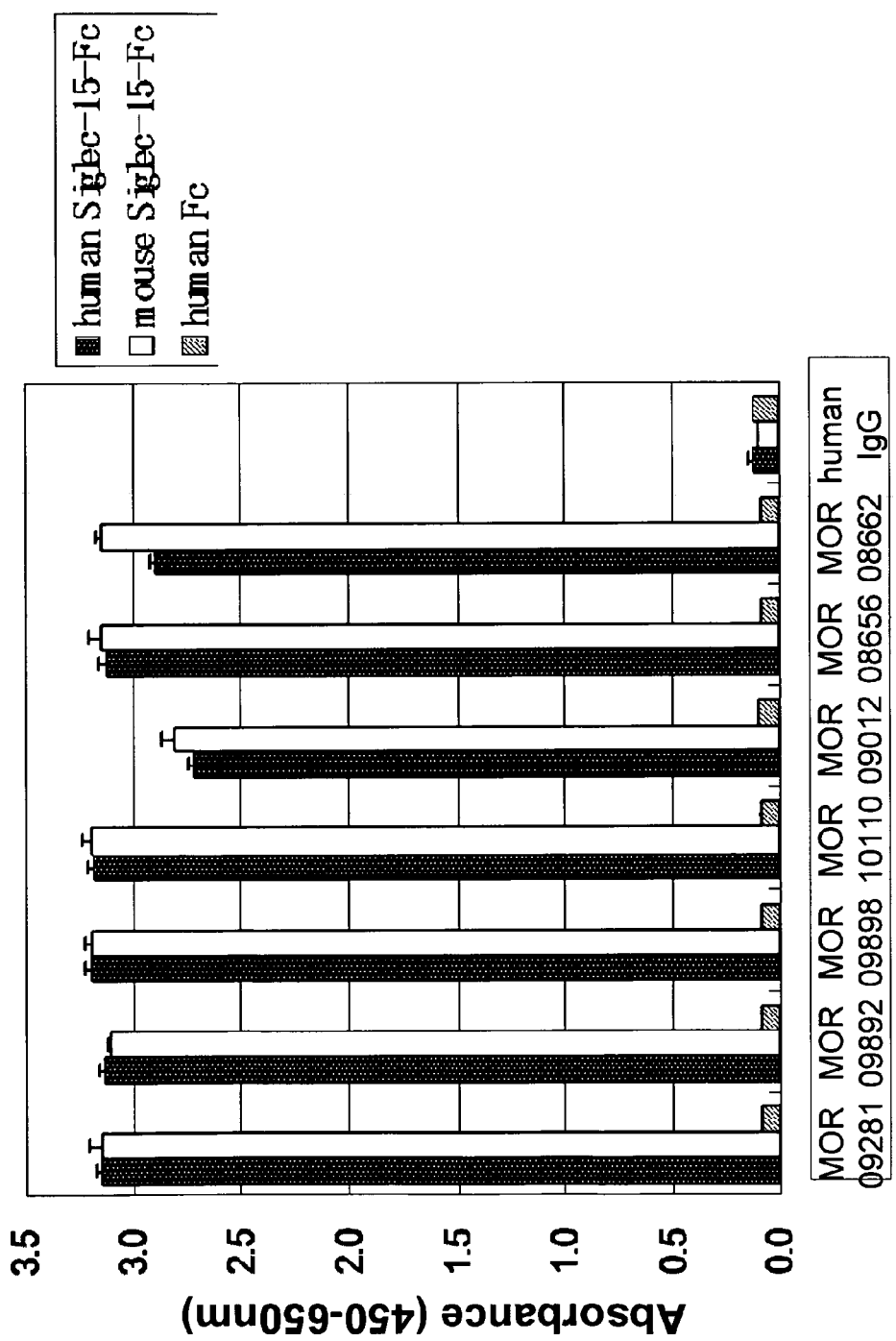
FIG. 1 is a graph showing the results of an ELISA assay to measure binding of antibodies MOR09281, MOR09892, MOR09898, MOR10110, MOR09012, MOR08656, MOR08662 and human IgG (negative control) to human Siglec-15-Fc, mouse Siglec-15-Fc and human Fc.
Figure 2:
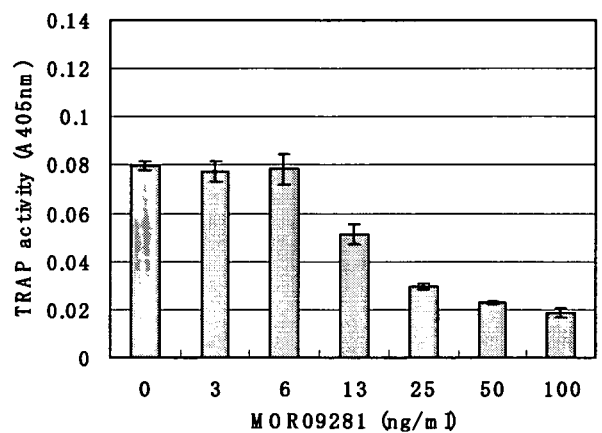
FIG. 2 is a graph showing the TRAP activity of mouse osteoclasts formed in the presence of antibody MOR09281.
Figure 3:
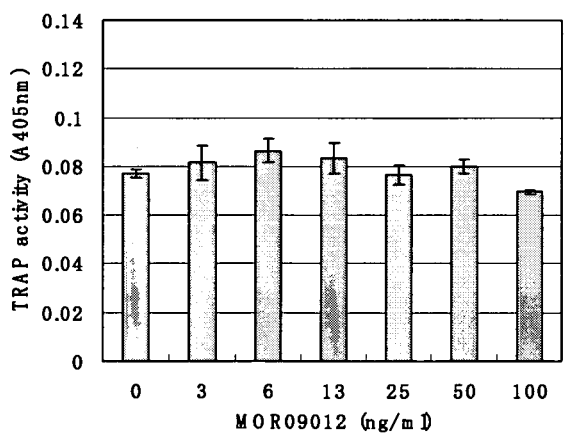
FIG. 3 is a graph showing the TRAP activity of mouse osteoclasts formed in the presence of antibody MOR09012 (parent antibody of MOR09892).
Figure 4:
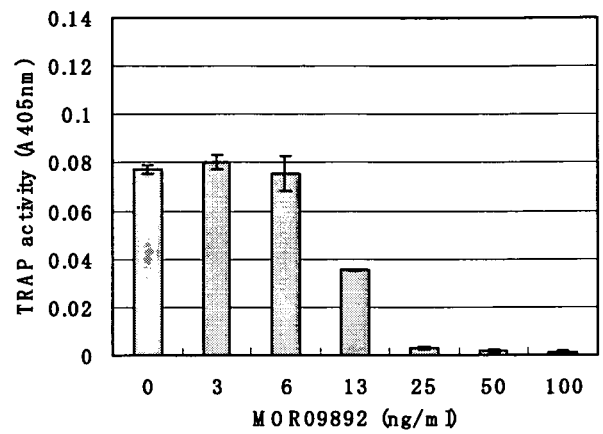
FIG. 4 is a graph showing the TRAP activity of mouse osteoclasts formed in the presence of antibody MOR09892.
Figure 5:
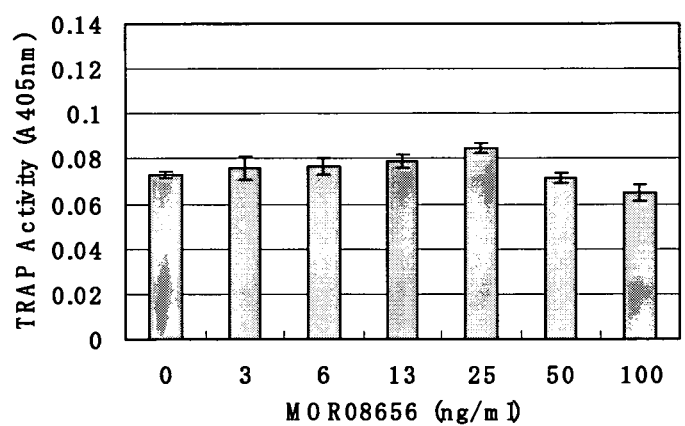
FIG. 5 is a graph showing the TRAP activity of mouse osteoclasts formed in the presence of antibody MOR08656 (parent antibody of MOR09898).
Figure 6:
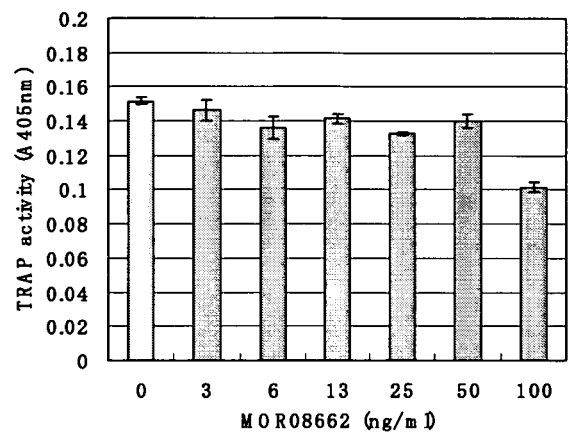
FIG. 6 is a graph showing the TRAP activity of mouse osteoclasts formed in the presence of antibody MOR08662 (parent antibody of MOR10110).
Figure 7:
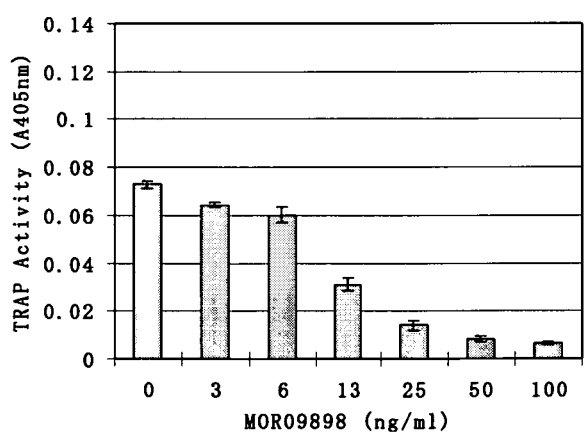
FIG. 7 is a graph showing the TRAP activity of mouse osteoclasts formed in the presence of antibody MOR09898.
Figure 8:
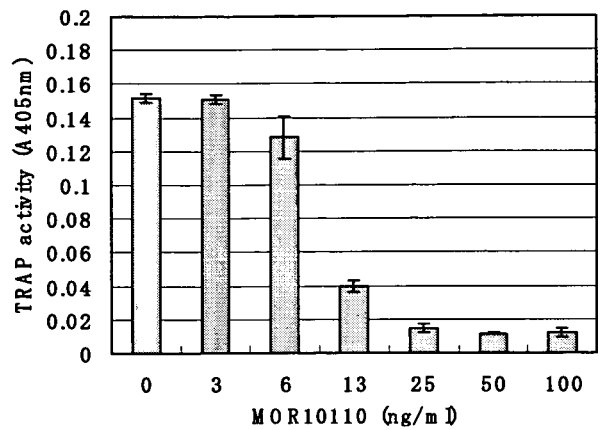
FIG. 8 is a graph showing the TRAP activity of mouse osteoclasts formed in the presence of antibody MOR10110.
Figure 9:
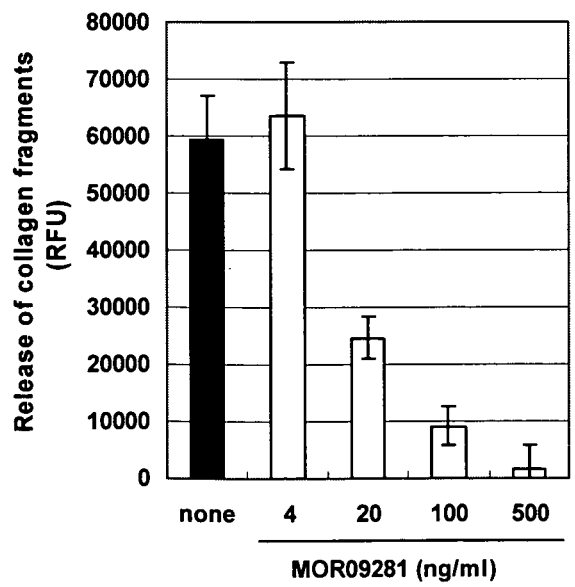
FIG. 9 is a graph showing the release of collagen fragments from the plate degraded by human osteoclast precursor cells when cultured in the presence of antibody MOR09281.
Figure 10:
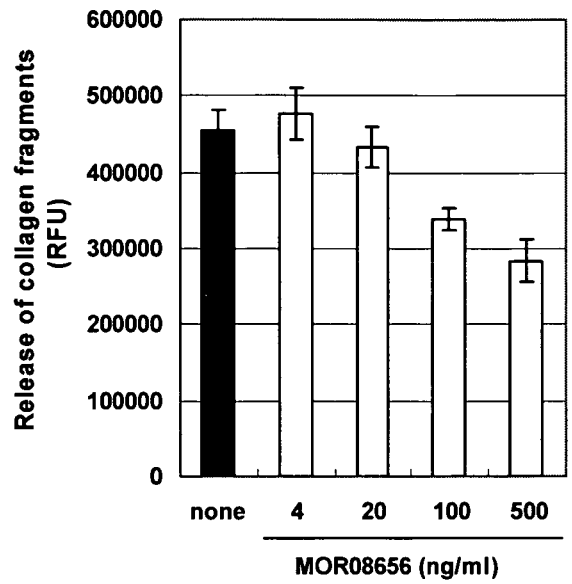
FIG. 10 is a graph showing the release of collagen fragments from the plate degraded by human osteoclast precursor cells when cultured in the presence of antibody MOR08656 (parent antibody of MOR09898).
Figure 11:
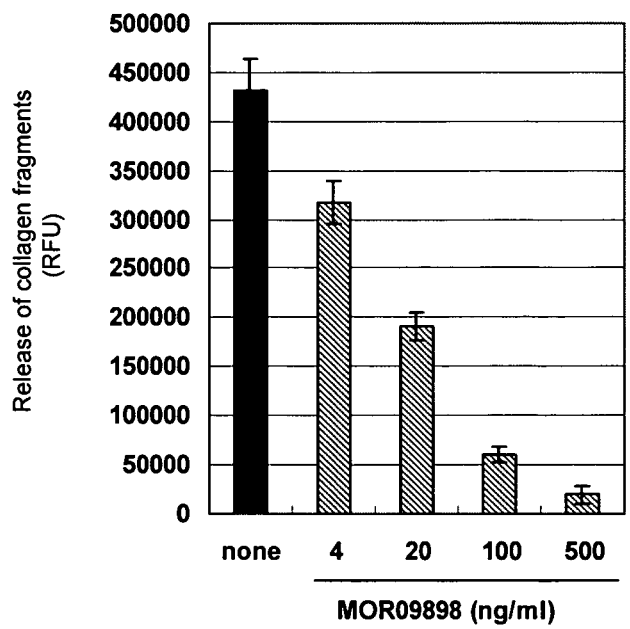
FIG. 11 is a graph showing the release of collagen fragments from the plate degraded by human osteoclast precursor cells when cultured in the presence of antibody MOR09898.
Figure 12:
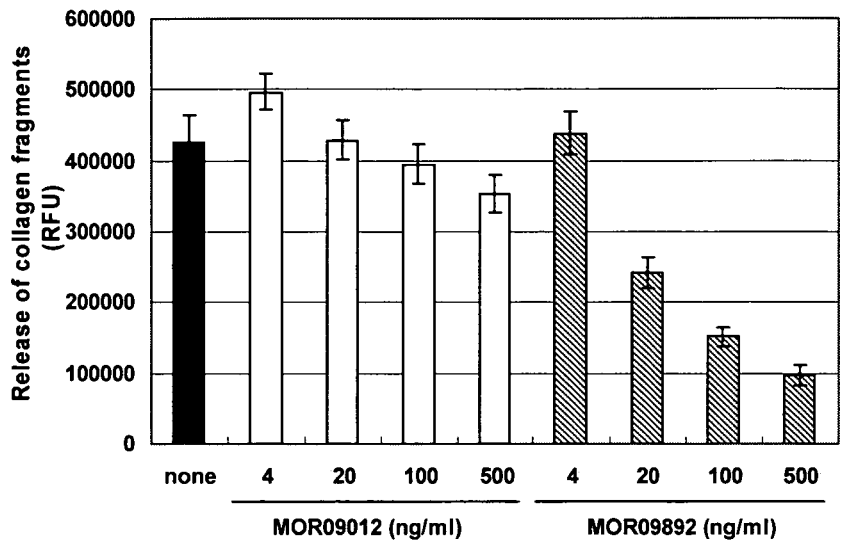
FIG. 12 is a graph showing the release of collagen fragments from the plate degraded by human osteoclast precursor cells when cultured in the presence of antibodies MOR09012 (parent antibody of MOR09892) and MOR09892.
Figure 13:
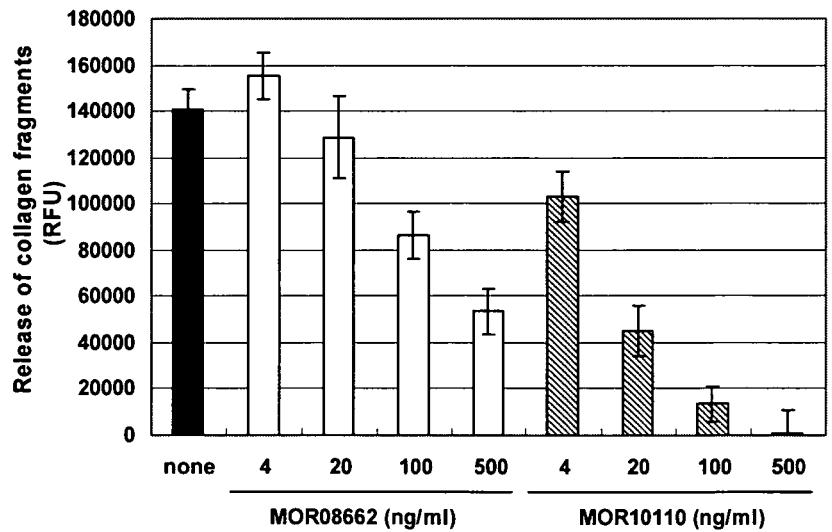
FIG. 13 is a graph showing the release of collagen fragments from the plate degraded by human osteoclast precursor cells when cultured in the presence of antibodies MOR08662 (parent antibody of MOR10110) and MOR10110.
Figure 42:
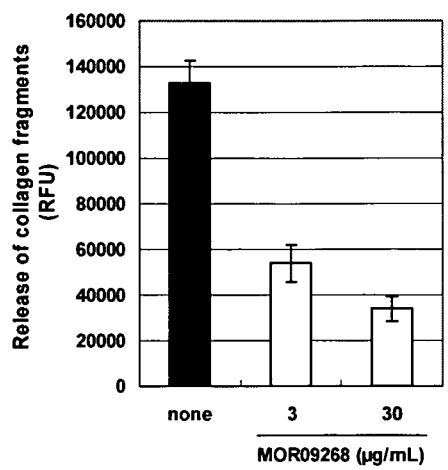
FIG. 42 is a graph showing the release of collagen fragments from the plate degraded by human osteoclast precursor cells when cultured in the presence of antibody MOR09268.
Figure 43:
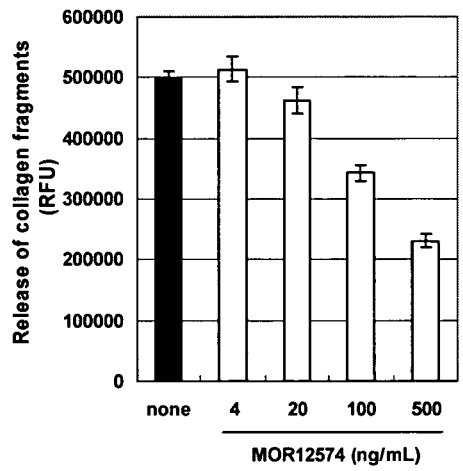
FIG. 43 is a graph showing the release of collagen fragments from the plate degraded by human osteoclast precursor cells when cultured in the presence of antibody MOR12574.
Figure 44:
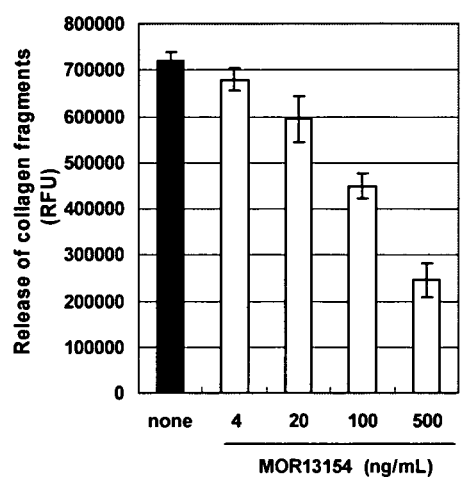
FIG. 44 is a graph showing the release of collagen fragments from the plate degraded by human osteoclast precursor cells when cultured in the presence of antibody MOR13154.
Figure 45:
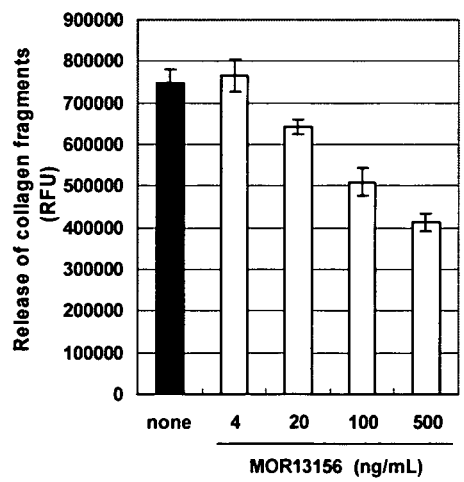
FIG. 45 is a graph showing the release of collagen fragments from the plate degraded by human osteoclast precursor cells when cultured in the presence of antibody MOR13156.

The term "gene" as used herein includes not only DNA, but also mRNA, cDNA and cRNA.

The term "polynucleotide" as used herein is used in the same meaning as a nucleic acid and also includes DNA, RNA, probes, oligonucleotides and primers.

The terms "polypeptide" and "protein" as used herein are used without distinction.

The term "RNA fraction" as used herein refers to a fraction containing RNA.

The term "cell" as used herein also includes cells in an animal individual and cultured cells.

The term "Siglec-15" as used herein is used in the same meaning as Siglec-15 protein.

The term "osteoclast formation" as used herein is used in the same meaning as "osteoclast differentiation" or "osteoclast maturation".

The term "functional fragment of an antibody" as used herein refers to a partial fragment of an antibody having an antigen-binding activity and includes Fab, F(ab')2, scFv and the like. The term also encompasses Fab' which is a monovalent fragment of a variable region of an antibody obtained by treating F(ab')2 under reducing conditions. However, the term is not limited to these molecules as long as the fragment has a binding affinity for an antigen. Further, these functional fragments include not only a fragment obtained by treating a full-length molecule of an antibody protein with an appropriate enzyme, but also a protein produced in an appropriate host cell using a genetically modified antibody gene.

It is known that a heavy or light chain of an antibody has three complementarity determining regions (CDRs). Complementarity Determining Regions are also known as hypervariable domains and these regions are hypervariable in the primary structure of a heavy or a light chain variable region. Such hypervariable domains exist as three divergent portions in the polypeptide of a heavy or light chain of an antibody. In this specification, the CDRs of a heavy chain are termed CDRH1, CDRH2 and CDRH3 in order from the amino terminus (N-terminus) of the polypeptide of the heavy chain. CDRs of a light chain are termed CDRL1, CDRL2 and CDRL3 in order from the amino terminus of the polypeptide of the light chain. These 6 CDRs are in close proximity within the tertiary structure of an antibody and determine the specificity of the binding to an antigen.

The phrase "hybridization is performed under stringent conditions" as used herein refers to hybridization being performed under the conditions under which identification can be effected by performing hybridization at 68° C. in a commercially available hybridization solution, such as ExpressHyb Hybridization Solution (manufactured by Clontech, Inc.) or performing hybridization at 68° C. in the presence of 0.7 to 1.0 M NaCl using a filter having DNA immobilized thereon, followed by performing washing at 68° C. using 0.1 to 2×SSC solution (1×SSC solution is composed of 150 mM NaCl and 15 mM sodium citrate) or under conditions equivalent thereto.

The term "capable of binding" when used in relation to an antibody with respect to Siglec-15 means that the antibody is able to bind the Siglec-15 preferentially under physiological conditions. In some embodiments, this is synonymous with the term "specific for". Thus in some embodiments, the antibody has greater affinity for Siglec-15 than for other related polypeptides, for example 1.5 fold, 2-fold, 5-fold, 10-fold, 100-fold, $10^3$-fold, $10^4$-fold, $10^5$-fold, $10^6$-fold greater affinity.

The term "several" as used herein means a number from 2 to 4 in some embodiments.

1. Siglec-15

Where Siglec-15 is to be used as an immunogen, Siglec-15 may be directly purified from monocytes or bone marrow cells of humans, non-human mammals (such as guinea pigs, rats, mice, rabbits, pigs, sheep, cattle or monkeys) or chickens and used, or a cell membrane fraction of the above-mentioned cells may be prepared and can be used. Furthermore, Siglec-15 can be obtained by in vitro synthesis thereof or production thereof in a host cell through genetic engineering. In such genetic engineering, more specifically, Siglec-15 cDNA is integrated into a vector capable of expressing Siglec-15 cDNA, and Siglec-15 is synthesized in a solution containing enzymes, substrates, and energy substances required for transcription and translation, or another prokaryotic or eucaryotic host cell is transformed to express Siglec-15, whereby the protein can be obtained.

The nucleotide sequence of human Siglec-15 cDNA has been registered in GenBank with the accession number of NM_213602. The nucleotide sequence of mouse Siglec-15 cDNA has been registered in GenBank with the accession number of XM_884636.

2. Anti-Siglec-15 Antibody

The general structure of antibodies is known in the art and will only be briefly summarised here. An immunoglobulin monomer comprises two heavy chains and two light chains connected by disulfide bonds. Each heavy chain is paired with one of the light chains to which it is directly bound via a disulfide bond. Each heavy chain comprises a constant region (which varies depending on the isotype of the antibody) and a variable region. The variable region comprises three hypervariable regions (or complementarity determining regions) which are designated CDRH1, CDRH2 and CDRH3 and which are supported within framework regions. Each light chain comprises a constant region and a variable region, with the variable region comprising three hypervariable regions (designated CDRL1, CDRL2 and CDRL3) supported by framework regions in an analogous manner to the variable region of the heavy chain.

The hypervariable regions of each pair of heavy and light chains mutually cooperate to provide an antigen binding site that is capable of binding a target antigen. The binding specificity of a pair of heavy and light chains is defined by the sequence of CDR1, CDR2 and CDR3 of the heavy and light chains. Thus once a set of CDR sequences (i.e. the sequence of CDR1, CDR2 and CDR3 for the heavy and light chains) is determined which gives rise to a particular binding specificity, the set of CDR sequences can, in principle, be inserted into the appropriate positions within any other antibody framework regions linked with any antibody constant regions in order to provide a different antibody with the same antigen binding specificity.

In preferred embodiments, there are provided antibodies MOR09281, MOR09892, MOR09898, MOR10110, MOR12574, MOR13154 and MOR13156, details of whose amino acid sequences are set forth in Tables 4 to 7 and 10 to 12. However, the present invention is not limited to these preferred antibodies.

In general terms, in the anti-Siglec 15 antibodies of the present invention, the sequences of CDR1 and CDR2 of the heavy and light chains conform with the consensus sequences set out in SEQ ID NOS: 71 to 74. Alternatively, the sequences of the CDR1 and CDR2 sequences of the heavy chain may conform with the consensus sequences set out in SEQ ID NOS: 106 and 107; the sequence of the CDR2 sequence of the light chain may conform with SEQ ID NO: 108 and the sequence of the CDR1 sequence of the light chain may conform with either SEQ ID NO: 73 or 83.

The sequence of the CDR3 sequence of the light chain may conform with the consensus sequence set out in SEQ ID NO: 109. It is particularly preferred that the antibody has the CDR3 sequence of the light chain conforming with the consensus sequence of SEQ ID NO: 109 and the CDR3 sequence of the heavy chain has the sequence of SEQ ID NO: 80.

Specific CDR1, CDR2 and CDR3 sequences from some of the preferred antibodies (MOR09281, MOR09892, MOR09898 and MOR10110) of the invention are set out in Table 8. Specific CDR1, CDR2 and CDR3 sequences from the other preferred antibodies (MOR12574, MOR13154 and MOR13156) of the invention are set out in Table 13. Thus there are provided antibodies comprising CDRs 1 to 3 having the sequences from these preferred antibodies. However, since there is a high level of sequence identity between sequences of the preferred antibodies of the invention, it is also within the scope of the invention to provide antibodies with CDR sequences from different preferred antibodies. For example, an antibody may be provided comprising a heavy chain having the sequence of CDR1 from MOR09281, CDR2 from MOR09892 and CDR3 from MOR09898 and light chain having the sequence of CDR1 from MOR10110, CDR2 from MOR09281 and CDR3 from MOR09892.

It is also to be understood that in some embodiments of the invention, the amino acid sequence of CDRs 1 to 3 is varied from those sequences provided in Tables 8 and 13 while still retaining at least 80% (or, in some embodiments, at least 90% or 95%) sequence identity therewith. In some embodiments, an amino acid residue at a position in a CDR of one antibody is swapped with the amino acid residue at the corresponding position in the same CDR of another antibody. For example, an antibody may be provided comprising a heavy chain in which the sequence of CDR1 comprises the amino acid sequence NYAMS (SEQ ID NO. 75) i.e. the sequence of CDR1 of the heavy chain of MOR09281 with the amino acid at position 3 substituted with the amino acid at position 3 from CDR1 of the heavy chain of MOR09892. In other embodiments, one or more amino acid residues in a CDR are substituted with another amino acid. The substitution may be "conservative" in the sense of being a substitution within the same family of amino acids. The naturally occurring amino acids may be divided into the following four families and conservative substitutions will take place within those families.

1) Amino acids with basic side chains: lysine, arginine, histidine.
2) Amino acids with acidic side chains: aspartic acid, glutamic acid
3) Amino acids with uncharged polar side chains: asparagine, glutamine, serine, threonine, tyrosine.
4) Amino acids with nonpolar side chains: glycine, alanine, valine, leucine, isoleucine, proline, phenylalanine, methionine, tryptophan, cysteine.

In still further embodiments, one or more amino acid residues are added to or deleted from one or more CDRs of an antibody. Such additions or deletions occur at the N or C termini of the CDR or at a position within the CDR.

By varying the amino acid sequence of the CDRs of an antibody by addition, deletion or substitution of amino acids, various effects such as increased binding affinity for the target antigen or reduced aggregation may be obtained.

It is to be appreciated that antibodies of the invention comprising such varied CDR sequences still bind Siglec-15 and inhibit osteoclast formation and/or osteoclastic bone resorption. This may be tested by way of the binding assays and biological activity assays disclosed in Examples 5 and 6 herein.

The constant regions of antibodies may also be varied from those specifically disclosed for antibodies MOR09281, MOR09892, MOR09898, MOR10110, MOR12574, MOR13154 and MOR13156. For example, antibodies may be provided with Fc regions of any isotype: IgA, IgD, IgE, IgG or IgM.

It is preferred that the antibody is a human antibody.

Antibodies, their manufacture and uses are well known and disclosed in, for example, Harlow, E. and Lane, D., *Antibodies: A Laboratory Manual*, Cold Spring Harbor Laboratory Press, Cold Spring Harbor, N.Y., 1999.

The antibodies may be generated using standard methods known in the art. Examples of antibodies include (but are not limited to) monoclonal, single chain, and functional fragments of antibodies.

A "functional fragment" of an antibody includes any fragment of an antibody which is capable of binding a target antigen and thus includes Fab fragments, F(ab')$_2$ fragments, Fab' fragments and Fv fragments.

Antibodies may be produced in a range of hosts, for example goats, rabbits, rats, mice, humans, and others. They may be immunized by injection with a target antigen (in this invention Siglec-15) or a fragment or oligopeptide thereof which has immunogenic properties. Depending on the host species, various adjuvants may be used to increase an immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (Bacille Calmette-Guerin) and *Corynebacterium parvum* are particularly useful.

Monoclonal antibodies, to Siglec-15 may be prepared using any technique which provides for the production of antibody molecules by continuous cell lines in culture.

These include, but are not limited to, the hybridoma technique, the human B-cell hybridoma technique, and the EBV-hybridoma technique (Koehler et al., 1975, Nature, 256: 495-497; Kosbor et al., 1983, Immunol. Today 4: 72; Cote et al., 1983, PNAS USA, 80: 2026-2030; Cole et al., 1985, *Monoclonal Antibodies and Cancer Therapy*, Alan R. Liss Inc., New York, pp. 77-96).

Alternatively, techniques for the production of single chain antibodies may be used. Single chain antibodies (scFvs) comprise a heavy chain variable region and a light chain variable region connected with a linker peptide (typically around 5 to 25 amino acids in length). scFvs may be synthesised using recombinant techniques, for example by expression of a vector encoding the scFv in a host organism such as *E. coli*.

Antibodies may also be produced by inducing in vivo production in the lymphocyte population or by screening recombinant immunoglobulin libraries or panels of highly specific binding reagents (Orlandi et al., 1989, PNAS USA, 86: 3833-3837; Winter, G. et al., 1991, Nature, 349: 293-299).

Antigen binding fragments may also be generated, for example the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse et al., 1989, Science, 256: 1275-1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between Siglec-15, or any fragment or oligopeptide thereof and its specific antibody. A two-site, monoclonal-based immunoassay utilizing monoclonal antibodies specific to two non-interfering Siglec-15 epitopes may be used, but a competitive binding assay may also be employed (Maddox et al., 1983, J. Exp. Med., 158: 1211-1216).

3. Medicine Containing Anti-Siglec-15 Antibody

The anti-Siglec-15 antibodies described in the above item "2. Anti-Siglec-15 antibody", neutralize the biological activity of Siglec-15. Such an antibody, which neutralizes the biological activity of Siglec-15, inhibits the biological activity of Siglec-15 in vivo (i.e., the differentiation and/or maturation of osteoclasts) and therefore can be used as a therapeutic and/or preventive agent for abnormal bone metabolism caused by abnormal differentiation and/or maturation of osteoclasts. The abnormal bone metabolism may be any disorder characterized by net bone loss (osteopenia or osteolysis). In general, the therapeutic and/or preventive effect of the anti-Siglec-15 antibody is applied in cases where inhibition of bone resorption is required. Examples of abnormal bone metabolism which can be treated and/or prevented by the anti-Siglec-15 antibody include osteoporosis (postmenopausal osteoporosis, senile osteoporosis, secondary osteoporosis due to the use of a therapeutic agent such as a steroid or an immunosuppressant, or osteoporosis accompanying rheumatoid arthritis), bone destruction accompanying rheumatoid arthritis, cancerous hypercalcemia, bone destruction accompanying multiple myeloma or cancer metastasis to bone, giant cell tumor, tooth loss due to periodontitis, osteolysis around a prosthetic joint, bone destruction in chronic osteomyelitis, Paget's disease of bone, renal osteodystrophy and osteogenesis imperfecta. However, the abnormal bone metabolism is not limited to these examples as long as it is a disease accompanied by net bone loss caused by osteoclasts.

The in vitro activity of the anti-Siglec-15 antibody in neutralizing the biological activity of Siglec-15 can be determined by, for example, the activity of inhibiting the differentiation of the cells which overexpress Siglec-15 into osteoclasts. For example, the anti-Siglec-15 antibody is added to RAW 264.7 cells or Raw 264 cells, which are a mouse monocyte-derived cell line, at various concentrations, and the activity of inhibiting the differentiation into osteoclasts by stimulation with RANKL or TNF-α can be determined. In a further example, the anti-Siglec-15 antibody is added to bone marrow-derived primary cultured cells at various concentrations, and the activity of inhibiting the differentiation into osteoclasts by stimulation with RANKL, TNF-α or active vitamin D$_3$ can be determined. In a further example, the anti-Siglec-15 antibody is added to normal human osteoclast precursor cells (Normal Human Natural Osteoclast Precursor Cells, available from Sanko Junyaku Co., Ltd., Cat. No. 2T-110) at various concentrations, and the activity of inhibiting the differentiation into osteoclasts by stimulation with RANKL or M-CSF can be determined. Such an inhibitory effect on osteoclast differentiation can be determined by using the inhibition of tartrate-resistant acid phosphatase (TRAP) activity of osteoclasts as an index. In a further example, the inhibitory effect on osteoclast differentiation can also be determined by using the inhibition of formation of TRAP-positive multinucleated osteoclasts, i.e., the inhibition of cell fusion of osteoclasts as an index. In a further example, in an experiment of a pit assay (Takada et al., Bone and Mineral, (1992) 17, 347-359) using femur- and/or tibia-derived cells, the in vitro activity of inhibiting bone resorption by osteoclasts can be determined by adding the anti-Siglec-15 antibody to femur- and/or tibia-derived cells at various concentrations, and observing pit formation on a dentine slice. As a system for determining the in vitro activity of inhibiting bone resorption by osteoclasts, it is also possible to use a plate coated with human collagen conjugated to europium. The in vivo therapeutic or preventive effect of the anti-Siglec-15 antibody on abnormal bone metabolism in an experimental animal can be confirmed by administering the anti-Siglec-15 antibody to a model animal of osteoporosis or a transgenic animal which overexpresses siglec-15 and measuring a change in osteoclasts.

The above-described antibody which neutralizes the biological activity of Siglec-15 is useful as a medicine, particularly as a pharmaceutical composition for treating or preventing abnormal bone metabolism such as osteoporosis, bone destruction accompanying rheumatoid arthritis or bone destruction accompanying cancer metastasis to bone, or as an antibody for immunological diagnosis of such a disease.

In the treatment of rheumatoid arthritis (RA), a major problem is bone loss accompanying the occurrence of the disease. It has been reported that in this bone loss accompanying RA, osteoclasts play a primary role. The cytokines considered to be most important for osteoclast induction (differentiation and maturation) and activation and the cause of bone destruction in RA are RANKL and TNF-α (Romas E. et al., Bone 30, pp. 340-346, 2002). OCIF/OPG which is a decoy receptor for RANKL can inhibit osteoclast formation induced by RANKL but does not inhibit osteoclast formation induced by TNF-α. On the other hand, the anti-Siglec-15 antibody according to the invention effectively inhibits osteoclast formation induced by both RANKL and TNF-α. Therefore, it is expected that the anti-Siglec-15 antibody of the invention can inhibit bone loss and bone destruction induced by TNF-α in RA or the like more strongly than an RANKL blocker (OCIF/OPG, an anti-RANKL antibody or the like).

As one example, for the treatment or prevention of abnormal bone metabolism, the anti-Siglec-15 antibody is administered alone or along with at least one other therapeutic agent for a bone-related disease. As another example, the anti-Siglec-15 antibody can be administered along with a therapeutically effective amount of a therapeutic agent for abnormal bone metabolism. The anti-Siglec-15 antibody and the therapeutic agent may be administered simultaneously, separately or sequentially. Examples of the therapeutic agent which can be administered along with the anti-Siglec-15 antibody include, but are not limited to, bisphosphonates, active vitamin D$_3$, calcitonin and derivatives thereof, hormone preparations such as estradiol, SERMs (selective estrogen receptor modulators), ipriflavone, vitamin K$_2$ (menatetrenone), calcium preparations, PTH (parathyroid hormone)

preparations, nonsteroidal anti-inflammatory agents, soluble TNF receptor preparations, anti-TNF-α antibodies or functional fragments of the antibodies, anti-PTHrP (parathyroid hormone-related protein) antibodies or functional fragments of the antibodies, IL-1 receptor antagonists, anti-IL-6 receptor antibodies or functional fragments of the antibodies, anti-RANKL antibodies or functional fragments of the antibodies and OCIF (osteoclastogenesis inhibitory factor). In another example, the therapeutic agent is a second different anti-Siglec-15 antibody of the present invention. That is to say, two different anti-Siglec-15 antibodies of the invention are administered. Depending on the state of abnormal bone metabolism or the intended degree of the treatment and/or prevention, two or three, or more types of therapeutic agents can be administered, and these therapeutic agents can be supplied all together by encapsulating them in the same preparation. These therapeutic agents and the anti-Siglec-15 antibody can be supplied all together by encapsulating them in the same preparation. Further, these therapeutic agents can be supplied all together by encapsulating them as a kit to be used for treatment and/or prevention. Further, these therapeutic agents and the anti-Siglec-15 antibody can be supplied separately. In the case of administration in gene therapy, a gene of a proteinaceous therapeutic agent for a bone disease and a gene of the anti-Siglec-15 antibody can be inserted downstream of the same promoter region or different promoter regions, and can be introduced into the same vector or different vectors.

By conjugating a therapeutic agent for a bone disease to the anti-Siglec-15 antibody or a fragment thereof, a targeted drug conjugate as described in M. C. Garnet "Targeted drug conjugates: principles and progress", Advanced Drug Delivery Reviews, (2001) 53, 171-216 can be produced. For achieving this purpose, other than the antibody molecule, any antibody fragment can be applied as long as it does not completely lose the ability to recognize osteoclasts, and examples thereof include fragments such as Fab, F(ab')2, and Fv. In the invention, the antibody and the fragment can be used in the same manner. The conjugate formed by the anti-Siglec-15 antibody or a fragment thereof and a therapeutic agent for a bone disease can be any of various forms described in M. C. Garnet "Targeted drug conjugates: principles and progress", Advanced Drug Delivery Reviews, (2001) 53, 171-216, G. T. Hermanson "Bioconjugate Techniques" Academic Press, California (1996), Putnam and J. Kopecek "Polymer Conjugates with Anticancer Activity" Advances in Polymer Science (1995) 122, 55-123 and the like. That is, a conjugate form in which the anti-Siglec-15 antibody and a therapeutic agent for a bone disease are conjugated to each other chemically and directly or via a spacer such as an oligopeptide and a conjugate formed via an appropriate drug carrier can be exemplified. Examples of the drug carrier include a liposome and a water-soluble polymer. More specific examples of the conjugate formed via such a drug carrier include a conjugate form in which the antibody and a therapeutic agent for a bone disease are incorporated in a liposome and the liposome and the antibody are conjugated to each other, and a conjugate form in which a therapeutic agent for a bone disease is conjugated to a water-soluble polymer (a compound having a molecular weight of from about 1000 to 100000) chemically and directly or via a spacer such as an oligopeptide and the antibody is conjugated to the water-soluble polymer. The conjugation of the antibody (or a fragment thereof) to a therapeutic agent for a bone disease or a drug carrier such as a liposome or a water-soluble polymer can be effected by a method known to those skilled in the art such as the method described in G. T. Hermanson "Bioconjugate Techniques" Academic Press, California (1996), Putnam and J. Kopecek "Polymer Conjugates with Anticancer Activity" Advances in Polymer Science (1995) 122, 55-123. The incorporation of a therapeutic agent for a bone disease in a liposome can be effected by a method known to those skilled in the art such as the method described in D. D. Lasic "Liposomes: From Physics to Applications" Elsevier Science Publishers B. V., Amsterdam (1993) or the like. The conjugation of a therapeutic agent for a bone disease to a water-soluble polymer can be effected by a method known to those skilled in the art such as the method described in D. Putnam and J. Kopecek "Polymer Conjugates with Anticancer Activity" Advances in Polymer Science (1995) 122, 55-123. A conjugate between the antibody (or a fragment thereof) and a proteinaceous therapeutic agent for a bone disease (or a fragment thereof) can be produced by a method known to those skilled in the art through genetic engineering other than the above-mentioned method.

The invention also provides a pharmaceutical composition containing a therapeutically and/or preventively effective amount of the anti-Siglec-15 antibody and a pharmaceutically acceptable diluent, carrier, solubilizing agent, emulsifying agent, preservative and/or adjuvant.

The invention also provides a pharmaceutical composition containing a therapeutically and/or preventively effective amount of the anti-Siglec-15 antibody, a therapeutically and/or preventively effective amount of at least one therapeutic agent for a bone disease, and a pharmaceutically acceptable diluent, carrier, solubilizing agent, emulsifying agent, preservative and/or adjuvant. Examples of the therapeutic agent for a bone disease include, but are not limited to, bisphosphonates, active vitamin $D_3$, calcitonin and derivatives thereof, hormone preparations such as estradiol, SERMs (selective estrogen receptor modulators), ipriflavone, vitamin $K_2$ (menatetrenone), calcium preparations, PTH (parathyroid hormone) preparations, nonsteroidal anti-inflammatory agents, soluble TNF receptor preparations, anti-TNF-α antibodies or functional fragments of the antibodies, anti-PTHrP (parathyroid hormone-related protein) antibodies or functional fragments of the antibodies, IL-1 receptor antagonists, anti-IL-6 receptor antibodies or functional fragments of the antibodies, anti-RANKL antibodies or functional fragments of the antibodies and OCIF (osteoclastogenesis inhibitory factor). In another example, the therapeutic agent is a second, different anti-Siglec-15 antibody of the invention. That is to say that the pharmaceutical composition comprises two different anti-Siglec-15 antibodies of the invention.

A substance to be used in a preparation acceptable in a pharmaceutical composition according to the present invention is preferably non-toxic to a person to whom the pharmaceutical composition is to be administered, in terms of the dose and concentration.

The pharmaceutical composition of the invention can contain a substance for pharmaceutical use which is capable of changing or maintaining the pH, osmotic pressure, viscosity, transparency, color, isotonicity, color, aseptic condition, stability, solubility, release rate, absorption rate, or permeability of the pharmaceutical composition or its components. Examples of the substance for pharmaceutical use include, but are not limited to, amino acids such as glycine, alanine, glutamine, asparagine, arginine and lysine; antimicrobial agents; antioxidants such as ascorbic acid, sodium sulfate and sodium hydrogen sulfite; buffers such as phosphate, citrate, borate buffers, bicarbonate and Tris-HCl solutions; fillers such as mannitol and glycine; chelating agents such as ethylenediamine tetraacetate (EDTA); complexing agents such as caffeine, polyvinylpyrrolidine, p-cyclodextrin and hydroxypropyl-β-cyclodextrin; expanders such as glucose, mannose and dextrin; other carbohydrates such as monosaccharides and disaccharides; coloring agents; flavors; diluents; emulsifying agents; hydrophilic polymers such as polyvinylpyrrolidine; preservatives such as low molecular weight polypeptides, base forming counter ions, benzalkonium chloride, benzoate, salicylic acid, thimerosal, phenethyl alcohol, methylparaben, propylparaben, chlorhexidine, sorbic acid, and hydrogen peroxide; solvents such as glycerin, propylene glycol and polyethylene glycol; sugar alcohols such as mannitol and sorbitol; suspending agents; surfactants such as sorbitan ester, polysorbates including polysorbate 20 and polysorbate 80, Triton, tromethamine, lecithin and cholesterol; stability enhancing agents such as sucrose and sorbitol; elasticity enhancing agents such as sodium chloride, potassium chloride and mannitol and sorbitol; transport agents; diluents; excipients; and/or pharmaceutical adjuvants. The addition amount of these substances for pharmaceutical use is preferably from 0.01 to 100 times, particularly preferably from 0.1 to 10 times the weight of the anti-Siglec-15 antibody. Those skilled in the art can appropriately determine a preferred formulation of the pharmaceutical composition in a preparation depending on the disease to be applied, the route of administration to be applied or the like.

The excipient or carrier in the pharmaceutical composition may be in the form of a liquid or a solid. An appropriate excipient or carrier may be injectable water, physiological saline, an artificial cerebral spinal fluid or other substance commonly used for parenteral administration. Further, neutral physiological saline or physiological saline containing serum albumin can also be used as a carrier. The pharmaceutical composition may contain a Tris buffer of pH 7.0 to 8.5 or an acetate buffer of pH 4.0 to 5.5 which may be supplemented with sorbitol or another compound. Examples of the pharmaceutical composition of the invention include a pharmaceutical composition containing the anti-Siglec-15 antibody and a pharmaceutical composition containing the anti-Siglec-15 antibody and at least one therapeutic agent for a bone disease. The pharmaceutical composition of the invention is prepared in the form of a lyophilized product or a liquid as a medicinal agent having a selected composition and a required purity. The pharmaceutical composition containing the anti-Siglec-15 antibody and the pharmaceutical composition containing the anti-Siglec-15 antibody and at least one therapeutic agent for abnormal bone metabolism can also be formed into a lyophilized product using an appropriate excipient such as sucrose.

The pharmaceutical composition of the invention can be prepared for parenteral administration or for gastrointestinal absorption through oral administration. The composition and concentration of a preparation can be determined depending on the administration method. To the extent that the affinity of the anti-Siglec-15 antibody contained in the pharmaceutical composition of the invention for Siglec-15 is higher, that is, as the dissociation constant (Kd value) for Siglec-15 is lower, the anti-Siglec-15 antibody can exhibit its drug efficacy at a lower dose for humans, and therefore, the dose of the pharmaceutical composition of the invention for humans can also be determined based on this result. As for the dose, in the case where a human anti-Siglec-15 antibody is administered to humans, the antibody may be administered at a dose of from about 0.1 to 100 mg/kg once per one to 180 days.

Examples of the dosage form of the pharmaceutical composition of the invention include injections, infusions, suppositories, transnasal agents, sublingual agents and percutaneous absorbents.

4. Other Products of the Invention

There is also provided a polynucleotide which comprises a sequence encoding an anti-Siglec-15 antibody described in the above item "2. Anti-Siglec-15 Antibody". Details of the nucleotide sequence encoding the preferred antibodies (MOR09281, MOR09892, MOR09898, MOR10110, MOR12574, MOR13154 and MOR13156) are provided in Tables 4 to 7 and 10 to 12. However, it is to be understood that the polynucleotides of the present invention are not limited to those set forth in Tables 4 to 7 and 10 to 12. In particular, as explained in above item 2, anti-Siglec-15 antibodies of the invention include those which comprise CDRs from different preferred antibodies and also includes antibodies which comprise CDRs comprising one or more amino acid additions, deletions or substitutions. The polynucleotides of the present invention include those which encode such antibodies. Furthermore, owing to the degeneracy of the nucleic acid code, nucleotide sequences aside from those set forth in Tables 4 to 7 and 10 to 12 also encode the same amino acid sequences.

Also provided is a polynucleotide which comprises a nucleotide sequence of a polynucleotide which hybridizes to a polynucleotide consisting of a nucleotide sequence complementary to a nucleotide sequence that encodes one of the antibodies set forth in above item 2, under stringent conditions. In this regard, the phrase "hybridization is performed under stringent conditions" is defined above.

The polynucleotide may also comprise other nucleotide sequences such as a promoter and/or other expression-regulating sequences, sequences which encode a polyadenylation tail, minimal untranslated regions and a Kozak consensus sequence.

In some embodiments, a vector comprising such a polynucleotide is provided. Exemplary vectors include plasmids, cosmids and viral vectors, including bacteriophage. In addition to the polynucleotide, itself, such vectors may include sequences such as an origin of replication, genetic markers, antibiotic resistance genes, cos sites, cloning sites and targeting sequences. In many embodiments, the vector comprises sufficient elements to replicate in a host cell and to express the polynucleotide sequence encoding the anti-Siglec-15 antibody in the host cell.

Thus in further embodiments, there is provided a transformed cell comprising a polynucleotide as described above (for example, incorporated into the genome of the cell) or comprising a vector as described above. Suitable host cells include bacterial cells such as *E. coli* and eukaryotic cells such as yeast cells or human cell lines. Such transformed cells may be used to synthesize a Siglec-15 antibody of the invention by culturing the cells, expressing nucleotide sequences encoding the antibody and then purifying the antibody from the culture medium.

EXAMPLES

Hereinafter, the invention will be more specifically described with reference to Examples, however, the invention is not limited thereto. Note that the respective operations regarding gene manipulation in the following Examples were performed according to the methods described in "Molecular Cloning" (written by Sambrook, J., Fritsch, E. F. and Maniatis, T., published by Cold Spring Harbor Laboratory Press in 1989), or in the case of using commercially available reagents or kits, performed according to the protocols attached thereto.

Example 1

Cell Culture and Transient Transfection

Human embryonic kidney (HEK) 293FreeStyle™ cells were grown in Freestyle 293 Medium (Invitrogen). For cell pannings, HEK 293FreeStyle™ cells were transfected with plasmid DNAs such as plasmid pcDNA3.1 (+)/human Siglec-15 (encoding human Siglec-15, accession number, Q6ZMC9), plasmid pcDNA3.1 (+)/mouse Siglec-15 (encoding mouse Siglec-15, accession number, NP_001094508) or pcDNA3.1(+) using 293fectin (Invitrogen) according to the supplier's instructions. Transfected HEK 293FreeStyle™ cells were harvested after 2 days-cultivation for further cell panning.

Recombinant Human Siglec-15-Fc and Mouse Siglec-15-Fc Preparation

An expression vector for soluble human Siglec-15/phIgFc was constructed by the Gateway technology (Invitrogen). A DNA fragment encoding the extracellular domain of human Siglec-15 (accession number, Q6ZMC9, 1-260) was amplified by PCR to construct an entry clone into pDNOR221 (Invitrogen). Next, an LR reaction was performed between this entry clone and a destination vector harboring a DNA encoding human Fc sequence. The DNA sequence of the human Siglec-15-Fc in the constructed plasmid was confirmed by DNA sequence analysis. Human Siglec-15-Fc was transiently expressed in HEK 293FreeStyle™ harboring the expression vector of soluble human Siglec-15/phIgFc. 1.5 L of the culture solution of HEK 293FreeStyle™ cells expressing soluble human Siglec-15-Fc was filtered through a Sterivex-GV filter (Millipore), then the filtrate was applied to a HiTrap Protein A column (Amersham Biosciences) which was previously equilibrated with Dulbecco's PBS (D-PBS, manufactured by Invitrogen, Inc.). Human Siglec-15-Fc was eluted with 0.1 M sodium citrate buffer (pH 3.0) and neutralized with 1 M Tris. A 2.5 ml aliquot of human Siglec-15-Fc fraction was applied to a PD-10 desalting column (Amersham Biosciences) which had previously been equilibrated with phosphate-buffered saline containing 50 mM arginine hydrochloride (pH 7.0, A-PBS), followed by elution with A-PBS, whereby 3.5 ml of a sample whose solvent was replaced with A-PBS was obtained. The samples prepared by the above-mentioned procedure were cryopreserved at −80° C. until use.

An expression vector for soluble mouse Siglec-15/phIgFc was constructed by the Gateway technology (Invitrogen). A DNA fragment encoding the extracellular domain of mouse Siglec-15 (Accession number, NP_001094508, 1-258) was amplified by PCR to construct an entry clone into pDNOR221 (Invitrogen). Next an LR reaction was performed between this entry clone and a destination vector harboring DNA encoding a human Fc sequence. The DNA sequence of the mouse Siglec-15-Fc in the constructed plasmid was confirmed by DNA sequence analysis. Mouse Siglec-15-Fc was transiently expressed in HEK 293FreeStyle™ harboring the expression vector of soluble mouse Siglec-15/phIgFc. 1.8 L of the culture solution of mouse Siglec-15-Fc-expressing HEK 293FreeStyle™ cells was filtered through a Sterivex-GV filter (Millipore), and the filtrate was applied to a HiTrap Protein A column (Amersham Biosciences) which had previously been equilibrated with Dulbecco's PBS (D-PBS, Invitrogen). Mouse Siglec-15-Fc was eluted with 0.1 M sodium citrate buffer (pH 3.0) and neutralized with 1 M Tris. The collected mouse Siglec-15-Fc fraction was concentrated to 2.5 ml with a centrifugal membrane concentrator Amicon Ultra-15 (Millipore). The buffer was exchanged with Otsuka Physiological Saline for Infection (Otsuka Pharmaceutical) containing 0.01% Tween-20. The sample was cryopreserved at −80° C. until use.

Antibody Generation from HuCAL Gold Libraries

A. Phage Display Library

For the generation of therapeutic antibodies against human Siglec-15, selections with the MorphoSys HuCAL GOLD phage display library were carried out. HuCAL GOLD® is a Fab library based on the HuCAL® concept (Knappik et al. (J. Mol. Biol., 296, 57-86, 2000); Krebs et al., J. Immunol. Methods, 254, 67-84, 2001; Rothe et al., J. Mol. Biol., 376 (4):1182-200, 2008), in which all six CDRs are diversified, and which employs the CysDisplay™ technology for linking Fab fragments to the phage surface (WO 01/05950).

B. Pannings with HuCAL GOLD®

MOR09012, MOR08656 and MOR08662 were isolated as follows. For the selections, the HuCAL GOLD® antibody library was subjected to whole cell panning using HEK 293FreeStyle™ cells transfected with either plasmid pcDNA3.1 (+)/human Siglec-15 or plasmid pcDNA3.1 (+)/mouse Siglec-15 using 293 fectin (Invitrogen) followed by pH-elution and a post-adsorption step on Siglec-15-negative HEK 293FreeStyle™ cells for depletion of irrelevant antibody-phages. Finally, the remaining antibody phages were used to infect E. coli cells which were then plated on agar plates and incubated overnight. The next day, the bacterial colonies were scraped off from the plates, the phages were rescued and amplified. The HuCAL GOLD® antibody library was subjected to capture panning using recombinant human Siglec-15-Fc captured by goat anti-human Fc antibody (Jackson Immuno Research, cat. No. 109-005-098) on 96-well Maxi-sorp plate (Nunc, clear). In order to eliminate human Fc and goat IgG binders, both human IgG (Jackson Immuno Research, cat No. 009-000-003) and Goat IgG (Jackson Immuno Research, cat No. 005-000-003) were added to the selection solution. After washing with Tween-20/PBS and PBS, bound phages were eluted. Mid-log phase E. coli cells were infected with the eluted phages and plated onto LB-agar supplemented with glucose and chloramphenicol (LB-CG). After overnight incubation, colonies were scraped off and kept in LB-CG containing 15% glycerol.

MOR09281 was isolated as follows. To obtain Fab with improved affinities, phage resulting from the solid phase Fc capture and differential whole cell pannings were selected for LCDR3 diversification followed by additional selection rounds. Output from all panning strategies was screened in a primary ELISA on recombinant human Siglec15-hFc. Positive clones were subjected to secondary ELISA and FACS screenings. Selected clones were consolidated and purified.

C. Micro Expression of HuCAL GOLD® Fab Antibodies in E. coli

Micro expression of Fab fragments encoded by pMORPH® x23_Fab in E. coli was carried out in a round bottom 96-well culture plate (Corning). E. coli colonies were inoculated in medium. The culture plates were incubated until the culture became slightly turbid. Then, additional medium was added. The culture plate was further incubated overnight. Next day, BEL buffer (protease inhibitor cocktail (Roche, cat No. 11873580001)) containing 2.5 mg/ml lysozyme (Roche) was added to each well of the culture plate and the culture plate was shaken. After lysis of the E. coli, skim milk/TBS (Takara Bio) solution was added and the culture plate was further shaken. The prepared lysate of E. coli was used for ELISA screening for human Siglec-15 binders.

D. ELISA Screening of Siglec-15 Binders

Wells of a 96-well MaxiSorp™ microtiter plate (Nunc) were coated with 1.25 µg/ml of goat anti-human Fc antibody (Jackson Immuno Research, cat No. 109-005-098) overnight. Next day, after washing with PBS the microtiter plate was blocked with skim milk/PBS. After washing with PBS, 1

μg/ml of recombinant human Siglec-15-Fc was added to the microtiter plate. The wells were washed three times with Tween-20/Tris buffered saline (Takara Bio, (TBST)) before adding the *E. coli* lysate as described above. The plate was shaken gently followed by washing with TBST. Then, alkaline phosphatase conjugated anti-human Fab (Jackson Immuno Research, Cat No. 109-035-097) was diluted with TBST and was added to the plate. The plate was shaken gently followed by washing with TBST. Binding was detected by Attophos Substrate Set (Roche) and fluorescence (Excitation: 440 nm; Emission: 550 nm) was measured with a plate reader (Molecular Devices, SpectraMax M5).

Example 2

Construction, Expression and Purification OF HuCAL® IgG2

A. Conversion to IgG2

In order to express full length IgG, variable domain fragments of heavy (VH) and light chains (VL) were subcloned from pMORPHx® 9 Fab expression vectors into appropriate pMOPRH® 2_h_Ig vectors for human IgG2. Restriction enzymes MfeI and BlpI were used for subcloning of the VH domain fragment into pMORP® 2_h_IgG2, EcoRV and BsiWI for subcloning of the VL domain fragment into pMORPH® 2_h_Igκ, and EcoRV and HpaI for subcloning of the VL domain fragment into pMORPH® 2_h_Igλ2. Subsequent to ligation, transformation and DNA preparation, the resulting IgG expression plasmids were characterized by restriction analysis and sequencing.

B. Transient Expression and Purification of Human IgG2

Eukaryotic HKB11 cells were transfected with equal amounts of IgG heavy and light chain expression vector (pMORPH® 2). The cell culture supernatant was generally harvested from 3 to 7 days post transfection. After sterile filtration, the solution was subjected to standard protein A affinity chromatography (MabSelect SURE, GE Healthcare). If not otherwise stated, buffer exchange was performed either to 1× Dulbecco's PBS (pH 7.2, Invitrogen) or to citrate buffer (100 mM citrate, 150 mM NaCl, pH 5.0) and samples were sterile filtered (0.2 μm pore size). Protein concentrations were determined by UV-spectrophotometry. Purity of IgG was analyzed under denaturing, reducing and non-reducing conditions in SDS-PAGE or by using Agilent BioAnalyzer and in native state by HP-SEC.

Example 3

Screening and Antibody Characterization

A. Capture ELISA on Siglec-15-FC

Wells of a 384-well MaxiSorp™ microtiter plate were coated with goat anti-human IgG (Dianova, Cat#109-005-098, diluted 1:1,000 in PBS). The next day, wells were washed and then blocked with MPBST on a microtiter plate shaker. The wells were washed with PBST before addition of recombinant human or mouse Siglec15-human Fc fusion protein. After incubation, pre-blocked BEL extracts (for preparations refer to Example 1C) or purified Fab/IgG were added. The plate was incubated on a microtiter plate shaker and then washed with PBST.

For detection of the antigen bound to the captured Fab, the plate was washed with PBST and anti-Fab-AP (Dianova, Cat#109-055-097, 1:5000 diluted in PBS) was added.

After incubation the plate was washed with TBST, Attophos (AttoPhos Substrate Set, Roche #11681982001, diluted 1:10 in TBS) was added and fluorescence was measured in a TECAN microtiter plate reader (emission: 535 nm; excitation: 430 nm).

B. FACS Analysis

HEK293T cells were detached with Versene (Invitrogen #15040066), washed and resuspended in FACS buffer (PBS/ 3% FCS). The non-adherent HEK293 FreeStyle™ cells were washed and resuspended in FACS buffer. $1\times10^5$-$1\times10^6$ cells/ well were transferred into a 96 round bottom well plate, pelleted for 5 min at 300×g and resuspended in diluted BEL extract (see Example 1C) or purified antibody. Cell-antibody mixtures were incubated for 1 h at 4° C. The cells were washed twice by centrifugation for 5 min at 300×g and subsequent suspension in FACS buffer. (During the course of the project, the number of washing steps was increased to five to prevent antibody binding to untransfected cells.) Cells were resuspended in detection antibody solution (diluted 1:100 in FACS buffer). After 1 h incubation at 4° C., cells were washed twice with FACS buffer, resuspended in FACS buffer and analyzed via FACS Array device. Data were analyzed via FlowJo software. MOR03207 (anti-lysozyme) antibody was used as negative control. Human antibodies were detected with goat anti-human PE (Jackson ImmunoResearch #109-116-097).

Example 4

Affinity Maturation of Candidate Antibodies

A. Generation of Affinity Maturation Libraries

To increase affinity and biological activity of selected antibody fragments, CDR3L and CDRH2 regions were optimized in parallel by cassette mutagenesis using trinucleotide directed mutagenesis (Virnekas et al. 1994), while the framework regions were kept constant. Prior to cloning for affinity maturation, all parental Fab fragments were transferred from the corresponding expression vector (pMORPH® x9_FH) into the CysDisplay® vector pMORPH® 25_LHC via XbaI/ EcoRI. After CDRL3 or CDRH2 diversification, ligation mixtures of the resulting seven different libraries were electroporated into 4 ml *E. coli* cells (Invitrogen, Carlsbad, Calif., USA) yielding ~$10^7$ to $10^8$ independent colonies per library. This library size ensured coverage of the theoretical diversity. Amplification of the library was performed as described before (Rauchenberger et al. 2003). For quality control, single clones were randomly picked and sequenced.

B. Solid-Phase Fc Capture Pannings $1\times10^{12}$ phage rescued from the affinity maturation libraries as described above, were introduced to the selection via solid phase Fc capture panning as described below.

The appropriate number of wells of a MaxiSorp™ plate (F96 MaxiSorp™, Nunc #442402) was coated overnight with 330 μl Fcγ fragment specific anti-human IgG, (10 μg/ml in PBS; Jackson Immuno Research, Cat#109-005-098). The following day, coated wells were washed with PBS and blocked with MPBST on a microtiter plate shaker. Subsequently, wells were washed with PBS and incubated with 330 μl antigen solution. The phage were pre-blocked in PBS solution containing milk powder, Tween 20 and 0.1 mg/ml goat gammaglobulin (Jackson Immuno Research, Cat#009-000-002) for 2 h at room temperature on a rotator. For the selection process the antigen solution was removed from the MaxiSorp™ plate and wells were washed with PBS. Pre-blocked phage were added to the corresponding wells and the plate was incubated on a microtiter plate shaker. Following incubation, phage solution was removed and wells were washed several times with PBST, and PBS. PBS was removed after the last washing step before continuing with elution. Specifically bound phage were eluted via DTT in Tris/HCl, pH 8.0 and a 10 min incubation period at room temperature. Eluates were used to infect log phase *E. coli* TG1 F+ cultures. Infected *E. coli* were plated onto LB agar plates supplemented with chloramphenicol and glucose and were incubated. The following day, bacterial colonies were scraped off and resuspended in YT media.

Selection rounds were applied in CDRL3 maturation pannings, and in CDRH2 maturation pannings. Panning stringency was increased in each selection round by decreasing antigen concentration and increasing the number and intensity of washing steps.

C. Differential Whole Cell Panning

Differential whole cell maturation pannings were essentially carried out as described below.

Differential whole cell pannings (dWCPs) were designed by alternation of solid phase Fc capture pannings on recombinant antigen (see Example 4B) and whole cell pannings on transfected cells as described below.

Whole cell pannings (WCPs) were performed using HEK293 FreeStyle™ cells transiently transfected with human Siglec-15. The Siglec-15-expressing cells were washed, resuspended and pre-blocked. ~1×10$^{12}$ phage rescued from each maturation library were pre-blocked. After blocking, 1×10$^6$ Siglec-15-expressing cells were pelleted, resuspended in pre-blocked phage solution and incubated. The cell number was reduced to 5×10$^5$ in the subsequent selection round. Non-specific phage were removed by washing steps, whereby washing stringency was increased during the panning process. For washing, cells were pelleted by centrifugation, resuspended and incubated on a rotator. After washing, the specifically bound phage were eluted from the cells. After centrifugation, the supernatant was removed from the cell pellet and its pH neutralized with 2 M Tris base (unbuffered). Infection of *E. coli* TG1 F+ with the selected phage was performed as described for solid phase pannings (see Example 4B). Rounds of selection were performed as Fc capture pannings, or as whole cell panning.

D. Parent Antibodies

MOR09012, MOR08656 and MOR08662 are the parent antibodies of MOR09892, MOR09898 or MOR10110, respectively. MOR09281 was selected as a candidate for the further analysis without the step of Affinity Maturation.

Information concerning the amino acid sequences of the antibodies, the nucleic acid sequences encoding them and the structures thereof is summarized in Tables 1 to 7.

TABLE 1

MOR08656

| | Chain | | | |
|---|---|---|---|---|
| | Heavy | | Light | |
| | Sequence Type | | | |
| | Nucleotide | Amino Acid | Nucleotide | Amino Acid |
| SEQ ID NO | 1 | 2 | 6 | 7 |
| FIG. | 14 | 15 | 16 | 17 |
| Signal Sequence* | 1-57 | 1-19 | 1-57 | 1-19 |
| Variable Region* | 58-411 | 20-137 | 58-384 | 20-128 |
| CDR1* | 148-162 | 50-54 | 124-156 | 42-52 |
| CDR2* | 205-255 | 69-85 | 202-222 | 68-74 |
| CDR3* | 352-378 | 118-126 | 319-345 | 107-115 |

TABLE 2

MOR08662

| | Chain | | | |
|---|---|---|---|---|
| | Heavy | | Light | |
| | Sequence Type | | | |
| | Nucleotide | Amino Acid | Nucleotide | Amino Acid |
| SEQ ID NO | 11 | 12 | 16 | 17 |
| FIG. | 18 | 19 | 20 | 21 |
| Signal Sequence* | 1-57 | 1-19 | 1-57 | 1-19 |
| Variable Region* | 58-408 | 20-136 | 58-387 | 20-129 |
| CDR1* | 148-162 | 50-54 | 124-156 | 42-52 |
| CDR2* | 205-255 | 69-85 | 202-222 | 68-74 |
| CDR3* | 352-375 | 118-125 | 319-348 | 107-116 |

TABLE 3

MOR09012

| | Chain | | | |
|---|---|---|---|---|
| | Heavy | | Light | |
| | Sequence Type | | | |
| | Nucleotide | Amino Acid | Nucleotide | Amino Acid |
| SEQ ID NO | 21 | 22 | 26 | 27 |
| FIG. | 22 | 23 | 24 | 25 |
| Signal Sequence* | 1-57 | 1-19 | 1-57 | 1-19 |
| Variable Region* | 58-405 | 20-135 | 58-390 | 20-130 |
| CDR1* | 148-162 | 50-54 | 124-156 | 42-52 |
| CDR2* | 205-255 | 69-85 | 202-222 | 68-74 |
| CDR3* | 352-372 | 118-124 | 319-351 | 107-117 |

TABLE 4

MOR09281

| | Chain | | | |
|---|---|---|---|---|
| | Heavy | | Light | |
| | Sequence Type | | | |
| | Nucleotide | Amino Acid | Nucleotide | Amino Acid |
| SEQ ID NO | 31 | 32 | 36 | 37 |
| FIG. | 26 | 27 | 28 | 29 |
| Signal Sequence* | 1-57 | 1-19 | 1-57 | 1-19 |
| Variable Region* | 58-408 | 20-136 | 58-387 | 20-129 |
| CDR1* | 148-162 | 50-54 | 124-156 | 42-52 |
| CDR2* | 205-255 | 69-85 | 202-222 | 68-74 |
| CDR3* | 352-375 | 118-125 | 319-348 | 107-116 |

TABLE 5

MOR09892

| | Chain | | | |
|---|---|---|---|---|
| | Heavy | | Light | |
| | Sequence Type | | | |
| | Nucleotide | Amino Acid | Nucleotide | Amino Acid |
| SEQ ID NO | 41 | 42 | 46 | 47 |
| FIG. | 30 | 31 | 32 | 33 |
| Signal Sequence* | 1-57 | 1-19 | 1-57 | 1-19 |
| Variable Region* | 58-405 | 20-135 | 58-387 | 20-129 |
| CDR1* | 148-162 | 50-54 | 124-156 | 42-52 |
| CDR2* | 205-255 | 69-85 | 202-222 | 68-74 |
| CDR3* | 352-372 | 118-124 | 319-348 | 107-116 |

TABLE 6

MOR09898

| | Chain | | | |
|---|---|---|---|---|
| | Heavy | | Light | |
| | Sequence Type | | | |
| | Nucleotide | Amino Acid | Nucleotide | Amino Acid |
| SEQ ID NO | 51 | 52 | 56 | 57 |
| FIG. | 34 | 35 | 36 | 37 |
| Signal Sequence* | 1-57 | 1-19 | 1-57 | 1-19 |
| Variable Region* | 58-411 | 20-137 | 58-387 | 20-129 |
| CDR1* | 148-162 | 50-54 | 124-156 | 42-52 |
| CDR2* | 205-255 | 69-85 | 202-222 | 68-74 |
| CDR3* | 352-378 | 118-126 | 319-348 | 107-116 |

TABLE 7

MOR10110

| | Chain | | | |
|---|---|---|---|---|
| | Heavy | | Light | |
| | Sequence Type | | | |
| | Nucleotide | Amino Acid | Nucleotide | Amino Acid |
| SEQ ID NO | 61 | 62 | 66 | 67 |
| FIG. | 38 | 39 | 40 | 41 |
| Signal Sequence* | 1-57 | 1-19 | 1-57 | 1-19 |
| Variable Region* | 58-408 | 20-136 | 58-387 | 20-129 |
| CDR1* | 148-162 | 50-54 | 124-156 | 42-52 |
| CDR2* | 205-255 | 69-85 | 202-222 | 68-74 |
| CDR3* | 352-375 | 118-125 | 319-348 | 107-116 |

*range of nucleotides or amino acid residues

The amino acid sequences of the complementarity determining regions (CDRs) of each of the antibodies are set out in Table 8.

TABLE 8

| Antibody | Chain | CDR | Sequence | SEQ ID NO. |
|---|---|---|---|---|
| MOR08656 | Heavy | CDR1 | NYWMT | 3 |
| | | CDR2 | FISYSGSTTYYADSVKG | 4 |
| | | CDR3 | EGTSSMFDV | 5 |
| | Light | CDR1 | SGDALRSYYAS | 8 |
| | | CDR2 | DDNKRPS | 9 |
| | | CDR3 | GSYDGTVHV | 10 |
| MOR08662 | Heavy | CDR1 | NYAMN | 13 |
| | | CDR2 | TISYIGSNTYYADSVKG | 14 |
| | | CDR3 | GAGLGYDV | 15 |
| | Light | CDR1 | SGDNLRSKYVY | 18 |
| | | CDR2 | DTNDRPS | 19 |
| | | CDR3 | QTYDMTSQDV | 20 |
| MOR09012 | Heavy | CDR1 | SYAMH | 23 |
| | | CDR2 | YISYSGSNTYYADSVKG | 24 |
| | | CDR3 | GWGGFDY | 25 |
| | Light | CDR1 | SGDNLPNRYVH | 28 |
| | | CDR2 | DDNNRPS | 29 |
| | | CDR3 | QTYDMFSMSDV | 30 |
| MOR09281 | Heavy | CDR1 | NYWMS | 33 |
| | | CDR2 | LISYSGSTTYYADSVKG | 34 |
| | | CDR3 | DTPIGMDF | 35 |
| | Light | CDR1 | SGDNLGSYYAY | 38 |
| | | CDR2 | GDNDRPS | 39 |
| | | CDR3 | SSYDIVQPYV | 40 |
| MOR09892 | Heavy | CDR1 | SYAMH | 43 |
| | | CDR2 | YISYSGSNTYYADSVKG | 44 |
| | | CDR3 | GWGGFDY | 45 |
| | Light | CDR1 | SGDNLPNRYVH | 48 |
| | | CDR2 | DDNNRPS | 49 |
| | | CDR3 | QSRDLHYSPV | 50 |
| MOR09898 | Heavy | CDR1 | NYWMT | 53 |
| | | CDR2 | FISYSGSTTYYADSVKG | 54 |
| | | CDR3 | EGTSSMFDV | 55 |
| | Light | CDR1 | SGDALRSYYAS | 58 |
| | | CDR2 | DDNKRPS | 59 |
| | | CDR3 | ASFTYMSDFV | 60 |
| MOR10110 | Heavy | CDR1 | NYAMN | 63 |
| | | CDR2 | YISYSSSNTYYADSVKG | 64 |
| | | CDR3 | GAGLGYDV | 65 |
| | Light | CDR1 | SGDNLRSKYVY | 68 |
| | | CDR2 | DTNDRPS | 69 |
| | | CDR3 | QTYDMTSQDV | 70 |

The amino acid sequences of CDR1 and CDR2 of antibodies MOR09281, MOR09892, MOR09898 and MOR10110 conform to the consensus sequences set out below.

Heavy chain CDR1 consensus sequence is $X_1YX_2MX_3$     (SEQ ID NO: 71)

wherein $X_1$ is N or S, $X_2$ is W or A and $X_3$ is S, H, T or N.

Heavy chain CDR2 consensus sequence is $X_4ISYSX_5SX_6TYYADSVKG$     (SEQ ID NO: 72)

wherein $X_4$ is L, Y or F, $X_5$ is S or G and $X_6$ is T or N.

Light chain CDR1 consensus sequence is

SGDX₇LX₈X₉X₁₀YX₁₁X₁₂    (SEQ ID NO: 73)

wherein $X_7$ is N or A, $X_8$ is G, P or R, $X_9$ is S or N, $X_{10}$ is Y, R or K, $X_{11}$ is A or V and $X_{12}$ is Y, H or S.

Light chain CDR2 consensus sequence is

X₁₃X₁₄NX₁₅RPS    (SEQ ID NO: 74)

wherein $X_{13}$ is G or D, $X_{14}$ is T or D and $X_{15}$ is N, D or K.

Example 5

Binding Activity Analysis

A. Binding Activity Analysis by ELISA 0.1 mL of 1 µg/ml recombinant human Siglec-15-Fc, mouse Siglec-15-Fc or human Fc (Jackson Immuno Research, #009-000-008) was added to the wells of a 96-well Immobilizer amino plate (Nunc) and the plate was kept overnight at 4° C. Next day, after washing with 0.05% Tween-20/PBS (PBST), the plate was blocked with 5% BSA/PBS for 1.5 hours at room temperature. After washing with PBST, 0.1 mL of 1 µg/ml anti-Siglec-15 antibodies (MOR09281, MOR09892, MOR09898, MOR10110, MOR09012, MOR08656, MOR08662) and human IgG (Jackson Immuno Research, Cat. No. 009-000-003 as a negative control) were added to the plate and the plate was kept for one hour at room temperature. After washing with PBST, 0.1 mL of peroxidise conjugated anti-human Fab antibody (Jackson Immuno Research, Cat. No. 112-035-097) diluted by 5,000 fold with PBST was added to the plate and the plate was kept for 1.5 hours at room temperature. After washing with PBST, binding was detected using ELISA POD ABTS Kit (Nacalai Tesque, Cat. No. 02893-60). Reaction time was 4 min. Absorbance of 450 nm and 650 nm was measured with a plate reader (Molecular Devices, SpectraMax M5). FIG. 1 shows the ELISA results. It was found that MOR09281, MOR09892, MOR09898, MOR10110, MOR09012, MOR08656 and MOR08662 bound to both recombinant human Siglec-15-Fc and mouse Siglec-15-Fc but not human Fc.

Example 6

Biological Assays

A. Mouse Osteoclast Formation Assay

A-1. Preparation of Mouse Bone Marrow Nonadherent Cells

The femur and tibia were resected from a male ddY mouse at the age of 5 to 8 weeks and soft tissues were removed. Both ends of the femur or tibia were cut off, and D-PBS was injected using a syringe with a 23-gauge injection needle to push out bone marrow cells. Centrifugation was performed at room temperature for 5 minutes at 1,000 rpm, and the supernatant was removed. To the cell pellet, 1 ml of a hemolytic buffer (Red Blood Cell Lysing Buffer, manufactured by Sigma Co., Ltd.) was added to suspend it, and the resulting suspension was left at room temperature for 5 minutes. Twenty ml of MEM-α medium (manufactured by Invitrogen, Inc.) containing 10% fetal bovine serum (FBS) was added thereto, and the suspension was centrifuged at room temperature for 5 minutes at 1,000 rpm, and the supernatant was removed. To the cell pellet, 10 ml of MEM-α medium containing 5 ng/ml of M-CSF (manufactured by R&D systems, Inc.) and 10% FBS was added to suspend it. Then, the resulting suspension was passed through a cell strainer (40 µm Nylon, manufactured by BD Falcon) to remove aggregates. The resulting cells were transferred to a 75 cm²-T flask (for the use of adherent cells) and cultured overnight in a $CO_2$ incubator. After the overnight culture, the cells which did not adhere to the T-flask were recovered and used as mouse bone marrow nonadherent cells.

A-2. Effect of Anti-Siglec-15 Antibody on Osteoclast Differentiation from Mouse Bone Marrow Nonadherent Cells (Stimulation with RANKL)

The effect of anti-Siglec-15 antibodies produced in Examples 1 and 4, was evaluated by an osteoclast differentiation assay by using mouse bone marrow nonadherent cells. Mouse bone marrow nonadherent cells prepared by the above-mentioned method in Example 6A-1 were prepared at $1.5 \times 10^5$ cells/ml in α-MEM medium containing 10% FBS and 10 ng/ml of M-CSF, and the resulting cell preparation was seeded in each well of a 96-well plate in an amount of 200 µl and the cells were cultured for 2 days in a $CO_2$ incubator. The old culture medium in the 96-well plate was removed, and 100 µl of MEM-α medium containing 10% FBS, 20 ng/ml human RANKL (RANKL, manufactured by Peprotech, Inc.), and 10 ng/ml M-CSF was added to each well. To the cell culture medium, each anti-Siglec-15 antibody (MOR09281, MOR09012, MOR09892, MOR08656, MOR09898, MOR08662, and MOR10110) was added at concentrations from 3 to 100 ng/ml, and the cells were cultured for an additional 3 days in a $CO_2$ incubator. After completion of the culturing, the activity of tartrate-resistant acid phosphatase (TRAP) of the formed osteoclasts was measured by the following procedure. The culture medium in each well of the 96-well plate was removed by suction, and 50 µl of 50 mM sodium citrate buffer (pH 6.1) containing 1% Triton X-100 was added to each well. Then, the plate was shaken for 5 minutes on a plate shaker to lyse the cells. To each well, 50 µl of a substrate solution (50 mM sodium citrate buffer (pH 6.1) containing 5 mg/ml p-nitrophenyl phosphate and 0.46% sodium tartrate) was added, and the plate was incubated at room temperature for 10 minutes. After the incubation, 50 µl of a 1 N sodium hydroxide solution was added to each well of the 96-well plate to stop the enzymatic reaction. After stopping the enzymatic reaction, an absorbance of each well at 405 nm was measured as an index of TRAP activity. The results are shown in FIGS. 2 to 8. A significant inhibition of TRAP activity was not observed for MOR09012 (parent antibody of MOR09892), MOR08656 (parent antibody of MOR09898), and MOR08662 (parent antibody for MOR10110). On the other hand, a significant inhibition of TRAP activity was observed for MOR09281, MOR09892, MOR09898, and MOR10110 at 13 ng/ml or higher concentrations in a dose-dependent manner. From the above results, it was shown that the anti-Siglec-15 antibodies (MOR09281, MOR09892, MOR09898, and MOR10110) have a potent inhibitory effect on osteoclast formation (osteoclast differentiation and maturation). Furthermore, it was also shown that affinity maturation of the parent antibodies (MOR09012, MOR08656, and MOR08662) produced antibodies (MOR09892, MOR09898, and MOR10110, respectively) that have higher inhibitory activity on osteoclast formation.

B. OsteoLyse Assay with Human Osteoclasts
B) Effect of Addition of Human Anti-Human Siglec-15 Monoclonal Antibodies on Bone Resorption Activity of Normal Human Osteoclast Precursor Cells (Evaluation Using Collagen-Coated Plate)

It is known that osteoclasts release a protease such as cathepsin K and degrade type I collagen which is a constitutional component of bone tissue. OsteoLyse Assay Kit (manufactured by Lonza, Inc., Cat. No. PA-1500) provides a 96-well plate coated with europium-conjugated human collagen (96-well OsteoLyse cell culture plate), and it is possible to evaluate the bone resorption activity of osteoclasts in vitro by measuring the amount of fluorescent collagen fragments released in the supernatant when osteoclasts are cultured in the plate.

Normal human osteoclast precursor cells (Normal Human Natural Osteoclast Precursor Cells, purchased from Sanko Junyaku Co., Ltd., Cat. No. 2T-110) were seeded in a 96-well OsteoLyse cell culture plate at $1\times10^4$ cells/well according to the protocol attached to the cells. As the medium, a minimal essential medium for osteoclast precursor cells (OPBM, purchased from Sanko Junyaku Co., Ltd., Cat. No. PT-8201) supplemented with an OPGM supplement set (Osteoclast SingleQuot™ Kit, purchased from Sanko Junyaku Co., Ltd., Cat. No. PT-9501) containing fetal bovine serum (final concentration: 10%), human RANKL (final concentration: 10 or 20 ng/ml), human M-CSF (final concentration: 33 ng/ml) and the like was used. To the resulting culture supernatant, the human anti-human Siglec-15 monoclonal antibodies (MOR09281, 09012, 09892, 08656, 09898, 08662 and 10110) prepared in Examples 1 and 4 was added to give a final concentration of 4, 20, 100, or 500 ng/ml, and the cells were cultured for 4 or 5 days in a $CO_2$ incubator. A 10 μl aliquot of the culture supernatant was collected, and 200 μl of Fluorophore Releasing Reagent included in the OsteoLyse Assay Kit was added thereto, and a fluorescence intensity (RFU) was measured using a time-resolved fluorescence fluorimeter (ALVO MX, manufactured by Perkin Elmer Inc., with excitation at 340 nm and emission at 615 nm), whereby the amount of free fluorescent collagen fragments released in the culture supernatant was determined. The results are shown in FIGS. 9 to 13. As a result, the amount of fluorescent collagen fragments increased by the addition of RANKL was reduced by the anti-Siglec-15 antibodies in a concentration-dependent manner within the range of from 4 ng/ml to 500 ng/ml. The key finding is that the affinity-improved antibodies (MOR09892, 09898 and 10110) inhibited the bone resorption activity at lower concentrations than respective parental antibodies (MOR09012, 08656 and 08662). These results suggest that improvement of the binding affinity of the antibody leads to the improvement of bioactivity as well.

Example 7

Preparation and Assays of Additional Antibodies

A. Preparation of Antibodies

MOR09268 was prepared in the same manner as in Example 1 in which MOR09281 was obtained and it was converted to IgG2 in accordance with Example 2. MOR09268 is the parental antibody of MOR12574, MOR13154 and MOR13156. Affinity maturations to generate these three antibodies were performed in accordance with the protocol described in Example 4.

Information concerning the amino acid sequences of the antibodies, the nucleic acid sequences encoding them and the structures thereof is summarized in Tables 9 to 12.

TABLE 9

| | MOR09268 | | | |
|---|---|---|---|---|
| | Chain | | | |
| | Heavy | | Light | |
| | Sequence Type | | | |
| | Nucleotide | Amino Acid | Nucleotide | Amino Acid |
| SEQ ID NO | 76 | 77 | 81 | 82 |
| FIG. | 46 | 47 | 48 | 49 |
| Signal Sequence* | 1-57 | 1-19 | 1-57 | 1-19 |
| Variable Region* | 58-414 | 20-138 | 58-399 | 20-133 |
| CDR1* | 148-162 | 50-54 | 124-165 | 42-55 |
| CDR2* | 205-255 | 69-85 | 211-231 | 71-77 |
| CDR3* | 352-381 | 118-127 | 328-360 | 110-120 |

TABLE 10

| | MOR12574 | | | |
|---|---|---|---|---|
| | Chain | | | |
| | Heavy | | Light | |
| | Sequence Type | | | |
| | Nucleotide | Amino Acid | Nucleotide | Amino Acid |
| SEQ ID NO | 76 | 77 | 86 | 87 |
| FIG. | 46 | 47 | 50 | 51 |
| Signal Sequence* | 1-57 | 1-19 | 1-57 | 1-19 |
| Variable Region* | 58-414 | 20-138 | 58-402 | 20-134 |
| CDR1* | 148-162 | 50-54 | 124-165 | 42-55 |
| CDR2* | 205-255 | 69-85 | 211-231 | 71-77 |
| CDR3* | 352-381 | 118-127 | 328-363 | 110-121 |

TABLE 11

| | MOR13154 | | | |
|---|---|---|---|---|
| | Chain | | | |
| | Heavy | | Light | |
| | Sequence Type | | | |
| | Nucleotide | Amino Acid | Nucleotide | Amino Acid |
| SEQ ID NO | 91 | 92 | 96 | 97 |
| FIG. | 52 | 53 | 54 | 55 |
| Signal Sequence* | 1-57 | 1-19 | 1-57 | 1-19 |
| Variable Region* | 58-414 | 20-138 | 58-399 | 20-133 |
| CDR1* | 148-162 | 50-54 | 124-165 | 42-55 |
| CDR2* | 205-255 | 69-85 | 211-231 | 71-77 |
| CDR3* | 352-381 | 118-127 | 328-360 | 110-120 |

TABLE 12

MOR13156

| | Chain | | | |
|---|---|---|---|---|
| | Heavy | | Light | |
| Sequence Type | | | | |
| | Nucleotide | Amino Acid | Nucleotide | Amino Acid |
| SEQ ID NO | 101 | 102 | 86 | 87 |
| FIG. | 56 | 57 | 50 | 51 |
| Signal Sequence* | 1-57 | 1-19 | 1-57 | 1-19 |
| Variable Region* | 58-420 | 20-140 | 58-402 | 20-134 |
| CDR1* | 148-162 | 50-54 | 124-165 | 42-55 |
| CDR2* | 205-261 | 69-87 | 211-231 | 71-77 |
| CDR3* | 358-387 | 120-129 | 328-363 | 110-121 |

*range of nucleotides or amino acid residues n.b. The heavy chains of antibodies MOR09268 and MOR12574 are identical. The light chains of antibodies MOR12574 and MOR13156 are identical.

The amino acid sequences of the complementarity determining regions (CDRs) of each of the antibodies are set out in Table 13.

TABLE 13

| Antibody | Chain | CDR | Sequence | SEQ ID NO. |
|---|---|---|---|---|
| MOR09268 | Heavy | CDR1 | TYAMH | 78 |
| | | CDR2 | NIAYSGSVTYYADSVKG | 79 |
| | | CDR3 | RGPGMGNMDI | 80 |
| | Light | CDR1 | TGTSSDVGDYNYVS | 83 |
| | | CDR2 | YVTNRPS | 84 |
| | | CDR3 | QSYDTGSFAMV | 85 |
| MOR12574 | Heavy | CDR1 | TYAMH | 78 |
| | | CDR2 | NIAYSGSVTYYADSVKG | 79 |
| | | CDR3 | RGPGMGNMDI | 80 |
| | Light | CDR1 | TGTSSDVGDYNYVS | 88 |
| | | CDR2 | YVTNRPS | 89 |
| | | CDR3 | QSYAPLPSSHIV | 90 |
| MOR13154 | Heavy | CDR1 | TYAMH | 93 |
| | | CDR2 | TIFGSSSTYYADSVKG | 94 |
| | | CDR3 | RGPGMGNMDI | 95 |
| | Light | CDR1 | TGTSSDVGDYNYVS | 98 |
| | | CDR2 | YVTNRPS | 99 |
| | | CDR3 | QSYAGASFNLV | 100 |
| MOR13156 | Heavy | CDR1 | TYAMH | 103 |
| | | CDR2 | TIEIKEAGYATNYAAGVKG | 104 |
| | | CDR3 | RGPGMGNMDI | 105 |
| | Light | CDR1 | TGTSSDVGDYNYVS | 88 |
| | | CDR2 | YVTNRPS | 89 |
| | | CDR3 | QSYAPLPSSHIV | 90 |

The amino acid sequences of CDR1 and CDR2 of the heavy chain and CDR2 of the light chain of antibodies MOR09281, MOR09892, MOR09898, MOR10110, MOR09268, MOR12574, MOR13154 and MOR13156 conform to the consensus sequences set out below.

Heavy chain CDR1 consensus sequence is $X_{16}YX_{17}MX_{18}$        (SEQ ID NO: 106)

wherein $X_{16}$ is N, S or T, $X_{17}$ is W or A and $X_{18}$ is S, H, T or N.

Heavy chain CDR2 consensus sequence is (SEQ ID NO: 107)
$X_{19}IX_{20}X_{21}X_{22}X_{23}X_{24}X_{25}X_{26}X_{27}TX_{28}YAX_{29}X_{30}VKG$ wherein $X_{19}$ is L, Y, F, N or T, $X_{20}$ is S, A, F or E, $X_{21}$ is Y, G or I, $X_{22}$ is K or no amino acid, $X_{23}$ is E or no amino acid, $X_{24}$ is S or A, $X_{25}$ is S or G, $X_{26}$ is S or Y, $X_{27}$ is T, N, V, S or A, $X_{28}$ is Y or N, $X_{29}$ is D or A and $X_{30}$ is S or G.

Light chain CDR2 consensus sequence is $X_{31}X_{32}X_{33}X_{34}RPS$        (SEQ ID NO: 108)

wherein $X_{31}$ is G, D or Y, $X_{32}$ is T, D or V, $X_{33}$ is N or T and $X_{34}$ is N, D or K.

Antibodies MOR12574, MOR13154 and MOR13156 all have the same light chain CDR1 sequence of:

TGTSSDVGDYNYVS        (SEQ ID NO: 83)

Antibodies MOR12574, MOR13154 and MOR13156 all have the same light chain CDR2 sequence of:

YVTNRPS        (SEQ ID NO: 89)

Antibodies MOR12574, MOR13154 and MOR13156 all have the same heavy chain CDR3 sequence of:

RGPGMGNMDI        (SEQ ID NO: 80)

The amino acid sequences of CDR3 of the light chain of antibodies MOR12574, MOR13154 and MOR13156 conform to the consensus sequences set out below.

$QSYAX_{35}X_{36}X_{37}X_{38}X_{39}X_{40}X_{41}V$        (SEQ ID NO: 109)

wherein $X_{35}$ is P or G, $X_{36}$ is L or A, $X_{37}$ is S or P, $X_{38}$ is S or F, $X_{39}$ is S or N, $X_{40}$ is H or no amino acid and $X_{41}$ is I or L.

B. OsteoLyse Assay with Human Osteoclasts

Effect of human anti-human Siglec-15 monoclonal antibodies on bone resorption activity of normal human osteoclast precursor cells (Evaluation using collagen-coated plate)

Normal human osteoclast precursor cells (Normal Human Natural Osteoclast Precursor Cells, purchased from Sanko Junyaku Co., Ltd., Cat. No. 2T-110) were seeded in a 96-well OsteoLyse cell culture plate (Lonza, Inc., Cat. No. PA-1500) at $1 \times 10^4$ cells/well according to the protocol attached to the cells. As the medium, a minimal essential medium for osteoclast precursor cells (OPBM, purchased from Sanko Junyaku Co., Ltd., Cat. No. PT-8201) supplemented with an OPGM supplement set (Osteoclast SingleQuot™ Kit, purchased from Sanko Junyaku Co., Ltd., Cat. No. PT-9501) containing fetal bovine serum (final concentration: 10%), human RANKL (final concentration: 10 or 20 ng/ml), human M-CSF (final concentration: 33 ng/ml) and the like was used. To the resulting culture supernatant, MOR09268 was added to give a final concentration of 3 or 30 μg/ml, and the cells were cultured for 6 days in a $CO_2$ incubator. Likewise MOR12574, MOR13154 or MOR13156 were added to the culture supernatant, to give a final concentration of 4, 20, 100, or 500 ng/ml, and the cells were cultured for 5 days in a $CO_2$ incubator. A 10 μl aliquot of the culture supernatant was collected, and 200 μl of Fluorophore Releasing Reagent included in the OsteoLyse Assay Kit was added thereto. Fluorescence intensity (RFU) was measured using a time-resolved fluorescence fluorimeter (ALVO MX, manufactured by Perkin Elmer Inc., with excitation at 340 nm and emission at 615 nm), whereby the amount of free fluorescent collagen fragments released in the culture supernatant was determined. The results for MOR09268, MOR12574, MOR13154 and MOR13156 are shown in FIGS. 42, 43, 44 and 45, respectively. As shown in FIGS. 42 to 45, the number of fluorescent collagen fragments increased by the addition of RANKL was reduced by the anti-Siglec-15 antibodies in a concentration-dependent manner.

Example 8

Evaluation of Biological Activity of Anti-Siglec-15 Monoclonal Antibody Using Ovariectomized Rats A. Protocol of Animal Experiment The ovaries on both sides are removed from female F344 rats (obtained from Charles River Laboratories Japan, Inc.) at the age of 12 weeks, and the rats are divided into two groups: a vehicle administration group; and an anti-Siglec-15 monoclonal antibody administration group. Further, as a sham operation group, one group is prepared. In the antibody administration group, the anti-Siglec-15 monoclonal antibody in Example 2 or 7 is intraperitoneally administered at a dose of 1 mg/kg three times a week repeatedly for 4 weeks from the next day of the operation. In the vehicle administration group and the sham operation group, PBS containing 0.01% Tween 20 is intraperitoneally administered as the vehicle. At 4 weeks after the initiation of administration, urine is collected for 24 hours under fasting conditions, and the urine samples are stored at −80° C. until measurement. After completion of the urine collection, the rats are euthanized, and the lumbar spine is excised from each rat.

B. Measurement of Lumbar Spine Bone Density

Soft tissues adhered to the excised lumbar spine are removed, and the 4th to 6th lumbar vertebrae are extracted. The extracted lumbar vertebrae are degreased and dehydrated by being shaken in ethanol and then air-dried, and the bone density is measured using a bone densitometer (DCS-600EX, manufactured by Aloka Co., Ltd.). A significant decrease in lumbar spine bone density will be observed in the ovariectomized group as compared with the sham operation group, however, in the antibody administration groups, a decrease in bone density due to ovariectomy will be significantly inhibited.

C. Measurement of Urinary Deoxypyridinoline Excretion

A variety of type I collagen crosslinked metabolites sharply reflect bone metabolic turnover, particularly bone resorption. Above all, deoxypyridinoline is localized mainly in bone collagen, and therefore, is considered to have high reliability as an index of bone resorption.

The cryopreserved urine sample is thawed, and insoluble matter is precipitated by a centrifugal operation, whereby a supernatant is obtained. The amount of deoxypyridinoline contained in this supernatant is measured using Osteolinks "DPD" (manufactured by DS Pharma Biomedical Co., Ltd.). Further, by using Creatinine Test Wako (manufactured by Wako Pure Chemical Industries, Ltd.), the content of creatinine in the supernatant is also measured, and the amount of deoxypyridinoline corrected for creatinine is calculated. The urinary deoxypyridinoline excretion will be significantly increased in the ovariectomized group as compared with the sham group, and therefore, it will be indicated that in the ovariectomized rats, osteoclastic bone resorption is increased. On the other hand, in the antibody administration groups, an increase in deoxypyridinoline excretion due to ovariectomy will be inhibited. From this result, it will also be confirmed in the animal models that the monoclonal antibodies specifically binding to Siglec-15 inhibit osteoclastic bone resorption, and it will be strongly indicated that due to the inhibitory effect on bone resorption, a decrease in lumbar spine bone density in the ovariectomized rats is inhibited.

INDUSTRIAL APPLICABILITY

The anti-Siglec-15 antibody of the invention has the ability to inhibit osteoclast differentiation or bone resorption activity, and a pharmaceutical composition containing the anti-Siglec-15 antibody can be a therapeutic or preventive agent for a disease of abnormal bone metabolism.

The invention claimed is:

1. An isolated antibody capable of binding Siglec-15 which inhibits osteoclast formation and/or osteoclastic bone resorption, or an antigen-binding fragment thereof comprising (a) a heavy chain comprising a CDRH1 comprising a sequence of SEQ ID NO: 106, a CDRH2 comprising a sequence of SEQ ID NO: 107, and a CDRH3 comprising a sequence of any one of SEQ ID NOS: 80, 55, 65, 35 or 45; and (b) a light chain comprising a CDRL1 comprising a sequence of SEQ ID NO: 83 or 73, a CDRL2 comprising a sequence of SEQ ID NO: 108, and a CDRL3 comprising a sequence of any one of SEQ ID NOS: 90, 60, 100, 70, 40, 50 or 109, wherein the antibody or antigen-binding fragment binds to and inhibits Siglec-15, thereby inhibiting osteoclast formation and/or osteoclastic bone resorption.

2. The isolated antibody or antigen-binding fragment thereof according to claim 1, wherein the CDRH1 comprises a sequence of any one of SEQ ID NOS: 78, 53, 63, 33 or 43.

3. The isolated antibody or antigen-binding fragment thereof according to claim 1, wherein the CDRH2 comprises a sequence of any one of SEQ ID NOS: 104, 54, 94, 64, 34, 44 or 79.

4. The isolated antibody or antigen-binding fragment thereof according to claim 1, wherein the CDRL1 comprises a sequence of any one of SEQ ID NOS: 88, 58, 68, 38 or 48.

5. The isolated antibody or antigen-binding fragment thereof according to claim 1, wherein the CDRL2 comprises a sequence of any one of SEQ ID NOS: 89, 59, 69, 39 or 49.

6. The isolated antibody or antigen-binding fragment thereof according to claim 1, wherein the sequences of CDRH1, CDRH2, CDRH3, CDRL1, CDRL2 and CDRL3 in the antibody comprise:
   a) SEQ ID NOS: 103, 104, 105, 88, 89 and 90, respectively;
   b) SEQ ID NOS: 53, 54, 55, 58, 59 and 60, respectively;
   c) SEQ ID NOS: 93, 94, 95, 98, 99 and 100, respectively;
   d) SEQ ID NOS: 63, 64, 65, 68, 69 and 70, respectively;
   e) SEQ ID NOS: 33, 34, 35, 38, 39 and 40, respectively;
   f) SEQ ID NOS: 43, 44, 45, 48, 49 and 50, respectively; or
   g) SEQ ID NOS: 78, 79, 80, 88, 89 and 90, respectively.

7. The isolated antibody or antigen-binding fragment thereof according to claim 1, wherein the antibody comprises:
   a heavy chain variable region selected from the group consisting of
   a1) an amino acid sequence comprising: amino acid residues 20 to 140 of SEQ ID NO: 102, amino acid residues 20 to 137 of SEQ ID NO: 52, amino acid residues 20 to 138 of SEQ ID NO: 92, amino acid residues 20 to 136 of SEQ ID NO: 62, amino acid residues 20 to 136 of SEQ ID NO: 32, amino acid residues 20 to 135 of SEQ ID NO: 42, or amino acid residues 20 to 138 of SEQ ID NO: 77;
   and
   a light chain variable region selected from the group consisting of
   b1) an amino acid sequence comprising: amino acid residues 20 to 134 of SEQ ID NO: 87, amino acid residues 20 to 129 of SEQ ID NO: 57, amino acid residues 20 to 133 of SEQ ID NO: 97, amino acid residues 20 to 129 of SEQ ID NO: 67, amino acid residues 20 to 129 of SEQ ID NO: 37, or amino acid residues 20 to 129 of SEQ ID NO: 47.

8. The isolated antibody or antigen-binding fragment thereof according to claim 1, wherein the antibody comprises:
a heavy chain selected from the group consisting of
a1) an amino acid sequence comprising the sequence of any one of SEQ ID NOS: 102, 52, 92, 62, 32, 42 or 77; and
a light chain selected from the group consisting of
b1) an amino acid sequence comprising the sequence of any one of SEQ ID NOS: 87, 57, 97, 67, 37 or 47.

9. The isolated antibody or antigen-binding fragment thereof according to claim 1, wherein the antibody comprises a heavy chain consisting of an amino acid sequence comprising SEQ ID NO: 102, and a light chain consisting of an amino acid sequence comprising SEQ ID NO: 87.

10. The isolated antibody or functional fragment thereof according to claim 1, wherein the antibody comprises a heavy chain consisting of an amino acid sequence comprising SEQ ID NO: 52, and a light chain consisting of an amino acid sequence comprising SEQ ID NO: 57.

11. The isolated antibody or functional fragment thereof according to claim 1, wherein the antibody comprises a heavy chain consisting of an amino acid sequence comprising SEQ ID NO: 92, and a light chain consisting of an amino acid sequence comprising SEQ ID NO: 97.

12. The isolated antibody or functional fragment thereof according to claim 1, wherein the antibody comprises a heavy chain consisting of an amino acid sequence comprising SEQ ID NO: 62, and a light chain consisting of an amino acid sequence comprising SEQ ID NO: 67.

13. The isolated antibody or functional fragment thereof according to claim 1, wherein the antibody comprises a heavy chain consisting of an amino acid sequence comprising SEQ ID NO: 32, and a light chain consisting of an amino acid sequence comprising SEQ ID NO: 37.

14. The isolated antibody or functional fragment thereof according to claim 1, wherein the antibody comprises a heavy chain consisting of an amino acid sequence comprising SEQ ID NO: 42, and a light chain consisting of an amino acid sequence comprising SEQ ID NO: 47.

15. The isolated antibody or functional fragment thereof according to claim 1, wherein the antibody comprises a heavy chain consisting of an amino acid sequence comprising SEQ ID NO: 77, and a light chain consisting of an amino acid sequence comprising SEQ ID NO: 87.

16. The isolated antibody or antigen-binding fragment thereof according to claim 1, wherein the antigen-binding fragment is selected from the group consisting of Fab, F(ab')2, Fab' and Fv.

17. The isolated antibody or antigen-binding fragment thereof according to claim 1, wherein the antigen-binding fragment is a scFv.

18. A method for treating a patient suffering from abnormal bone metabolism comprising administering a therapeutically effective amount of the isolated antibody or antigen-binding fragment thereof according to claim 1, wherein the abnormal bone metabolism is characterized by insufficient bone mass or density.

19. A pharmaceutical composition comprising at least one antibody or antigen-binding fragment thereof according to claim 1.

20. The pharmaceutical composition according to claim 19, wherein the composition is a therapeutic agent for abnormal bone metabolism, wherein the abnormal bone metabolism is characterized by insufficient bone mass or density.

21. A pharmaceutical composition for treating abnormal bone metabolism comprising at least one antibody or antigen-binding fragment thereof according to claim 1, and at least one member selected from the group consisting of bisphosphonates, active vitamin $D_3$, calcitonin, hormones, ipriflavone, vitamin $K_2$ (menatetrenone), calcium, PTH (parathyroid hormone), nonsteroidal anti-inflammatory agents, soluble TNF receptor, anti-TNF-α antibodies or antigen-binding fragments thereof, anti-PTHrP (parathyroid hormone-related protein) antibodies or antigen-binding fragments thereof, anti-IL-6 receptor antibodies or antigen-binding fragments thereof, anti-RANKL antibodies or antigen-binding fragments thereof, and OCIF (osteoclastogenesis inhibitory factor).

22. The method of claim 18, wherein the abnormal bone metabolism is selected from the group consisting of: osteoporosis, bone destruction accompanying rheumatoid arthritis, cancerous hypercalcemia, bone destruction accompanying multiple myeloma or cancer metastasis to bone, giant cell tumor, tooth loss due to periodontitis, osteolysis around a prosthetic joint, bone destruction in chronic osteomyelitis, Paget's disease of bone, renal osteodystrophy and osteogenesis imperfecta.

23. The method according to claim 22, characterized in that the abnormal bone metabolism is osteoporosis, bone destruction accompanying rheumatoid arthritis or bone destruction accompanying cancer metastasis to bone.

24. The method according to claim 23, characterized in that the osteoporosis is postmenopausal osteoporosis, senile osteoporosis, secondary osteoporosis due to the use of a therapeutic agent, or osteoporosis accompanying rheumatoid arthritis.

25. A polynucleotide which comprises a nucleotide sequence that encodes the antibody or functional antigen-binding fragment thereof according to claim 1.

26. The polynucleotide according to claim 25, wherein the nucleotide sequences encoding CDRH1, CDRH2, CDRH3, CDRL1, CDRL2 and CDRL3 comprise:
a) nucleotides 148 to 162 of SEQ ID NO: 101, nucleotides 205 to 261 of SEQ ID NO: 101, nucleotides 358 to 387 of SEQ ID NO: 101, nucleotides 124 to 165 of SEQ ID NO: 86, nucleotides 211 to 231 of SEQ ID NO: 86 and nucleotides 328 to 363 of SEQ ID NO: 86, respectively;
b) nucleotides 148 to 162 of SEQ ID NO: 51, nucleotides 205 to 255 of SEQ ID NO: 51, nucleotides 352 to 378 of SEQ ID NO: 51, nucleotides 124 to 156 of SEQ ID NO: 56, nucleotides 202 to 222 of SEQ ID NO: 56 and nucleotides 319 to 348 of SEQ ID NO: 56, respectively;
c) nucleotides 148 to 162 of SEQ ID NO: 91, nucleotides 205 to 255 of SEQ ID NO: 91, nucleotides 352 to 381 of SEQ ID NO: 91, nucleotides 124 to 165 of SEQ ID NO: 96, nucleotides 211 to 231 of SEQ ID NO: 96 and nucleotides 328 to 360 of SEQ ID NO: 96, respectively;
d) nucleotides 148 to 162 of SEQ ID NO: 61, nucleotides 205 to 255 of SEQ ID NO: 61, nucleotides 352 to 375 of SEQ ID NO: 61, nucleotides 124 to 156 of SEQ ID NO: 66, nucleotides 202 to 222 of SEQ ID NO: 66 and nucleotides 319 to 348 of SEQ ID NO: 66, respectively;
e) nucleotides 148 to 162 of SEQ ID NO: 31, nucleotides 205 to 255 of SEQ ID NO: 31, nucleotides 352 to 375 of SEQ ID NO: 31, nucleotides 124 to 156 of SEQ ID NO: 36, nucleotides 202 to 222 of SEQ ID NO: 36 and nucleotides 319 to 348 of SEQ ID NO: 36, respectively;
f) nucleotides 148 to 162 of SEQ ID NO: 41, nucleotides 205 to 255 of SEQ ID NO: 41, nucleotides 352 to 372 of SEQ ID NO: 41, nucleotides 124 to 156 of SEQ ID NO: 46, nucleotides 202 to 222 of SEQ ID NO: 46 and nucleotides 319 to 348 of SEQ ID NO: 46, respectively; or g) nucleotides 148 to 162 of SEQ ID NO: 76, nucleotides 205 to 255 of SEQ ID NO: 76, nucleotides 352 to 381 of SEQ ID NO: 76, nucleotides 124 to 165 of SEQ ID NO: 86, nucleotides 211 to 231 of SEQ ID NO: 86 and nucleotides 328 to 363 of SEQ ID NO: 86, respectively.

27. The polynucleotide according to claim 25, wherein the polynucleotide comprises:
a nucleotide sequence encoding a heavy chain variable region comprising: nucleotides 58 to 420 of SEQ ID NO: 101, nucleotides 58 to 411 of SEQ ID NO: 51, nucleotides 58 to 414 of SEQ ID NO: 91, nucleotides 58 to 408 of SEQ ID NO: 61, nucleotides 58 to 408 of SEQ ID NO: 31, nucleotides 58 to 405 of SEQ ID NO: 41 or nucleotides 58 to 414 of SEQ ID NO: 76; and
a nucleotide sequence encoding a light chain variable region comprising: nucleotides 58 to 402 of SEQ ID NO: 86, nucleotides 58 to 387 of SEQ ID NO: 56, nucleotides 58 to 399 of SEQ ID NO: 96, nucleotides 58 to 387 of SEQ ID NO: 66, nucleotides 58 to 387 of SEQ ID NO: 36 or nucleotides 58 to 387 of SEQ ID NO: 46.

28. The polynucleotide according to claim 27, wherein the polynucleotide comprises:
a nucleotide sequence encoding a heavy chain comprising the nucleotide sequence of any one of SEQ ID NOS: 101, 51, 91, 61, 31, 41 or 76; and
a nucleotide sequence encoding a light chain comprising the nucleotide sequence of any one of SEQ ID NOS: 86, 56, 96, 66, 36 or 46.

29. A vector comprising at least one polynucleotide according to claim 25.

30. A transformed cell comprising at least one polynucleotide according to claim 25.

31. A transformed cell comprising at least one vector according to claim 29.

32. A method of producing the isolated antibody or antigen-binding fragment of claim 1, comprising (i)-culturing a transformed cell that comprises at least one polynucleotide encoding (a) a heavy chain comprising a CDRH1 comprising a sequence of SEQ ID NO: 106, a CDRH2 comprising a sequence of SEQ ID NO: 107, and a CDRH3 comprising a sequence of any one of SEQ ID NOS: 80, 55, 65, 35 or 45; and (b) a light chain comprising a CDRL1 comprising a sequence of SEQ ID NO: 83 or 73, a CDRL2 comprising a sequence of SEQ ID NO: 108, and a CDRL3 comprising a sequence of any one of SEQ ID NOS: 90, 60, 100, 70, 40, 50 or 109, (ii) collecting culturing materials, and (iii) purifying said antibody from said culturing materials.

33. The pharmaceutical composition according to claim 20, wherein the abnormal bone metabolism is selected from the group consisting of: osteoporosis, bone destruction accompanying rheumatoid arthritis, cancerous hypercalcemia, bone destruction accompanying multiple myeloma or cancer metastasis to bone, giant cell tumor, tooth loss due to periodontitis, osteolysis around a prosthetic joint, bone destruction in chronic osteomyelitis, Paget's disease of bone, renal osteodystrophy and osteogenesis imperfecta.

34. The pharmaceutical composition according to claim 21, wherein the abnormal bone metabolism is selected from the group consisting of: osteoporosis, bone destruction accompanying rheumatoid arthritis, cancerous hypercalcemia, bone destruction accompanying multiple myeloma or cancer metastasis to bone, giant cell tumor, tooth loss due to periodontitis, osteolysis around a prosthetic joint, bone destruction in chronic osteomyelitis, Paget's disease of bone, renal osteodystrophy and osteogenesis imperfecta.

35. The pharmaceutical composition according to claim 33, wherein the abnormal bone metabolism is osteoporosis, bone destruction accompanying rheumatoid arthritis or bone destruction accompanying cancer metastasis to bone.

36. The pharmaceutical composition according to claim 34, wherein the abnormal bone metabolism is osteoporosis, bone destruction accompanying rheumatoid arthritis or bone destruction accompanying cancer metastasis to bone.

37. The pharmaceutical composition according to claim 35, wherein the osteoporosis is postmenopausal osteoporosis, senile osteoporosis, secondary osteoporosis due to the use of a therapeutic agent, or osteoporosis accompanying rheumatoid arthritis.

38. The pharmaceutical composition according to claim 36, wherein the osteoporosis is postmenopausal osteoporosis, senile osteoporosis, secondary osteoporosis due to the use of a therapeutic agent, or osteoporosis accompanying rheumatoid arthritis.

39. The pharmaceutical composition according to claim 21, wherein the hormone is estradiol.

40. The pharmaceutical composition according to claim 24, wherein the secondary osteoporosis is due to the use of a steroid or an immunosuppressant.

41. The pharmaceutical composition according to claim 37, wherein the secondary osteoporosis is due to the use of a steroid or an immunosuppressant.

42. The pharmaceutical composition according to claim 38, wherein the secondary osteoporosis is due to the use of a steroid or an immunosuppressant.

* * * * *